US008653330B2

(12) United States Patent
van der Knaap

(10) Patent No.: US 8,653,330 B2
(45) Date of Patent: Feb. 18, 2014

(54) COMPOSITIONS AND METHODS FOR ALTERING THE MORPHOLOGY OF PLANTS

(75) Inventor: Esther van der Knaap, Shreve, OH (US)

(73) Assignee: National Science Foundation, Arlington, VA (US)

(*) Notice: Subject to any disclaimer, the term of this patent is extended or adjusted under 35 U.S.C. 154(b) by 664 days.

(21) Appl. No.: 12/678,359

(22) PCT Filed: Sep. 19, 2008

(86) PCT No.: PCT/US2008/076936
§ 371 (c)(1), (2), (4) Date: May 28, 2010

(87) PCT Pub. No.: WO2009/039330
PCT Pub. Date: Mar. 26, 2009

(65) Prior Publication Data

US 2010/0269217 A1 Oct. 21, 2010

Related U.S. Application Data

(60) Provisional application No. 60/994,349, filed on Sep. 19, 2007.

(51) Int. Cl.

| | |
|---|---|
| *C12N 15/82* | (2006.01) |
| *C12N 15/87* | (2006.01) |
| *A01H 1/00* | (2006.01) |
| *A01H 1/02* | (2006.01) |
| *A01H 1/06* | (2006.01) |
| *A01H 5/00* | (2006.01) |
| *C12N 5/04* | (2006.01) |

(52) U.S. Cl.
USPC ........ 800/290; 800/260; 800/317.4; 435/468; 435/411

(58) Field of Classification Search
USPC ........................................................ 800/290
See application file for complete search history.

(56) References Cited

U.S. PATENT DOCUMENTS

| | | | |
|---|---|---|---|
| 6,706,866 B1 | 3/2004 | Thomashow et al. | |
| 2004/0031072 A1* | 2/2004 | La Rosa et al. | 800/278 |
| 2004/0123351 A1 | 6/2004 | Silvestri | |
| 2005/0044592 A1 | 2/2005 | Nelissen et al. | |
| 2007/0016976 A1 | 1/2007 | Katagiri et al. | |
| 2007/0101454 A1 | 5/2007 | Jiang et al. | |

FOREIGN PATENT DOCUMENTS

WO 2009039330 A3 3/2009

OTHER PUBLICATIONS

Van der Knaap and Tanksley, Identification and characterization of a novel locus controlling early fruit development in tomato, 103 Theor Appl Genet 353-358 (2001).*
Tanksley, The Genetic, Developmental, and Molecular Bases of Fruit Size and Shape Variation in Tomato, 16 Plant Cell Supp., S181-S189 (2004).*

(Continued)

*Primary Examiner* — Cynthia Collins
*Assistant Examiner* — Rebecca Coobs
(74) *Attorney, Agent, or Firm* — MacMillan, Sobanski & Todd, LLC

(57) ABSTRACT

Compounds, methods for producing them and methods for varying the morphology of plants are disclosed. More particularly, a SUN gene can be used to alter the shape of fruit in a plant such as a tomato plant.

5 Claims, 40 Drawing Sheets

(56) References Cited

OTHER PUBLICATIONS

Van der Knaap et al., High-resolution Fine Mapping and Fluorescence in situ Hybridization Analysis of sun, a Locus Controlling Tomato Fruit Shape, Reveals a Region of the Tomato Genome Prone to DNA Rearrangements, 168 Genetics 2127-2410 (2004).*

Levy et al., Arabidopsis IQD1, a novel calmodulin-binding nuclear protein, stimulates glucosinolate accumulation and plant defense, 43 Plant Journal 79-96 (2005).*

Guo et al. (Protein tolerance to random amino acid change, 101 PNAS 9205-9210 (2004)).*

Tuinstra et al. (Heterogeneous inbred family (HIF) analysis: a method for developing near-isogenic lices that differ at quantitative trait loci, 95 Theor Appl Genet 1005-1011 (1997)).*

Tam et al., The distribution of copia-type retrotransposons and the evolutionary history of tomato and related wild species, 20 J of Evolutionary Biology, 1056-1072, 1057 at bridge of Columns (2007).*

Miller and Tanksley, RFLP analysis of phylogenetic relationships and genetic variation in the genus *Lycopersicon*, 80 Theor Appl Genet, 437-448, 440 (1990).*

PCT International Preliminary Report, PCT/US2008/076936 filed Sep. 19, 2008, dated Apr. 1, 2010.

Levy, M. et al., "Arabidopsis IQD1, A Novel Calmodulin-Binding Nuclear Protein, Stimulates Glucosinolate Accumulation and Plant Defense," The Plant Journal, 2005, pp. 79-96, vol. 43.

NCBI Sequence Viewer, Feb. 10, 2009, BQ116231-EST601807, Mixed Potato Tissue, www.ncbi.nlm.nih.gov.

NCBI Sequence Viewer, Feb. 10, 2009, DU865501-82099, Tomato Hind III BAC Library, www.ncbi.nlm.nih.gov.

Tian, M. et al., "A *Phytophthora infestans* Cystatin-Like Protein Targets a Novel Tomato Papain-Like Apoplastic Protease," Plant Physiology, Jan. 2007, pp. 364-377, vol. 143.

Van Der Knaap, E. et al., "Identification and Characterization of a Novel Locus Controlling Early Fruit Development in Tomato," Theoretical and Applied Genetics, 2001, pp. 353-358, vol. 103.

Database EMBL (Online), "EST469148 Tomato Shoot/Meristem *Lycopersicon esculentum* cDNA Clone cTOF2K7 5' Sequence, mRNA Sequence," Feb. 3, 2001, Retrieved from EBI Accession No. EMBL:BG123512 Database Accession No. BG123512, XP002594944.

European Search Report, Application No. 08831817.5 dated Sep. 7, 2010.

Van Der Knaap et al., "High-Resolution Fine Mapping and Fluorescence in Situ Hybridization Analysis of sun, a Locus Controlling Tomato Fruit Shape, Reveals a Region of the Tomato Genome Prone to DNA Rearrangements," Genetics, Dec. 2004, pp. 2127-2140, vol. 168.

Paran et al., "Genetic and Molecular Regulation of Fruit and Plant Domestication Traits in Tomato and Pepper," Journal of Experimental Botany, 2007, pp. 1-12.

Xiao, et al., "A Retrotransposon-Mediated Gene Duplication Underlies Morphological Variation of Tomato Fruit," Science, 2008, p. 1527, vol. 319.

Xiao, et al., "A Retrotransposon-Mediated Gene Duplication Underlies Morphological Variation of Tomato Fruit," Supporting Online Materials, Science, 2008, p. 1527, vol. 319.

Van Der Knaap, E. et al., "High-Resolution Fine Mapping and Fluorescence in situ Hybridization Analysis of sun, a Locus Controlling Tomato Fruit Shape, Reveals a Region of the Tomato Genome Prone to DNA Rearrangements," Genetics, Dec. 2004, vol. 168, No. 4, pp. 2127-2140, XP009127717.

Xiao, H. et al., "A Retrotransposon-Mediated Gene Duplication Underlies Morphological Variation of Tomato Fruit," Science, Mar. 2008, vol. 319, No. 5869, pp. 1527-1530.

Database EMBL, "EST469148 Tomato Shoot/Meristem *Lycopersicon esculentum* cDNA Clone cT0F2K7 5' Sequence, mRNA Sequence," Feb. 3, 2001, Retrieved from EBI Accession No. EMBL: BG123512, Database Accession No. BG123512, XP002594944.

* cited by examiner

*35S:IQD12*

*RNAi:IQD12*

| Genetic analysis, segregation at *sun* | - | + | + | + | + | + | + | - | - | - | - | - |
|---|---|---|---|---|---|---|---|---|---|---|---|---|
| Molecular analysis at *ovate* | - | - | - | - | + | - | - | - | - | + | - | + |
| Fruit shape index | 0.98 | 1.53 | 2.22 | 1.67 | 2.78 | 1.88 | 1.80 | 1.13 | ND | 1.30 | 0.84 | 1.36 |

Formation of one large retro-element mRNA

Integration of Rider into chromosome 7

Structure at the *sun* locus on chromosome 7

Lines, T2 (T1)
Plant No.
IQD12
eIF4a6
Mature fruit shape index

Lines, T2 (T1) 07S27 (pp) 07S26 (ee) 07S21 (097-005) 07S23 (105-014)

Plant No. 6 8 9 6 8 9 3 4 6 12 5 2 3 4 5 6 7 1

IQD12 eIF4a6

**Table 1 Mature fruit shape index, *IQD12* transcript levels and progeny testing of selected transformants in the round-fruited LA1589 background.**

| Pedigree | Parental line | Construct | Transgene copy number | Mature fruit shape index | *IQD12* transcript levels[a] | Progeny testing pedigree | Average fruit shape index $kan^R$ | Average fruit shape index $kan^S$ | *IQD12* transcript levels[b] |
|---|---|---|---|---|---|---|---|---|---|
| 052 171-001 | LA1589pp | pHX2 | ~5 | 1.01 | ND | | | | |
| 052 171-006 | LA1589pp | pHX2 | ~5 | 1.02 | ND | | | | |
| 052 171-008 | LA1589pp | pHX2 | ~5 | 0.99 | 0.20 | | | | |
| 052 171-009 | LA1589pp | pHX2 | 1 | 0.99 | ND | | | | |
| 052 171-012 | LA1589pp | pHX2 | ~4 | 1.03 | 0.54 | | | | |
| 052 171-013 | LA1589pp | pHX2 | 1 | 0.97 | 0.11 | | | | |
| 052 175-001 | LA1589pp | pHX2 | 2 | 0.92 | 0.03 | | | | |
| 052 175-004 | LA1589pp | pHX2 | 1 | 0.95 | 0.11 | | | | |
| 052 175-005 | LA1589pp | pHX2 | 1 | 0.96 | 0.02 | | | | |
| 052 175-006 | LA1589pp | pHX2 | ~10 | 0.92 | 0.08 | | | | |
| 052 206-002 | LA1589pp | pHX4 | 2 | 1 | 0.09 | | | | |
| 052 206-003 | LA1589pp | pHX4 | 1 | 0.99 | 0.20 | | | | |
| **052 206-004** | LA1589pp | pHX4 | 1 | 1.11 | 1.70 | 06S496 | 1.17 | 1.02 | 0.31 |
| **052 206-005** | LA1589pp | pHX4 | 1 or 2 | 1.1 | 1.03 | 06S497 | 1.23 | 1 | 1.42 |
| 052 206-006 | LA1589pp | pHX4 | 10+ | ND | ND | | | | |
| **052 206-007** | LA1589pp | pHX4 | 1 | 1.08 | 2.30 | 06S498 | 1.18 | 0.95 | 0.83 |
| 052 206-008 | LA1589pp | pHX4 | 2 | 1 | 0 | | | | |
| **052 206-009** | LA1589pp | pHX4 | 3 | 1.13 | 2.97 | 06S499 | 1.14 | 0.92 | 0.61 |
| 052 206-010 | LA1589pp | pHX4 | 1 | 1.01 | ND | | | | |
| **052 217-001** | LA1589pp | pHX4 | 2 | 1.04 | 1.60 | 06S500 | 1.21 | ND | 0.45 |
| **052 217-002** | LA1589pp | pHX4 | 1 | 1.08 | 3.08 | 06S501 | 1.15 | 0.93 | 0.65 |
| 052 217-004 | LA1589pp | pHX4 | 1 | 1.04 | ND | | Fruit shape index ee | Fruit shape index pp | |
| | | | | | | LA1589 NIL | 1.33 | 0.97 | 1 |

ND, not determined. The fruit shape index is calculated on an average of 10-20 fruit per plant. In bold are the primary transformant plants that exhibited an increase in fruit shape index and were selected for progeny testing.

[a]Transcript levels were determined by measuring the amount of radioactive probe signal from *IQD12* divided by the signal from *eIF4□6* using phosphorimager analysis. The expression value indicated is relative to the expression of the other samples in the column.

[b]Transcript levels were determined in the plants carrying the transgene (kanR) by measuring the amount of radioactive probe signal from *IQD12* divided by the signal from *eIF4□6* using phosphorimager analysis. The transcript level of *IQD12* in the transgenic lines is expressed relative to that of the NIL carrying the Sun1642 allele of *sun*, which is set at "1".

Figure 10

**Table 2 Mature fruit shape index of pHX2 and pHX4 primary transformants in the round-fruited Sun1642 background carrying the LA1589 allele of *sun*.**

| Pedigree | Parental line | Construct | Transgene copy number | Mature fruit shape index |
|---|---|---|---|---|
| 052 172-001 | Sun1642pp | pHX2 | ND | ND |
| 052 172-002 | Sun1642pp | pHX2 | ND | 0.93±0.09 |
| 052 172-003 | Sun1642pp | pHX2 | ND | ND |
| 052 172-004 | Sun1642pp | pHX2 | ND | ND |
| 052 172-005 | Sun1642pp | pHX2 | ND | 0.91±0.05 |
| 052 172-006 | Sun1642pp | pHX2 | ND | ND |
| 052 183-001 | Sun1642pp | pHX2 | ND | 0.97±0.04 |
| 052 183-002 | Sun1642pp | pHX2 | ND | ND |
| 052 204-001 | Sun1642pp | pHX2 | ND | 1±0.06 |
| 052 204-002 | Sun1642pp | pHX2 | ND | 0.75±0.28 |
| 052 204-004 | Sun1642pp | pHX2 | ND | 0.94±0.06 |
| 052 204-005 | Sun1642pp | pHX2 | ND | ND |
| 052 204-006 | Sun1642pp | pHX2 | ND | ND |
| 052 204-007 | Sun1642pp | pHX2 | ND | 1.01±0.06 |
| 052 204-008 | Sun1642pp | pHX2 | ND | 0.99±0.04 |
| 052 187-001 | Sun1642pp | pHX4 | 1 | ND |
| 052 187-002 | Sun1642pp | pHX4 | 1 | ND |
| 052 187-003 | Sun1642pp | pHX4 | 2? | 0.95±0.12 |
| **052 187-004** | Sun1642pp | pHX4 | 1 or 2 | 1.09±0.09 |
| **052 187-005** | Sun1642pp | pHX4 | 2 | 1.04±0.06 |
| 052 187-006 | Sun1642pp | pHX4 | 2 | 0.87±0.02 |
| **052 187-008** | Sun1642pp | pHX4 | 3 | 1.23±0.04 |
| **052 205-001** | Sun1642pp | pHX4 | 1 | 1.07±0.04 |
| 052 205-002 | Sun1642pp | pHX4 | 1 | 0.99±0.04 |
| **052 205-003** | Sun1642pp | pHX4 | 1 | 1.12±0.04 |
| 052 205-005 | Sun1642pp | pHX4 | 1 | 0.98±0.08 |
| **052 205-006** | Sun1642pp | pHX4 | 3? | 1.13±0.05 |
| 052 205-007 | Sun1642pp | pHX4 | 1 | 0.99±0.06 |
| **052 205-008** | Sun1642pp | pHX4 | 2? | 1.02±0.01 |

ND, not determined because of lack of fruit set. Primary transgenic plants were grown in the greenhouse. The average fruit shape index and the standard deviation are indicated. In bold are the plants that exhibited larger fruit shape indices compared to control.

Figure 11

| Table 3 Fruit shape index of plants that over or underexpress *IQD12.* | | | | | | | | |
|---|---|---|---|---|---|---|---|---|
| **Pedigree** | **Parental line** | **Construct** | **Transgene copy number** | **Fruit shape index** | **Progeny testing pedigree** | **Average fruit shape index kan$^R$ or Bar$^R$** | **Ave fruit shape index kan$^S$ or Bar$^S$** | ***IQD12* transcript levels[a]** |
| ***P35S:IQD12*** | | | | | | | | |
| 062 109-014 | LA1589pp | EK69 | 1 | 1.02±0.01 | | | | |
| **062 109-016** | LA1589pp | EK69 | 2 | 2.11±0.11 | | | | |
| **062 109-017** | LA1589pp | EK69 | 1 | 4.26±0.72 | 07S15 | 3.39±0.09 | 1.00±0.02 | 10.9 |
| 062 109-018 | LA1589pp | EK69 | 2 | 0.92±0.02 | | | | |
| **062 109-019** | LA1589pp | EK69 | 1 | 3.92±0.46 | 07S16 | 3.62±0.25 | 1.00±0.03 | 12.3 |
| 062 109-020 | LA1589pp | EK69 | 3? | 0.94±0.02 | | | | |
| 062 109-021 | LA1589pp | EK69 | 2 or 3 | 0.98±0.01 | | | | |
| 062 109-022 | LA1589pp | EK69 | 2 or 3 | 0.94±0.03 | | | | |
| **062 109-023** | LA1589pp | EK69 | 1 | 3.4±0.37 | 07S17 | 2.85±0.16 | 0.98±0.03 | 6.3 |
| 062 109-024 | LA1589pp | EK69 | 3 to 5 | 0.93±0.03 | | | | |
| **062 109-026** | LA1589pp | EK69 | 1 or 2 | 2.15±0.23 | | | | |
| 062 109-027 | LA1589pp | EK69 | 3 | 1.02±0.02 | | | | |
| **062 109-028** | LA1589pp | EK69 | 1 | 4.13±0.95 | 07S18 | 3.49±0.69 | 0.97±0.02 | 16.9 |
| ***RNAi:IQD12*** | | | | | | | | |
| **062 97-001** | LA1589ee | pHX8 | 2 | 1.07±0.03 | 07S19 | 1.01±0.02 | ND | 0.36 |
| 062 97-002 | LA1589ee | pHX8 | 1 | 1.2±0.02 | | | | |
| 062 97-003 | LA1589ee | pHX8 | 2 | 1.4±0.07 | | | | |
| **062 97-004** | LA1589ee | pHX8 | 3 | 1.1±0.05 | 07S20 | 1.12±0.09 | ND | 0.33 |
| **062 97-005** | LA1589ee | pHX8 | 2? | 1.07±0.05 | 07S21 | 1.04±0.04 | 1.36 | 0.37 |
| 062 97-006 | LA1589ee | pHX8 | 3 | 1.2±0.05 | | | | |
| **062 97-007** | LA1589ee | pHX8 | 3 | 1.02±0.02 | 07S22 | 0.98±0.02 | ND | 0.61 |
| 062 105-013 | LA1589ee | pHX8 | 1? | 1.31±0.07 | | | | |
| **062 105-014** | LA1589ee | pHX8 | 2 | 1.01±0.02 | 07S23 | 0.97±0.04 | 1.38 | 0.27 |
| 062 105-015 | LA1589ee | pHX8 | 1 | 1.24±0.10 | | | | |
| 062 105-016 | LA1589ee | pHX8 | 1 | 1.66±0.10 | | | | |
| **062 105-017** | LA1589ee | pHX8 | 1 | 1.1±0.06 | 07S24 | 1.15±0.13 | 1.50±0.04 | 0.71 |
| 062 105-018 | LA1589ee | pHX8 | 1 | 1.24±0.04 | | | | |
| **062 105-020** | LA1589ee | pHX8 | 2 | 0.95±0.04 | 07S25 | 0.97±0.04 | ND | 0.27 |
| | | | | | | Fruit shape index ee | Fruit shape index pp | |
| | | | | | LA1589 NILs | 1.51±0.06 | 0.97±0.03 | 1 |

ND, not determined. The fruit shape index is calculated on an average of 10-20 fruit per plant. In bold are the primary transformant plants that exhibited an obvious increase or decrease in fruit shape index and were selected for progeny testing.

[a]Transcript levels were determined in the plants carrying the transgenes by measuring the amount of radioactive probe signal from *IQD12* divided by the signal from *eIF4a6* using phosphorimager analysis. The transcript level of *IQD12* in the transgenic lines is expressed relative to that of the NIL carrying the Sun1642 allele of *sun*, which is set at "1". For *35S::IQD12* lines, *IQD12* transcript levels may be underestimated due to oversaturated signals.

Figure 12

Table 4 List of Primers

| SEQ ID NO | *Gene* | primer name | Sequence (5'->3') | Fragment size (bp) |
|---|---|---|---|---|
| 14 | *DEFL1* | BT012682F1 | CGAAAGATTTTCCGGTGGTA | |
| 15 | | BT012682R1 | TTTTTACAAACAAAACTAGCATTACAA | 175 |
| 16 | *HYP1* | CDS3F | GCGGTTGTGTTGTCATATCG | |
| 17 | | CDS3R | GCGAAGAAAATTGGGATGAA | 496 |
| 18 | *HYP2* | CDS4F | GAGGCACCATCTTGGAATGT | |
| 19 | | CDS4R | TGAGTGCAGCTAGGCTTGAA | 420 |
| 20 | *SDL1-like* | CME16F | CAGGGTTTGAAGGAATCTGG | |
| 21 | | CME16R | CCACGAATTTCCTTGCAGTT | 190 |
| 22 | *IQD12* | CME5F | CACCAAGAAAAGCAGGGTTG | |
| 23 | *for probe labeling* | CME5R | GATTCTGTGGCTGCCATGTA | 250 |
| 24 | *IQD12* | EP519 | TACAAGGATCCAAATTTTGCATGTCCTTCA | |
| 25 | *for overexpression* | EP520 | ACAAGGATCCGGCTTGGACACTTCGTTAT | 1412 |
| 26 | *IQD12* | EP527 | TTTGGATCCATTTAAATTATGACAGCGCCAGAACAAG | |
| 27 | *for silencing* | EP528 | TTTGGCGCGCCTCTAGAGACCTCCTGGTCTCATGGAA | 512 |
| 28 | *eIF4a6* | eIF4*a*6F | CAGCTTTTGCCACCAAAAAT | |
| 29 | *loading control* | eIF4a6R | TCTGATCCATGTCTCCGTGA | 325 |
| 30 | *Ovate* | EP158 | CACGACGTTGTAAAACGACAATGCTTTCCGTTCAACGAC | |
| 31 | dCAPS, *Dde*I | EP159 | CGTCGGTTTCTACGTCATCA | 240 |
| 32 | *KanR* | EP551 | TGAATGAACTGCAGGACGAG | |
| 33 | | EP552 | ATACTTTCTCGGCAGGAGCA | 171 |
| 34 | *CHS* | EP687 | AGCGAGCTAGCAAAATTCCA | |
| 35 | | EP688 | AGCATGCAAAAACCCTCAAT | 489 |
| 36 | *Fragment that identified phage clone EK36* | EP8 | GCAGCACTTTGCACCATCT | |
| 37 | | EP9 | TGAATGGTTGCAGTGCGTA | 342 |
| 38 | *To map the duplication; Eco*RV *RFLP* | EP45 | TTTACCCGATGTGAAAACGA | |
| 38 | | EP46 | CATCAATAGTCCAAGGGGAAA | 320 |
| 40 | *Maps between EK59 and EK57; Sca*I *RFLP* | EP293 | CATCTTGGCCCTTACTCTGG | |
| 41 | | EP294 | AATGACACAGCGGAACTCAA | 271 |
| | | | | |
| | | | | |

| |
|---|
| *primers to score the sun alleles in the NILs* |
| *cos103 primers (to genotype F2 pops Fig 5)* |

Figure 13

| Table 5 - Comparison of leaf, flower and fruit traits between *sun* NILs | | | | | | |
|---|---|---|---|---|---|---|
| **Traits** | **LA589 NILs** | | | **Sun1642 NILs** | | |
| | **LA1589ee** | **LA1589pp** | ***p* value** | **Sun1642ee** | **Sun1642pp** | ***p* value** |
| **Hypocotyl length (cm)** | 3.45+/-0.24 | 3.47+/-0.34 | 0.878 | 4.46+/-0.42 | 4.20+/-0.14 | 0.181 |
| **Internode length (cm)** | 6.75+/-0.99 | 7.50+/-0.18 | 0.168 | - | - | - |
| **Leaflet number** | 11.88+/-0.26 | 11.33+/-0.86 | 0.204 | - | - | - |
| **Leaflet shape** | 2.31+/-0.23 | 2.04+/-0.08 | **0.002** | 2.23+/-0.15 | 1.76+/-0.14 | **0.001** |
| **Floral organ shape (L/W)** | | | | | | |
| **Sepal** | 7.02+/-0.38 | 5.57+/-0.20 | **<0.001** | 9.75+/-2.68 | 6.81+/-0.73 | **0.002** |
| **Petal** | 4.94+/-0.22 | 4.71+/-0.16 | 0.107 | 3.20+/-0.84 | 2.86+/-0.09 | **0.012** |
| **Stamen** | 6.09+/-0.73 | 6.21+/-0.58 | 0.789 | 3.84+/-1.00 | 3.28+/-0.16 | **0.005** |
| **Ovary** | 1.24+/-0.06 | 1.15+/-0.06 | **0.036** | 1.17+/-0.31 | 1.05+/-0.03 | **<0.001** |
| **Seed number per fruit** | 18.76+/-4.63 | 19.31+/-1.55 | 0.807 | 72.8+/-12.2 | 79.4+/-9.1 | 0.440 |
| **Seed weight (mg per 100 seeds)** | 96.5+/-6.4 | 128.0+/-7.2 | **<0.001** | 343.6+/-11.7 | 373.3+/-10.2 | **0.003** |
| **Fruit weight (grams)** | 1.08+/-0.09 | 1.11+/-0.08 | 0.653 | 105.4+/-9.5 | 101.2+/-5.2 | 0.415 |
| **Mature fruit shape** | | | | | | |
| **Fruit Height (cm)** | 1.30+/-0.09 | 1.05+/-0.05 | **<0.001** | 8.14+/-0.39 | 5.47+/-0.25 | **<0.001** |
| **Fruit Width (cm)** | 1.00+/-0.06 | 1.07+/-0.06 | 0.090 | 5.19+/-0.13 | 6.27+/-0.12 | **<0.001** |
| **Fruit shape index** | 1.30+/-0.03 | 0.98+/-0.01 | **<0.001** | 1.58+/-0.08 | 0.87+/-0.03 | **<0.001** |

Figure 21

**Table 6 - Phenotypes of LA1589 NILs and one transgenic line expressing *SUN* under its own promoter**

| Genotype | Leaflet shape index | Seed number per fruit | Seed weight (mg per 100 seeds) | Fruit weight (grams) | Fruit Height (cm) | Fruit Width (cm) | Fruit shape index |
|---|---|---|---|---|---|---|---|
| LA1589ee (n=4) | 2.35+/-0.06[a] | 18.14+/-2.07[a] | 125.89+/-1.92[a] | 0.78+/-0.15[a] | 1.41+/-0.03[a] | 1.04+/-0.06[a] | 1.37+/-0.07[a] |
| LA1589pp (n=3) | 2.06+/-0.07[b] | 17.06+/-1.94[a] | 147.05+/-7.09[b] | 0.81+/-0.07[a] | 1.02+/-0.04[b] | 1.08+/-0.05[a] | 0.94+/-0.02[c] |
| 06S497 (n=4) | 2.34+/-0.05[a] | 15.40+/-3.15[a] | 126.42+/-5.47[a] | 0.70+/-0.06[a] | 1.18+/-0.15[b] | 1.01+/-0.06[a] | 1.16+/-0.10[b] |
| 06S497-5 | 2.33+/-0.18 | ND | ND | ND | 0.95 | 0.93 | 1.03 |
| 06S497-8 | 2.29+/-0.08 | 13.62+/-4.87 | 127.37+/-2.73 | 0.65+/-0.20 | 1.27 | 1.03 | 1.23 |
| 06S497-16 | 2.41+/-0.43 | 13.53+/-0.19 | 131.36+/-11.24 | 0.66+/-0.06 | 1.25 | 1.01 | 1.23 |
| 06S497-17 | 2.32+/-0.12 | 19.04+/-0.06 | 120.54+/-12.14 | 0.77+/-0.09 | 1.24 | 1.08 | 1.15 |

Figure 22

SEQUENCE LISTING

<160> NUMBER OF SEQ ID NOS: 41

<210> SEQ ID NO 1
<211> LENGTH: 61605
<212> TYPE: DNA
<213> ORGANISM: Solanum lycopersicum

<400> SEQUENCE: 1
aagctttctg ctgcttactt ttgggattaa ttaattaatt aattaccata taattacttt 60
tccatacatt ggattaatta aagaaaacta atcaccactt aacagaatca ttcaccacgc 120
cgttgctttt gactattttg ttataatgtt aagttaaaga tgaacactaa ttaacttaga 180
ttggacattt aatttattga ttaagctgtt aaaattataa ttataatatt aaaattattg 240
ttatgtttta aattgtgtgc aattaatttg tctttcgtaa attaaaggaa ctaagattat 300
tattacagtc attaattacc tagttttaat ttttaaaatt attactttaa gggtaccaaa 360
tcatgtgtac tttataatat gattcttgtt tagtcatatt ttaccaattt attttgacat 420
tttttgggtt tcatcattgc gaataattaa acacgttagc tttgtgctat aaacaatcag 480
tgaaattatg gttggtatta tccgcaataa caataatatg tttggtaaaa ttttacgata 540
aaatctaagg aggatacata tttatctcat gaaaataaaa aaaaaattgt atctttgtca 600
tgtccgaaaa cccgcataaa attgtgaaat attggtccaa atgataaatc aaattcccct 660
atttcaactt atttatcgta ctttcttaaa tagttatttc aaattattta tctttgtaca 720
aattcaatac aaaatatatg tatgtatatt tcctcgaaaa gttaatacaa gaaagtccta 780

```
acaagtactt ctagaagtac atgtataggt gaaaacttac aattgaaaaa tgtcgtggta    840
aaatttgatt cgaatcatta atttttttta aaaaaattat atattcacaa ttttaaaaca    900
tattttttta cttgactaac gaaattttat ctcgtaaaat atttattatc tctgaacatg    960
agaacaagta aaaagaaaac aaatcccacc ttccaagtca ttttcactac attttactaa   1020
ggccaaagta ctatagacat gactccactc ttaaccaatt gcatgtgcat tagtcatggc   1080
gtgggtggcc acttttcctt attcttcatc ttttttaaaa aaattttaac cgttacagtt   1140
atatatttga taaaacgttt tctataagaa gatttttttat ttaaagattc aaaagcaaaa   1200
tctttgatta aagataaaat aattttattt gactcaccca ttctttggtg ttgacgtggt   1260
cgtacaaatc aaaactcgat aaataatagg ttgatccatg aatttttcct ttcttacagt   1320
tagtttgtta tgtaaattaa ttaaaagatg aaatcctttt tatattctaa agatcaaatt   1380
taagatgttt aattaaagat agaaagaatt aatgaaatag cctaccccac atcctccgat   1440
gattcttgtt tttataattc tttttgattg ataactgaga agtctcggag tacacgcaac   1500
atatagttcg aaactcgaca aataataaat cgaccccttgt atccttctcc aacaattagt   1560
tcttatattt gtcatgtagt aaattcatta caggatgaaa tgcattttat ggagaggatt   1620
ctgattctag agatcaaatt caatatcttt cgttatggaa agaaatcaaa cgtcctacct   1680
cacttccccc cttgcagttc ttgtcgttat tattcttttt gactgatagc tgagagatct   1740
cagagtgcac gcaacataca gtctaaaact cagtaaacga taattaatgg ccccacccct   1800
tttatctttc tagctagaat gacgtattct tttatatcga caatattcaa acttgtaacg   1860
tatgttgtta ttcacatatc acatgttatg ttcttaccgc taaacgaaag ccccaaaggc   1920
cttcaattgt tcttactctc tcttctaaat aataaaataa taatcactta aatatgaaca   1980
agaagggaaa gaattgaaaa accaaaaaag cattgaagaa agtcttgtta ccaagcaaac   2040
aatatttctc catggaatct aaaattgatt gatatttgag ctctcacttt actagacatg   2100
catcatgacc cttgtattat gcattgtctc aatatttagg acaccaaagg tcccccactc   2160
tcaagataaa aagaacaaaa ataccccact actttaggct ctattgcaaa atgctatctt   2220
tcttttatgt tacatatatc atagaagaat tctgaaaaat aatgtactac attttctatc   2280
tattatgctc gtttcgtttc gtttcaattt gtttcttgta ctttcctttt cgattcatct   2340
aaaatatttt ttcccctttt tgtggcaact cttttgatta tgattttcta catgttatgt   2400
ttaagactat gatgtttaat taaaatacat ttatgtcatt caatatatag ttaccttttt   2460
attttttttta attatatatc aaataaaaat cagacaaata aataaatcgt aactacggga   2520
gtagctatta tagctttgtg ttgatatata tatatatttt ttacctacaa aatgaaacat   2580
gagtgctcta gtttaggcca aagctagctg ctagccaatt cgaatgaaac agtgatcatt   2640
gggaaataac tatcgactgg gccccacctg agaggcgatt tatctaacgc catccctagg   2700
tggggctcac acaaatttga ctagggaaca aacgagagtt ccctagctca gaaatgttaa   2760
ggttaaaacc tttctaatgg agtctaacaa cttggttcca cgcgatccca gccaatgtaa   2820
gactcataat ccataggtcg tgctttgatt acaagtctca ggcttgagct ccaaatagag   2880
acttaacaat aggtcttagg tttgagacag aaatagagcc tttttaatag taaaagtgtt   2940
gggatatata cacactatta aacgtgattt ataatttatc atgataagaa taatttaaat   3000
taatttttga aattatttcc atatattata gagattgaat aatatatggt caggtaccac   3060
tcagggatgg ttggatttgc aatcgagacc taagagtgag gagttgttgg attttcatat   3120
ttttgtttcg ttttgtttga agaattctta gttcagtatc actctacctt tcttcatttt   3180
```

```
cgcgcttaga ccaagcattt taaatctaga tagtctcact aactaaacga aaaaaaagac   3240
tcgattaatc aaagggatac tacgagtcct gtgtcctaca catcagttcc aactactaaa   3300
caattaaatc cacaattgtc atctttgtga atcttctttt tatacgtaac acgactttct   3360
aatatgattt tccgattagg atgatgaatg tttaattaac tgaccactct tcgctctata   3420
tccatgcaag ccatggagta ttctccatgg aacaattagt aaaattaatc aaaagatgtt   3480
ttctactaag tttttattgt tcctattttt atttattttt ataatactaa tgtatatata   3540
atgattacta tatattcaca aaatgagtgt gcggtcatat aagatcagat aaaattaaaa   3600
atcaccaaag gcataatatt aagtgtaaaa gaaccaaaca tcgaagagaa gttgcaattt   3660
ttatgaaata ccaaactagt agagtagtta cgaaatctga aatataacat tttgtattat   3720
aatacaataa agtgtgcaca ttatattttg tggttcatat ataataggca acggaacaaa   3780
tacatactac atcaaaattt aattattctt tattgtatat aagcaacaat aacagtaata   3840
tcatcaactt ttcctcctct atgtcgtccc ttagatgctc ttgcatatgg tgtatctgca   3900
tatctatcaa atgaattgta caatgcaatg tttgcaattt tcttagccaa ttcctttggt   3960
ttcaacttgt cgtttatcgc tctttgaaca atttcctcta tctcactatc attcatatta   4020
tcaagcatcc catccgtccc agccatcaaa atatcatcca tctcgacgtt tagttccatc   4080
tcatgagcaa cactaggatt gtccttgcag tttcccaatt gatatggaca cccatatcct   4140
ctttgttgta ttggcgactt gtatataatt tttccctttc tgattagtaa aaatccacta   4200
tcaccaacat tagcagcaac tatactactt ctctctgagt ttagagatat aatgcaagct   4260
gtagacgatc ctcttgaatg tgtgtttctg taagcttctt caagaaccct tttagggttc   4320
acgtgacctt tcatcgcttc actatccgta gcgatacgtg aattcttcat aagctctctt   4380
gcgtatattc cagcgtcaat cccatgtttt gcccagccac caacgccatc agcaacgcca   4440
atagtttggt ataattcatg tatgaagtta gcatcgtcac ctaaaggctt ctttggatcg   4500
tctttgggta tgtatacaga tccagccatt atttttaggc atggtagtaa ctctttgtta   4560
ctagattcaa ctactctctt ttcgacattg acaaattcat tatcttgact aaatttgagt   4620
ttcttgttgc tgtgattttc cagttgatca ttagcttgat gagaagtgaa gtctaaatac   4680
ctcttgtagc gtggcaggtt gaaaagttca tcgaaattga tggaggaata ttgatcatga   4740
cctaatgaag aaatataggc agccattgtt gtattgattg aaaaactttg ggaagtaaaa   4800
aattatgtga tacaaaaaat tatgtgaagg gttaacatat atatatacac acacagatta   4860
cgctgcaatc ctatttagaa taggtaatgg aaaagcaatt tatggtaact aattaaatgg   4920
aatatttaga aactagcgtg taatctaaaa gaaaaaggga tttggaaaca aagtatgata   4980
actaactaaa ataacaattt ttggaaacaa tgtaaaacaa ctagaagtaa gtaatcctca   5040
cgcgtacggg catgaaaaga aagtgaaatt ttaatccaaa ctcatggaag atttccttat   5100
ggacgcagaa ataataaatt ttacttatag agtcgacgag aaataaataa ataaataaat   5160
aaacgcagat aagatcacaa tgcgcatgta tatatgccta gcacaactgt aaaattcata   5220
aaactgcatg gagatgaggg cagaatgcaa ttcgcataaa tggtgaaagg tttaaatgag   5280
atgatagtca agcaaatcaa aacttgaaac ctaacaccga agattttcca ctgggaaaac   5340
agaatgggca cttgattcaa aatggctacg cgattgaagg tcgattcttc ttcccatagc   5400
agatgtctga caaaactgcc cagattaagg ctgctgcgtg gttgctgctg cagctggccg   5460
agggttctgc tgatgtgcgg ctagctgaac actaggtggt gggtgtgcag tagcttgata   5520
aggtggagga ggatattgat gataaggtgg aggaggtggt ggcatatatc cataagctgg   5580
```

```
acgataataa ggtgggtaaa attgacctgg aggtggtggc cctccaggtg gatatgcata   5640
atggtgtcct tgttgatgat cagaaccgat tttattttca ccaggaccag atcctgcagt   5700
tgaactagat gccccttcct gggatgcaat tacggcaccc atcctttgtg gatccattga   5760
tggataatat ggtctgtctt gctgaggcat cgggggtatg ttgaagtaag gcatggatgg   5820
aggttggtcc tgagtgcctg gtggctgaag aggctgattc tgctgctgtg atacgactgc   5880
tctaggcaac aaaccactgt gagttagagc agcctgctgt cttgcttcat cagagacctc   5940
ggactctggc ttgggaactt gaggtctccc ccagagtagc ttcagtctca ggccctttat   6000
caccagcttg tttgcaagtt cctcagctgc cttcaccgca ccttctctag tcgtgtaagt   6060
tacaaaagca caaccacgct ggaccaccat tttaatggac tcaatttcac catgtgcata   6120
aaaatggtcc ctaaggtcct gctcagtgat tcttgcatca acaccaccca catagagggt   6180
tctaatgctc tcgtcatcag gggctccaa tgaaggcatt tcacctgctt tattaagtag   6240
ctttaaagcc actggatcat tgactctgca agcatttaag atacatcagt gaagattttg   6300
tcagtcaaaa atgtaggata aatacatctc tgtaaatgag aacagggtat ataataagca   6360
aaagaaaagt gaccagcaaa tagatgtcat caataatcag cctagccatc acgtaatctt   6420
ggagagacaa agtaagatga gtttcaaaag tgcatagagt atttaattca ttggtcatga   6480
agaaaatggt atctatctag agttaagtgt ctgaacttaa ttatgtctat aaccatggag   6540
atgactgggt tctgcattct tgccagtttc ggcaattatt tgaacctcaa caagctgtta   6600
aatcacatga aaaagcattc acaaaacatt tcttctagga cttccattgg tgatcgagtg   6660
caaggatttg aacaagatgg cattaaagaa atttaaacaa ggctctactc caaaaaaaaa   6720
aatacttaaa taacgtataa ctcaaacaca agcagagagg attgagaaac cagaaaggaa   6780
taagtcacgg aataaagtat gggaatgaag actaccagtg gtagaaagca attacaccac   6840
acattcacac aagcattttt tagctgcaaa actataaaaa aatgattata atatattgac   6900
agcaggacga ctttgtatgt cagatctgag ataaatttac atgtttatat atgtttttgt   6960
ttataaattc aatgagggta aacaagcaac tcaatataag ctattcacct cctgagtcag   7020
ttgaccaagt ccacatactg tcttcccaca ttgagatata ttttacttaa gttgttttgc   7080
ttctcctttc taacatgata aatgagaaca taatctctgg gtcaattccc ctttttttcct   7140
cctacttgct gaactgatgt attatttagt tatacaacaa catacccagt gtaatcccac   7200
aacgatgtat tatttactat tttatataac attgtgtggc catgaatcgc tggccttcat   7260
cccatattag cattgcaact gagggaaaca gataatgtgt ctacagtgac tagtaagtct   7320
tctaaaaaaa gtgactagta agtcttcatg aacatatcaa cagaaaagtg aaccgccatt   7380
ctcacacccc aagcaaaatt aaagaccaga aaccctatca caaatatgtc aatacagata   7440
tatgagcatc attccaaaaa ggagaatttc acatcagcga caaagaatca gactggcata   7500
cccatagtaa cggtctttga tattttgctg tgacaattcc cctgtttcag gcatctcatg   7560
ccggtaagga cactccaaac ctcttgtaca ttgaccacgt atgtagaaac tgcaaacatg   7620
tgcccgattt ctcttgtagt atggagttgt tctttgaagc ttcatgatag tatcatttgc   7680
acggactttt ccatatgaag attcataatc aataccagcc cttgcctgga caaaaattta   7740
agtattactt tggggaaaac caagaaaaca gcattttttt tttgtgcttc ttgaaaattc   7800
taagccctta ttttcaccag gttcaatttc ttctcctaat ttaaaactgc accccatccc   7860
taagtagttc ccagcaagat ttggatcgga ggtgtgtggg gcggggtggg gggtggggta   7920
agtaaattaa atataagttg ggctttcact tagtaaatca catacccttc ggtcatgctc   7980
```

-continued

```
ctctgcaaaa tattctctat ttacgtcact ctttgggatg gcatcatttg agttgatact   8040
gagagcagtg tctcggacct gaacaggcaa accatattca agatctaaca ggcaaacttg   8100
acaaacattc ttcaatttgc tgcaggtctg acagatctca gactttttgt atctcgcatc   8160
ccgaccaggc ctccacctga acactgtgaa gggtcgcgtg cagatcttgc actccttgtc   8220
ataatctgct tttgtctgta caaaaaccat aacaaaatca aaagtcagat agtgaaattg   8280
gagaaagaaa gattatagta gaggacatgc agctaaaacc aaaacaaagt caaaggcccg   8340
acttattcta ctgccaaaat ggagactctt tgagcaagaa attaattcct aatatgtatg   8400
gagagagtaa acatcgtaac aatgtgccaa aagtagtggc aaatcaggag aagctgtcga   8460
tgagtaaagg tccaaacaaa gagcttcaga aagccacaat gattataatg taagtggtct   8520
tgcctagcta cacgtaaata gaattcaaaa tacagtttac tgcagctagc acaaagataa   8580
gcaattaaat aaatgctacc agagattaac agtccttaca gaaaggctaa tagcctttcc   8640
tgtagagcaa atctgacaaa caacttactt aaaaatttga taaaacacta cgttgctgcc   8700
tccatcaaag gatccagcca cattcttcac gcacttcaca ttcttaagga acgctacatt   8760
aggaattgga ctccgtgatc tttcaaggtt gagaaatgac agtctttacc cttttaaact   8820
tcaataaagc cccccccccc ccccttcttt atttgatttt gcacaataaa cacatatatt   8880
tctacaacta ctgatcattc ctactgtatt aataaattgg ggcacttgaa ataaatgaat   8940
tcttaaaaaa tcacctaaaa aattctgaaa atgaacttct agttgtattc agagtaacct   9000
tactatattc ccctaaaacc atatcaatca accaatcatt caacttcgcc ttattcacat   9060
actttactgt tgcctatttg aatctgcaat ctccatcaac tctagcctct ttgcacctat   9120
attcacctat aactacaacc agaaatttct caacttcttc gccgaataaa gtttcctacc   9180
cttccacctc aaatctcaat agcagatagg agcaatgcaa ataagaaaaa cattcctcga   9240
gtatattttc aatttgtagt cagcaaccaa aggactggag attattataa accctaggac   9300
cattcacggc ctttaccata acaaaaattg aaacgaagaa cttaccattc gcacataggg   9360
actgtcaccg agacacgact cgcatataat agggaaatca gatcgttccc atccatcagc   9420
ttcagcatct ctcagcaacc tatgcgccat cgttttctaa ttcctaaact tcaatctgca   9480
aaacaaatga acttttaaaa gctcattcca agctatttat tacatattct ataagaatct   9540
taacctaaag aaacagaaat ctgaaaaaag gtgagaaatc aatagtacct gattaagagc   9600
aacttaggct agtgaaagtt atttgaatgc caaaatctcg cttagcagac tcaattttat   9660
atagagctca gagacggcgg agatggctgt tgtcgacggc ggagagaaga accttccgac   9720
gaaggacagc gaggcaaata gcccagctca gccgggcgaa gagagataag aagacctttt   9780
tcaagttgat ttccgttatt ttgaatttta aaactattaa ttaattaaaa aaataaattt   9840
aatttttatc atgataaaaa tagaaaaaaa agtaatttaa ataatttttt ttatatataa   9900
atatatatta caacaataca tcgatgaaat ccacaagccc attctctttg tatgaaaagt   9960
aggaatagga aatgtcgtag gtaaagctgt ccagtactac attcgtaagc ctttcatgta  10020
ttgcatgcgt ttattaaatc agctcaatca taaaatacta tataaaatat gattatgata  10080
gtcatttccc taactacttc aatgattaat ttacatcctg tccttgttat agtataattc  10140
aatctaaaca gtaccttgtg ttataattga gaaattttat tgctcggatc gtctagtcaa  10200
caaccatgaa aggacaccct ttttttttcaa gagagaattt gtttctgaaa gacaatttgc  10260
ttcttgaagc caccaaagaa aaaaatggcc taaatctata aaagcagaat aagttgaact  10320
ggaaattaca gaatatcagc agatgttagg ttcaaagaat tatcaataac aatgtctaaa  10380
```

```
atccttcccc atcaacaatg aattatccca aactagactt agccatctca tacgccaaga  10440
aacatgcagc atttgcaggg acactacgtc ccatagcagg tccaaagccc ttgtaaaggc  10500
ctttgactcc ctccgatgcc aagatcttct tgaatgcatc aaaaaagcca gagaattttg  10560
ggtttttata gtcatcgatt tggattacac tcttgatcac gtctgttgga tacaccgaaa  10620
tccagaagga accaccagcc aggccacctg ctacaataag agaacctctt cccaaccctg  10680
aagtgtctgt gcctcctgca aagtactgct ttagtgcttc atacatgcca aacatagcag  10740
catttccggg gatttcacgt gccatggtgg gaaacaagcc cttgaagaga cccatcatgc  10800
ctccttcgga tcgaagaaca tgtcttgcta catccattgg ccctgcatat ttcactgcca  10860
cagcagctga gcctacactt gccaatgcac cctgagcttg caatctacag tcatgtaatt  10920
taacgagtaa attgacaagt atagaagttg attcctagta gttttgatca tttgaccgaa  10980
caatggtaac aaaaagttga aaagtagata atgcacatgt cactactaag gatacaacat  11040
ggcaaaaata agcaagggaa actttgtgaa ggctgaatta taatgcacta gaaacaaacc  11100
tgcattttat aagctcagtt gggcaagcaa gaaaagagac agcagttccg gcaacagccc  11160
cacaaacaac ttgctggctc acagtaagag ggactccagg ttcagacctc aagaatgcct  11220
ctgtttgacc tctcacggtg aagagcagag cattaaaggc tgcaacagtg gcaagtgggg  11280
ctcccatgcc tttgaacagc cccccggcac cttccgcagc taatgtttgc cggacagcat  11340
ctatagcacc agaatatttt ggaagctgcc ctggaagtgg agtaggctgg ctttgaagct  11400
tgacctttat ggtatcaaaa gggtgaccaa cgaccaattg tgctacacca cctacagtcc  11460
cagctgttaa atccttggct atatcaccca ttggaaaatc tgaaaaaaag aaaaggggga  11520
aaaacaattc tcagtctaaa tgtaagctat tagctactgt attcactgtt tacaattctc  11580
aattgtagaa aaagaatgat ttgctgggaa ggagcggacc tcaagagtat attatcaaag  11640
ttaagcttaa agcttctgct aaaagttggt gcagtggaaa aaagaacatt aatctttaca  11700
gtcaatagcc atgaacctat atagtaaaca acactaggcg tcattgatgt aataacaagt  11760
ccagcttggg tgtttgtgga gtgaccacaa atttatgagt aaatagcacc aaaaagaatc  11820
caggtaaagt tcttctcaac gatattattc acaattttac acctcccagc ctgaggcact  11880
ctgataatca gaaactgata tgtcagatga caaaaaaaaa cagatcaaaa gtttgtatgc  11940
taactctaat tctctagata attttgacat tggtgtccta tgaaagtcgc ctagtttaaa  12000
accaaagtga tcaaactgct tctgcctaca aattatctac acacaacgct tgacaaaagg  12060
aaagagtgag acagctagtt agaactccag tactatccca ttatcatttg ctcattcata  12120
gtaaggaagg actagattca caaatttctc cctgtataac cgcctaacca aaaacaaaga  12180
agcaaaaaaa atagacatgt acaagaatct cttcctttga ttctcgactt ttcttctcct  12240
tgataaacat attaaaacgt aaggtccaaa aacatgtact cgaagaggag aaaattggaa  12300
atctagtggt gataataata ctcttcatca gatagagcag aaattctaaa agctaactga  12360
gattgaagac cttgagagaa ataaactaat ctgattctat ttctttaaag ttcaagctca  12420
aagcagactc cgaggtacaa attagtttta aggaaggaaa aaaccatgaa gaagatattc  12480
tagagatttc ttatggtttt gagcttgatg aatcttgaat ttatctaaat tgctctcctc  12540
atgttcgctc accagctttg aaagaatcca agcagggagc tcttggagag catcccaacc  12600
cttacaactt ataatagtcc cacaagacaa atgacacccc attaactgaa ggttgtcact  12660
tttttacggt tttacccacg agagagctaa ttccagcatc aaattcaaac atagaagaac  12720
tagaaaacat gtcgtaactt aactatcatg ttattcacaa atgcctcaga aatcaaagct  12780
```

-continued

```
gctgaaaagt agtcatcggg aaggcaattc cctctagtga actatatata gtccaccctc  12840
gatagagatt ccaaacataa aacaattacc ttcaaaagta aatagctata tcaagaaagt  12900
gaagtgaaat tacagaatct agatgcaaaa attcacaata cataagagtg gaaaggcaat  12960
cctttatgct aaccacaaac aaaaaccaat accgtgcatt ccatcagaca cctaaaagtt  13020
caaatgcagt cctaagccac aagcaaccaa ttcgcacaac catagaaatt catagaaaca  13080
atggtatagg ggtttagaga aagactacaa cgacaactat gatcaaattt taagccttaa  13140
cctggctgat ttctctttat acaagaagaa tatccaacat gacggatccc cgatttatca  13200
agatctagat gcaatctgaa actaacagtt gagcaatgta acactcaatc acgcaaacaa  13260
agcaaacgtg cacatcaaga tatgacatac agaaacaaat cccacaaagg aaaactagaa  13320
acatagacat aaaggtgtct gatttctgac ataaatacaa aggtgaaaaa taccaaatga  13380
acatcactca atgtccattt tcagcacgtc aacttctagt ttcctaaaaa ggtatataat  13440
ttcaccaaat tttaacaaaa gtatacactt tatactaata aaagattcta ctggtaaagt  13500
ataagcctta ccctagctag ttatgaatgt ccaccaagtc aaccaaatga attccacaat  13560
ctgaaatcta cataaaagca gtgtatcagt agcaaacata tacatcaaca agatagacat  13620
gaaggaacaa atcccagaaa gaataagcaa aaggggtttg atataaaaga aaaaagatac  13680
ccaaatgata tcactcaatg cccattatca tcagtacatc aaaggtggag tctttttcca  13740
tattttaaca aagttataag ctcggtggac taatgtgtac ctgataaatc tgatagtaaa  13800
agaatcttga atttcaatta cagccacatg aatgaaattc aagaaacgac aataatggga  13860
tttagaaatt tggtggccaa tagctgtaaa gacacaattt ttaattagat aggggagatg  13920
aggacacaaa ttttgagcaa atttcagcct cttttctcct cccaactcaa gatcttgaga  13980
gagatggaag aaagctccta taatattggg tcactctttg ctatataaag ggaatataca  14040
aattgcaggg ctaccaccaa ccccatttac ctataatagc gcatcccctg attttgacag  14100
atttactacc ttctctagtt tcaattcacc tgacacaatc ttcgatttca atttaataaa  14160
attatttata attttataaa agtataaaat ataaatattt tattttattt attgtttatg  14220
tcttttaatt ttgatatata cgagtaagta atactccttt ttgtgtgctt aattatttgt  14280
tcaaatttct tttttggtta tttctaatct tttctccgtc ttaataaatc aagaaatgac  14340
aaaaagattt acctattata tcctcaatta attattttta aaaaaaataa cgcttcttga  14400
aactcttaaa tttttaattc attcatttca taattaatag gggtaaaatg gtaaactcac  14460
aatatcaatc atagttcttt taataagtgt gtcaattcaa aagttgacaa gtaattagga  14520
acagaatgat tatttaaatt tgtattgata tgaacaaaga aatacacata tcgtacgtga  14580
tattctacct aatgattcgc atcttacacg atttatatgt ggtgtttgat tatgtcacat  14640
aaaataccta aatttatttt atttaatttt atacaaattt aaatacatag ttatatatat  14700
tgaaaaaatc atattttatg cagctaaatg cgtttggtgg agtgatttta aaagtttttt  14760
tttcctaaaa aactcgatca cttatgtgct ttacacggat gcatcatctc accaaacttg  14820
tcaccttctt cttctactaa taatacaaaa ctaaacatat aaatggtaat ttattgaatg  14880
gtagctaatg gaaaagatta atagaaatta gaaaattaat gtgtatctta ttaaaaaaaa  14940
aatcaaagtc aaatcaaatt aaattaaata ttaggatatc taattgtagc atagattatc  15000
aagagggtcc tttattctta ggatggcaat caatatttgt tatactataa aaatattaat  15060
aatgtaattc aattcatctt agcctaataa tgtttgattt taaaagtcat atatcgttat  15120
ggtatgttaa tatctccatg atcattgcta tatagtaatc tatattttag gtatagtaaa  15180
```

```
atcacgatcg aactcttgta gcaaaatatt gttactcttt tttattactt aaatattaaa  15240
tttcacacta ttcaaacctt tttttttttt tttgttaata gttattttac ttacaataaa  15300
cattttacct tatatgtaat gaattttaga attgaggggt ttaccatatt atagtaaagg  15360
atcattcaaa agtattactt aaaatgaatg aactggttgt atcatgtata taatataaca  15420
aaaacatctt atcttagtaa tttaagtaat atcacatata acatacacat actaatattt  15480
gcaaaaaata aattttgctc caaaaatgct aatttggaaa tattcatcac ttcatgttcc  15540
aaaaattgaa gcaaatatta ataatatgaa atttaacctt gaaaataaac tctaaagaag  15600
taggacagaa aaagatgata caatgttgat tgccttaata ttagtactat tagtttatgc  15660
acttgcatta catgtgtatt caattaaatt aaacataaat tgttttaaat tggcattata  15720
ttaaaaaaaa attataattc aattacatga atattgttta tttttcaaac aaaaaatata  15780
tatacttttg gatatcaata acaaattaaa atagatgaca acaaaatatt tcttctccaa  15840
atgagacaaa aaatgtaaat atttagtact ttaaaatcct ataatcaaaa acacaaataa  15900
atatatatat atatatatat tcttatctca tgtgttaatt atcacaaagt tcagaaaaaa  15960
gaagaaagat gaaaaatgaa aagaatttga tagcacttgt tagaattaat taaaataaaa  16020
tgaaggttac agttaataat caatattatt tattattatt attattatta ttattattat  16080
tattattatt attaaggcat catatcaaat attgaacctt actaaattat tttttttaaaa  16140
aatgagtttc gaatacaaaa atttaacatc aacggagtga catacaactt aaaatatgaa  16200
atcgtataaa aaattgaaac attgaaattt gtctttctca aaattagata gaagaataaa  16260
aataaataaa gatatatcat tatttcttca gtgaattaaa ttagttatta ataatttatt  16320
tgtatgttac tttctccact ttaaattagt ctatgtgttt caatcttgta aacccccttaa  16380
gaaaaacatt gataaaaatg tagttttatg tattttatgt tatattccct ttgaaaaata  16440
aatataaata agtaactaac aaaatcacaa aaacaaatta aataactatt attatcaata  16500
cagtacaata atttaattgt taaaaaggac aagtaaaatc taattaatat atttttacaa  16560
gttacattac acaagtatat tagtaaagag tcatgatgtt ataatttgat tcgtgaccct  16620
atattttaca ttcaaataaa tgatgttatt tactacaatt gttttcattt ttatagataa  16680
ctaatgtacg gacaatccaa aaattacaag acaatgtgta taatcaagag ttatataagt  16740
gcgaattaat catgatctaa atatatgaaa atattaataa atttttaaaa taacctgatt  16800
tttattaata catgaatcat attaaattgc ttgtaaattt caaaataata tttaaaattt  16860
ctcaaaaaat atttgttttt gttttttctt ttttgcattt gaacattaat tacggcataa  16920
taactttagt ttctaagcat gaattattag aggaacgatg ttaatttagt gaatgatcat  16980
ttaatttttt tagaaatatt taatatttaa ttaattagtt ttttaattaa aaaattataa  17040
tatatgttag gggtaaaata cttattcaaa tttgcaattt agtgcttccc actttgatat  17100
gatgattaaa ttaaatatac atatgaaccg tgaactgtag atgttaaata ttattaaatt  17160
gaatatttta attatgaatt aaactaagaa agtgcaaaat ttttgtgttg caaatgacat  17220
attttctccg cttccaattt attgatattt actaaaaaga aagtttactg aaattactat  17280
aagtgaaaat taaaaaaatt gaaagttgaa ataccaaaaa attcttataa aattgcgtta  17340
ctgcaataat gacattaaaa aaaagttact ctaaattaaa atattataaa atatttattt  17400
aattatatac ttagacaata attatataat attatacaac actagaaaac ccaaaaatta  17460
tagtaaatag tattcataca attaagagat aatgcacaaa tactccctca acatatgttc  17520
gaaatctcag agacacactt gtactatact aaggtcctat tacctttgat tttattttat  17580
```

```
taataatttt ctaccccttt tcacctacct gacactatct tgctgattga cttttttca  17640
agctaatgcc acgaggccaa aaaagagtag aaaattaatt ataaaataag ttcaggaaga  17700
taataggacc ttagtatagt ataaatgtgt atctacaatt tcgggcataa gttgaaggat  17760
acttgtgtat ttcccctata gttaataaac tagttaatag agagagacta tatacacatg  17820
tcattaatat atgaataact tgaacgttta gttagtaaaa cgtgtatttc gaatttctat  17880
aaatttaata ggatgattat ttctcaagtt tttaatgtga taatattgtt actttacgaa  17940
taaaactagg ttttaaaatt taattaatta cctcgttaac agataaaaat tgatataaaa  18000
ctaataactt cgtcaacccg aaactacatg aagattaagc ataataatat tacatttaac  18060
taatgtgatt acgttctcta gatggatgta aagattattg atatattaat ttgtactcat  18120
tattatttat aagtattata tatttattaa taatatttat aggagtagtt attttttaaa  18180
attactaatg tatgatgaat aatactcttt ccaaatacac tttttctag ttagttccat  18240
aaaaaaaata tttaattaca ttattaaaat tttatccata ttgtatcttt agttatcaat  18300
atttattatt actattttta tttgtaatat ttgtaggagt acttattttt aaaattacta  18360
atgtgtcata aataatactc tttctaggat acactttttt tttagttaat ctcatattat  18420
atctatactt atttggaaaa ataataataa agctatattc ttctatttta acaaaagata  18480
tttattttta ttttaagaat aattttaaaa cattaaaaga tcacataact tgaaaataga  18540
aaaagaatta tatttgttag tactactttt aattataata ttcataggag tacttatttt  18600
taaaattacc aatgtgtgat aaataatact ctttcctaga tacatcttta gttaatctca  18660
taaagaataa tgaaatttta tccatattat atatatatac taatttgaaa aaacaataat  18720
aaaactttat tcttctattt ttaaaaatta ttttatttta aaaatattac aagattacat  18780
aacttaaaaa tagaaaaaaa tataatatta aaatatacgt acacacacac catctataaa  18840
accgtttaga gaaaaaagtt ttttgttgta tatgataacc atattttatt agaatacaaa  18900
tcgttaatcc ttatggatta gcgcaattta attatgataa attacatgaa ttcgagatta  18960
tcaaagctat aaaacaaaaa caccattaac gtcttctata aagcttcagt ttcaactctg  19020
catgaatcat ctcactctgt atatatatac atatgtatat atagaccgag atttcgatac  19080
aaataataaa aaaagaaaca atcaaagagt ttcttataga aattcttcat ttttttttc  19140
tttgaatttt acaaatggcg ggtcttttcg ctactctaag aagacccacc aacatttctt  19200
catcgaattt tcaatcatcc tctgtttttg cttctcgttt gctctattta ctcaccgtta  19260
tttctgtatc gcttgctgtt ttcgcttatg ttcttcaatg gcgtggcggg ttacccgacc  19320
cgactaccca atggataccc ggtgacgatc cgaatgaggc tgggtccaaa cccgtacggt  19380
tatcgtcttc ttcctctggt tgtgcagata tccttggaca gagccgtacg gcgtcgttcc  19440
cgtatttcag ggattggaag tttgattttg ggtcttctcc ttccgggtcg gatcttagac  19500
ccaaggtttg tttttatcaa gtttttattta taccctgttc tgtttacttt ttctttgcga  19560
gttattttgt tgtgtgtttg ttatcgataa cttcatgttg aagtatttag ttattaactt  19620
tcgtttagtt tgaagaaaaa aatggacatg tttatgtttt ttattagcca agtgtctggt  19680
attgtggatg aattgtggaa aagttcattt gatgatgatg gggtccacct gtttgataaa  19740
atcaaagtta tttgttgttg gcattttcta attgtataga atctggttgt aaggctgtgt  19800
aaacgtcata ctccactgag agatttggtt gtgctagaat tgggttgtaa cgctgcgtat  19860
agactagact ctgcttgtga gtttacaccg cgtatgttta atagaaaaaa gacaattctt  19920
gaaatggtag caggcgcaaa gctagcagtt gcagaatttg gtagatttgt attctaggca  19980
```

```
gttgataaaa atgaagcact ttgaaaggat atgctaattt gtttaactgg tgtgcttatg  20040
ctattcatac tccaacattc taagtaggtc atttggttgt tgattagagt atagcagata  20100
ttagttacgc agagattggt tgttcgaggt ttagatattc catcttctat acagcataaa  20160
gtagtgaata gatttccttt taacttatac acgtattagt tgtaattgat tctaacttgc  20220
taaccaaaag ttgtgtttag tgtgttgaat tttatatatt agcaaaaaat tactgcccca  20280
aatatggtac aaattctgcg gtgatttaat acatgaatga ctcacatcct aaccagcaac  20340
caaacataca tattttactg ttggttttgg ctctgttcat gcttttaatg agtgcagttg  20400
ggctggagaa ttagcacctc attttttcgc atgtttttct ctaaatgaag aattgcaatc  20460
ttatagttgg tcttcactat tctttctccc cccgccctct ttattttctt gtagttaaat  20520
tattctatat cagtatccta agagacttgt tacctttgct tgatgttaga tatcgattac  20580
tacaagtact tccgctggct tagagcagat cctgccatgg atgttttatc ataaggtcat  20640
tggcgtgaca aactttttcc tgtttgtgga gggaaaagct gcatctcccg atgtatctaa  20700
agtgctaaaa tctattccag taagtgttca tatctcctta atatttccat tgtcgtgttg  20760
aacattttgt ttcatcactt ctaccatttt gtgtatttgg acttgtcgta tttcttctgt  20820
tgattatata caaaatgtgt gtgctctgca gggtgtaaga gttatatata gaacaaaaga  20880
actagagaat gtacaagcca aaaggtaagc ggtctttgcc tatatataca ttttctgtgc  20940
ctaaactatg aagatgaggt ctttgttcag tagagtagac gttatttcct attgctttga  21000
gaaatgtttt tatcccttcc gtgggtttat gttctttatt tagcctcgta tgattcattt  21060
tctttatgtt gctaatggat gcaagtaata gtcgatgata gaaactattt atccaaagca  21120
aagcttattg acgaacatat gttagcatgg gtcaacaagt ttccaaaact tgttgggagt  21180
tccttacata gcaacgtaat atatatcagg agtaactaca atgcacgggt ggagggggtt  21240
gatgtggacc gtctaattta cctattaata gcaagcagta attaccttgg gtagtggtga  21300
caacagattc tctattctat ttgtcttgag actaataata gacttggttc ctagaaggga  21360
aagagggaag gttaaatgag agtgaagttc attgattatt taccctacgt ggagcaccga  21420
gtatttaatt cactttattt gatgtattgg aaggtaagta aataagacat acttctctca  21480
gtcccccttg gtaaacaaga gaaataactc tttcacctct cgtctcccaa ccctttctcc  21540
tttcaaccca agcgacattg tatgacgtat gtttcaagtc attcatcttg agtaagcttg  21600
gatctgtttt gagtgtaata tgactaatgt agtgaaaaat ggtaatagac tttaatgaag  21660
aagtgattat tcaagttact aacttaaata gaactaaatt tggagagtga aatttccata  21720
caagctagta aaaatgctct gttccctata tttcatctca cgtctcaatt aagtaagctt  21780
attatctgac atactgatga tctataatgt gttgtgtcct agtcggattt ggaatgagac  21840
gtggctggct ggattctttt accaaccatg caaccatgag ttatttgtca agcagactct  21900
taacatggaa atggccatcg tcatggcaag ggtatgattg caataacttc catctgtttc  21960
cagttatggt taccttttga tccactatat tgcctagtaa ctctacagga agctggcgtg  22020
gactggatca ttcatctcga caccgatgag ctaatgcatc cagctggaac tagtgagtat  22080
tctttacgga aacttttggc agatatacct gaagatgttg acatggtcat ctttcctaac  22140
tatgtaagta attgagctct aggctgtctt ttaactgtgt ctaagcatgt aattacatgc  22200
cgaatagtca aaacgcatgc atttgattcg ttttcatttt ctgcggtctt ttttcatgtc  22260
aatatcttct ctgatgatga caaatatttc aggagagcag tgttgagaga gatgatgtga  22320
aggaaccttt tagtgaagta agatatcttt cactgtatcc ttttttctta tctttcaagt  22380
```

```
tctagtatta aaattcaatc gtttggctag gaacatcctc cacctctata catgaataaa  22440
tttagatttt cttaaaataa atttggataa ttctattacc caatacttga gaatggagca  22500
acagctagta gtcaaagagt caccgctttc cagacgaatg aaaaagaagg ttgcgttgga  22560
gttagacatt gtggaggcaa gaaaggaaaa ttgtacctag cgaacacaag gagcttgagt  22620
gttaaaattt tttagagaga gtttgcgtag tctgtaattt attttaatta ttgtgcaact  22680
aaagttcttt tagactgttt accagcaatg catctgtatc atgtggtagg tctcgatgtt  22740
caagaagaat tatgaccatc tcacaaagga aatgtacttt ggaagctaca aggaagcaac  22800
tcgtggtaat cccaactact ttttgactta tggaaatggc aaatcagctg ctcgagttca  22860
agatcatctt cgtcctaatg gtgctcatag atggcacaac tacatgaaaa gcccaaagta  22920
tgcttgttct gcatgttact tgttttcctt tatctctatt tcgtttctta tttattccca  22980
gtcctataga atcactgttt tatcgaagtt gaaaacatac ttgtaatgtt gtcatatttt  23040
ttcacttctt tggtgtgatt gtcttcgctt gtataatgaa aatgtatttt cttattattg  23100
tagagagatc aaactgggag aggctgctgt tttgcactac acataccccca aattttcaga  23160
tttaacctca cgacgagatc gttgtggatg taaacctact aaagaagatg tgaaaagatg  23220
cttcatgcta gaattcgaca gagctgtgag taataggcag tctgttatta aaacaacaaa  23280
tgtttttggg gtcaaaaaga tggactgtat agtttgtttg ttgataattt tcatcttcac  23340
attgcaggct tttataatag cttcgactct gacagaggag gagatgcttg actggtagta  23400
attcttttaa cttccattcc atcgaattca tgctaatcct tatactactt atttcgtgaa  23460
atccttccct tgttatactg taaaatctta tttcatactg atctgtagtc cgcgtggtgc  23520
ttgatttctt tttggtttgt atattatgct gacagaacct ttattggatt aggtaccgtg  23580
aacatgttgt ttggacggat aaaacactca tccagaagct tatcaagaag ggcatattga  23640
cgcgcatata tactcccatg gtaagatcaa cttatattg attgcggaag ctccttttga  23700
gtttatattg agggtcatga atcctaagaa gctgaactca tagtaacttt tgtttttcgg  23760
tctgtgtagg ccattgtaca gggtttgaag gaatctggtg ttttcgtttc tattattgct  23820
tcagcacata gagatgtcat aaaagacgag tctctatctt cttctgctgg aaacagaaat  23880
gcttccggat atcctcatat tactgatact tttcccagaa agatgggtcg tatattggaa  23940
tctcaatcaa ctgcaaggaa attcgtggac tttagtacaa ctgatcatca ggcaattcca  24000
cccgaatcac ctcctggcat ggatggaatt gatctcgcag atacaaaata ccttctgaac  24060
aatagctctt cttgaagaag tatacttaca tacccctctt gggaaaatag gtgtgtacat  24120
tagttctgtc atactccata gagttgttcg agtatcatat catagagaat gaagtattct  24180
tcatctttta aaagttcgat atgtatacat gacagaatgc tttggagaat gacaatctta  24240
tcgatataca agaatagatc tcttccatgc ctcaaatctt tcgatgatgt tctaactatt  24300
actcgtctgt tttttcttt attagaactg agtatgattc ttagattgtt gttaagtaat  24360
ttggttctga atccagtagt tctggtccag aaattataca agtgcttgtg cataaagggt  24420
gatgttacat ttgttgtaat gcttatttgt tatgttttag atacactact tttgaactag  24480
caatcagatg aagtagagat ttaagaaata aaagtatatt cattgatttg attatatgaa  24540
acaatttcac taaacaaaac tacattgttg acaagaagta gactaagaga gcaactgaga  24600
tagccattcc ttgttttgtc ccataaattt atcaaaatca cttaattcat ctaataaaca  24660
ctcgtcgttg tttgttggtt cgacttgata agcattacct gctgtctctt caacattctg  24720
cagcacttgc tcttcctgat aaggaaaaac taattcacca ttcatattcc cttcattcat  24780
```

```
tgcagcatcg ttcccttgaa ccattggaaa cgtgacgatt agctgagaaa gttgatgatc  24840
ctccataggc cactgcggtt gtgttgtcat atcgttccta ttctcatcat cacatccaac  24900
ataccctgat tcaatatttt gcattggctt cacaatctgt tgaggaagtt gatcactata  24960
tccaaattca ttaggccctt ggggtactag tgtatcatca catccaacat accccgatcc  25020
aacattttgc attggattca caatctgttg aggaaattga tcaccatatc caaattcatt  25080
aggcccttgg ggtagtagta gtgtatcatc accatcacca tcatcatatc cactgccagt  25140
tgttgtaggc atatgatttc ttgatttttt aactttacac ctaatgtagc acaaaacaac  25200
atccttgtgc ttcatcacac ctctgttact caacaacttt attaccttgt cgtcaagact  25260
atactctttc atgatccaag aaacgtcgtt aactacatcc tttttatttt cttcatagtt  25320
ataagttttt ttcatcccaa ttttcttcgc acctattgac tttcctttgc tcttcccttt  25380
ccaacttcct cctcccacca aagtccgact aaaccttgta tcgcgtttct ttaatttagt  25440
aaaaaaatat ttagtaccgg atgagtcttc cagtaactcc catggcttct tacttccgta  25500
aagttcttca aattcaatat ctttacaaac gtagttttta gaaacaacaa atttaatcaa  25560
gtagcgaatg agctgttcat cagtgggtcg aaacctgact ccaaattcag cgtctggaga  25620
ttcaattgcc ataactattg atgagagtag aaacaaactt tattagtttt aggcaatggc  25680
tctaaataac gatatatgat taacgtacgt gatgtattat tagcaagaac tgtattgatg  25740
cccaaagccc tatatattat attatgacgt taaggttagt taaaaaatgg aaaccaaatt  25800
taagaataat taggaaacgt aaatgcaaaa actttccttt tatatttcaa gattagttac  25860
ttaaaatcat tctaatacaa acgtaatgca aaaactttcc atatataata aatttaaagt  25920
ctcctttttt ttgtttcatt atataaatca gttattaact gtaatgcaaa tatttttttt  25980
tatttttttt tctattttat tcccgtactt caactttagt ttgaccataa aagtttgggt  26040
caattgtttt ttctgatata ttgcttattt ttttatatag tttcattaat tgttaatata  26100
atttaaattg tttgttttaa tattatcagt attatgtagt taattaggtt ttgccacttt  26160
tattgccgca aaatcctatt tagaataggt aatggaaaag caaaaacttg tcttagataa  26220
taaatttaaa atttgatgaa taaataaata atcaataatt atatgataag tacgggtgtt  26280
tataagttga ttacaattgg aaattggaac ttcgaaacgt aagcactgtt ttgcattttc  26340
gattgagaaa tgaaagcatt ttttatgaca taatacataa atagattctt ttaacttgat  26400
ttcaattaat atttatattt tttagaattt tgagtgtgca caaataaata tttatacttt  26460
tataaaactg agcaaattaa catattcgat agggataatt gtatataata aatagcaaac  26520
taataaccca aaataaatgg agtagctacg gtttgattta attgtgctcc atagcaaacg  26580
ttagccaaag tttgtcagtc gcctctctcc caaaaatctc gctcgccact ctccaattct  26640
cgcttgccac tctccctatg cttgcctctc tcgctttgta cacagaagtg tgtaaattgt  26700
gtttctgttt tgtataaagc gagagaaaat tgtatataca catgcaaaaa catatatctt  26760
cgtgctatac acttaattat gcaatttata aacattttac tttgattcaa ttgtagacaa  26820
atgcaaattt tatacaaata cttcaatgaa aaaggccaac aaattatata attgcgaatt  26880
atacaattgc agtgaaatac aattttctct cgctttatac aacagaagtg tatatattgt  26940
gtttctgttt ttgtataaag cgagagaaaa acatatatct tcttcctata cacttataat  27000
tatgcaatat acatacattt tacttcgatt caattgtata caaagcaaat tttatgcaaa  27060
tattgcagcg aaataggcag cgaattatac aattgcagtg aaattggata acgaattata  27120
caattgcagc gaaataggcc agcgaattat acaatttagg ccaacgaatt atacaattgt  27180
```

-continued

```
atatgtatag cgaattatac agtttatgtt tgctatggag cgtaattatt caaactttga  27240
tatagcatac aaatatgaat tttttatttg ctatatgtga aagttgccct atttaatatc  27300
ctatgtgtaa aaaaataatg ttatggggtg ataacgtcaa aattttgaaa atagtataat  27360
tatcgttgca ttatatttaa caataataat aaataaaaat atttagcgac atgtcacatg  27420
ttgatatttt acataaattt tctttgttta gagcaacaat tacataaaca tggtttgttc  27480
atattgaata tctcaacttc attatttagg aagggtaaaa tagtaaatta ttaccttttt  27540
attaagctat cgatttatcc aataattcaa tagtaaaatt aacatcgaac caataactca  27600
aaaacataca aaacggactc cttgatagca atttgttgat gtaggtaact tattttgaca  27660
taatattata gctaatttca cgatttaaat ccatgatgat acatcatata tatatatagt  27720
gtcttaattt ttggcctcta atatgtagtg tcttaatttt tggcctctaa tattttgctg  27780
gaccacttaa ttctttagga gtggcaaaaa tatagtggtt tgcctgtaat acaattttgt  27840
aatattaact ggacttcctc taaactacat tgtcaaatga aaaggttgtg tggagctttc  27900
tgattgggta gaatattaat tttttttca aaataaataa ttaatctgac ctagtaaaca  27960
aatatacatc atttttaaat atataaatca gcctaaacta ttgaaaactc aggtttgctt  28020
catgtgaaca ttgtccaatt ttttttaatt actttattat tattattatt attattttat  28080
ttttattatt aatagaaaag gactacttct ccatgtttat actgccacat caatcagaat  28140
tttttttttg tttaatgagt tactactatt agaaaaaaaa taaaatatat aattaaaagg  28200
aaatcactta agttggcaat tttcatgctt taaactttga atctcatgaa tcatgatcaa  28260
gaactgggat aaagactcca tatataaaca aatgattaga tgaagtcata aaaggaacag  28320
gagacatgac ggagtggtaa gtactcaatc attaaaaaaa atttatagcg cgtatacaag  28380
caaatggtaa gataacgtat tctggatagt cttgacacaa taacgtgttg tagccggtga  28440
tttcaaggct cttaaaagag ccaagacacg caaattttta gtgttcacat gttcgcaacg  28500
atccaaattt agtcagccct aatatgaata acggacactg ggtggcgatt caaatttagt  28560
cagccctaat ctcactacca gtattaatga agaaggattt ctcgcggcga tctaacttta  28620
atcagcccta atatggatag cgaacactgg gtggtgatcc aaatttagtc agccctaatc  28680
tcactatcag tataaatgaa ctatgattct agcagcgatc caaatttaat caatcctaat  28740
atggatagca gacactgagt ggcgatccaa gtttagtcag acctaatatg gatatcggac  28800
gctaggcgga aaattaaacc ttatataaac aattggttat agaaagtttt aaaaggaaca  28860
tgagagttga caagtgagaa aacagaacaa aagcagatag atgaagtgct gactttgaca  28920
actactaaat ctcttcattt aatattctta tgaattttat aacaacttca tggtaggcaa  28980
ctttttagtt tgacattctt tgattcctta agactttttc aagtaaatag atttgattat  29040
gaagtttata tatatgaagt tccacactca ctagcaaaaa ccccacaaaa acacaaaaca  29100
aagtcttttt acaacttcaa aaaaaaaatg gaaggacaaa caggacaaca agaggagtta  29160
tttgtagaaa ttgatcaaaa aacagatgat caaacatata gcgatggtga agcagcatca  29220
tgtacaacag atggtaacga aatagttaat gttattgtca cgtctgatcc gatcttgcaa  29280
ggagaatcta tgccaagaag gtatacatac tcgtggagaa ggcgaataca gaaagtttta  29340
cctctattga agacggatga atacaacaga cacgagtatg atccgaaagt agtttcatta  29400
ggaccttacc atcatggtaa gacagagcta cagctagcag aggatttcaa gcatatagcc  29460
cttgaaatgt ttgtatcggg tagcagcaga gacgtagctt atttctataa caagatactt  29520
gaagttgttg acaatgcaag aagttgttat gtcgatggct ccacggacaa gtacaatgat  29580
```

```
catgaatttg ccttaatgat gcttcttgat gcttgcttta ttatcaacca tatcgagcta  29640
agcacaacgg ataggtataa caaactcaga accacgaggc accatcttgg aatgttggcg  29700
ttatcaacaa cagttcgtga tatgtttttg cttgagaatc aaatcccatt ttggatactg  29760
aagctcttga ttagcttacg atatgacaaa gatgaaggag atgaattgct cgagatgttc  29820
ttgaatttca ccctttttcgg tgaatatgaa caagaagggg aaatgagtca caaccatgta  29880
gaagagccac tccatcttct tgaagcattt agaacaagac ttgtttcaca acagagtgaa  29940
gtacggagct ttcaccgtac ttgcacacct caatggctaa aaaggaagaa aagtataagc  30000
aatgaacgcg ttaacatgaa aagctacatt cactcttttc gttcagtaac cgatcttaaa  30060
gcaaaaggta ttcaattcaa gcctagctgc actcattcac tcaaggacat aaagttcaaa  30120
tcaagatact tctatggaca gcttgtactt ccaacttggt atgtttctat ctacactaag  30180
gcgttcttct taaacatgat agcctacgag atgtgtccaa atacagttac tgatcgcgct  30240
gtgacatcat acgtatactt catgaaatca ctaatagaga gtccaaggga tgtcaaggaa  30300
ctacgcgaaa tgcaaatact attcaacatg cttggtagcg acgaggaagt ggcaagaatg  30360
tacaaagaga tcaatacgta tggagtgaac aacgcgcaca ttttctacaa tgtgaaagaa  30420
aagattcaag aacactataa taacaaggcg aaaacatgga tagcagagct tatacacact  30480
tactttagga gtccatggac tgctttagca ttacttgcag ctactttctt gctttgcttg  30540
acttttacac aaacttattt tacaataaat cccaatccta gattatgaga aaatatttgt  30600
aactatttga gaaattttgt ggtagagtac tagtttctta tcttgtttgc tgttacaaga  30660
aaataaagat gcttttgtga tatagatatc tctcataaaa ttatttttca cgtatacttt  30720
atagatgttg aacttcgatc cttggattag ttcttgtatt tattttttca tattttgaac  30780
taaaattaag agggttaatt gggccgggtc acttcacctt gaagaccaag aaccaatcgg  30840
gttcaaaatc cacctcggta atcggaacca gcactatttg tgatttgata gtatagggtt  30900
aaccaactag cccagcccgg aatgcccaat tgttaagtct aaaatttaaa attatatttc  30960
aaaatcgtta agtatttaaa aaaacactac aatataaaaa gttattttta aattaaaacc  31020
cgaccctata tggcccaaaa ttatgcgggt tacatcaaac ccaaaccgat tggattcgat  31080
atctgatcgg gttccataat cagtgaacca gcccgggcca actcaatgcc accctcggtg  31140
aaaatttca ctttttcacg ggttcaatca aaatagaagg aaaaaaactg aaatacacgt  31200
cttatgtttt tttttttca atgtctccta tttctaaaaa cctcttaaat aatttatttt  31260
tctcccaatg tatttaatgt atccgagtta catattaatg tatcctaact atatattatg  31320
tattcgattt attttataat gtattcgagc tacatattat gtatttgggc taatttttaa  31380
tatatccaag ctacatatta tgtattcaat ttatgttata atgtattcga gatactcttt  31440
aatgtattca aaaggtataa agtataagga attattataa ttaaaaaaaa tagagataaa  31500
atgaaatata tttttgcact atgaaattta agtgaattat acaaaataga atattacgat  31560
agaagggcct aaagttgaac tgagagtagg ttcttttgaa atgtattggg cctcatcttg  31620
gcccttactc tggtaacaaa cattccattt taattttttt tttttatcac ttggcttttt  31680
tcatcattta acattgtatt atgaaacaaa atatatttag taataaatac tcaaacaata  31740
ttgatgagtg tatatacatc tctaatccat agttatagct tataggctga atccatcggt  31800
agctttctaa agttgacatt aattttcatt taaattagac tttgttcatc ttacacacct  31860
catgttgagt tccgctgtgt catttgacac tttttgatga cttgatatat tgtgtgtgtt  31920
gcatccattt tgagtgcgtg aggggtcttt ttttgtgtgg atatttttaa tttttttcct  31980
```

-continued

```
tcttcacttt ttagccttac cacttattcc acatttccca atgaaaattc atgataaaaa  32040
actttacaaa atatgaaaag attttttaga acaagacata catttttttc aaaaaaaaat  32100
tggaaaaatg tcatatataa ttttcaaaat caattaaaaa aaacctaaaa tctaatgatt  32160
ttttaaaaaa aattggaaga agaatcaaga aaatgattgt agagttgagg aggcaaaagg  32220
gacgcaagac agatgggctt agggtgggat gatataaggt ggggtggagt ggtacaaact  32280
aggtaatttt atttatttat ttttgctaaa aaattagtta ttttttgata ctttatttta  32340
aaattattat ttttacattt aaatgtcaaa tatcagcttt tatagtcatc atgtcatgtt  32400
atccgcaagt gtgttacaca ctctttgtaa ttttagctga ttggcaaaaa ggtgccaaaa  32460
taacatagcg gtcccctact tgaggtgttt aaaatgacta cttgaagtgt ctaattgaaa  32520
attgatgtca tatttaaggg gttgccgatg ggttcaacct atcttttata tatacgatta  32580
tatacaattt atacaatgtc aatacattac ctaaaagtaa atttatgtgt atttttgttt  32640
cttttcgctc agggtgcacc aagttcgaaa agaatgagga tacaacgtaa gcattagtga  32700
ttgattctac tatttaaagt tgaatttata agttacttga agacaattat atcgtcaaat  32760
aggatcataa acaaactatc ttaacacaag tattagttat tgtctagatt tgctttcatc  32820
aaactcaaat aaatattaat taatgagaat tattatacct ttttatatta aaataaacta  32880
tactcggagt ttacttaaaa caataaagaa tatttgctgc tctggacaga ctcaaatagg  32940
ggacctatca taagtacaac cacaacttat aagtaatcat atttttttta aaaaaattaa  33000
aatattagta atcttatatt taatgtttaa aataactgtg tatttgaaac tttctgctat  33060
tcattccatg cttaaattct ttttatcatt acactaatta atttcccaaa ttgtttttgc  33120
atgtaatgat ccttcatgga ttggtcccat ttttattttt ttttaaaact caaatgttga  33180
taatctccaa tcagacatat gattagtgga acatgtgatc ttctagctag tgacaactct  33240
gcatatgtga gtttatttat tttatcgagt ttcaatcgaa atagagtata acgatatatt  33300
tataaattat gttaattttc aagtaaaaat aattctgaaa tgaaaatgaa gaagtataga  33360
gaatcgatat tacttttcat ttgtattttg tataaatatta ctatatgtgt actgtttaaa  33420
tagttaatct cgatttattt gagatcgaag cacaatggtt agatagttta tcattatagc  33480
ctttttgtat tgaataattg aaagaagcat taaaaaaatc aatttaaggg cttttgcaat  33540
tatgaccttt cacattttc actaagatat atataattaa catgcatgaa gaaaagtgtt  33600
accttttctc tatctttcat ttgtcaaatg gaaactttat tatttaaaga acacatataa  33660
ttcccaaaaa agatttaaaa aatataaagg ctaaaaattc aattattttg gattatatcc  33720
ttgattacca aaattgagtc cattaaataa ctcaaaaaga taaatgctac tttccaaaag  33780
gtggatagat attcacatgg tttatctatg acccaaaaat atatgggact agtgatatag  33840
atacaaaagc ggctcaatta aattaatggc ctaaattttt tttttttttt aatctaacga  33900
ttttaaaaag taaactaacc taaaatgtat tataggtaaa aataaaactc catcctccct  33960
taaccttccc tagagatatt ggttcgaaaa tctcgctaga aagtgctttc ctcgatctta  34020
catgtctcaa aaccaaacaa aaaaaaattg aaagcctaaa gttctctctt tagtgacttg  34080
actgcatata caatataatt ttttaacgaa ggattttaat tgcattctat atcagtggtc  34140
tcttcacctc tgaccaagtg atgatgatga gtattacttg gaagctgaaa gtatactgtt  34200
ggatttgcta ggtgaaaaaa acaaaagaga atatactaaa atagttttaa cacattgtga  34260
aaattttcaa attttggtat catttttata cagctaccaa aaaataatca taagttgtac  34320
tactaattaa aactttatat ttcttccgtt taaaaaagaa tgaccttgtt gtgcggaatt  34380
```

```
tgagataata cgagaaaata taaacgcgaa aaataagaca acagatttac gtggttcacc  34440
aacaaattgg ctacgtccac gggaagagag ggagcagttt tattatggag aggcaaaaac  34500
agaattacag aatagggttt cccatagcgt ctatatatag tgctaagcta cgccctaaca  34560
ggcttgggcc caacatacag aatcaacaga aaattaaggg cccaatacaa caacattgta  34620
taccgtcggc ccgggggcgt ctccgccccc ccggaccccc aggccagggg gcgcgtcgcc  34680
cccctggacc ccccgactcg ctgaccgggc agcgagaccc ccgtcctttc tgtttgtagc  34740
gggtccgatt caaggcattc aacaaatctc caccttgact tgaattctcc gaacagattc  34800
ttcagacgca ctatgatagt gccaagcctc cccctcttcc tcagagttgc cccgcagggc  34860
aattaacagc ttctgatgtt gagcaagtcc aaacagtgtt gaaacttgct ctgtggaacc  34920
ggctttgtga acatatcagc aggattatca gcagttccta ctttcttcac cttgattctc  34980
ttctcacttc ttagaaaatg ataccttacg tcaatatgct tggttctctc atgatggact  35040
tgatccttgg ctagacaaat tgcgctcaaa ctgtcacaat acaccgtagc ctgatcatga  35100
tgcagaccaa gatcactaac cagccctttc aaccaaatcc cttcttttgc agcctctgtc  35160
aaggccatgt actccgcttc cgtagtagac aaagtcactg taggttgcaa agttgccttc  35220
caactgacga cagatcctcc aagggtaaac acatagccag tcatcgatct tcttgtgtca  35280
acatctccag catagtctga atcagaatag ccagtaacca agcactgagt atcacctcca  35340
taaatgagac caacgtcaga tgtacctcta aggtaccgga aaattctctt cacagcctgc  35400
caatgttctc tccctggttg tcccatgaat ctgctcacta cactgactgc atgtgctaaa  35460
tctggccttg tacagaccat agcatacatc aaacttccta cggcactggc ataagggact  35520
cgtgacatat actccttctc ttcttctgac tgtggagcga acatggcagt gagatggata  35580
ttggcagcac tgggggtatc aatgggctta gatgaagaca tgccaaacct cgccaagacc  35640
ttctgaatgt agcttctctg tgacaagaaa agtttccttc tctctctgtc tctaatgatc  35700
tccatcccta aaatcttccg agcggctccc agatccttca tctcaaactc agcactaagt  35760
aaacccttca gcttctgaat gtcatacttc ttctttgcag ctatcaacat atcatctaca  35820
taaagcacca gatagatgaa tgaatcatca ttgagcctat tgtagtagac acaacaatca  35880
tatgagctcc gagtatagcc caacttcacc atatagctgt caaacctttt ataccactgc  35940
cttggagact gcttaagtcc atataaggac ttcttcaact tgcagacgtg attttccttc  36000
cctggaactt ggaaaccatc cggctgagtc atgtatatct cttcctccaa ctctccatgt  36060
agaaacgctg tcttcacatc aagttgttca agctccagat tctgatgtgc aactatcgct  36120
agtaacactc ggatggaagt atgtctgacc actggtgaga agatctcatt atagtccact  36180
ccctctcttt ggttgaaacc tctggcaaca accctggctt tatacttgac tccttctgct  36240
ggtgatatcc cttccttctt cttgaaaacc catttgcaag taataatctt tctccccgaa  36300
ggctgtatga ccagatccca tgtctgattc ttgtgtaggg actccatctc atctcccata  36360
gcggcaaacc atttttcaga atcagaactt aaaatggctt ctttgtaagt agacggctca  36420
gatgtatcta cctcttcagc aacctgcagt gcataaccca ccatgtcctc aaaaccatac  36480
ctcgtaggtg gccgaactcc aaccctcctt ggccgatctt gagctatact ctgatggata  36540
tctgatggca tagattctgg aatatcagtt tcagtctgtg gctcttgatc ctcctcttca  36600
ggttccttta aatcgctctc gttctgaatg acttgaaact ccacctgttt gtcaagactc  36660
ccagtttctg acgtagttgt aggcttcaca atggttctaa gcagaggact ttcatcaaag  36720
acaacgttcc tgctcataat aaccctcttt tctgctggag accagattct gaaacctttc  36780
```

```
actccatctc cgtagcccac aaatactccc tttttagctc ttggttctaa cttaccttca  36840
ctgacgtgat agtaagccgt acaaccaaaa gctttcagat ttgaataatc agcagctttt  36900
ccagaccaca tctccatagg tgtcttgcac tgtatacctg tatgtggtcc gcggttaatc  36960
aagtagcaag ctgtactaac cgcttctgcc cagaatcttc tatctagccc agcattagag  37020
agcatgcacc ttgctctctc cagaagtgtt tgattcatcc gctcagctac accgttctgc  37080
tgtggtgtat ttctgactgt gcgatgtcga gcaatccctt catccttaca gaattgatca  37140
aattcagacc aacagaattc cagcccatta tcagttcgca acctcttgat cttcttccct  37200
gtttgatttt ccatcaaaat tttccactcc ttgaacttct ggaaggcttc acttttatgc  37260
ttcatcatgt acacccaagt catccttgag tagtcatcaa taatggacac aaaaaatctg  37320
cagcctccca aagactcaac acggcatgga ccccagcaat cagaatggat ataatcaagt  37380
gtgccttttg ttctatgaat ggcctttgga aacttgttgc gatgtagttt tccaaaaaca  37440
caatgttcac aaaactctag gctcttaacc ttatgaccag caagtaaatc ctcctttgac  37500
agaatttgca tccctctttc acccatatga ccaagtctta tgtgccataa cttagtcata  37560
tccttctggt gaaattctga cgatgcaaca tgggctgaac ctgtaaccgt ggaaccttgt  37620
agaaaataca aagtaccacg catgacacct ttcagaatca aatttgaacc cttccagacc  37680
cgcaagactc catcttttcc cgaccagctg aatcccttgc tgtccaaaag actgagagat  37740
atcagatttt tcgtcatcaa tggaacgtgc ctgacctcgt tcaatgtgca gaagctaccg  37800
tcatgtgtcc ttatcttgat cgagcctgtc ccaaccacct tgcagacaga actgttggcc  37860
atcgagatgc tgcctccgtc tacctgctca taagtcgtga accactctct cctaggacag  37920
atgtgatagg atgccccaga atcaagaacc cacacatctg aatgatgagt gtgctcatcc  37980
gcaactaggg caatatcttc ttcagaattg gtgtcttctt cagcaacagc agcagacact  38040
gattgttttt ccgattgctt cttcttcttc ggacaatcaa atttccaatg tcccttctcc  38100
ttgcagtaat tacaaacatc atccggcttt gcacccttcg acatcggctt atttttcttt  38160
ccgccgtttt tccttccctt tctgctactg gtgaacagac cggaaggctg tatgtccgta  38220
cttgtgccgt tagccttatg ccgtaattcc ctgctatgaa gggctgatct gacttcttcc  38280
agtgacacag tatctttccc aacaatgaac gattgaacaa aattctcaaa cgacattggg  38340
agagatacta acagaatcag ggcagcatct tcatcctcga tcttcacatc gatattacgc  38400
aattctaata acaaagtatt caattgctct aagtgttccc tgagttgtgt accttcagcc  38460
attcgtaaac cgaatagacg ttgtttcaga agcagcttgt tggttagaga ttttgtcatg  38520
tacaaactct ccagcttcaa ccacagacca gcagcagtct cttcatccga gacctccgtg  38580
atgacgtcat ccgcgagaca cagcatgatc gtcgagtgcg ccttttcctc cagaatcgcc  38640
atctcaggag taacgacggc gttcttgtct ttcgacaacg gcgcccagaa gccttgctgt  38700
ttcaacaagg cccgcatctt gatctgccat aaactgaaac tgttcctccc tgtgaatttg  38760
tcgattttca cgttcaaagc agacatctcg aattctccaa gaacaccgat taaccgagag  38820
gctctgatac caatttgttg tgcggaattt gagataatac gagaaaatat aaacgcgaaa  38880
aataagacaa cagatttacg tggttcacca acaaattggc tacgtccacg ggaagagagg  38940
gagcagtttt attatggaga ggcaaaaaca gaattacaga atagggtttc ccatagcgtc  39000
tatatatagt gctaagctac gccctaacag gcttgggccc aacatacaga atcaacagaa  39060
aattaagggc ccaatacaac aacattgtat accgtcggcc cgggggcgtc tccgcccccc  39120
cggacccccca ggccaggggg cgcgtcgccc ccctggaccc cccgactcgc tgaccgggca  39180
```

```
gcgagacccc cgtcctttct gtttgtagcg ggtccgattc aaggcattca acagacctaa  39240
tttgacttaa aacggaattt aagaaaagaa agaaattttt ttaatcttat ggttctaaat  39300
caaagttgtg tcaaatgtat caaaatgcgt tttaatcttg tggtcttttt catatcacgt  39360
ggaaagttaa aattaaaatg ttactgaaaa aagaaaaggg tcattctttt ttaaacagac  39420
taaaaaatga aataaaatta ttctttttaa aacgaagggg ataataaaca ataacaacaa  39480
gaagtaaaat gtcgcaaatt acccaacatg ttgcacaaaa atctgttcaa ttaatgttct  39540
cttcatgact taattcttat taaagatgga tagctttgat agaaagcgtt ttatccctga  39600
cattttaaga tgagactttt cgatacgaat ctagatttaa tcagatccta acacgggtac  39660
gattcacagg ttaaatcagt aaataaattc aaagcagaaa gagacatttg aaaaggtcaa  39720
ttcacagtta ggaaaatgac agttagaaaa taaggacaga gggcccttta ataagaagta  39780
tatgatgtta aaagagactt cccacaagtc acctccaaaa gtagttaaaa ataatagaaa  39840
gttgaaacat caattctttt ttccctttta ataaccgcga tgttcaagtc agctttcgcg  39900
cgcctcaact tataattcca agaaatatct gtcattggaa tcgcttacta tttttgaatt  39960
tccaaaaata gatcaaaata actggggata ttatgtgatt tattagtatt ctaaatctta  40020
gtttctttcg cgtgccgtac cttaggattc gtgctattgc taggtaactc tgtccatcaa  40080
gaccgaaaca aatgagaaaa atcacctagt gtattttttt gtctccgcaa ctgttgtcta  40140
aaggtacctt ttttcactct tcaatatatt tcatatactc cacggcacat ggtgtggttc  40200
tcaaagcata agtgaggtca gtgtttctta ctggatataa atagacataa atttggggag  40260
aaaatgaaac cacatggaac aacaaaacaa cactattatt attattattc aagaatcact  40320
agcaagactg gttaattaat gttaccaaat tttgcatgtc cttcaaattg atcattttta  40380
gtcacccttt cctacaattg cactaggtat gtgttttaaa ttttgtgatt actcatatta  40440
ttaatatatg attccaagat tgtaagctca tttagccatc acatgaacaa ttttgctgat  40500
gtaagacaat tgttgttttc tgctgttata gtaggttaaa gaatagacta atgaaacccc  40560
tctcgtgaga tagtttttgg agttgaggta gacttagata ccttatagtt tacatggtat  40620
cagagttacg ttgatccgag ctcctagtcc atggtcttag agtggattag agtcttacat  40680
ggacttggga aatccttccc tcacgctcca atttgcttat attacgcgag atgctagctg  40740
tcctattgag gcagtttttg tttttatatt gtagctctgc agcattttgt tgtatatgga  40800
atagaaatgc ctctgaaata cttttctata tctgtttgat tgctgaagga ctattgaatg  40860
ggaaagcgaa gaaactggtt tacctttgtc aagagacttt tcattcctga aacagaatca  40920
acagcagatc aaaaggtttg aatttcaaga tttctgttgc ttagtagtgt gagtgaatct  40980
tcggatatct aaactggaaa tttatgaaaa atatttcaga aaccaaagag atggagatgt  41040
tgttttctga gaaagttcaa gttgaggaaa tgtcctgcta taacatcagc acctcagcaa  41100
acgttacctg aggcgaaagg aacacctcag caaacgttaa ctgaggcgaa agaacagcaa  41160
agaaaacatg cttttgcagt tgctatagca acggcagcag ctgctgaggc tgctgtagct  41220
gctgctaatg ctgctgctga tgttattcgt ctaacagatg ctccaagtga attcaaaagg  41280
aaacgcaaac aagctgctat tagaatccaa agtgcttatc gcgctcacct ggtaaaacat  41340
cctctctggt agctctagta ctttcactca tacaatttca ctgtgaactt gttgcagaga  41400
cgcttttaaa tgcagaaaga ttgaaaatta gttagtcatt caagacaaaa cttaaaggat  41460
agtatgggaa aaggtaggcc agtttggata tagcaggatt aaacgcccag tgctctacca  41520
gctgagctac acacctaaaa aatgataatc aagtaaacaa gtattgatac agaaaaaagg  41580
```

```
cctgcccctt tactctcatc ttattaaagg agcacgacta tttattatga ggcttgtact  41640

acagagcaag tggaagctcc gaaggtcaca cttttttttt ttttttgcct tttggctgtt  41700

aatcatatta gtcataaggt agtctatcac ctcggttgga aagaaaatct tattggttgg  41760

aaaatccctc tccgctagta aaactcttct cttatggcgg ctactaattc tttttccttt  41820

catctctcaa aaaaactttc cgagatttgg tgaaatgaac tggtgtctga tctatgtccc  41880

tgtgaaatgt tgtgcaggcc cagaaagcat taagggctct aaagggtgtt gtgaagcttc  41940

aagcagtgat tagaggtgaa attgtgagag gaagactcat tgccaaactg aagttcatgt  42000

tgccacttca tcaaaagtca aaaacaagag ttaatcaaat tagagtccct actttgaag   42060

atcatcatga caagaaactc atcaatagtc caagggaaat tatgaaagct aaagaactaa  42120

aggtaagatc aatcattcat tctcttttgt ttaattaagt ttccaaacat tagttcaact  42180

atactaaatc tataaaagag acctactaac acatcttatt atgactttta tggtttggaa  42240

ctgtaatatg gtttttgtt tttttggcag cttaaatgca agagccttag cacttggaat  42300

ttcaacttag cttcagaaca agacagtgaa gccttgtggt caagaagaga agaagccatt  42360

gacaaaagag agcatttgat gaaatactcg ttttcacatc gggtaaagtc attacttgtt  42420

atacagacac tgcaattaca cttgtcaatg tattataaaa tgttgtagca gttaacctgc  42480

cttatttct agaatactaa tctcacattt tatgaacgat tatttataat atatttttag  42540

gtaagctgat agtatattgc ttcttttagg agagaagaaa cgatcaaact ctacaagact  42600

tactaaacag aaagcaaaac agaagaagct acaggattga ccagttagta gaacttgacg  42660

caccaagaaa agcagggttg ttagagaaat tgagatcatt tacagactca aatgttcctc  42720

taactgatat ggatggaatg acacagcttc aagtgagaaa aatgcataga tcagattgta  42780

tagaggacct acattctcct tcttcacttc caagaagatc attttctaat gcaaaacgaa  42840

aatcaaacgt tgatgataac tcattaccaa gttctcctat atttcctact tacatggcag  42900

ccacagaatc tgcaaaggca aaaacaaggt caaacagcac agcgaagcaa cacctaaggt  42960

tacacgagac attgtcaggt caacattctc cttataacct caagatttct tcttggagat  43020

tgtctaatgg tgaaatgtat gacagcgcca gaacaagcag aacttctagc agttatatgt  43080

taatatagaa ggtgttttac aaggattgaa gaacatgagt gttgtacatt attactatct  43140

ttgataacga agtgtccaag ccggtttgct ctcacctctg ctagttcacc gagtgttgtt  43200

aacttctaca agtaccagta ccagtactag gtaactctgt tcaccaaaga tgaatgtgta  43260

cattatcaac ctgtttatgc aagcaaggga gcgcagaaac tcctagattt gcagcattac  43320

ttctggacat gaaaacaatc agaaaaatgg agctattatt ggagcttcaa acttcttcag  43380

taatctatct acagttgatt gatgaaagat tactggtttt aacacttttt tatatagact  43440

tgccacaatg tgtatatata gttcaagttt ttttcccttt ccctgtttgt tttcccttgt  43500

ttcatttatt tattgatttg taaagttgtt tccatgagac caggaggtca caggggtaag  43560

attctgtaca atagaccata tggtctcgag ccttcaccag accgcacata gcggggagct  43620

tagtgcactg ggctgttgtt cttttttttt ttttttgctt ctgagttgat atactggagg  43680

aagaattgtt gtttgatggc cattcacctg gaagcatttc caagtttggt aattgcatag  43740

aggtttaatc tttgccttct gtatttacat aggtttattt cttttgattt cttccttcaa  43800

agttcaaacc acctctttat tatttcatgt aaaatccttc aaaaaaaaat gaacttacac  43860

caaaatttat gtcttacctt tcttacaaaa ccattgatgt tgaaactaag gaaaatggat  43920

tggaccaacc atatgtagaa gaaatatagc aagtttactc caactttcac tacttatgtt  43980
```

-continued

```
aacacattga acacttgaga aacaaaatcc attggaagct cctcatttct acaggcttaa  44040
aatgtctatg gtatatccaa tgtaacagaa taacacatgt gaggcacact gttctcctca  44100
actgagattg acagatttca catactacaa atttgtaaac ttttggaaca taacgcaata  44160
ggcaagataa tgacatttga caagaagtat caactgtaat gctcaaatta ccagataagt  44220
gaatgagata gtcggaaatg tctgatccac gacgataaaa tctataccag taaaagtagc  44280
cctcctgtat gttttgaact aatgataaca ttcagtccag caacaactct gctgacctca  44340
aatctagaag ccaaataaaa ttacttgacc atgaggcaga aagaagattc acaaaattct  44400
agaaggacaa agcatttgct ggaatcatca ctcgcaaagg ccaaagttgg aagatttgta  44460
tgtccattgt ccaccttcaa gagaaattgt gtctccagta tatgtgtgcc tcgcaaacag  44520
tagaagaggg aagtctataa gcaggctatt tgggtagctt ggtttgaggt tgcagatgcc  44580
tgattgagga aataaactcc catttgcttc ttttcatgaa gatggcttta cttcaaaggg  44640
acgtcgcacg atagtgttgc agaaggaggc aacacaaatc ttggtgttga tttaaaccag  44700
aaaatgacta tctaatcagt tttcttttct ccgttattgt tcatgaatag ctgatctctt  44760
aaagtttcaa ctatcttagc taaaatgtca ccatttgaag ctagataatc ttcagcgtcc  44820
tgtctactat ttaaaacctg tccatcaatg aagtagctcc ctccttcttt cagaacgact  44880
tcatgttcac aagccaattc caaaacctca ggttcaatgc aaaagcctcc gccgtactgt  44940
atgctcagtt cagcttctgt tgctgcagga gctagcttat ttttaaccac ctttacgcag  45000
atcctaagac cagtaatctg gatatttcaa gcaaacaatc atatattcaa aagacaatta  45060
gcaaagccag tgaaaaaaac aacatgaaac tcatctagga ccagtccatc tgaaatgaag  45120
ggaataagca aaacaaagaa aagcaggtga atataaggat taacatagca gacatgactc  45180
cagatgattc atactacaga atagcagaag aagcccaagc tcttccattt tgctagaggg  45240
agtagcacag taatagtaag tccacacaat ttaagcaaaa ctgtaaacca atgttacttg  45300
atcacagact gagaagtctt tcaattgtga atccacacaa tttaagcaga actgtgaacc  45360
aatgtaactt gatcacagac tgagaagtct tccaatctga aatcagtacg ctctgactca  45420
gtaaatgagt taaactgcag atcaatagct catactcgtg tatattaatt agttcctatt  45480
caatgaacat ctcaaatatc caaaatgagg tagttcttat attctcttca acaaatagca  45540
catctgtttc catagagcaa cttaaatgac tttgagtttt tttacctaga acacttcact  45600
tgtttatttg gacaaatatt tgtggcaaat taaagaagtc agttgaggaa tatcatattc  45660
tccttctcat gttccaaaga aagagaacag agtgacagat tcagaataat tcatacaacc  45720
ttctgaaaga atcgtgacct caagaatcta ggttgtaaca tctaagaaac aaagtaaaca  45780
atttttagta taaggaagcc catttgggat tattatcatt ataggttaat aaaaatatat  45840
ttctgaaggt gcgagtcaat gagtcagaaa catgcaatat gtaccttatg cctggtctta  45900
agcaattgtt ttctgatcgt tctaagccgt atggcagcat aaaaaggcaa agcatttcca  45960
ccacaagtta cttcatccat acacccggag cctcgaacta atcctttgtt agatcttctt  46020
acctaaatag agggcagatc agtatgccaa gctgttacag aaagcaaata gcaatgaaaa  46080
atgtgttcta gtaaccagat cagacctgat taatgaaaat aattagtgtg ctagagttgc  46140
ctaacgaata atgaatttta cgtagtgctt gtgtcataat ctttgattgc aagcctttag  46200
gagagtcaca taacgtagca tcaatctcaa gttggggaac aagagctgcc acctgttaat  46260
agaaaagaaa ttaaaaccct tcagaggcaa agatggttga tcatttacta ggaaaattgg  46320
agcaaaagaa tcaaccttga attataaagg aaagcactta cactatcaac cacgattaca  46380
```

-continued

```
tccatggatc cactttttgt cagggtatta acaatactca gcaaattctc agcagaatct  46440

ggctgcgaaa taaggagatt ttctacattt accccctattg cttcggcaag agaggggttc  46500

attccatttt cgacatccag atatgcacaa taacctatca gtacaaaaga aataggatga  46560

gaggaaacaa atttgaaaat tatagaggat ggaaatactg aaatggctat aaagatttca  46620

cactgacaat tctggatatc attatctcgt gataaacatt gaaatgtttc cttctaaaag  46680

gtaaatgatc tttaccttcg aaagctagaa tcactttctt gttcactttt aatttaactt  46740

tttaaagtac tcttattgaa aaaaagtaat ggactgttca acgccaatca gtacatctga  46800

agataatgat gtttagtatc ataactgtct aaagtctttt tacctgatca tactatggtg  46860

catctcgttt caaggcttta aagtgtgtct ttgccaacac tacgattaac aatcactttt  46920

atgtcaaact aaataaaaaa ataactcact gtttcccagt cacaattaaa gaacaagatc  46980

agcataaatc ttcttttgag agtttcccga gatttaaaac aaacttagaa gcacttaatc  47040

catttctaag ccaatcaaat atgctcatta tataaacaca aaaaagttac agccatgata  47100

attatgaaaa agacaaaaag ttaggagagt attcaactgg caaggataaa ctttttgttc  47160

attatatcaa taggtgccgt ttaaaataaa caaaggcata aaatatgtaa atatctataa  47220

agcatcacgt ttatagtaag agctcagtat atttttcacc tccaagcttt tgagcctctc  47280

taattacatg aagggcaagt gttgtcttcc cagatgcttc ttgtccgtaa atttcaacaa  47340

ttcttccctt tagaaggaaa ttcaaatgaa ctgcaactgt taataccagc aatattctta  47400

agacgagaat agtatcagta atttgattca gagaagcact ggacactaaa atcattatac  47460

agattaatac aaactcaaaa cacataaaga agtactctga tacagagaag caacaagcac  47520

tcaaatcata aattttataa ctagacatct catgaaacga ccatggcacc tgaggacttc  47580

caccctaacc caaaggagga acaatgttac aaattgcact ttgataaagc atagaatcgg  47640

ctattatcca atgacatatc catttagtga accctcaccg aagaaaagaa ggaaaagcta  47700

ggcacgtaat tatactcaga aattatgcaa ttttaaacct ttaaaagaac acttttaaat  47760

tcgatgcaaa ccttaaaaaa gtcggttgag aacagcagct gatttacaaa tcaaatccag  47820

gtataagtta agataactaa agactatact ttcctgatcc tcctccttcc cttttcccct  47880

caaaagaaat gaccccaact tctaataagg ggaaaatgca aaccctaatc aacaatctta  47940

tttcaagaga tctacgtcca tggccctttg aacatacagt atatcagcta ttactgtttt  48000

cgattacaaa atttaggcaa cagcacgtca gaaccacatg atgaccacat ttttacaact  48060

ggcgtcaatg acaaatttat gtttggaata aaaacgtaat cactttatat aaaatcacct  48120

taggtaatcc tccaagccca agtgctagat caagcctcaa tgagcccgta ggtattacag  48180

gagtacgtct agcaccaaag aagcgctgca aggacaacct tgattctttg caaaaatcgc  48240

cttcaagctg cgagagggcc gaatgcagtg cactggcttt ctctgatgtt ttggtgtcat  48300

cttggatttc gtcaagttca ccttctgaag atttcattag ataacatggt tggagttatt  48360

ctagcaaaag acactgaatg ctccaggagt atgataaagg atgaaactac aaggaaagct  48420

caagcagttt aacaccaata ggttgctccc actaacaact gtatgttgga gacaagctac  48480

tggatttctg acaaataact gagcattatt atacatatat tcactaattg agaaggtaat  48540

ctcgcctatc ttcctatttg tccaattttc tgccaattgt tttttgcttt gcaagtatat  48600

ggatatcttt acctcaacaa aacattatgt tcgatacttc gtttaaacat atagaataat  48660

tccacatact agaagatgca aaatatattc cacgaaggaa agttgtgcct atgtgagcta  48720

gctacatcac tgagaatgag ttatcatcct aaaaaagcta tcaactacac atcaacatgt  48780
```

```
tcaatattct tggaaaaact gattaattcc ttctccccaa tactgatata tcaagggttg  48840
atgtctacgc gtgaacctct tttaatcttt gactaatcag gaaacaagat acttctacgg  48900
tgccgttctt ctattaaaac tctctagccc acattattca ccctctttcc ccctttctca  48960
gtcagagtta cttggatgac attgaataat cgaagaaaac ctcacattgt tgagaataca  49020
attaaataac agaagtgtgc tctctctaac aactaaagct tatagatgag atggtcacac  49080
acttaacaca tatggagatt atgcatagaa tgccaagaag gggactcaag gagaaaacct  49140
aaaatattct agcctggcaa caaggtacag cacaattcag ccatcacaga gtttggaaaa  49200
caagataaag atggtatatc acagaagcac caaacagtta acaacttgca aacaagtact  49260
cataccaacc cttatatccc caccccccca aaaaaatgaa ctttttatta caaaaacaaa  49320
aaaagattag aactttacaa tcataagaaa aaacctaaac aagtaaagat agttttttat  49380
tacctgctga agatgcataa gcactaagca tccttctcca aaccattcca ttctgatagt  49440
aacagttaac cccaaaaaat caaaaaaaaa aaaacacata attagccaaa actaagaaca  49500
ctacacttag gaatgaattc ttagtcaaaa acaataaacc ccataactcc aaaaaagtat  49560
acctttttac ttatatatat gtaaagagag taaaaattac ctccggtttg aaggaagata  49620
aggggaaaac agaaaggcaa cgagaggaag aggaaatgaa acgaagaaat tgaagcacca  49680
ttgtttttc actagggcat ctgtgccact ccaactttgg agcttttagc agctgtatta  49740
tagtcttgcc attaatctac aaacagagct tttcattttt cttttaatct ttttcaagaa  49800
agataagggg caaaataaaa agaaaaatct tttctttttt agtaattaac aaagtggtaa  49860
gtatatcttt atcgtttatc aaagtttttg aatcagaaaa gtgcgaaatc actgaatcat  49920
cttcattatt tttgatgtga aatttaattt aaattaaatt ttaatgtaga tatcaaatat  49980
acaaaggtaa atcaaaaagt ttataaataa aaaaaaagtt tatagaaatt tagagaagtt  50040
aatagcttga aaataagtcg tcctattaat gtgtttgtaa gcttaaatat ttcctagctt  50100
accatctaat ataggatcaa tttgcatttt tatgtgtatt tattcatggt tcaacttaaa  50160
tacctcaata catatacatt attatgtcaa aaataaaata attaacctac tttaactcat  50220
attaatattg tatactacaa caacaacaaa aaattactca ccttggtatt tatatcaaag  50280
attatatttt tattgttttc aaatgttaaa tttatgtgaa agtaaatctt taattagtta  50340
gtaagcttaa atgattaaaa aaaaattaaa acatgtcaag aattcttgtt tttttttttg  50400
tctctgccct tattttcttt acccactaat tattcaaata taattttagg ggaaaaatag  50460
atctgacgaa actgtttgat ttttcataag aatctgtcta ctactacttc atagtaaaaa  50520
tcaaagttta ttaattgtat gcacctaaca ttatttgact ttctcaaact caaaatacac  50580
agttctcttg atttttgtag gctgggaaaa tctttggaag caaatcaaga ttcaatatcc  50640
atagtaagca gctatgtctt tagcaatttc tcagctttct tgtttttctt caatcaatcg  50700
cagattagta cagtttcaca gtcgaccatt gcaaccatgt tctacttttt ccttaaaggt  50760
acaatctttt cccttttttt acatcaagaa ttgatttttt tggaacccca gaattttgtt  50820
tgtccattat ctgttgccaa gacatttttt cctcttaatt tcatttgggg tattgggaaa  50880
ctagtggttt ctgatgaatg ttagggatgc atccatttct ttgagcttga accatgttat  50940
agttgaaatt ttgtttgaag tatgtgttta tgttgttagt tggtatccat agtttcaaga  51000
atggtgatga acctcacaga actagttgat cctctttctc ccttgctaac taccaaagaa  51060
cttcgctgtc actagtaaat tagatcatcc ccactaaaag actagctctt ttagttcctt  51120
attttttcag tttgtatatg tctgtgtctg tcggttgtct atatgaaaga tcttcattcc  51180
```

```
tttcaccgga aggagcagac tttgttctaa ggggtatcgg gttccattct aaatagtgcc  51240
ttaagcatga aagaaatgaa attatgtggt atgttatcgt gtataagaga aagcttgcgt  51300
cttgaatctg cctgtaactg tttgggggct agtgctgggg aaatgaaaga attttaagag  51360
atgttgtgtt gctctgttta ttgagtaccc ttgtatgttt tttctccagt gatatattgt  51420
gtaagactgt aagctttgtc gtggtgatca tttagagctt caatcatctt tttttgttga  51480
taagatttca tctttagaga cttatcttct aagtagtgtc tcctactctc ctgataaact  51540
tatatagcat attcagcaat catatggttg gacacaaaag aatgggccca aataaagtag  51600
aatggtatta tagatttata tagtcgaccc caaccagttt gtgattgagc cttgaggcat  51660
agttgattga ttggttgata tgttttgacc actaaaatta cttactttta atgtgatcat  51720
aatttattca gcgaaagatt gatgcatact tccccccttct gaatatgatt ttgctcataa  51780
aatagatgaa agatggagcc tgaaactact tctatattta tctttacaaa acaagcatat  51840
aacatctaaa cttaggccag agtggacctc tgggagccta atttttcaaa tctaaaatac  51900
ccttaaatct tcaatgatgc ttccatacaa agtatactca attgatctct tattgttctt  51960
ctgattttag gagttgtacc ttctgtaagc tagtgtatac tttccctctc gctcttttc  52020
tttctatgtt ttcttgaagc aaactcagag ttaaatgtta atttgtttga catttagta  52080
cggtgcctga cattttgttc tctagggaag tgactcgcca tgtggagtct gtattccttc  52140
acttagacaa acttcgttta tcatggattt caggtaatct ctatgagtaa cgatgtacat  52200
ggcacagatg aatccagttt aaagagccgg accactttaa gttatgcaac tgattcatcg  52260
caatcactta atgggacttc atcaaactca tattctgcac cagaagaata tgtctctgag  52320
aaagaaataa atgagtcagt gcaagagaac tccagcagcc agccaaaaaa ggctgcaaaa  52380
attcatgatt tctgtttagg aattcccttt ggtgagtttc atcttatact ctgaggaggc  52440
agaggacatc taatgcttct ctattaagag gttccatatt tcatatttct ctttacaatg  52500
tgtctagtgg tacaaactag tgtcaatttt tcacctttgc cacatcatct cccatttttt  52560
gttaacttgg tcccttgtcc actggtgaat tcagccagtt tagactttag aggtctttag  52620
aatctcttta tatttagccc atcacatatt agttgatttt gttctttttt tagaaaaaaa  52680
tcctccgtga tctcgctgat tattgaataa gaagatgaag gtgacacact atgctctcca  52740
cctttcttca aatgaaatct tagtgtattt ccttcaagta atttctaaac atttccaagt  52800
caagaatgcc acttatgaac tgtaacaatg tgctgatgac tcaatccttg gtccttttct  52860
taaatccaag agtcagttga aagtagaact ttattgattt actaacagaa aaatgaagag  52920
aacttgattt tatagactag gatcaagagt tgttatgtaa aggtcttttc tttattggaa  52980
atttaagcct attcattcac ttctcatctg tcaattctgt tatgaacatc aggataaatg  53040
tttattacat ttcttttaac ctgcaagacc gccaattctg gaaaatgtat ctcatatgtg  53100
agtgggcaac acttatctgg ctatacccat gttaggtgca catgtaataa acttggtaca  53160
tttcttaagc atttccttga gggggtgctc taaatatagg cacatcaata gataagtctt  53220
tcaatgttct acagtactga cactagacta cttttaacta ttgtattgta catagcgtct  53280
ataaaagcac taggcataag atacaatgat ttgacatttt cgcaatctct tctgttactt  53340
cttagagatc tggtaataac tcattgattc tcttcacagg tggttttgtt ttcacgggag  53400
gatttattgg ttttatttc tcaagaaatc ctgccacatt aagcagtggt gttctttttg  53460
gaggtgcatt attggccctc agcaccatta gcatgaaggt gtggcgggaa gggaaaacta  53520
gctttccgtt catattgggt caagcaggta tttgccgttt attctgcctc atctctttgt  53580
```

```
ggctgttgga cagtctgcat gttattggtt gtgaaccggg aacacttcct tagggcataa  53640
atcgtaaatc tcttccgatc tgatatcagt tttaaaattc tatgtgatca tagatatgtt  53700
taatgtttat tactccataa ttcaataaca atggcatcca taatgtgata gacctatgga  53760
ccgatgtcac attgatatca gttgccaagg ctaaatttta ttttttgtgc acttcaaatt  53820
ttaacaactt ccatccacag tttgatcttg catttttcga tttaactttt caaaatacgc  53880
tgctactaat tgaaattaat tcagtgtttg gattcacttt tacgtattgt gtctatacaa  53940
ttgcatatct tctatagagt tgcatatttt tatgaactcc atcttttctg gtccctgacc  54000
tgctaatacg tatagcagaa tatatcttcc ttccgctaat tcctgatttt ccccttctgt  54060
tgtcctgcag tacttgctgc gacccttctg tggaagaata tgcagacctt ctcactggta  54120
attcttcata ttgccaaaga ctttctgttg gcttattccc aggattgcat tattaaaaag  54180
gtctttttgt tttgtttttg cagacaggaa aattgttccc tactggcttc tttgctgcca  54240
tcaggtattg cagcgtcttc ttttctttct tctcttctcg agtattcatt accaggtgta  54300
actgtgcaat gttatcttca atttgttgtt aaactttaca gcgctgcaat gttctgcttc  54360
tactcttatg tgatactctc tgggggtaat ccaccaccta agaagttgaa ggcatctaca  54420
tcaggggcat attagtgaaa atctcgacac ctgttgacag ttttagagtg agcaaatctg  54480
ttaatttgcg cgagttacat gttgtctatg agggagagtg aacaacgttt cgataatgtt  54540
ggtcttggaa tgtagaatga atttgctaaa atgtcatagg agtttgttca ttagcaactt  54600
gctggtggca caatgaatgt tataatagtt tggattatac aaattgttac ttatgtatga  54660
atcattttaa gtacttgaag catagaatac agtattttct cttcatattt tctcttccta  54720
ttgttgttct atagagtagt ttctttcaat tcaaagttta tattttgggt tttctttctt  54780
ttcccttgtt aatttttgag aaatttagag tttttgttaa ttgatttgga tatataacat  54840
catcaactac gcctcaattc caacctagtt atatttagac gcggttatac aattttttca  54900
tgggattgaa ccggattgac cgactagtag taaaatctta tagagaaatc gtcatttata  54960
tcctctgtta taagtttgcc gtatcatata catgatctcg cacaacataa ttaaagtgag  55020
ggctttgatg atcggcaaat gcttctcccg tataactaat cgtatgaggt aggatgcttg  55080
tgaaaaaact aagcaattta aaaaaaaaat gaaatgtttg aaatttgacg aagaattttc  55140
tatcaaagaa ctagatatat atacatagat gagtagatta ataatccata ttgaagtatt  55200
ttgacaattt taatttgatc cttacttggt tatgatataa tattaatgat tatactaaaa  55260
tgagtttaag ttttaccaat aatacactcc caaaaaagat tatcatacaa ttaaaattaa  55320
cttaattatt attataaata aaggatatta ctatccacga taaaaaaaat agtaactaat  55380
tcactatcga taatattcat tggtaactaa ttaattaatt cctattttaa tgccatacat  55440
cccccataaa ttcctaaaat aacgcataaa ttttctatat aaatttcaca ttttttcttc  55500
catttttgta gttgctagca ccttttttgag tttttttttt aaaataaaaa aatcacattt  55560
ttaaaaaaaa aattatatat taaaaggtta tccagcacca ccatcatcac cacctgaacc  55620
gccactgtat aacggccggc aaccttacac aaccaccaaa catgaccaac acaaatttct  55680
tcccaatttt gtttgcattt atcttcattt catcatacac aatatgcaat gctaatgaag  55740
ttggtatgtt attttattca atcgaaaaaa ttatatagat ataaatatgt caaaaaaaaa  55800
ttatgtttat gtattatatg aattataatt gattcccctt taatgttttt taataatttg  55860
aaaatttcga ttcaattata tatatgtatc atagataatt ctttcttgat gttttatatc  55920
agaaaaggat tagaattatt cttaagttat tggacgttga atattaattt aatacctaaa  55980
```

```
acaaactaaa ggtaaaatta ttctattttt ttatgatttt aaggtaagta taaccctttt  56040
ctgaatttta atttcacctt ttttgaccat gcgattttgt tttttctttc ttattgaatt  56100
atgtttttgt ataaaatatt tttgtattgt atttgattat taattatctt tttttgcgac  56160
acaatactaa cagatgatga gtcaaaattt aattacttgt tgggaacaac agaaggacca  56220
gaaagttggg gtacgattaa attcgaatgg aaattatgtg aaactggatt atttcagtct  56280
cccgttaatt tccgtaataa gagtgtgaaa attaccacta ctatccctct tttgaaacct  56340
aactacaaaa atgcccctgc tatgatagtt aacagaggtc atgatatcaa ggtacgtaac  56400
tctaaaataa ttatggtaca tttcatattt ataaaaaaaa aaattattta aacccctaat  56460
tatagtttat tcgataaatc ctttatttat taagtctata agctattaga ttgagtcgat  56520
taaaagtgca tttcatttat gatatgaata taatatataa gttaaatcat caaatataaa  56580
ttttgaacct ttttattata gtatatgata tttatcttct tgaaatttct gaatccgctc  56640
ggataaataa tgagtccaat cgagtttttt gggacagttg caatgggaag cagatgcagg  56700
aagtatcaac attgatggta ctgagtacag attacaacaa tgccattggc atactccttc  56760
tgagcacaaa gttgatggaa aaaggtttgt atatattata gtatttttat ctcgatttac  56820
gtgacatatt tcatttttcg tgagttaaac agcttaaatt tgattaagaa tttgcttata  56880
aaatcttcaa aaattttaaa atgaaattta tttactatga aaaaagtact ataagtcaca  56940
ataattgaca atttaaaaaa tataaaaaaa tatatatggt caaagattga cttgttttaa  57000
atctcgaaag tcgaaatgtg tcacataaat taagacagaa taagtaattg ttatttgagt  57060
ttgctagcta attggagatc tagttgaaac ttaaatttaa gtattaatta gttgatatat  57120
atcgaaagca aaaatgctga cacgaataac gaaaaatctt ttacagtttt ggtatggaag  57180
cccatatggt tcatcagagt gatgatggta gattagctgt ggttgctata cccttcaaaa  57240
ttggagcgcc taacccttt cttgatcagg tatctaattt tttctatgtt tgatattcgc  57300
gtaatattta tctaatttga aggataatga caagtttatg tcacttgatt tggcgttgaa  57360
cacgtgtcat cgatcatatc acttcacttc aatctaatgt cataaatttt gttgtcatta  57420
tcttctttgt ctattcaact atgtaatcac attcaatgaa ggattgttat tacttgacct  57480
tatcaaaata attgtatatt aaattaattt ttaaatattt taacgaaatt tttgattttg  57540
cgaccagtta ataggccacg tgaagagagt tgatgataag ggtcttaaat tgggacttgt  57600
taaccctcaa caacttggag tcaaagctga acctttctat agatacattg gttcactcac  57660
tgttccacca tgcactgagg gtattatttg gagtgtatta tacgaggtat tcatttgaaa  57720
attatttata aaaattatat tattatacaa aaaggggaaa aagatatttt attttatttt  57780
taatttgcaa tcattgacta ttttattggc taatttaggc aaggactgtg tcaatggaac  57840
aaatgatggc actaagaaat gctgttcatg atgtaagtat taaacttctc ttttagataa  57900
tgtttgagtt agctgattaa aaataactca taaacatcga atgttgaaaa tataactttt  57960
taattttatg aataaaaaaa tatacgtaga tagaaatatt aaaattaatc ataagatgtt  58020
agtacgtgtg gtatcacatg ttaaactatt ttagattaaa aaagtcgtgc atagattcga  58080
aagggagtct ttcaagaagt agtaaaattg tctctcaagt tcgaacttta aagaaaaaat  58140
cattgatata tttatattaa gatagattgt ctaatcacac tcgttttagt gctctctttt  58200
atcaaaccct gtcaatattg gatgctttat gcgattttaa tattattatt attatttttt  58260
ttttacaggg atttgaagca aatgcaagac cagttcaagg cttacataga agaccagtgt  58320
atctagctat gtaaagatag atgatggcat gttaattttt taagaaaaaa aaagtgtttc  58380
```

```
ttcattgcaa tattgttgta attatttaaa tatagcctat ttatggtggt caagtaattg  58440
gaaattatct tttaaataga tatatttgaa aaccaattaa aagtcacata tatatagttg  58500
agatgaggtt cacatgtata tctcaaagca aatatatata tatatatata tatatatata  58560
tatatatata tatatatata tatatatata tatatatata tgcttgtctc ttttttttc  58620
ttttcaaaac atgcacgcta tcttatttta cgtatcgata gcacaaaaaa tatttatttt  58680
tacataatca gattatttat aactcagtta aaacttaaaa gagaaaaata gaggaaaaca  58740
attatcttct cttcaagttg agttcttgta tagcacaaga ggttatttgt tttttatata  58800
atcaagaaat aatcaaagtt gaataataca tgatttgaaa tttgtgagtc gtgattaatg  58860
actttgtttg cattcttctt cacgtgaata ttagagtttt atttgtaata gtttaaaatt  58920
tgtggtatac gacgtataac gtatataata cgtgttgcat ttatgacata tgatacgtaa  58980
ctaacagaaa aacgtgtatt ctcgtctata aatattgcat atatataata tgacatacga  59040
tacgtaagca aacataataa atgttgtgtg ctttctatta atacaattat gttgtacaaa  59100
tgcaaaatgt agcatcatta gcataaagta attgaccaat taatcccttt gcttccatta  59160
atagtcaaag ttagaagtta aattttgttt aaacatgtaa tttagatttt aatttttttt  59220
tattaatatg aaaatacgat aatttatgaa aactatttac gcttgtcaat tctaaacaat  59280
cttattaaat taatacttca taattcataa gtaaaatatt ataaatatga ttttatagaa  59340
gtagtaaact gtagattgat ttctaattaa tatgattgac aacaagaaag taaattaagt  59400
tgactaattc tcaaacttga ctcataagtc aaaactcaaa aagtaattta atgaagtata  59460
aatatatgtt tatagttaat gtttaaatgt ctaattatat atgtaggaat taatcacttt  59520
gtactctttt ttttttgtct gtgtaataca aagaataaag tactttttgg gccttttca  59580
ctttttattt ttgtggattt cttttctttt tctttttaat tttttctttc tcatttgaaa  59640
aataaagtac ctcaattgat tgtgaaattt gtttcccttc ttatatatta tagtatagtc  59700
taaataaaat atgggattga ttttaagtct atcaaaaaat tgtctaaata taaatttatc  59760
aagcaggatc aataattaac atcacattta attcttgtaa catctttatt taattctttt  59820
aatataataa aaacacgagt tacacattta tttttcttga tactattatg agagtgtgta  59880
aatttttgag ttaaagagta aaaacatatt taaagtatgt attactccct ctatttcatt  59940
tagtttgtca tttttttata tgcatattaa gaaattataa ataaaaagat aatttcacta  60000
attaattcct ttcaaaaaat tttggatatt ttaaatacaa atgtaaacac ttgaaaaaaa  60060
tttaatcata agaaaatata gaaaaaaact gaattaacga tttcttgatt tattaagata  60120
aacaactaat atgagataat tatttttagt aattaagata atcaattaat aagtgaagga  60180
gagagagaaa atttcgaatc tacaccattg aaagtaattt ttctatctga actatcatta  60240
attgattggc gaaacacacc tatatataca tttattagac aaaaatattt gtgtaaaaat  60300
gtttgtaagc atgtttactc gtaaaatctt gatccactta acatatatca tgactctatt  60360
tgcgtatgca ttaatatttt aaatatatat taagttgact tctttaaaac atttaactct  60420
ccctttcata gatatcaata acacgacata agcaagacta cgactaacaa agatagacaa  60480
gaaaatggtg gttttcattg ttagaataaa ttaatttata cattaataaa ttcaaaactt  60540
taacctaaca ttcatttatt tttagatttg ctatgaattc gatcgaatta tttttcacat  60600
agaatgtcac gtgacaaaag ttttaaataa atgagagagt atacatatat catcataaac  60660
taatcgagat gtgtgttggg tcatagttca gatagcaaac tcataccttt aatatttcac  60720
gtgtgaaaat aaaaaattaa gataatttaa atatattttt gacacttaac acttactcct  60780
```

```
tttttctata ttaactgatc atttttctaa aatggacact ccactttaaa aaatcaagaa  60840

aatactaatt aatttttttc tctatattat cttgcaagga attatcttct tttttataat  60900

ttaaaatagg aattttattt tttaccttat ttggtattcc ccttaaataa ttcaaattat  60960

gggggaaaaa gtttattttt tttaaaaaat tatttgtttc tctttcttcc acctatacac  61020

acatctaaca aaaattccca aaaagcacac acattgcata ctaaaaaacc aaataaaaaa  61080

acatagtgaa agatttcctc aatctgagga aaaacaaaac acacattccc atcaacaaga  61140

tttactcatt gaaattttct tgaaattcct tcacaaattc aagaattcac ttacccacaa  61200

acccaaaaat gtcatcagca caatcagaaa aacaaaccct tttcattgct tcacttatca  61260

tcttctggta ctcatccaac attggtgtcc ttctcctaaa caaattatta ctctcaaact  61320

atggtttttc tttccctatt ttcctcacaa tgtgtcatat gtcagcttgt gctgttctta  61380

gctatgtttc cattgttttc ttaaagattg taccttttca gaggatcaaa tcaaggtctc  61440

aattcttaag aattgctact cttagcattg tcttttgtgg gtctgttgtg ggtgggaaca  61500

tttctttaag gtatcttcct gtatcattca atcaagctgt cggtgcaacg acaccgtttt  61560

tcacagcttt gtttgcttat ctgatcactc agaagaggga agctt                 61605
```

```
<210> SEQ ID NO 2
<211> LENGTH: 68840
<212> TYPE: DNA
<213> ORGANISM: Solanum lycopersicum

<400> SEQUENCE: 2

tcctgaaatt gatgcagaaa agattagccc agctagtaca ttatacttgt tttcctttct     60

aagaaaatgc agtataataa taatacaaaa aatagaaatt caacaactgc aataattcct    120

cagtcccgaa ttagttgaat attctatata aaatcccaac atcaatttta ttccatctcc    180

gtcatttttt ccaatactta ataatttgta gtacaccttt aaaaagaatc agagtgagtt    240

aagaaacgaa ataatgaaga agtcagatgg ctaaaaaatg aacctttgaa agttgatatc    300

aaacgcagac aacaaggtgg ggaatgttaa tcccccataa caaaaggtgg aagaatctac    360

agttgtggag cacaagagag aatatctccg cagaggcaat gataacaagg agagcataaa    420

tgagaaaacc ctatcattta gggttctttt atattcacat ggtctgacca cttttgggct    480

gaccaactcc tttttggtat atttatgtgt ggatccgttt aggagcccat ttttattaaa    540

taaaatggac catgagtcca tatttaaact ttcaaaaagg gatatcggta gttttcaatg    600

tcaattgtgg tgttcggtcc atttccacaa ctatacttga ttggtttggt tttacccaaa    660

aaaattgtca attcgagatc aaaccaaccc gatatcatat atataatttt gaaatttata    720

attttttata cataaaaata tttactttct attattttta aaaaaatttc ttacactttt    780

tcatagtttt tatcttttat catattattt ctagtttcta agacttgatt ttgaatagtc    840

caataaaggt tatagttcat agatattagt aactctaaca aaactcaaat taaaatcaaa    900

tcaatactag tgctaaaaaa tgttatttaa aaagtaagaa tgataataat atctgttctt    960

taattttgca caagtgaatt catcctcact tcgaagatca tgcaaaatat aaataataca   1020

ctatattatt taaatagaag ggatattata tataataata atgtctttat cttatatttt   1080

tgtgtgcacg cacgtgcgcg tttatgtgtg tgcatgtgat gtgtgaattt tagttgaaaa   1140

ttctaaatgc tttttgaggg tttcttctaa catgaaaaac attactattt ttcattctaa   1200

gaatatgcag tatagtaata atacataaat aggaatttaa caagtataat aaaatacctc   1260

aattctgaat tagttgaatt ttgcatataa aatctcaata tcaattttat tccatctcca   1320
```

```
ccattttttc caatacttaa taatttgtag tacaccttca aacaaaaaga agagtcagtt   1380
gagaaacaag acaatgaaga tgccagatgg ctaaaaaaat gaacctttga aagttgatct   1440
ccacagcaac aagatcaagg tggaatatgt taatcccgca taatcaaagg gggaagaagc   1500
tacagttgtg gagcacaaga gacaacatct ccgtagaggc gatgagaaca atgagaagaa   1560
gaggcggaga gcattaatca gaaaactcta tcatagaggg ttctttcata ctcacctagt   1620
ctgaccactt cagggccgac caactctttt tttggtatat ttatgtgtgg atccatttat   1680
gagcccattt ttattaagta aaatggccca tgagtccata tttaaactta aaaaggaggg   1740
atatcggttt tcaatgtcag ttgtggtttt cgtccatttc cacaatcatg gttgattagt   1800
ttggttttac ctaaaaaaat atcaattcga cattaaacca acccgacatt atatatataa   1860
tttttaaaat tataattttt tatgcataaa aatatttact ttgaataatt ttttagaata   1920
tttcttatac tttttcatag tttttatctt ttatgatatt atttcttgtt tctaagactt   1980
gaattttgaa tggtctaata aaggttatag tccacagata ttagtaactt taacaaaatc   2040
aaattaaaat caaatcaata ctagtgctaa aaaaagttac ttcaacacta agaatgataa   2100
taatatttat tctttgattt taaataatac actatatatt taaaaagaag ggtattata    2160
tgtataataa tgtctttatc ttatattttg tacgtgtgcg cgtacttgtg cgtgtgcgcg   2220
tgaatttaat tgaaaatttt aaatacttct gagggttcct tatgacatga gaaacattat   2280
cttttttttc ctttctaaga gtatgcagta tagtaataat atctatctat ctatctatct   2340
atctatatat atatatatat atatatatat atatatatat atatatatat atatatatat   2400
ataggaattt aacaattgta ataatacctc attcctgaat tagttggatt ttacatataa   2460
aatctcaaaa ttttatttca tctccatcaa tttttcaaat acttaataat ttgtagtaca   2520
ccttcaagca gaaagaagag tcagttgaga aacgaaacaa tgaagatgtc agatggctaa   2580
aaaaatgaac ctttgaaagt taacctcaaa agcaacaaca atagcaacaa catcaaggtg   2640
gggaatttaa tcctccataa ccaaaggggg aagaagctac agttgtggag cacaagagag   2700
aacatctcgg cagaggcgat tagaacaatg agaagaagag gtggagagca caaatcataa   2760
aaccctatca ttagggttct tttatattca cctggtttga ccacttctgg accgaccaac   2820
tctttttggg gatatttatg tgtgtattta tcttatcttt tgattatgca cgtacatgcg   2880
tgtgcgtgtg catgtgcgtg cgtgtacgtg tgattttagt tgaaaagttt aaattctttt   2940
ttgagggttt cttcttacat aaaaaaaaata taaaataaat tatagtatac cttcctacaa   3000
atgggtagaa gtataatttg gttgcatagg gaaaaaaaaa cattattttt tacatgtaat   3060
catctttttt agaagtgaag gaatattctt gtaatttata atgatttcaa aataaataac   3120
ataaatatac tattttcaaa gtaaaaagaa gaagaagaaa taaataaata tactttgaag   3180
aattgattag atatattgag attgtttatt atcttatatt tttattgtaa ataaataatg   3240
gttacaatta aatagcgagt aatattttaa ttgtggaaat ttctacagac gtatttatcc   3300
atacaatata tatttgacta catatacata catcatcttc ttattttaaa tttttgtgat   3360
aagtctagca ctaattttgt aataatttat ataatttatt tgcgtaggta aatttgactt   3420
tattcatttc aattttttca ctattctcta accaaatatg aaccgtaatt atgtttacta   3480
aattaaattt tgttaaaata taataaacaa ttattatgga gtcatatgaa attaatacaa   3540
caaaaatatt ttatcgaaaa cattctaaat tgtagtatgc atgttttgtt atattgattg   3600
aggttcaacc aattatgata acaaaaatat tttatagatt catagagttc tttacaaaag   3660
aacattatta catatcaatt gagataatct aaattggaat aggattggtg gagtgcacca   3720
```

```
ggccaagaat atggtggaac atcatgggaa tgattgaaga tcccgatagt aagctaccgt   3780
aatggacctt ccccttaaa aaatagaatt aatatcgtgt gagtcaatga ttcatatatt   3840
aaatattaaa ttgataagaa catatactac acttgataat aaactcacat tcatttatga   3900
aagcttttat atttaatttg ttttaaataa aattccaaca taaatgacga aagaagactc   3960
ccgtggttgg ttatgaatgt cgctaatgac ttaagtgact ctagatgcat tggcattacc   4020
tcagttattt tgaatatttt tatgacatct attgtcacta aatgtctctt ttgttatagt   4080
gccttgaatc tgttaatgca aaatatttct tacatcaatc atatattata ttaaataaaa   4140
gctgctaaaa ttacacatct cacatttcga tgaagcttac ttgtaggtgc tccatctatt   4200
ccatatgaaa ttattttttg agtctttttc tttttcaaaa taattaaatt ttataggttt   4260
tttttttca tatttgtcct tttctttagt gaatttttat agtttccagg gcatttattg   4320
agtctacatt ctaacaccat gtaactaact attaactaag ttgtttttc ttttttacc   4380
ttatgtaaca aactaacttc ttgaccacta atcataactt aattccaata gtctaacaaa   4440
tggctacata gataccttag ttgtctaaca tatatacatc acgtttcaat aaggatatat   4500
cagctctaaa tcacaaaaaa tatttttcac tcatgtcatg catattgttt gaatttgatt   4560
tgtacaaacc ctagctttag catgttatag agatttactc catgaatatg acgattaaat   4620
ggattgatga tcttactgac ctagctttta gtatatagtc gatccctctc taatcttaga   4680
tagtggattt ttgggtatta atcatgactt ttcattttga aattgtgaca aatgcaccac   4740
atatattata attgatctta catttgcaat tttattggat atcaaatatt taaaataaga   4800
tcttgttagt aaattgacag aatcattaag caccagtggt ctagtggtag aatagtaccc   4860
tgccacggta cagacccggg ttcgattccc ggctggtgca ttatattttt tgtctttctt   4920
acgagattca tctaaatcct tggagaaaaa tttcgttttg ttatttctcc caccccatcc   4980
gaggaggatc aatagtgatc tcactcaccc tctaacatga ctcaacccca taacctcttc   5040
gtttgatggt ggatattttc aaccacttga gctaatctca tactcgtcta attaaagtca   5100
tccagacaaa gcaagtttgg ccaagtccat tgccttttcc accatattgt atcgatttca   5160
atcaaaaaat gtagaggtta ttataacttc acaaaaatcc taaaaaattc ttcaactaac   5220
aatcaaaaga aaggcttaca actagaattg gtggggtgtg ccaagccaag gcaatagtgc   5280
aacgcctaga cgacacttga aggtaccaat agcaagctac catgatgaac cttcccctca   5340
aaaaatagag ttaatatcgt gtgagtcaat gactcacata tcagatatta aactgataag   5400
aacagatact acacttgatc ttagccaaaa ggccgagaaa ggtataattt ttaatgattt   5460
ggtaggactc attttgtatc ctatttgtca ataggagttc ttttgtccag tcaatgtggg   5520
actagaagag gaactattta aataagctat aggaaaatga agacaattag acaaataaca   5580
aaataatata tgctctttat tttaattttg tgtaggtaca tgttacattt gtaatatttc   5640
ttgacactag cttcaaacat cttggtaggc cttttgccaa cttaagattc ttatatatat   5700
ataagaatcg ataactcttg acacaagtta aaaaatttta atttaggcgt tgcaaaaatt   5760
ttctgaggtg atgtatgttc taatcctact agtctcatta ttaattttct tattacaatc   5820
attgaaactt cttataattt tttaatgaag aggtatcggg tgacactcct tagtcaagtg   5880
catctttatt tctatcacta tattataaag atgataacgt tattttcaat aaatttttaa   5940
gtcgaataaa ataacaaata atacgataac ctaaaagtaa tatgaacatg cctaatcttt   6000
tttgattttc agactggtga tgtccttttt ttcttttgac attgtaacac atatggaagt   6060
gcaataattt tcacaaaaag acaaattcaa tgacttatca tgactatagt ttccttattt   6120
```

-continued

```
tattttcttt tttttcaaat atataatgct ttccacacag gaatagaaat tattattatt   6180
atttttttact gtgtcctcct tttttttacc tactgtaaaa ttagtggcca caagttaaat   6240
agttgaatat aatatctaca gactccacca accaaattat tacttccgcg tcttatatta   6300
gttattcata ttattaaaaa taattttctt tttgtatttg gtaaatgcta tttttaacca   6360
aacttagatc gtgactgttc attatttcta atcgtcttat tcaatcactc taaatctaaa   6420
gtaaaatcga taaaaatttc ttaattcttt gtgtattagc gaatttaaat gcaaattgtc   6480
tttttgcctg tggtagtttg gtgagctttc gcttttccaa gttacatatg aattaataaa   6540
atctaagata aaattaatta tatttttata gttaatcttt ttaaaaagtg taaataagtt   6600
tataaagttt caaaataaat tattactaag gggtaaatt agtaaaacta tcattcttat   6660
tcataatttc gtaagagaca tgtaaagaaa aagaagcaac taatatacgg gacaaaggga   6720
atacagtaat gatagttgtc actaaccata atttcactaa tttacatgta cataagccga   6780
tattcaaatt tggtctaaga taacaagtta atcagatgta tagatcggat ttgagctttg   6840
agtatggaga aaaaattgat tggaagcact atccctgaat ggttgcagtg cgtacttcag   6900
atttattcag agctctaaaa cggacctcaa acattgaatg aaaaataaaa aaatgaatat   6960
acacatctag acactttaat ttgatctcaa tttgtctcca acttatcccc attatatatg   7020
ttgtacaccc ttcactaatg tgatacataa atttagaagg tgtggcgata tacatacgat   7080
cttaatttat gtatacaccc gaccttaatt taggtataag tctgtatatc aacactagct   7140
acaagaccga aagttaaagt gaaaagtaag tatttcaata atcaaatatc tcgaattcga   7200
gatggtgcaa agtgctgcat tcgaacacta actacaagat caaaaagtta gagagaagag   7260
taaacattgt tataatctga tatctcaaat tcgaaataat ttttgatcaa aactatttag   7320
gtcccaaaat tgcattttgt agtctagtgc aatgtgcaat agtgcttaat tataaatgat   7380
atttgagatg tcaattttag aataatggag atatatatgc tggtccacca tatcttttat   7440
cttttacctt tgtgtttcag agttcagacc aagttgttgc aaagttttaa tttgtttacg   7500
tatcgatata gattgtgata tagtgattga attattttat ttttaattag agattttaaa   7560
tttgagtaaa tgtatattga aaatatcttg ttgaaagcat atctttaaat agatcttgca   7620
gtgtgcgatt taaatttaat cgagatttta atgtgactcg aaatatcgag tataaagtca   7680
aaaaaaaaaa tactttgcgt gaaaaaaatc acaaagttaa aggggctatc tatgtatttg   7740
gccttttcta ttttattgtg tccttttttt tttttaattt gatctagttt tctctttagc   7800
tttttattta ttttttgttt taatttttca cgtaatatat ttaagattat agaattaata   7860
aatattttac ttcctccgcc ttaaaaagag tcaccaagtt tggcttgaca cgagaagagt   7920
aaatcttgtg attctaaatt caaattattt tatatataga aaattgtctt ttaatcttgt   7980
ggtattaaac atgtcacatg aaaaactaaa aataaatgtt acaaattaaa ttttcttttc   8040
agacaaacta aaaagaaaaa aatactattc tttttaaaat aaaaaaataa tatacttaac   8100
atatttttaa tttaaaatca taacatttta atttatttta ttaaatacca aacaaaataa   8160
attaaaataa cttttatctt tacctccact ttttaagtag cttaaattcc caccaaccta   8220
caccgtagac ctttgtacca tgagtagtga tattaatata tttttttcgt tcgttttata   8280
ttatttgatc tctgttaatt taatatattt ttgaagaaaa ttttaattaa aaatatattt   8340
ttttaaaatt aaaaatgata ttctgcattt taaatttgaa tactgctatt ctttccgttt   8400
taaaataatt atcatatttt atttcttaaa catcaaatta agatataaaa ttatatattt   8460
aaacgcataa tataatttat aaatttaaaa ttttaaacgt tgccgacatc gaaatctctg   8520
```

```
aataataata aaagataaag acagcatgat atatgtcaga tgataattca attattggtc   8580
ataaataatg acagataata attttgcact ttattacctt tttttttttt ttttttttg   8640
ctttttaatg attattttt tcaccaattc aatatcacac gtatacgaaa tttgacaaat   8700
gttgaagtgt tatattagct aaattacaaa tatagtacta aggtgttatt atcagcttta   8760
atcaatcaac tatttcaata attaatcata ttactagctc aaattcagac aaagtgtttg   8820
gtgaaatgaa atatcagtta aacactttaa caaataaaat ttaacattta gatacatgtt   8880
aaactttcga atttcacgaa aaatataaag attcttgagt taatgtgttt gaatgtgcat   8940
ctctctcaaa attcaaacgt ttagtactga ttaattgaca tcaaatttga acgaaaaata   9000
aacaaaaatc tcaccaagac cccgtctcct ttttaagttt ttgaccaaac taagccatta   9060
ttataactat ttattttatt tatataaaaa aattaatttt tttatagatt atttaacttg   9120
atgatacaaa agatcttgtg atataatggg atgacacata ataatgatct ttatcatgat   9180
aaaatttgaa cttgtgatat aatgacacat agtctcaatc tagatttgtc cataaagaaa   9240
aattatttaa aattgctttt tacttggtgc agtagataaa attatttttt aaaaaaaata   9300
aattttaatt ttaaattaaa tgttaaaatt aaagtattat gtgatacaat tttattttta   9360
aaaaatcttc ttattgtaat atgaactaat aaataaactt ataagatatt caacttattt   9420
ttttatttta tatcttactt ctaaatttat ctaaataaga ataaaaattt tgaacaatat   9480
aagcatagga tataaatgtc ttttaaattt tatgatgtta aaaatattac gtaagatatt   9540
gaaatttaaa agttaagtac tgattataat aaactaacct cttccacacg accaatatct   9600
tctcatttta actgttattt tggcttttaa aaaattacca ttttagaaat ttaagattta   9660
agctatccat tttttcgact tggttttcta atatttttat ttatttatca ttattattga   9720
aagattaaat tttttttatc cctttctgaa agttttttta ttttttttgtg attcgaacca   9780
cgatcttaag ttgaaggacg gaagtgaacg atgtttacta tttatcatat atctgccttt   9840
tcttaacgac ataaaagagt taagatgata attaaaatac tatgaatgga ataatattat   9900
ttttaagata aattaaaaaa taaagagtat gtatgtatgc acatatagtt taattcaaac   9960
gatcgataaa aaagaaaaaa aatatgtatc atttacttaa ttgtatcatc ttccacaagg  10020
aaaaatccct ataaaaagaa aatgacatac tccatgcgtt tctttattat tgtatttgtt  10080
taatcagtag tgaaattaaa aattttaaaa aaaatatatt taaaatttga aaaataaata  10140
tacgatctag tgaaaaaggg ttcaacatct attatatata tctacaaaat aattttaacc  10200
acatataaat aataatattt tcaccgaaga gatgaaccct aaatatatgt cgcctccgct  10260
cctgcttcta gccatgattg aaatagctac gggttattac tttttttcct caatttttta  10320
atttaattat ataaaaaata aaacactttc tatcaaaaat tactatcgct ttcgaatcat  10380
tttaaaatat cttttatatt ttccgttaaa gttgtcaata ttgtcatgcc attatatttt  10440
ttcttagtag tcctcgttaa agttgtcaat attgtcatac tgtaatattt ttttaaatat  10500
atttttaaat gtaataaaaa tatttgatct aacaatatta tgttgtcatt tgataatcga  10560
tgggttgtgc agtttgggtc aattagtgtg gcttgtacat tttttttttta tttttactaa  10620
attaaaaact ttatgaaatt aaaaacttta ttaaatttat aattaatatt gttattgaaa  10680
aaatgaaaaa gtaagacaca taataaattg caaagtaggg agttattact gtaacaaaaa  10740
tattattagc aataattaat ttttaattat ttattaaata tttattttta gcgacaatta  10800
tcactctttg tatatgtctc taaagccttt agcgacatta attctaatga cacttaacta  10860
atgttgataa aaactttaaa acttttatgt caatatttaa tgtcgctaaa aattaatttt  10920
```

-continued

```
attacagtga atgtactttt atgctttatg aaaacaataa tatatatacg gttgcattct  10980
tttgaataat ttacactatg attgttcaaa gatatgtaat attactaatt ttgtttgtaa  11040
aactaaactt ataatcttta tgtgtgtatt tcttgttttt ctaaaatatt atggataaaa  11100
tctgtttttg gacctctaat ttttactatc tttatttcta acaattatta ttattattac  11160
tattattatt attattatta ttattattat gagaagttta tttttttaaa ctcctttagg  11220
agcttctatc attttttgct catttaatga ctcgaatcta caattttaaa ttagaaataa  11280
aaatatttat tatctgatca atcccctctt aacaaacata tccttaacac tagagaaata  11340
tatagtttat ttatttattt aacaatattc aaattctcaa aatcatctaa taattaaata  11400
ggaataactt aataaataat accttatatc ttgtttttct taatgacatt agaaaaagaa  11460
gctaaaaata aaacaataca aaagtgataa tattcttttt aaaaataaat ttaaaaagtc  11520
taaattaaaa cacatgtgat atatacttag tttaatccaa actatgaata aaaaagaatt  11580
ttttttttat cttccacaag ataagacttt agagctctat aaaaccacat gtatactagt  11640
ctaaatatct ctcacattac attaaaaaaa ataaattatt atttcttctc tctctcaaaa  11700
aaattgtgaa aatggcacaa tccattcgtt tctttgctac tttgtttctt ctagccatgc  11760
ttgttatggc tactggttag acttctatct tttttattta ggttacgttc aaaatttatt  11820
agcttttcga tattatgtcg ataatgttat cgaataaatc actttctatc aaaaatatcg  11880
ataattcaag tcatctcctc acattttta gttatttcta gtaaaaaatt taaatatcgt  11940
accataatat ttgttgtgcg gaatttgaga taatacgaga aaatataaac gcgaaaaata  12000
agacaacaga tttacgtggt tcaccaacaa attggctacg tccacgggaa gagagggagc  12060
agttttatta tggagaggca aaaacagaat tacagaatag ggtttcccat agcgtctata  12120
tatagtgcta agctacgccc taacaggctt gggcccaaca tacagaatca acagaaaatt  12180
aagggcccaa tacaacaaca ttgtataccg tcggcccggg ggcgtctccg cccccccgga  12240
cccccaggcc agggggcgcg tcgcccccct ggaccccccg actcgctgac cgggcagcga  12300
gacccccgtc ctttctgttt gtagcgggtc cgattcaagg cattcaacag acctaatttg  12360
acttaaaacg gaatttaaga aaagaaagaa attttttttaa tcttatggtt ctaaatcaaa  12420
gttgtgtcaa atgtatcaaa atgcgtttta atcttgtggt ctttttcata tcacgtggaa  12480
agttaaaatt aaaatgttac tgaaaaaaga aaagggtcat tcttttttaa acagactaaa  12540
aaatgaaata aaattattct ttttaaaacg aaggggataa taaacaataa caacaagaag  12600
taaaatgtcg caaattaccc aacatgttgc acaaaaatct gttcaattaa tgttctcttc  12660
atgacttaat tcttattaaa gatggatagc tttgatagaa agcgttttat ccctgacatt  12720
ttaagatgag actttcgat acgaatctag atttaatcag atcctaacac gggtacgatt  12780
cacaggttaa atcagtaaat aaattcaaag cagaaagaga catttgaaaa ggtcaattca  12840
cagttaggaa aatgacagtt agaaaataag gacagagggc cctttaataa gaagtatatg  12900
atgttaaaag agacttccca caagtcacct ccaaaagtag ttaaaaataa tagaaagttg  12960
aaacatcaat tcttttttcc cttttaataa ccgcgatgtt caagtcagct ttcgcgcgcc  13020
tcaacttata attccaagaa atatctgtca ttggaatcgc ttactatttt tgaatttcca  13080
aaaatagatc aaaataactg gggatattat gtgatttatt agtattctaa atcttagttt  13140
ctttcgcgtg ccgtacctta ggattcgtgc tattgctagg taactctgtc catcaagacc  13200
gaaacaaatg agaaaaatca cctagtgtat ttttttgtct ccgcaactgt tgtctaaagg  13260
tacctttttt cactcttcaa tatatttcat atactccacg gcacatggtg tggttctcaa  13320
```

```
agcataagtg aggtcagtgt ttcttactgg atataaatag acataaattt ggggagaaaa  13380
tgaaaccaca tggaacaaca aaacaacact attattatta ttattcaaga atcactagca  13440
agactggtta attaatgtta ccaaattttg catgtccttc aaattgatca tttttagtca  13500
ccctttccta caattgcact aggtatgtgt tttaaatttt gtgattactc atattattaa  13560
tatatgattc caagattgta agctcattta gccatcacat gaacaatttt gctgatgtaa  13620
gacaattgtt gttttctgct gttatagtag gttaaagaat agactaatga aacccctctc  13680
gtgagatagt ttttggagtt gaggtagact tagatacctt atagtttaca tggtatcaga  13740
gttacgttga tccgagctcc tagtccatgg tcttagagtg gattagagtc ttacatggac  13800
ttgggaaatc cttccctcac gctccaattt gcttatatta cgcgagatgc tagctgtcct  13860
attgaggcag tttttgtttt tatattgtag ctctgcagca ttttgttgta tatggaatag  13920
aaatgcctct gaaatacttt tctatatctg tttgattgct gaaggactat tgaatgggaa  13980
agcgaagaaa ctggtttacc tttgtcaaga gacttttcat tcctgaaaca gaatcaacag  14040
cagatcaaaa ggtttgaatt tcaagatttc tgttgcttag tagtgtgagt gaatcttcgg  14100
atatctaaac tggaaattta tgaaaaatat ttcagaaacc aaagagatgg agatgttgtt  14160
ttctgagaaa gttcaagttg aggaaatgtc ctgctataac atcagcacct cagcaaacgt  14220
tacctgaggc gaaaggaaca cctcagcaaa cgttaactga ggcgaaagaa cagcaaagaa  14280
aacatgcttt tgcagttgct atagcaacgg cagcagctgc tgaggctgct gtagctgctg  14340
ctaatgctgc tgctgatgtt attcgtctaa cagatgctcc aagtgaattc aaaaggaaac  14400
gcaaacaagc tgctattaga atccaaagtg cttatcgcgc tcacctggta aaacatcctc  14460
tctggtagct ctagtacttt cactcataca atttcactgt gaacttgttg cagagacgct  14520
tttaaatgca gaaagattga aaattagtta gtcattcaag acaaaactta aaggatagta  14580
tgggaaaagg taggccagtt tggatatagc aggattaaac gcccagtgct ctaccagctg  14640
agctacacac ctaaaaaatg ataatcaagt aaacaagtat tgatacagaa aaaaggcctg  14700
cccctttact ctcatcttat taaaggagca cgactattta ttatgaggct tgtactacag  14760
agcaagtgga agctccgaag gtcacacttt tttttttttt ttgccttttg gctgttaatc  14820
atattagtca taaggtagtc tatcacctcg gttggaaaga aaatcttatt ggttggaaaa  14880
tccctctccg ctagtaaaac tcttctctta tggcggctac taattctttt tcctttcatc  14940
tctcaaaaaa actttccgag atttggtgaa atgaactggt gtctgatcta tgtccctgtg  15000
aaatgttgtg caggcccaga aagcattaag ggctctaaag ggtgttgtga agcttcaagc  15060
agtgattaga ggtgaaattg tgagaggaag actcattgcc aaactgaagt tcatgttgcc  15120
acttcatcaa aagtcaaaaa caagagttaa tcaaattaga gtccctactt ttgaagatca  15180
tcatgacaag aaactcatca atagtccaag ggaaattatg aaagctaaag aactaaaggt  15240
aagatcaatc attcattctc ttttgtttaa ttaagtttcc aaacattagt tcaactatac  15300
taaatctata aaagagacct actaacacat cttattatga cttttatggt ttggaactgt  15360
aatatggttt tttgtttttt tggcagctta aatgcaagag ccttagcact tggaatttca  15420
acttagcttc agaacaagac agtgaagcct tgtggtcaag aagagaagaa gccattgaca  15480
aaagagagca tttgatgaaa tactcgtttt cacatcgggt aaagtcatta cttgttatac  15540
agacactgca attacacttg tcaatgtatt ataaaatgtt gtagcagtta acctgcctta  15600
ttttctagaa tactaatctc acattttatg aacgattatt tataatatat ttttaggtaa  15660
gctgatagta tattgcttct tttaggagag aagaaacgat caaactctac aagacttact  15720
```

-continued

```
aaacagaaag caaaacagaa gaagctacag gattgaccag ttagtagaac ttgacgcacc  15780
aagaaaagca gggttgttag agaaattgag atcatttaca gactcaaatg ttcctctaac  15840
tgatatggat ggaatgacac agcttcaagt gagaaaaatg catagatcag attgtataga  15900
ggacctacat tctccttctt cacttccaag aagatcattt tctaatgcaa aacgaaaatc  15960
aaacgttgat gataactcat taccaagttc tcctatattt cctacttaca tggcagccac  16020
agaatctgca aaggcaaaaa caaggtcaaa cagcacagcg aagcaacacc taaggttaca  16080
cgagacattg tcaggtcaac attctcctta taacctcaag atttcttctt ggagattgtc  16140
taatggtgaa atgtatgaca gcgccagaac aagcagaact tctagcagtt atatgttaat  16200
atagaaggtg ttttacaagg attgaagaac atgagtgttg tacattatta ctatctttga  16260
taacgaagtg tccaagccgg tttgctctca cctctgctag ttcaccgagt gttgttaact  16320
tctacaagta ccagtaccag tactaggtaa ctctgttcac caaagatgaa tgtgtacatt  16380
atcaacctgt ttatgcaagc aagggagcgc agaaactcct agatttgcag cattacttct  16440
ggacatgaaa acaatcagaa aaatggagct attattggag cttcaaactt cttcagtaat  16500
ctatctacag ttgattgatg aaagattact ggttttaaca ctttttttata tagacttgcc  16560
acaatgtgta tatatagttc aagttttttt ccctttccct gtttgttttc ccttgtttca  16620
tttatttatt gatttgtaaa gttgtttcca tgagaccagg aggtcacagg ggtaagattc  16680
tgtacaatag accatatggt ctcgagcctt caccagaccg cacatagcgg ggagcttagt  16740
gcactgggct gttgttcttt ttttttttt ttgcttctga gttgatatac tggaggaaga  16800
attgttgttt gatggccatt cacctggaag catttccaag tttggtaatt gcatagaggt  16860
ttaatctttg ccttctgtat ttacataggt ttatttcttt tgatttcttc cttcaaagtt  16920
caaaccacct ctttattatt tcatgtaaaa tccttcaaaa aaaaatgaac ttacaccaaa  16980
atttatgtct tacctttctt acaaaaccat tgatgttgaa actaaggaaa atggattgga  17040
ccaaccatat gtagaagaaa tatagcaagt ttactccaac tttcactact tatgttaaca  17100
cattgaacac ttgagaaaca aaatccattg gaagctcctc atttctacag gcttaaaatg  17160
tctatggtat atccaatgta acagaataac acatgtgagg cacactgttc tcctcaactg  17220
agattgacag atttcacata ctacaaattt gtaaactttt ggaacataac gcaataggca  17280
agataatgac atttgacaag aagtatcaac tgtaatgctc aaattaccag ataagtgaat  17340
gagatagtcg gaaatgtctg atccacgacg ataaaatcta taccagtaaa agtagccctc  17400
ctgtatgttt tgaactaatg ataacattca gtccagcaac aactctgctg acctcaaatc  17460
tagaagccaa ataaaattac ttgaccatga ggcttagata ttggttgttc gaggtttaga  17520
tattccatct tctatacagc ataaagtagt gaatagattt ccttttaact tatacacgta  17580
ttagttgtaa ttgattctaa cttgctaacc aaaagttgtg tttagtgtgt tgaattttat  17640
atattagcaa aaaattactg ccccaaatat ggtacaaatt ctgcggtgat ttaatacatg  17700
aatgactcac atcctaacca gcaaccaaac atacatattt tactgttggt tttggctctg  17760
ttcatgcttt taatgagtgc agttgggctg gagaattagc acctcatttt ttcgcatgtt  17820
tttctctaaa tgaagaattg caatcttata gttggtcttc actattcttt ctcccccgc  17880
cctctttatt ttcttgtagt taaattattc tatatcagta tcctaagaga cttgttacct  17940
ttgcttgatg ttagatatcg attactacaa gtacttccgc tggcttagag cagatcctgc  18000
catggatgtt ttatcataag gtcattggcg tgacaaactt tttcctgttt gtggagggaa  18060
aagctgcatc tcccgatgta tctaaagtgc taaaatctat tccagtaagt gttcatatct  18120
```

-continued

```
ccttaatatt tccattgtcg tgttgaacat tttgtttcat cacttctacc attttgtgta  18180
tttggacttg tcgtatttct tctgttgatt atatacaaaa tgtgtgtgct ctgcagggtg  18240
taagagttat atatagaaca aaagaactag agaatgtaca agccaaaagg taagcggtct  18300
ttgcctatat atacattttc tgtgcctaaa ctatgaagat gaggtctttg ttcagtagag  18360
tagacgttat ttcctattgc tttgagaaat gtttttatcc cttccgtggg tttatgttct  18420
ttatttagcc tcgtatgatt cattttcttt atgttgctaa tggatgcaag taatagtcga  18480
tgatagaaac tatttatcca aagcaaagct tattgacgaa catatgttag catgggtcaa  18540
caagtttcca aaacttgttg ggagttcctt acatagcaac gtaatatata tcaggagtaa  18600
ctacaatgca cgggtggagg gggttgatgt ggaccgtcta atttacctat taatagcaag  18660
cagtaattac cttgggtagt ggtgacaaca gattctctat tctatttgtc ttgagactaa  18720
taatagactt ggttcctaga agggaaagag ggaaggttaa atgagagtga agttcattga  18780
ttatttaccc tacgtggagc accgagtatt taattcactt tatttgatgt attggaaggt  18840
aagtaaataa gacatacttc tctcagtccc ccttggtaaa caagagaaat aactctttca  18900
cctctcgtct cccaaccctt tctcctttca acccaagcga cattgtatga cgtatgtttc  18960
aagtcattca tcttgagtaa gcttggatct gttttgagtg taatatgact aatgtagtga  19020
aaaatggtaa tagactttaa tgaagaagtg attattcaag ttactaactt aaatagaact  19080
aaatttggag agtgaaattt ccatacaagc tagtaaaaat gctctgttcc ctatatttca  19140
tctcacgtct caattaagta agcttattat ctgacatact gatgatctat aatgtgttgt  19200
gtcctagtcg gatttggaat gagacgtggc tggctggatt cttttaccaa ccatgcaacc  19260
atgagttatt tgtcaagcag actcttaaca tggaaatggc catcgtcatg gcaagggtat  19320
gattgcaata acttccatct gtttccagtt atggttacct tttgatccac tatattgcct  19380
agtaactcta caggaagctg gcgtggactg gatcattcat ctcgacaccg atgagctaat  19440
gcatccagct ggaactagtg agtattcttt acggaaactt ttggcagata tacctgaaga  19500
tgttgacatg gtcatctttc ctaactatgt aagtaattga gctctaggct gtcttttaac  19560
tgtgtctaag catgtaatta catgccgaat agtcaaaacg catgcatttg attcgttttc  19620
attttctgcg gtctttttc atgtcaatat cttctctgat gatgacaaat atttcaggag  19680
agcagtgttg agagagatga tgtgaaggaa ccttttagtg aagtaagata tctttcactg  19740
tatccttttt tcttatcttt caagttctag tattaaaatt caatcgtttg gctaggaaca  19800
tcctccacct ctatacatga ataaatttag attttcttaa aataaatttg gataattcta  19860
ttacccaata cttgagaatg gagcaacagc tagtagtcaa agagtcaccg ctttccagac  19920
gaatgaaaaa gaaggttgcg ttggagttag acattgtgga ggcaagaaag gaaaattgta  19980
cctagcgaac acaaggagct tgagtgttaa aattttttag agagagtttg cgtagtctgt  20040
aatttatttt aattattgtg caactaaagt tcttttagac tgtttaccag caatgcatct  20100
gtatcatgtg gtaggtctcg atgttcaaga agaattatga ccatctcaca aaggaaatgt  20160
actttggaag ctacaaggaa gcaactcgtg gtaatcccaa ctactttttg acttatggaa  20220
atggcaaatc agctgctcga gttcaagatc atcttcgtcc taatggtgct catagatggc  20280
acaactacat gaaaagccca aagtatgctt gttctgcatg ttacttgttt tcctttatct  20340
ctatttcgtt tcttatttat tcccagtcct atagaatcac tgttttatcg aagttgaaaa  20400
catacttgta atgttgtcat attttttcac ttctttggtg tgattgtctt cgcttgtata  20460
atgaaaatgt attttcttat tattgtagag agatcaaact gggagaggct gctgttttgc  20520
```

```
actacacata ccccaaattt tcagatttaa cctcacgacg agatcgttgt ggatgtaaac  20580
ctactaaaga agatgtgaaa agatgcttca tgctagaatt cgacagagct gtgagtaata  20640
ggcagtctgt tattaaaaca acaaatgttt ttggggtcaa aaagatggac tgtatagttt  20700
gtttgttgat aattttcatc ttcacattgc aggcttttat aatagcttcg actctgacag  20760
aggaggagat gcttgactgg tagtaattct tttaacttcc attccatcga attcatgcta  20820
atccttatac tacttatttc gtgaaatcct tcccttgtta tactgtaaaa tcttatttca  20880
tactgatctg tagtccgcgt ggtgcttgat ttctttttgg tttgtatatt atgctgacag  20940
aacctttatt ggattaggta ccgtgaacat gttgtttgga cggataaaac actcatccag  21000
aagcttatca agaagggcat attgacgcgc atatatactc ccatggtaag atcaacttat  21060
atttgattgc ggaagctcct tttgagttta tattgagggt catgaatcct aagaagctga  21120
actcatagta acttttgttt ttcggtctgt gtaggccatt gtacagggtt tgaaggaatc  21180
tggtgttttc gtttctatta ttgcttcagc acatagagat gtcataaaag acgagtctct  21240
atcttcttct gctggaaaca gaaatgcttc cggatatcct catattactg atacttttcc  21300
cagaaagatg ggtcgtatat tggaatctca atcaactgca aggaaattcg tggactttag  21360
tacaactgat catcaggcaa ttccacccga atcacctcct ggcatggatg gaattgatct  21420
cgcagataca aaataccttc tgaacaatag ctcttcttga agaagtatac ttacataccc  21480
ctcttgggaa aataggtgtg tacattagtt ctgtcatact ccatagagtt gttcgagtat  21540
catatcatag agaatgaagt attcttcatc ttttaaaagt tcgatatgta tacatgacag  21600
aatgctttgg agaatgacaa tcttatcgat atacaagaat agatctcttc catgcctcaa  21660
atctttcgat gatgttctaa ctattactcg tctgtttttt tctttattag aactgagtat  21720
gattcttaga ttgttgttaa gtaatttggt tctgaatcca gtagttctgg tccagaaatt  21780
atacaagtgc ttgtgcataa agggtgatgt tacatttgtt gtaatgctta tttgttatgt  21840
tttagataca ctacttttga actagcaatc agatgaagta gagatttaag aaataaaagt  21900
atattcattg atttgattat atgaaacaat ttcactaaac aaaactacat tgttgacaag  21960
aagtagacta agagagcaac tgagatagcc attccttgtt ttgtcccata aatttatcaa  22020
aatcacttaa ttcatctaat aaacactcgt cgttgtttgt tggttcgact tgataagcat  22080
tacctgctgt ctcttcaaca ttctgcagca cttgctcttc ctgataagga aaaactaatt  22140
caccattcat attcccttca ttcattgcag catcgttccc ttgaaccatt ggaaacgtga  22200
cgattagctg agaaagttga tgatcctcca taggccactg cggttgtgtt gtcatatcgt  22260
tcctattctc atcatcacat ccaacatacc ctgattcaat attttgcatt ggcttcacaa  22320
tctgttgagg aagttgatca ctatatccaa attcattagg cccttggggt actagtgtat  22380
catcacatcc aacatacccc gatccaacat tttgcattgg attcacaatc tgttgaggaa  22440
attgatcacc atatccaaat tcattaggcc cttggggtag tagtagtgta tcatcaccat  22500
caccatcatc atatccactg ccagttgttg taggcatatg atttcttgat tttttaactt  22560
tacacctaat gtagcacaaa acaacatcct tgtgcttcat cacacctctg ttactcaaca  22620
actttattac cttgtcgtca agactatact ctttcatgat ccaagaaacg tcgttaacta  22680
catccttttt attttcttca tagttataag ttttttttcat cccaattttc ttcgcaccta  22740
ttgactttcc tttgctcttc cctttccaac ttcctcctcc caccaaagtc cgactaaacc  22800
ttgtatcgcg tttctttaat ttagtaaaaa aatatttagt accggatgag tcttccagta  22860
actcccatgg cttcttactt ccgtaaagtt cttcaaattc aatatcttta caaacgtagt  22920
```

```
ttttagaaac aacaaattta atcaagtagc gaatgagctg ttcatcagtg ggtcgaaacc  22980
tgactccaaa ttcagcgtct ggagattcaa ttgccataac tattgatgag agtagaaaca  23040
aactttatta gttttaggca atggctctaa ataacgatat atgattaacg tacgtgatgt  23100
attattagca agaactgtat tgatgcccaa agccctatat attatattat gacgttaagg  23160
ttagttaaaa aatggaaacc aaatttaaga ataattagga aacgtaaatg caaaaacttt  23220
ccttttatat ttcaagatta gttacttaaa atcattctaa tacaaacgta atgcaaaaac  23280
tttccatata taataaattt aaagtctcct ttttttgtt tcattatata aatcagttat  23340
taactgtaat gcaaatattt ttttttattt ttttttctat tttattcccg tacttcaact  23400
ttagtttgac cataaaagtt tgggtcaatt gttttttctg atatattgct tattttttta  23460
tatagtttca ttaattgtta atataattta aattgtttgt tttaatatta tcagtattat  23520
gtagttaatt aggttttgcc acttttattg ccgcaaaatc ctatttagaa taggtaatgg  23580
aaaagcaaaa acttgtctta gataataaat ttaaaattg atgaataaat aaataatcaa  23640
taattatatg ataagtacgg gtgtttataa gttgattaca attggaaatt ggaacttcga  23700
aacgtaagca ctgttttgca ttttcgattg agaaatgaaa gcattttttta tgacataata  23760
cataaataga ttcttttaac ttgatttcaa ttaatattta tatttttag aattttgagt  23820
gtgcacaaat aaatatttat acttttataa aactgagcaa attaacatat tcgataggga  23880
taattgtata taataaatag caaactaata acccaaaata aatggagtag ctacggtttg  23940
atttaattgt gctccatagc aaacgttagc caaagtttgt cagtcgcctc tctcccaaaa  24000
atctcgctcg ccactctcca attctcgctt gccactctcc ctatgcttgc ctctctcgct  24060
ttgtacacag aagtgtgtaa attgtgtttc tgttttgtat aaagcgagag aaaattgtat  24120
atacacatgc aaaaacatat atcttcgtgc tatacactta attatgcaat ttataaacat  24180
tttactttga ttcaattgta gacaaatgca aattttatac aaatacttca atgaaaaagg  24240
ccaacaaatt atataattgc gaattataca attgcagtga aatacaattt tctctcgctt  24300
tatacaacag aagtgtatat attgtgtttc tgtttttgta taaagcgaga gaaaaacata  24360
tatcttcttc ctatacactt ataattatgc aatatacata cattttactt cgattcaatt  24420
gtatacaaag caaattttat gcaaatattg cagcgaaata ggcagcgaat tatacaattg  24480
cagtgaaatt ggataacgaa ttatacaatt gcagcgaaat aggccagcga attatacaat  24540
ttaggccaac gaattataca attgtatatg tatagcgaat tatacagttt atgtttgcta  24600
tggagcgtaa ttattcaaac tttgatatag catacaaata tgaatttttt atttgctata  24660
tgtgaaagtt gccctattta atatcctatg tgtaaaaaaa taatgttatg gggtgataac  24720
gtcaaaattt tgaaaatagt ataattatcg ttgcattata tttaacaata ataataaata  24780
aaaatattta gcgacatgtc acatgttgat attttacata aattttcttt gtttagagca  24840
acaattacat aaacatggtt tgttcatatt gaatatctca acttcattat ttaggaaggg  24900
taaaatagta aattattacc tttttattaa gctatcgatt tatccaataa ttcaatagta  24960
aaattaacat cgaaccaata actcaaaaac atacaaaacg gactccttga tagcaatttg  25020
ttgatgtagg taacttattt tgacataata ttatagctaa tttcacgatt taaatccatg  25080
atgatacatc atatatatat atagtgtctt aatttttggc ctctaatatg tagtgtctta  25140
atttttggcc tctaatattt tgctggacca cttaattctt taggagtggc aaaaatatag  25200
tggtttgcct gtaatacaat tttgtaatat taactggact tcctctaaac tacattgtca  25260
aatgaaaagg ttgtgtggag ctttctgatt gggtagaata ttaatttttt tttcaaaata  25320
```

```
aataattaat ctgacctagt aaacaaatat acatcatttt taaatatata aatcagccta  25380
aactattgaa aactcaggtt tgcttcatgt gaacattgtc caattttttt taattacttt  25440
attattatta ttattattat tttattttta ttattaatag aaaaggacta cttctccatg  25500
tttatactgc cacatcaatc agaatttttt ttttgtttaa tgagttacta ctattagaaa  25560
aaaaataaaa tatataatta aaaggaaatc acttaagttg gcaattttca tgctttaaac  25620
tttgaatctc atgaatcatg atcaagaact gggataaaga ctccatatat aaacaaatga  25680
ttagatgaag tcataaaagg aacaggagac atgacggagt ggtaagtact caatcattaa  25740
aaaaaattta tagcgcgtat acaagcaaat ggtaagataa cgtattctgg atagtcttga  25800
cacaataacg tgttgtagcc ggtgatttca aggctcttaa aagagccaag acacgcaaat  25860
ttttagtgtt cacatgttcg caacgatcca aatttagtca gccctaatat gaataacgga  25920
cactgggtgg cgattcaaat ttagtcagcc ctaatctcac taccagtatt aatgaagaag  25980
gatttctcgc ggcgatctaa ctttaatcag ccctaatatg gatagcgaac actgggtggt  26040
gatccaaatt tagtcagccc taatctcact atcagtataa atgaactatg attctagcag  26100
cgatccaaat ttaatcaatc ctaatatgga tagcagacac tgagtggcga tccaagttta  26160
gtcagaccta atatggatat cggacgctag gcggaaaatt aaaccttata taaacaattg  26220
gttatagaaa gttttaaaag gaacatgaga gttgacaagt gagaaaacag aacaaaagca  26280
gatagatgaa gtgctgactt tgacaactac taaatctctt catttaatat tcttatgaat  26340
tttataacaa cttcatggta ggcaactttt tagtttgaca ttctttgatt ccttaagact  26400
ttttcaagta aatagatttg attatgaagt ttatatatat gaagttccac actcactagc  26460
aaaaacccca caaaaacaca aaacaaagtc tttttacaac ttcaaaaaaa aaatggaagg  26520
acaaacagga caacaagagg agttatttgt agaaattgat caaaaaacag atgatcaaac  26580
atatagcgat ggtgaagcag catcatgtac aacagatggt aacgaaatag ttaatgttat  26640
tgtcacgtct gatccgatct tgcaaggaga atctatgcca agaaggtata catactcgtg  26700
gagaaggcga atacagaaag ttttacctct attgaagacg gatgaataca acagacacga  26760
gtatgatccg aaagtagttt cattaggacc ttaccatcat ggtaagacag agctacagct  26820
agcagaggat ttcaagcata tagcccttga aatgtttgta tcgggtagca gcagagacgt  26880
agcttatttc tataacaaga tacttgaagt tgttgacaat gcaagaagtt gttatgtcga  26940
tggctccacg gacaagtaca atgatcatga atttgcctta atgatgcttc ttgatgcttg  27000
ctttattatc aaccatatcg agctaagcac aacggatagg tataacaaac tcagaaccac  27060
gaggcaccat cttggaatgt tggcgttatc aacaacagtt cgtgatatgt ttttgcttga  27120
gaatcaaatc ccattttgga tactgaagct cttgattagc ttacgatatg acaaagatga  27180
aggagatgaa ttgctcgaga tgttcttgaa tttcaccctt ttcggtgaat atgaacaaga  27240
aggggaaatg agtcacaacc atgtagaaga gccactccat cttcttgaag catttagaac  27300
aagacttgtt tcacaacaga gtgaagtacg gagctttcac cgtacttgca cacctcaatg  27360
gctaaaaagg aagaaaagta taagcaatga acgcgttaac atgaaaagct acattcactc  27420
ttttcgttca gtaaccgatc ttaaagcaaa aggtattcaa ttcaagccta gctgcactca  27480
ttcactcaag gacataaagt tcaaatcaag atacttctat ggacagcttg tacttccaac  27540
ttggtatgtt tctatctaca ctaaggcgtt cttcttaaac atgatagcct acgagatgtg  27600
tccaaataca gttactgatc gcgctgtgac atcatacgta tacttcatga aatcactaat  27660
agagagtcca agggatgtca aggaactacg cgaaatgcaa atactattca acatgcttgg  27720
```

```
tagcgacgag gaagtggcaa gaatgtacaa agagatcaat acgtatggag tgaacaacgc  27780
gcacattttc tacaatgtga aagaaaagat tcaagaacac tataataaca aggcgaaaac  27840
atggatagca gagcttatac acacttactt taggagtcca tggactgctt tagcattact  27900
tgcagctact ttcttgcttt gcttgacttt tacacaaact tattttacaa taaatcccaa  27960
tcctagatta tgagaaaata tttgtaacta tttgagaaat tttgtggtag agtactagtt  28020
tcttatcttg tttgctgtta caagaaaata aagatgcttt tgtgatatag atatctctca  28080
taaaattatt tttcacgtat actttataga tgttgaactt cgatccttgg attagttctt  28140
gtatttattt tttcatattt tgaactaaaa ttaagagggt taattgggcc gggtcacttc  28200
accttgaaga ccaagaacca atcgggttca aaatccacct cggtaatcgg aaccagcact  28260
atttgtgatt tgatagtata gggttaacca actagcccag cccggaatgc ccaattgtta  28320
agtctaaaat ttaaaattat atttcaaaat cgttaagtat ttaaaaaaac actacaatat  28380
aaaaagttat ttttaaatta aaacccgacc ctatatggcc caaaattatg cgggttacat  28440
caaacccaaa ccgattggat tcgatatctg atcgggttcc ataatcagtg aaccagcccg  28500
ggccaactca atgccaccct cggtgaaaat tttcactttt tcacgggttc aatcaaaata  28560
gaaggaaaaa aactgaaata cacgtcttat gttttttttt tttcaatgtc tcctatttct  28620
aaaaacctct taaataattt atttttctcc caatgtattt aatgtatccg agttacatat  28680
taatgtatcc taactatata ttatgtattc gatttatttt ataatgtatt cgagctacat  28740
attatgtatt tgggctaatt tttaatatat ccaagctaca tattatgtat tcaatttatg  28800
ttataatgta ttcgagatac tctttaatgt attcaaaagg tataaagtat aaggaattat  28860
tataattaaa aaaaatagag ataaaatgaa atatattttt gcactatgaa atttaagtga  28920
attatacaaa atagaatatt acgatagaag ggcctaaagt tgaactgaga gtaggttctt  28980
ttgaaatgta ttgggcctca tcttggccct tactctggta acaaacattc catttttaatt  29040
ttttttttt atcacttggc tttttcatc atttaacatt gtattatgaa acaaaatata  29100
tttagtaata aatactcaaa caatattgat gagtgtatat acatctctaa tccatagtta  29160
tagcttatag gctgaatcca tcggtagctt tctaaagttg acattaattt tcatttaaat  29220
tagactttgt tcatcttaca cacctcatgt tgagttccgc tgtgtcattt gacacttttt  29280
gatgacttga tatattgtgt gtgttgcatc cattttgagt gcgtgagggg tctttttttg  29340
tgtggatatt tttaattttt ttccttcttc actttttagc cttaccactt attccacatt  29400
tcccaatgaa aattcatgat aaaaaacttt acaaaatatg aaaagatttt ttagaacaag  29460
acatacattt ttttcaaaaa aaaattggaa aaatgtcata tataattttc aaaatcaatt  29520
aaaaaaaacc taaaatctaa tgattttta aaaaaaattg gaagaagaat caagaaaatg  29580
attgtagagt tgaggaggca aaagggacgc aagacagatg ggcttagggt gggatgatat  29640
aaggtggggt ggagtggtac aaactaggta attttattta tttatttttg ctaaaaaatt  29700
agttattttt tgatacttta ttttaaaatt attatttta catttaaatg tcaaatatca  29760
gcttttatag tcatcatgtc atgttatccg caagtgtgtt acacactctt tgtaatttta  29820
gctgattggc aaaaaggtgc caaaataaca tagcggtccc ctacttgagg tgtttaaaat  29880
gactacttga agtgtctaat tgaaaattga tgtcatattt aaggggttgc cgatgggttc  29940
aacctatctt ttatatatac gattatatac aatttataca atgtcaatac attacctaaa  30000
agtaaattta tgtgtatttt tgtttctttt cgctcagggt gcaccaagtt cgaaaagaat  30060
gaggatacaa cgtaagcatt agtgattgat tctactattt aaagttgaat ttataagtta  30120
```

```
cttgaagaca attatatcgt caaataggat cataaacaaa ctatcttaac acaagtatta
gttattgtct agatttgctt tcatcaaact caaataaata ttaattaatg agaattatta
tacctttta tattaaaata aactatactc ggagtttact taaaacaata aagaatattt
gctgctctgg acagactcaa ataggggacc tatcataagt acaaccacaa cttataagta
atcatatttt ttttaaaaaa attaaaatat tagtaatctt atatttaatg tttaaaataa
ctgtgtattt gaaactttct gctattcatt ccatgcttaa attcttttta tcattacact
aattaatttc ccaaattgtt tttgcatgta atgatccttc atggattggt cccattttta
ttttttttta aaactcaaat gttgataatc tccaatcaga catatgatta gtggaacatg
tgatcttcta gctagtgaca actctgcata tgtgagttta tttattttat cgagtttcaa
tcgaaataga gtataacgat atatttataa attatgttaa ttttcaagta aaaataattc
tgaaatgaaa atgaagaagt atagagaatc gatattactt ttcatttgta ttttgtataa
tattactata tgtgtactgt ttaaatagtt aatctcgatt tatttgagat cgaagcacaa
tggttagata gtttatcatt atagcctttt tgtattgaat aattgaaaga agcattaaaa
aaatcaattt aagggctttt gcaattatga cctttcacat ttttcactaa gatatatata
attaacatgc atgaagaaaa gtgttacctt ttctctatct ttcatttgtc aaatggaaac
tttattattt aaagaacaca tataattccc aaaaaagatt taaaaaatat aaaggctaaa
aattcaatta ttttggatta tatccttgat taccaaaatt gagtccatta aataactcaa
aaagataaat gctactttcc aaaaggtgga tagatattca catggtttat ctatgaccca
aaaatatatg ggactagtga tatagataca aaagcggctc aattaaatta atggcctaaa
ttttttttt tttttaatct aacgatttta aaaagtaaac taacctaaaa tgtattatag
gtaaaaataa aactccatcc tcccttaacc ttccctagag atattggttc gaaaatctcg
ctagaaagtg ctttcctcga tcttacatgt ctcaaaacca aacaaaaaaa aattgaaagc
ctaaagttct ctctttagtg acttgactgc atatacaata taatttttta acgaaggatt
ttaattgcat tctatatcag tggtctcttc acctctgacc aagtgatgat gatgagtatt
acttggaagc tgaaagtata ctgttggatt tgctaggtga aaaaaacaaa agagaatata
ctaaaatagt tttaacacat tgtgaaaatt ttcaaatttt ggtatcattt ttatacagct
accaaaaaat aatcataagt tgtactacta attaaaactt tatatttctt ccgtttaaaa
aagaatgacc ttgttgtgcg gaatttgaga taatacgaga aaatataaac gcgaaaaata
agacaacaga tttacgtggt tcaccaacaa attggctacg tccacgggaa gagagggagc
agttttatta tggagaggca aaaacagaat tacagaatag ggtttcccat agcgtctata
tatagtgcta agctacgccc taacaggctt gggcccaaca tacagaatca acagaaaatt
aagggcccaa tacaacaaca ttgtataccg tcggcccggg ggcgtctccg cccccccgga
cccccaggcc agggggcgcg tcgccccccct ggaccccccg actcgctgac cgggcagcga
gacccccgtc ctttctgttt gtagcgggtc cgattcaagg cattcaacaa atctccacct
tgacttgaat tctccgaaca gattcttcag acgcactatg atagtgccaa gcctcccccct
cttcctcaga gttgccccgc agggcaatta acagcttctg atgttgagca agtccaaaca
gtgttgaaac ttgctctgtg gaaccggctt tgtgaacata tcagcaggat tatcagcagt
tcctactttc ttcaccttga ttctcttctc acttcttaga aaatgatacc ttacgtcaat
atgcttggtt ctctcatgat ggacttgatc cttggctaga caaattgcgc tcaaactgtc
acaatacacc gtagcctgat catgatgcag accaagatca ctaaccagcc ctttcaacca
```

```
aatcccttct tttgcagcct ctgtcaaggc catgtactcc gcttccgtag tagacaaagt  32580
cactgtaggt tgcaaagttg ccttccaact gacgacagat cctccaaggg taaacacata  32640
gccagtcatc gatcttcttg tgtcaacatc tccagcatag tctgaatcag aatagccagt  32700
aaccaagcac tgagtatcac ctccataaat gagaccaacg tcagatgtac ctctaaggta  32760
ccggaaaatt ctcttcacag cctgccaatg ttctctccct ggttgtccca tgaatctgct  32820
cactacactg actgcatgtg ctaaatctgg ccttgtacag accatagcat acatcaaact  32880
tcctacggca ctggcataag ggactcgtga catatactcc ttctcttctt ctgactgtgg  32940
agcgaacatg gcagtgagat ggatattggc agcactgggg gtatcaatgg gcttagatga  33000
agacatgcca aacctcgcca agaccttctg aatgtagctt ctctgtgaca agaaaagttt  33060
ccttctctct ctgtctctaa tgatctccat ccctaaaatc ttccgagcgg ctcccagatc  33120
cttcatctca aactcagcac taagtaaacc cttcagcttc tgaatgtcat acttcttctt  33180
tgcagctatc aacatatcat ctacataaag caccagatag atgaatgaat catcattgag  33240
cctattgtag tagacacaac aatcatatga gctccgagta tagcccaact tcaccatata  33300
gctgtcaaac cttttatacc actgccttgg agactgctta agtccatata aggacttctt  33360
caacttgcag acgtgatttt ccttccctgg aacttggaaa ccatccggct gagtcatgta  33420
tatctcttcc tccaactctc catgtagaaa cgctgtcttc acatcaagtt gttcaagctc  33480
cagattctga tgtgcaacta tcgctagtaa cactcggatg gaagtatgtc tgaccactgg  33540
tgagaagatc tcattatagt ccactccctc tctttggttg aaacctctgg caacaaccct  33600
ggctttatac ttgactcctt ctgctggtga tatcccttcc ttcttcttga aaacccattt  33660
gcaagtaata atctttctcc ccgaaggctg tatgaccaga tcccatgtct gattcttgtg  33720
tagggactcc atctcatctc ccatagcggc aaaccatttt tcagaatcag aacttaaaat  33780
ggcttctttg taagtagacg gctcagatgt atctacctct tcagcaacct gcagtgcata  33840
acccaccatg tcctcaaaac catacctcgt aggtggccga actccaaccc tccttggccg  33900
atcttgagct atactctgat ggatatctga tggcatagat tctggaatat cagtttcagt  33960
ctgtggctct tgatcctcct cttcaggttc ctttaaatcg ctctcgttct gaatgacttg  34020
aaactccacc tgtttgtcaa gactcccagt ttctgacgta gttgtaggct tcacaatggt  34080
tctaagcaga ggactttcat caaagacaac gttcctgctc ataataaccc tcttttctgc  34140
tggagaccag attctgaaac ctttcactcc atctccgtag cccacaaata ctcccttttt  34200
agctcttggt tctaacttac cttcactgac gtgatagtaa gccgtacaac caaaagcttt  34260
cagatttgaa taatcagcag cttttccaga ccacatctcc ataggtgtct tgcactgtat  34320
acctgtatgt ggtccgcggt taatcaagta gcaagctgta ctaaccgctt ctgcccagaa  34380
tcttctatct agcccagcat tagagagcat gcaccttgct ctctccagaa gtgtttgatt  34440
catccgctca gctacaccgt tctgctgtgg tgtatttctg actgtgcgat gtcgagcaat  34500
cccttcatcc ttacagaatt gatcaaattc agaccaacag aattccagcc cattatcagt  34560
tcgcaacctc ttgatcttct tccctgtttg attttccatc aaaattttcc actccttgaa  34620
cttctggaag gcttcacttt tatgcttcat catgtacacc caagtcatcc ttgagtagtc  34680
atcaataatg gacacaaaaa atctgcagcc tcccaaagac tcaacacggc atggacccca  34740
gcaatcagaa tggatataat caagtgtgcc ttttgttcta tgaatggcct ttggaaactt  34800
gttgcgatgt agttttccaa aaacacaatg ttcacaaaac tctaggctct taaccttatg  34860
accagcaagt aaatcctcct ttgacagaat ttgcatccct ctttcaccca tatgaccaag  34920
```

```
tcttatgtgc cataacttag tcatatcctt ctggtgaaat tctgacgatg caacatgggc  34980
tgaacctgta accgtggaac cttgtagaaa atacaaagta ccacgcatga cacctttcag  35040
aatcaaattt gaaccccttcc agacccgcaa gactccatct tttcccgacc agctgaatcc  35100
cttgctgtcc aaaagactga gagatatcag atttttcgtc atcaatggaa cgtgcctgac  35160
ctcgttcaat gtgcagaagc taccgtcatg tgtccttatc ttgatcgagc ctgtcccaac  35220
caccttgcag acagaactgt tggccatcga gatgctgcct ccgtctacct gctcataagt  35280
cgtgaaccac tctctcctag gacagatgtg ataggatgcc ccagaatcaa gaacccacac  35340
atctgaatga tgagtgtgct catccgcaac tagggcaata tcttcttcag aattggtgtc  35400
ttcttcagca acagcagcag acactgattg tttttccgat tgcttcttct tcttcggaca  35460
atcaaatttc caatgtccct tctccttgca gtaattacaa acatcatccg gctttgcacc  35520
cttcgacatc ggcttatttt tctttccgcc gtttttcctt ccctttctgc tactggtgaa  35580
cagaccggaa ggctgtatgt ccgtacttgt gccgttagcc ttatgccgta attccctgct  35640
atgaagggct gatctgactt cttccagtga cacagtatct ttcccaacaa tgaacgattg  35700
aacaaaattc tcaaacgaca ttgggagaga tactaacaga atcagggcag catcttcatc  35760
ctcgatcttc acatcgatat tacgcaattc taataacaaa gtattcaatt gctctaagtg  35820
ttccctgagt tgtgtacctt cagccattcg taaaccgaat agacgttgtt tcagaagcag  35880
cttgttggtt agagattttg tcatgtacaa actctccagc ttcaaccaca gaccagcagc  35940
agtctcttca tccgagacct ccgtgatgac gtcatccgcg agacacagca tgatcgtcga  36000
gtgcgccttt tcctccagaa tcgccatctc aggagtaacg acggcgttct tgtctttcga  36060
caacggcgcc cagaagcctt gctgtttcaa caaggcccgc atcttgatct gccataaact  36120
gaaactgttc ctccctgtga atttgtcgat tttcacgttc aaagcagaca tctcgaattc  36180
tccaagaaca ccgattaacc gagaggctct gataccaatt tgttgtgcgg aatttgagat  36240
aatacgagaa aatataaacg cgaaaaataa gacaacagat ttacgtggtt caccaacaaa  36300
ttggctacgt ccacgggaag agagggagca gttttattat ggagaggcaa aaacagaatt  36360
acagaatagg gtttcccata gcgtctatat atagtgctaa gctacgccct aacaggcttg  36420
ggcccaacat acagaatcaa cagaaaatta agggcccaat acaacaacat tgtataccgt  36480
cggcccgggg gcgtctccgc ccccccggac ccccaggcca gggggcgcgt cgcccccctg  36540
gacccccccga ctcgctgacc gggcagcgag acccccgtcc tttctgtttg tagcgggtcc  36600
gattcaaggc attcaacaat attgttattt ttttcctcta aagtttgggt gaggtggggg  36660
tgggggtggg ggtgggggga ctattttgtt tatatatatt ttgactaggg ttaaaattta  36720
agaatataag aaagattttt tatttaaagt aaaaatgtgt aaatacatta atcttacgcc  36780
attatttaga agttggtttt tataatattc aaattaaaaa tttagtaaca ttcatttcga  36840
aacagattaa aaaaataata atgcgtataa attgcaaagt agagagtatc acgctttgat  36900
ttgttgttta aagtaactcg tacgtaacta atatgatttt attttcacag aaatgggacc  36960
aacgagaatc gtagaggcaa gacattgtga gtcgttgagc catcgtttca agggaccatg  37020
tgtgagcgat aagaattgtg cctcggtttg cgagaccgaa agattttccg gtggtaattg  37080
ccgtggattc cgtcgccgtt gcttttgcac caagccatgc taaataaata attttgattt  37140
ttatgtgtaa aagaagaagt ttgagaagaa aaaaaatatt atgtaatttt gaataaagat  37200
gtattgtaat gctagttttg tttgtaaaaa ctagttgtga tctttgaatt tgtatgcaat  37260
tatggtgcac tagacttgta attcttcatg tggtgtattt ttatttttat ttttgaaata  37320
```

-continued

```
ttatagataa aatttgtctt ttagcctttt tgttagtaag ttttaataaa atattcttcg  37380
atgcggaatc aagaatcgat catttctttt tattaagtat tttgaaatgt gaaagcgata  37440
aattgataat tttatgagga agtttctgtg cggaatcaag aatcgatcat ttcttttaat  37500
taagtatttt taactgtgaa agcgataaat tgataatttt atgaggaagt ttctgtattc  37560
tttctgattc atgtctgagt aatttttttt ttgctataag tacagtattt tcataagcat  37620
ggagtaaaaa aaaaatacct tctatcattt ttgttgtagt tgatcattca caacgatatt  37680
ttattagaca tatttaatct ttaattaaag tattaattaa tttttcttct tctttaatat  37740
aagtttacaa tttttcgtaa ataggaatat tggttaaagt ctaagctagg ggttatttga  37800
atggcaatgg aatggacaaa ttattctact tcataatttt tagtagataa aattattttt  37860
ggcacaaatc ttacgccatg cgttcaatac gaaatctgaa aagctgcggg gatgacaaaa  37920
agagggcact ttcctatgtt gcaccggaaa aagacttaag agacaagcgt cttctcttag  37980
gtttttttct ctcgcgcccg tcaccacttg acccgcatta gaggggaaaa ttaacaaaac  38040
gagaaaagaa agagggaaga aaagtagcat cttattatat tattattatt agaaatacaa  38100
atagtaaaat ttaaattcaa aaaaatttaa tatttctcaa ttaaatatga tattttattt  38160
caaaattatt acttatcact ttattatttc acgacccttt agaaataaag gagatccatc  38220
aagatatgtt ggatagtaat tcaattattg gtcaagtggt tcataaaatc acgacatata  38280
ataataattg ttcatctttt tttttttcg ataaactcaa gattcttttt gataaattat  38340
taatgatata tttaaagtca ttaaattaat ttttttata tatcacagaa tttaaaattc  38400
tttcaaatat cataaacaga cactaatttt gaatttatat tttaaaaaaa atactatatt  38460
gtatatcttt ttgtagttga atctccataa gttttagaat atttcaaatt cgatttgatc  38520
atttaacggt gtatcttata aagtgtgcat gtaaatgaca tatatagaag gaataatttt  38580
aaaactcaag ctaaaagtta aaatagagtt caaaaagaag agaaactaaa gtaaaattaa  38640
aagtaaatta ggggatgaag ttagacaaag taaaaataaa tctttttaa aaaatattgt  38700
tatttcaata ttcgatattt atattgaaat ctgattaatt taaatttgtg tcgaatagag  38760
tccatttcga gagatatcac tctctgaact tttttatct aaaactcgaa ctcaaacttc  38820
tatacaaaat aaatttttgt atctaactaa tcgtcgtctt tttaacgtca ttttaattac  38880
tttgatgtgt ttttagtttc attgatttta aaaattatgg gagattttt aattttaaag  38940
taaaagatat attcaatatg ttaaaatatt ctttaaattt ttatatttta aatatatcat  39000
atgagatatt taaattatag agtcatttgt atacaaaata atattctttt ttaatataga  39060
aaaagtaaat aaataaattg aggtatattt attcacatag gttgtttaat tactttacta  39120
aacttataat atgatgtaca tcatagactt atttggtaat cgaaatgaga taaataaaaa  39180
tatcttatga gaacaaccat tatataaatt catttgatca ttaattttaa atattttttg  39240
tttaattgaa aatttacgga gtcaaagtta aaaattgagt tgtgattagt tatatttctt  39300
ataaaatata tttaaaaata atgtccatac ttaaacgtac ttaaatataa tttcaaatta  39360
aataatgagt cataagtttt tttctaaagg aaaaaagggt ctgatatacc cctcaacttt  39420
atcatttgga gctgatatat tcctcgttat aaaagtggct catatatgtc cttaccctta  39480
tacaaatggc tcacatatac ccctgccgtt acaaaatggc tcatatatac ccttcattta  39540
acggaagtta aaaaattagt tttaaattta tatttattac ttctaatttt tttaaagaaa  39600
ttatttagtg gtatatatga ttcttctatc aaagttcaag gtatattttc attttttca  39660
tgcatcaatt attttttgac ttcttttatt ataattattt gagtttctta ttcttatttt  39720
```

gtttttcttt tcattcctta gtttaaagaa aaaaaattaa actatttttt ttgtgtgtgt 39780
attataattt aatttcgtat tcaaagaaaa aatttggtca tctacaataa gttttgcaag 39840
aatattagtg aaatataaat aaatttgatt atcaaaataa taattataaa ttagtcattg 39900
aaacaaaaaa aagtcaaaaa aaaatatgtt tgacgatgat taaatttact catatgagat 39960
tatatttttt tagaaaataa aaataaaaat gtagattaaa attatttttt tccatttccg 40020
ttagatgaaa agggtatata tgagccattt atttacaaat agaggtatat atgaaccact 40080
ctcataataa gggtatatca gctctaaatg acaaagttgg gggtatatca gaccattttt 40140
ccttttctaa atttgatata caagaaaaaa aaaagaataa caacttttat agccaaaccc 40200
cgatcgtaat aaatcttttt agttaataat tataactaaa taccaaataa atatcgagat 40260
tattatttct tatctcacca atcaatttaa attagtccat atatttataa attatatcga 40320
taaacaacaa agtataaaaa cgtgatttta cctaccaaaa atattccaac aaacttttag 40380
tacaagttca cgagacactc attttagcat cttttatctt attataaaaa gccacacaaa 40440
tattaggtct aacataatat caaaaaataa aaattgaaaa aatttgtttg tgaaaattaa 40500
tggcaaactc catgcgttta tttgctacta tgttacttct agcaatgctt gtcatggcta 40560
ctggttcggc ttcttcttcc ttataattta attttttta acgattcgat atttgaaatc 40620
gaaccggtct gactcttctc gcgtcatgtt atgtctgcaa ggacatttac atgatctgat 40680
tcgagatttc tgattaaaac caagagaaaa tattccgatc atttcatcat gttccgtata 40740
gtaccataat ataatatgat actcctttct ccccaatttt catgatacat ttggaatttc 40800
gataaattaa gttttatttt gactgaattt ttaaatattt taagttgtta gctatgattt 40860
ataatagttt ttatgaattt ctatttacat atataaattt ttttaaaatt tctatgtttg 40920
aatttacgct caaaatttag aagttttgaa tatccattcg tatcattttt gtgtgttttt 40980
tagttaactc gaaatttgag actgcaaaaa gatttttgaa ttttttttgt tctaattata 41040
atagtgtgca tagtgtatcc ttcaagtcta atcctatagc taacatggtc aacatttttt 41100
tttttataat tttaaatttt ggattcgatt ttttctttta acatgcttgt atgatatcat 41160
gaccttgata agcaacttat aacacttcga tgtattttag gaccaatgag aattgttgag 41220
gcaagaactt gtgagtctca gagtcatcgt ttcaaaggac catgtgtgag tgagaagaat 41280
tgtgcctcgg tatgtgagac cgaaggattt tccggtggtg attgtcgtgg attccgtcgc 41340
cgttgctttt gcactaggcc atgctaaatt aagagtattt tatattcacc atatgtatcg 41400
gaaatactca tgaatgaata aaagacacta taattgttca aagatgtata gtgctagttt 41460
tgtttgtaaa aactagtcat ggtctttgaa ttatatgcaa ttatggtgca ctagacttat 41520
aattcatgtg gtgtgtttct tgttttatgc aatattatga ataaaatttt tcattatatc 41580
actaatctta gtgtttgtat tttggggtga tctaattttt gccctaaaaa tgattatctc 41640
aaattaagag taatatttag aatatgaatt aataaagatg aagtatttat tatgattatc 41700
caaacaactt atgcgaggtg aattacattt attgccgcat aacctaatta ttacaaatag 41760
gattttactg tagaaataat gctatactcc attattccac cctgttatca acttatcgtc 41820
ctattaatct gaattatcgc ggtataaaat aggattctaa tagagtgata acttttacat 41880
atagcaaacg taaaaatcat atttgcatgc tatagctata gtttgcataa ttgtgtttca 41940
tagaaaacat atatatgtat atttcgctat acatatacaa agaaaatagt tgtataattc 42000
gctatacata tacaaagaaa gcagttgtat aattcgctat atatatacaa aagaaagaag 42060
ttgtatacaa aagatcagtt gtattgtgta tgtataaaac gagaaagaaa gaaagactga 42120

-continued

```
agaaaaatgg gcagggaaat atttgtatt gtataattat aagtgtatag gacgaatgta  42180
tatgcatttg tgtgtgtata tacaattttc tctcgcttta tacaaataaa aatacaattt  42240
atacatttct tttctgtttg tatacgtgat ataggcgagg gtggcgagct agatctggga  42300
caataacaac tgagatctgg gataggggag agagggaacg aaaatatatg tttatataca  42360
attttctctc tatttataca aacacaaaca cattttatac atttgtgttt gtataaaagt  42420
gagagaggca agcgagactt ccaccaaaca agagtagcaa gcgagatttc accagacgaa  42480
aatagcaaga attggctata gggtacaatt aaatcaaatt aaaaaccgtt aaataagtgg  42540
tcaattttga accaaaaggt ggatgacaag ggtattttgg acccaatagg tgggtgagaa  42600
gggaattttg gagccaatag gtggatggag ggtaatttta taccatttcc aatactttga  42660
ggatattttg ggccctttc cgtacattat atctgcatgc atacaacatc tcatcctaac  42720
tcaaagttgc gcgaatacaa tatttgattg taataattat atatatatgt atgtgtttca  42780
aagcagaaaa tgaatgcatg tatgtatggt caattatatg tgtatgtata tatgaaagta  42840
gcagttgact atgggttctt ttttatattg gatctctgat taaatttgga ttgtgcatta  42900
taggacccat ttgagggtgg cgctcccaaa ttctaacaag attttctcca aactcaaggc  42960
tcgaacccga gacctctagt caagaatgca acagtctcat cattccacca taacctatgt  43020
tggtaacatt gttaccaatc gaatatgaaa aagttgaaaa atagattttg aaaaatattt  43080
tcctccataa caaaaattat cccgttttga tttcatactt aaactattga agtgcaattt  43140
tatacctaaa ttatcacaca ttagcttgag aaacacacat cagtagtgtg taataagagc  43200
gctctctctc ttcttttttt ttttttaaa aaaaatgaac taataaatatg acattttaca  43260
tcaataaaaa atttcacctc gataaaaatt aaatcaacta ttaaatctta gttaaagtca  43320
aaattaaagt atcaccatct caaaaaataa aactcatttt tttaaaattt aaaaatttaa  43380
tttcttttcc tttaattaag gaatatctca atataaataa gattttgact aaagtaatta  43440
ggtttgacaa cagaaaactt ttaaaactcc ttgcatcata tcttcatgta atttactttc  43500
attttatctc catttacttt ataattaaaa atgaattaat tgtgtctatt atgagctaat  43560
tgtttggctg acttttgaag ggaaatatgt catatattta ttttataaga gatttttttt  43620
ttttttttt actttataag aggccagctt gatgcttttc attatcataa attttatgca  43680
taagattaaa aaatattaag atggaacatt tgtttaaagt ttttttctc ctcgtgttat  43740
ttttcgttga aaattcaggt aacaattctt ttaattactt actagacttc tagactatat  43800
atataaactt ttttcaatcg aaaaattaat caactacatt ttaattcaaa gctagttgag  43860
attgattaat atatgaatca tttatatatg ttatgattta ttcatttcat gtattaccct  43920
tataattctt catattaagt taattttgag gtatttttta tttttcaaac tgacttaatt  43980
gtttagtttc aagacccatt tttagagtgt tcttccaatt ttacccttcg ttagttagta  44040
ttagaattaa tgattaatta atatttagtt attttaatta taaatttgac aataattaat  44100
aagggtaaga acggaaaatt gtgttcagtt tatgtcttaa tttacttttc ttaaaagggt  44160
gtaaaacacc tcagaaatta acttaatatg gaatggagag actaaatgat actccgtccg  44220
tccctattta cttgtccata tttcatcttt tagttgtccc tatttatttg tccattttga  44280
caaatcaaga aagcacaatt tattttccta ttataccctc atttatactt tttgaaaatt  44340
cttaagtttt aattcatgct ttttgaaacc ataattaata agggtaaaat tgtaactcta  44400
ctatgcttat tatcgttacc ttaatgtgtg tgtcatttct aaagcggaaa actaaacagg  44460
ggcggaggga gtaccttttt atttttctta taacttatgg acctatggac cactatctaa  44520
```

```
atatatctta tggggaatcg aaaatagtat tggaaaatgt tagatgacaa tctaaaaatt  44580
attataaaca ttaagcgata atctaaattt tttttataaa ttagataaat atatgaacaa  44640
acatcatacg ttacataata ttgtttaaaa tatcgctacg atcatagtaa tatgtagatc  44700
gagatcgcta attatcatct tatttttatt ataacagagg cagggaattg tgttgaatgg  44760
agcaaaacct atcagtggca atgttttgat actaataagt gtagagaggc ttgcataagt  44820
gaaggtttta cagatggatg gtgtgcttat ttgataagat atagacgatg tgcttgtaca  44880
aagccatgtc tttttaataa taattagtat ttttttgcta aaatatgtgt taaattataa  44940
agtttaacaa acaaacaaaa aaatatagtt aattagcctc taatcttatg taatcctttg  45000
atcataaatt atgaaatggc attttaatga ttttcatatt acattctacc tctttgtgtt  45060
tgtttggaac gaagggaaat aagtgaattt ttttatttaa aaaattgtgt tcgatatgta  45120
agtaaaaata tatattattt ttaatatatt taagaaagtg tgtgtgcggg gggggggggg  45180
gggggggggt gattaggagt ggagtgagga tgaggatgaa gtcacaagtg gcgaaatcag  45240
aaatttagtg ctgatcaaga tttaatatat gcatatgaaa aataattttt tgatgaaaat  45300
gttcgactga tcatccgtca ctatacatgt ctacaccagt aaatatcact tgtgaaaatt  45360
gttctcatgt gcttccatca ggaatttttt ttaattcatt ttttaaagaa cttatttttc  45420
ttaaatattt ttgtcaatta atcataaaaa aataaaaaaa aatgttttcc ttcgtaccaa  45480
aaacacccta aatttctacc tctttctccc ttggataatt tgtgttttta atacaactag  45540
acaagcttat tatatctttt taaattaaat ccaatttgta gtgaagtgag taaagttttg  45600
attagtttat ctaacattat atccacaatc tttgcataat caaacttatt tttgcatcaa  45660
ctagctgacc cttaatgttt aagcataatt atctgatgtt gaaaatctat tactccctcc  45720
gtccagaatt atttgttatg atttttattt ttagagttaa attataaaaa ctttgactaa  45780
tgttttaaga tgtatttttt catcatatta atatgcaaaa aattgtaatt tatagtactt  45840
ttcatgtagt tttaaaatat ttattttttg gtttacaata tcgaattaat gtgatttaat  45900
ttacctttaa aattaatcaa attaactttc gataagcgca atatgacaaa caattctaaa  45960
tggaaagagt atatattttg aggcagagct agaacatgca accttataag ttctaaatat  46020
gggctgattg taaagcaact agtaagtaac tttctaactc tatgcatagt agaaagtcta  46080
atattgaccg attgtttgtc gtatctaggg gtgtacaaaa tcgaatcaaa ttgcaaattg  46140
agtcaaataa aaaaaatctg attagtgatt tggtttgatt tggtttggcg ttgaaaaaaa  46200
aacccccgac tatatttggg tttgtttgat atcaactaaa aaaaaaaacc cgagataaaa  46260
ccaaccagac attatatata taattttaaa atttttattt tatgcgtaaa aatacttact  46320
ttgatataat ttttaaatat ctcttatact ttttcatagt ttttatattt taatataatt  46380
atttcatgtt tggaagttag aattcttaac gatttaataa gattatagac tatacatgtt  46440
gataattata ataaagttta agaaaaaatc aaattaatac taatgcaaaa aggaaattca  46500
tgacaataat attgaatatt tgttttttag ttttacatag atttagataa ttaaaataca  46560
tgatgtaatt tttttttaat atttagtcat gtaaaaaaaa tttaatatgc aaaaaaatgt  46620
aatttataat actttttatg tagttttaga ttatctgttt tttggtttaa aatatcgaat  46680
taatgtgatc taatttataa aattaatcaa attaactttc gataagcgta acatgacaaa  46740
ttattctgaa cgaaggaaat atatattttg aggcagagct agaatgtgca accttataag  46800
ttctaacgag gaaaagggta tatgtgagcc atttgtttac aagtaagggt atatatgagc  46860
cacttttata acgaggggta tatcagctcc aaatgacaaa gttgaggggt atatcagact  46920
```

-continued

```
cttttcctta aaatatataa tacaaataaa gtttttggtt aaagcaacta gaaagtaact  46980
ttctaactct atgcatcata gaaagtctaa tattgaccga ttgtcgaaaa tttaattaaa  47040
tcgtaaattg agtcaaattg aaaaaaaatc tgactagtga tttggtgttg gaaaattttt  47100
tttgactatg tttgggttgg attggtttca actataaaaa tcaacccgac attatatata  47160
taattttaaa attttatttt atacgtaaaa atatttactt tgatataatt tttaaatatt  47220
tcttatattt ttttcatagt ttttatgttt gaatataatt atttcatgtt tggaaattag  47280
aattcttaat gatttaataa gattatagtc tatacatgtt ggtaattata ataaagttta  47340
agaagaaaat tcaaattaat actaatacaa aaaggaaatt catgaaaata atattaaata  47400
tttatttttt agttttacat agatttagat aattaaaaca catgatctaa ttttactttc  47460
ttttaatatc tagtcatgta agtgatactt actaaactta ttttagcatg atttagtact  47520
ttaaattatg atcaatttca ttttggctta ttaatttgca atatttgttt tacgcgattt  47580
tattattatt attatttgga tatattagtg tcattaatta tatatcatat ttttgttatt  47640
ttcttgagaa ataacttaga tagttgcatt ttggtaggac taaagatata tttgaagtac  47700
aagtaaatta tatgtatgta tgaatacttt atcgaaaaaa ccgaaaaccc cgaaattgaa  47760
aaatccaatt tttattggtt tataagttca aaaacccgac acaaatggtt tggtttgata  47820
tttgaaaaac tcaaaccaat ccgatcatat acacccctag tcgtactttt ctctttagtg  47880
aatttataaa aataagattt tgatttaagc aaattaggtt ttactgaacc ataggtaact  47940
ttctaactga actgtagata atagataact ttataacttg tgcgtgatta aaaagcctag  48000
tatgagttgg ttgatcgtct gacctttcta ttttctggcc catatctttt taaacaaggc  48060
ccaataccct tcaccaatgt agtggtatta accttatatt tgtgtattta ctttcatctc  48120
atctctattg aatttataat caatatgaaa ttgacagtac atgcaaaatg ttaaaagagt  48180
attcaaaatt gattaattgc gcgatcgaaa gtctacaatg aacttaatcg tttgattgac  48240
ttttaagaga aaattacaag caaacatata ttgtcacgta tcttctttat atattaagag  48300
gcctggatgc ttttcatcat caaaaatttt tagtagaaga ttaaaacaaa ataaaaataa  48360
aaataaacta aagatggaac atttttttaa agtcatattt ctccttgtgt tgatttccat  48420
tggatacgca ggtaataatt ctttaatttc ctactagact atatatatat atatatataa  48480
gtaccactat gaataataat acgtagatcg agatcgctaa ttatcatttt atttttattt  48540
ttataacaga ggcaaaggat tgtgttgagt ggagcaaaac atacaagggg ttttgtagag  48600
ctcaaaagtg cagagatgct tgcataagtg aaggttttac aaatggatat tgtgtttctt  48660
tgagaagata cagaagatgt tcttgctcaa aaccatgtat tttcaataat tatctaccat  48720
aattaatatt tttctaaatt atgtgtttaa ttatgaggtt taacaacaaa aaaatatata  48780
taaaagtcca taatcaatat ttacttgtct taattctatc tctttttgtt tttgttttat  48840
tatacaaaaa taaatgtatg taggtcgctc tctctttaaa tatatatata tatatatata  48900
tatatgagtt cgaagttcaa gttctagagg atttgcaata cattaaagaa agtcgaaact  48960
caaatactaa aaattgattt gtcacaaatg aactttatat caagtggata atatctcaaa  49020
agaattgaag catcgaaagg aattgaatct taatttagaa ggctatttgg atatgatttg  49080
agttagtttt aacttgaaat tttagttgaa gttcgaagtt acaattaaat tgtattgaag  49140
ttggattata attatatgtt gagatggtat gaaaattatt ttaaatttgc ttgtgtgctt  49200
tatagttgtg ttaaatttat atggatatta tatgatggtt ctatcaatgt attgtattaa  49260
atttttggaa atcaacatga actttataca aaattgggaa aatgcactag tactccccta  49320
```

```
cactatgatc aaaatcacag agacacacct taactaacac aaaaattata cagttatata  49380
catatgtata tcaattttat ataaaaaaaa ttgtgaccca aaattctaag ccttgacgag  49440
atatacatat atcatatcga tttcacacaa tcttcataca tgaaaaaaat atgagtgaaa  49500
ttttaaggct cgagtaaaat taattcatat atattttgaa aaaataactc ctactatatt  49560
ttggtaaata aaaatctcct attacatgtg ataacactat aaatctaatt tggtatataa  49620
agaaaaattc ccaattgcca aatttattca tatttcaatt atcaattgat tcaagaaaga  49680
agacatgtca aagaatgaaa ataatacatg cctaatttca tgcttttata tggattttga  49740
cttgtaataa ttattttttt atatgcaatt ttatttcaat tttccttttt tttgttagac  49800
ataacatgtg taatagagtg tggcaaagga gtctcccccc tttcctcatt ttcatgttta  49860
aaacatatca actttcagca ttattcatgt tggctctctt gttagcataa ttttcttgac  49920
cctatatact taattattat tttttaaaaa aaagaaagca aaataaataa ttaagcacaa  49980
ttatcgagac tcgtctcgat atgcatactc aaaattggag tgttcacttg tcaactaaaa  50040
aggccagatt caaatgcttg tttatataaa tatcttttga aaatcttctt tttttttct  50100
taaatttcat actcaatcaa acacaacgta aaatgagaga tgttatatgt tgtgtttaga  50160
atagtaaatc agaaatactg ttaagatgaa aagaaagaaa atatccaagt ccacttaatt  50220
atttactgtg ttcataagaa atttaatccc ttcactgtat tcgaggtcga gattgtagat  50280
tatttcctta taggataaaa tagatatatt tattaaagaa gtagtggtac ctctcacttc  50340
aataacttat gcaaactcaa aagttagcaa tgaaaaatca cacagactct actttgttcg  50400
taagaaaata tatatgtaga agaaaaagaa aaacgataca aaagactgag agggaacctc  50460
tctatttaca tccaacgata ggtgtgaact cacatgtaca gaaatatttg ttcggaagga  50520
acatgccctt ctgtaacaat ttacgttact attttatatt tagtaataat ttaactttaa  50580
acttctcttt ttatctttat tgagatattc cctccgttca cttttccttt tggcaatatt  50640
aaaaagtaaa atttcacttt taacttttcc actttagcat ctaaaaaata attaaattaa  50700
aacgatctct tattttcatg ttttatcctt aacatttaac tataaaagcc cccttactat  50760
actcaatttc tcaaaatata tttccctttc tctctctata attttctctc tctaaaaaga  50820
ttggacaatc tatgcatttg tttgcaactt tcttcattgt accaatgctg cttttgtcta  50880
atggtttgcc ttctttcttc gtaatattta ttttattata tagtttaatt ttattctatg  50940
tgttaataat gtataagaat ttttataagt ataaatgttt aaatataact ctttaacttt  51000
ttgatttagt ctacctttaa agtttgataa ctagcaagaa cttggattac tgaaaaatct  51060
aattgatata taaaaaaatg gcttataacc tctgttgtta cacaaatgac ccacattgat  51120
agtttggtta tgtatataaa tgaaataaca aatcgttaaa atatgaaact cacgaagaaa  51180
ataatagttt caatgtgtca taaaatactt ttactaacat acgatgtata aatttaaata  51240
tttgtggtaa aaggtagtag taccacccga gactatatat gactcaaatt ttagaaacac  51300
accttatcta tactaaggtc ttattaccct tccgaactaa attttttgta attttaattt  51360
gtacaccttt tcggcttatg tggcatttaa atatctccca cacgccacaa ctgcgtggag  51420
tcacgggtgt gccacataat ccaaaaggtg tataatatta tatataaggg caacttaatg  51480
caattggagc tctgaaattt caatttgagg cctaaaatat aaatgtagga acaaacttcg  51540
tatacgtatt tattcaaaat taatttccct tacactattc aaatgaaaat tattagtact  51600
taatgttgtt ttttcagtta ttgattttag gtaagatttt atcaactcaa tattgaaaaa  51660
acatcctttc agtgagataa ttattatatg aattgctaac ataatcctat aagtagcgtt  51720
```

```
gataaatatt aaataaagat aagagttaga accacaaaat gagattcaag aaaatgatga  51780
cttgatttac cccatttcta tatgtttgct gtaatgcttg aaacaaacaa aaaagaatct  51840
gtaattctct ttgttcaaca ctataaattc ttatttttaa tgaaagacta catatgttaa  51900
actgagtaaa ataatatata cttcttaaaa gtaatacttt ttatcgtaac taatcaattt  51960
tttctataaa aatttaacac atatttattt atgataaaaa tttgggcccc ccaaattgcc  52020
ttattttgca aaggcaagag ccggcactga atatatataa aataagttca cgagataata  52080
gattctgttg agatttcgat catagtcaag ggatacttat gtcttctccc aatatttatt  52140
gataatatat ggttctcgat ttttgatgtt tgcgtacatt aattgataga tatgggacct  52200
atgagctgtg gtgtagaggc aagaacttgt gagccacaga gtcacagttt caaggggcca  52260
tgtagtaggg acagcaactg cgccaccgtt tgccagacgg aaggattcat tggcggcgat  52320
tgccgtggcc ttcgccgcca atgtttttgt actacagaat gttagaagaa agtttctaaa  52380
tgatcttttt tacagtctat gtatttgttt acttgttaag atatctaatg ataaataatg  52440
ttgtttaatc aacaaaaaaa agtgactgac taacctcata taaatatata atacatatgg  52500
tgcttttgtt acgattcaaa atcttaggtc atgattttcc ctaagagtca cgatctaggc  52560
ataccaaaat tatttatcga ggaagaaaaa ataagttcag gatagtaaat ttcatcatta  52620
aagcgaacga tacatgtaag aatattttta actaggagaa tatttattct atatttgtcc  52680
ttttcccttt gtttttttaat aataaaaaat aaaatctcct tgtaataaga aatagaacta  52740
attaatttat taattatgac ggttcaccgg ccttttctgc tcactcgtag aggttgggac  52800
ctcataaagg aatagcgagg gagtccactg aacattttag ctattggcgg gaaattcgct  52860
cttgtcaggt gaataacaat cgtttcgtca tagtactact tattcatact ggaattactc  52920
aacggattct tttaatgtat catttctggg tccaacgaaa ttcattgata tagaaagaag  52980
ccctatcata taaagatttt tttcttgtga gctactaggt cacactttgg ccaagcacgt  53040
actaccattg gcagagccac atgtagttga cacccccttca tcgaaaaatt acattgtgta  53100
gctagagtaa gatatcttca cgaatcgcct tggtgttgca ctactgcctt gacttagcac  53160
acccccacca attctagtcc taaaccattc acgttacaag tgatgaggac aaactcccta  53220
taataatgta atttcttagt caattctaac atttttgaaa tttaaaaata atttaagtta  53280
aacttataat ttttttaaaa tatttttggt atgtaggcta tcgactcacg tggtactttg  53340
gcctaacaca cctctaaaaa cttatgagaa aaaacattcc ctaaatgatg taacttttta  53400
gccaattcca agaaacatga taacttttta aattttcaaa aaaaatattt aactttgaac  53460
ttttaatttt acgcttaatg agaagctttt tagatattca atgtaattga atgatcttaa  53520
gtttaaaaaa aattcattta tttcttaaat tttcgtttat attaagatat tgtcacataa  53580
attaaaataa aataactaat gtcttgcatg tgattcatat atttgatatt ttacacatat  53640
gcaattaata attccaaaat gtttaatttt atcttcaagc attgaactca ccaacaaatt  53700
aagatctata atattggatc atgtgaaggc caatgtatta catcaaacta ctatataatg  53760
tacgttgtta attgaaagaa cataggaagg gaaaaaacac aaaaagaaga atggaatgag  53820
aagcagaact cggagaaacg agataaaaaa aaaatcggac acttcataac aattagtata  53880
aaccttttttt tttgttaaac cctagttctt tttaaccggt tttcaattaa gcatgaatct  53940
caaacaaaat ttgctaatat tttactatgt tcaataatct caactaaatc agtatcgtta  54000
agatgaaggg cacaaatacc taattttggg gcttccattt aagtggtagc cacattttttt  54060
attttataaa attacaaata tatccacttt tgaaccactt caaatatact cgatttaagt  54120
```

-continued

```
aaaaataatt ttaacaaagc tcgacttcag acatataatg acttgttaag atcgatttct  54180
gaatacatac ctaactttag aattaggaaa gataacttaa agcttttatg tggattttga  54240
cttataacaa tttttacatc tttataaagg agaaaattcc tctcaaattc ttctttttgt  54300
taggcataac atgtgtaata gagtgtgaca tgagaggaga cccctttttc tcattctcaa  54360
gttgtaacac atatcactct tcgacattat ttatgctcgc ggattcaaaa tttaaaattt  54420
atacagaaaa aaatgataaa cggatgaagt agttaatgtt ttagaaaatt aatatataat  54480
tagttattta tgttcacctt tattcttact ctataactaa atggagaggg aattaaatca  54540
aagagaaaat tagtaattta atcaaattat cctttttagtt aatgttttta ttaagggacg  54600
tgtaaaaaaa aatatgacaa ataagatgaa ccaaaagaat cacaaatctt caagtcctac  54660
tcccttcttt tcaaatatgt acttgtcacg attttatttt gagaatcaaa cgatatgaaa  54720
ttagatcagt taatatgaga aaaattacaa tttttagcat tttctataaa aattttaatt  54780
ttaaaatatt aaattaattt aagctaaaaa ttattcatta tcaatcttga aaaatgaatt  54840
atgacaacta tttaaaaaat atttgaaatt aaatttcgtg tctaatcaaa tagtcaggta  54900
aatgtgcatg tataaatacc cccctttgct tactccttgt cttaaccaat tctcaatata  54960
tttctcaaat tgcatttttc tttctctatt tgaagatggc acactctatc cgtttgtttg  55020
caactttctt ccttgtagca atgctactgc ttttatccac tggtttgtct tctttattta  55080
tattatttaa ttttattata tagttttata atattagctc tacgtcaaaa tttagctcaa  55140
tgagagaaaa ttgtccaatt tatgttaaga agtcttagtc ctctcattca ccttcaatgt  55200
gagagtatcc ttttttcata accctccaca cacaaatcga aacataattc tatactgaag  55260
tgtgaacagt ttattcgaaa actcaatatc atatttttta aaattttaat atcatgatgt  55320
atgaatttta gacttgagac aacccaaaat tagttcaaag tacaataaca aaagagacat  55380
tatccaaaca caatatgata ttgtagcatg aacacccgat atcatatgat ttgattctaa  55440
tatcatgata tatgaatttt ggacttaaca aaacccaaaa atagctcaaa acactataac  55500
aaaagagaca ttacccaaac acgatctgac actgaggcat gaacattcga taatccgtta  55560
tcatatgttt tgattctaat atcatgatat atatgaattt tggacttgac acaatcaaaa  55620
atcagctcaa ggcactataa caaaagagac gttatctaaa cacaatttgc tactgaagca  55680
tgaacacccc aaatttggga ctcaacacaa cccaaaatta gctcaaggca ctatgttttg  55740
attctaatat catgatatat gaatttcgga ctcaacacaa ttcaaaatta gctcaaggca  55800
ctataacaaa agagacatta ctcaaacacg agccgatact gaagcatgaa caattctaca  55860
attctagaca ttacccaaac acgatccgat actgaagcat gaacaattct agacattacc  55920
caaacacgat ccaatactga agcacgaaca attcttgttg ctatacaatt atattaaata  55980
tatcctagtt atcttatcca cgaccgatgt gggagtcttg tttcatcatt cataacatgt  56040
ttggctaaaa ttgaacagag atgggaccaa ttagcagtgc agaggcaaga acttgtgagt  56100
cacagagcaa cagtttcaag gggacatgtg ttagggacag caactgcgcc accgtttgcc  56160
agactgaagg cttcatcggc ggcaactgtc gtggcttccg tcgccgttgc ttttgcacca  56220
gaaactgtta gaacatatag agtttctaca tgaaatactc atcatgcatt catgataaat  56280
aatgatgttc tattctatca ataaaaaaga gagactagat atatatagtc tcatatttat  56340
ttatatataa tatgtggtta cgatcaaaaa tcataggtca tgattggcta atctagtatc  56400
tgtttttatt agtttaatat gtgaatcatc gacgaagcac atgatgtgtt gccttagcgt  56460
tgcacttact gccttgactt ggctaatcta gtacatgatc gatcctaaca tcttttgaat  56520
```

```
ttatgatatt acaagttcgg gaggggtaaa aaaggaattt aattacatgt actttttttag  56580
ttaggagtat ttgcttactt tttcttctct taaatcgttt tattcgccgc tctttgatca  56640
attatctagc acttctagtc ccacactgac tagaaagaga gattttatgt aaaatattgc  56700
catataaaat agcgcggtat agaatatgaa aaatcatacc tttctcggcc ttttggctaa  56760
gatcaagtgt agtatctgtt cttatcagtt taatatctga tatgtgagtc attgactcac  56820
acgatattaa ctctattttt tttgggtgaa ggttcatcat ggtagcttgc tattgggacc  56880
ttcaagtgtc gtctaggcgt tgcactactg ccttggcctg gcacacccca ccaattctag  56940
ttgtaagcct ttctttcaat tgttagttga ggacttctta ggatttttgt gtagttataa  57000
aaacctctac atttttggag caaaatcgat acaatatggt ggagaaggca atggacttgg  57060
ccaaacttgc tttgtctgga tgattttaat tagacgtgta tgtgagatta aagtgattga  57120
gaatatccat gatcaattga ggaggttacg ggttgagtca tgttggaggg tgagtgagat  57180
cgtcactatt gatcctcctc ggatggggtg ggggaaataa caaaacgaaa tttttctcaa  57240
aggattttag atgaatctcg taagaacgac aaaaaatata atgcaccagc cgggaatcga  57300
acccgggtct gtaccgtggc agggtactat tctaccacta gaccactggt gcttgatgac  57360
tttgtttatt tattaaataa ctacatattt gatatcaata aaattgcaaa tgtaagatca  57420
agtgtagtat atgtggtgca tttgtcacaa tttcaaaatt attagtcatg attaatgacc  57480
aaaaatccac tatctagatt agagagggat cgactacgat gctaaagcca ggtccgtaag  57540
atcatcaatc cacttgatcg tcatatccat ggagtaaatc tcgataaggt actaaagcta  57600
cggtttgtac aaagcaaata caaacaatat acatgacatg tgtgaaaata aattttgtga  57660
tttagaaatg atatattaaa acgtgatata ttatatgtta gacaacaagg tatctatgta  57720
gccatttgtt agactattgg aattaagtta tgattagtgg tcaagaagtt gttagtctgt  57780
tacataggta aaaaaaagaa aaaaacaagt tagttaatag ttagttactt agtgttagaa  57840
tgtagactca ataatgcccc tggaaactat aaaatttcac taaagaaaag gacaaatatg  57900
aagaaaaaaa aactataaat ttaattattt tgaaaaagta agactcaaaa aatcatttca  57960
tatggaaaat tgatcgaaat gaaataaagt gttgagattt tatatgtaaa atccaactaa  58020
ttcagaaatg ggtattatta cagttgttaa atttctatat atgtattatt actatactgc  58080
atactcttag aaaggaaaaa gaaagataac gtttctcatg tcagaaggaa ccctcaaaag  58140
tatttaaaat tttcaactaa attcatacgc acacatatgc accatcacac gcaatcacaa  58200
ggacacgcgc acgcgcacaa tatataagat aaagacatca ttatacatat aatacccctt  58260
ctatttaaat atatagtgta ttatttatat tttgcatgat cttgcgaagc gaggatgagt  58320
tcacttgtat aacatcaaag aataaatatt attatcattc ttagtgttga agtaactttg  58380
tttagcacta gtattgattt gattttaatt cgagttttgt tagagttact aatatctatg  58440
gactataacc ttaattagac cattcaaaat tcaagtctta gaaacaagaa ataatatgat  58500
aaaagataaa aactatgaaa aagtataaga aatattttta aaaattattc aaagtaaata  58560
tttttatgca taaaaaataa tagttttaaa aaatatatat ataatgtcgg gtccgtttga  58620
tctcgaattg acattttttt aggtaaaaca aaactaatca accacatttg tggaaatgga  58680
ccgaaaacca caattgacat tgaaaactgc cgatatccct tctttttaag tttaaatatg  58740
aactcatggt ccattttact taataaaaat gggctcataa atgggtccac acatattcca  58800
ccttgatctt gttgctgtgg agatcaatta gaaaggttca ttttttttagc catctggcat  58860
cttcattgtc tcgtttctga actgactctt ctttttgttt gaaagtgtac tacaaattat  58920
```

```
taagtattgg aaaaaatgat ggagatggaa taaaattgat attgagattt tatctgcaaa  58980
atccaactaa ttcaaaattg aggtattatt atacttgtta aattcctgta tatgtattat  59040
tactatactg catattctta gaacgaaaaa aaaacataat atttttcatg ttagaagaaa  59100
ccctcaaaaa gtatttaaaa ttttcaatta aaattcatac gcacgcacac gcaaacgcgc  59160
acgtgcgcgc gcacacaaaa tataagataa aggcattatt attatatata ataccccttc  59220
tatttaaata atatatagtg cattatttat attttgcagg atctccgaag tgaggatgaa  59280
ttcacttgtg caaaattaaa gaacagatag tattatcatt cttagtgttt aaataacatt  59340
ttctaacact agtattgatt tgattttaat ttgagttttg ttagagttac tattatctat  59400
gaactataac ctttattgga ttattcaaaa tcaagtctta gaaactggaa ataatatgat  59460
aaaagataaa aactatgaaa aagtataaga aatattttta aaaataatac aaagtaaata  59520
tttttatgta taaaaaatta taatttcaaa aaatatatgt ataatgtcga attggtttga  59580
tctcaaattg acattttttt tgggtaaaac caaaccaatc aagtatagtt gtgaaaatgg  59640
accgaaccac aattgacatt gaaaactacc tatattcctt ttttaaagtt taaatatgga  59700
ctcattattt aataaaaatg ggctcctaaa cagatccaca tataaatata ccaaaaaaga  59760
gttggtcggc ccaaaagtgg tcagaccacg tgaatataaa agaaccctaa atgatagggt  59820
tttctcattt gtgctctcct tgttatcatc gcctccgcgg agatgttcta tcttgtgctc  59880
cacaattgta gcttcttccc cctttagtta tgggggatta acattcccca ccttgatgtt  59940
gttgagtttg atatcaaatt tcaaaggttc attttttagc catctgactt cttcattgtt  60000
tcgtttctca actcactctg attcttgttt gaaggtgtac tacaaattat taagttttgg  60060
agaaaatggc agagatggaa taaaattgat gttgggattt tatatagaat attcaactaa  60120
ttcgagattg aggtattatt gcagtttttg aatttctatt tgtttgtatt attactatac  60180
tgcattttct tagaaaggaa aacaaaagta taatgtacta gctgggctaa tcttatctgc  60240
atcaatttca ggatccaaaa tagagtagaa aatcctacaa ttatcagcag cattacgtgt  60300
gaaaaagtat tcagactctc ttgttctagt ctaatctcaa ttctggaacc ttctatttca  60360
ggagacagtt gcaactcttg gatagctaca aacgtttaac tacggatggt aataatacta  60420
atacttcgtt tcattatatt ttcttctcct atttataatt atgatgatat atgttgaatt  60480
cgatgtgtta tgtttccact ctttcaacaa aattatttct acgcctatag gaagaaggta  60540
gtcgaattag ccttatataa atgataaaga aaagacattt cataagattt gtttaactga  60600
aaattataag agattcataa aaaataggtg acacactttc ttatacgatc attgtagtaa  60660
ttgttcatgg actaaaaaga ttttgtcaag acattacatt ggctgaagaa cttaatgttg  60720
tcattaccaa tatacttcca tccccctgcc ccccgccctc caaaaattat aataataata  60780
ataataataa taacaataat atatacatat atatatcaat taaatcttga ctaatgaaac  60840
ttaagattca aggagcaaag tatcatctgt tgtttggcga atctcacgaa attataaatt  60900
ggaaaaccta catgaggacc tatttggtgg aaagtaatac agagttgtga gattcaacct  60960
cttccgtttc tatcgctaat cctagtgaaa attatttaac tactacattg actcagacaa  61020
atgttaatca gtcaccttat tgctcttgat ctcctttacc acttaaagaa ttagaaggct  61080
tgaattaaca aaaatacaaa agagcaggtg aagattagga gaaaagtatc gattgattag  61140
gtggttgagt gtctcggatg taaacagatt tttggcagag attttgaagg ttgggcaaaa  61200
tggacaacat tgatcaaaag gaagaagtgg ttgtccaatt tgcccaagca tcaaaacctt  61260
tgccaaattc tctaaattcc tagcattcaa ctaccgaatc aaacaatact cttctcctaa  61320
```

-continued

```
tcttcagctg ctcttctgca ttattagtgc gagccttctg atctccaact ggtcaaagag  61380
atcaagaaca ataatactat gagtctcact caacatagat tttctccttg ccaagtctgg  61440
cttctaatta tatctcttat atatctaatc tttcactaag gtgattcatt gaaattttgt  61500
gaaagtcgat ttagtagttg gattcttttc acaatcatca acaagagaaa caaaagaggc  61560
tgagtccaac atctcttcat caccttttac caaatgggtc ctcatgtagg ttttttaatt  61620
cacgatttcg tgagattcac cgaacaaatg acacttgctc ccttaatcat aagtttcatc  61680
aatcaaaatt taattaatag ttgtttaagg aaaaaatgga agtatactga tatcatcaca  61740
atctgaaatg gcagagaaaa aaaagaatga aactaaatat caatattatt accatcatta  61800
gttaaacttc tacaatctaa agagttgtaa cctagtgttt tcaaagacct tttttgggca  61860
aatctcaggg tggccatacc aaaaaccttc gggcacaaat tgataagtcc tagaattggg  61920
cataagcact aagcataaaa caataagttc tggtgtaaaa acgtgtgccc taagtgtttc  61980
ttaagtattt tttttaatct tttttttttg ctttaaatca attctttttg taattattgg  62040
cgtagtgata tttctcaaat agtaattatt atactttttt ttctttatct caaataaaaa  62100
tcataataat ttccctatat attataataa aaaaaattac tagtaaagtc attgaaagtt  62160
taattttact tttgattatt ttcttagtaa taaaattata aaattaaata tacatgagat  62220
tatgccccat agatccatta gattactccc catgtctcaa gacttacgcc tcatcccgta  62280
ctacataaaa cgtctcgtct catgccccta cctttcaaaa ctctagttat tgtctcgtga  62340
gatagaaggt tccaaactta agtccagact agaacaaagg agactaaata ctctttcaca  62400
tgtaatttta ctgatatcct attagatctt gaaattgatg cagataagat cggtacaata  62460
caaaaacagc aattcaacaa ttgcaataat gtctcaatcc tgaattagtt gggtttcaca  62520
tgtaaattct caacatcaat tttattccat cttcaccaaa aaaaatctag agtaaataat  62580
ttgtacaatt aaacaaacta gagatactgg tgtttttcaa tatcgattat gatttttcggt  62640
ccattccata atcatgaaac tctactaacc acgtagatat tggataacct aatgaaatac  62700
ttttcgtatt agaagatatt gaacttaatc atcgatgact tttatcaatc aataaacaaa  62760
atccttcaac gaatcaaaaa ataaatcaaa aactttgttt caataccttta attttgatat  62820
atgaacttct tagagtccat ctaattggcc aggcacacac ttttatccca cactgcttag  62880
aaagagagat ttaatttaac aagtgatata tgaaatagcc cggcataaca aatggaaacc  62940
catacctttc tcggcctttt ggctaagatc aagtgtagta tctgttctta tcagtttaat  63000
atctgatatg tgagtcaatg actcgcacga tattaactct atttttttag gggaaaggtt  63060
catcacgata gcttgctatt ggtaccttca agtgtcgcct aggcgttgca ctactgcctt  63120
ggcctggcac atcccaccaa ttctaattct aaaatctttt gtttcaaaat agtacacagt  63180
ttgtcccttc taatatttgg atatttgata cataacagct ctctctatgc cccattccaa  63240
gtaacacttt ttaactaaac ctatataaac tataaagttt tagcagagtc aattttagta  63300
tgatccgata tataatcaga ccgaattcga tttctcatct ggtaacctcc aacaacatta  63360
aaaaataata atggaaaaag ataggctcag atgcactatt ttatagtcta ttaatatcag  63420
acaaggtgag gacccaaagt tctcactaac tgtgcaattt tatcttcact gcactcacat  63480
agaatgtatc agaggggagt tgaacctggg tctgtactgt gacagggtat tactctacca  63540
ctagaccatt cgcgcttgac atttaaagaa tacactcgca aagtatcacc cctaatgtaa  63600
gatcaagtgt agtatctgtt cgtattaata tatacattaa actctatttt tgaggaggat  63660
atccatagga tagcttgcta ttgggatttg ggaccttcaa gtgtcctttg gcgttgcact  63720
```

```
ttgtttatcg atttttgga actataaaag gtcattctca acattatcaa aagatttaat 63780
gtgtgttact aatcgacaaa tctttaatga ttcatgaaaa ataatttgtg tttcttatta 63840
gttttcaata tttattcaca acaaaggaat atgaggggaa ggttcattac ggtagctttg 63900
ctaacgtagc ctaggtgttg cactactact tggcttggtg cactgttttt caaggttctg 63960
gacaaagata attagtactt gggatttttg ttcaagttat tatcaacctt ttaacattta 64020
tgaagcaaga tcgatacgtt acgtggaaaa tgttatgtag tcaacaaatt gtaatttaca 64080
tttgttgttt tctatcttat tttggattaa atgaaaacct taataagata acctttgttt 64140
cttcatagca gaatgttaga ttataagaaa aagtagttaa atttgatgac atctttgatc 64200
aactgttaat ttcagcaaaa ttgttgaaac tagtttgcag ccaacaaaac tttaacagaa 64260
aaaaaatttc atttactttg atttaaaatc atattataga tgattactgt gattatatac 64320
aaaaatatag aggatattca agtcccacac tgactgcaaa gagagatttt atgtaacaac 64380
taacatataa aatagtgtgg cataagacat agaaaatcat acctttctcg gccttttggc 64440
taagatcaag tgtagtatct gttcttatca gtttaatatc tgatacgtga gtcattgatt 64500
cacacgatat taactctatt ttttgagggg aaaggttcac cacggtagct tgctattggg 64560
accttcaaga gttgccttgg tgttgcgcta ctgccttggc ctggctcacc ccaccaattc 64620
tacttctaaa gaccttttgg ttcacaatag cacacaattt gtcccttcta atattgggca 64680
gtttgatcca taaaagctca tatccaatgc attaaaataa aatcagatac tgaactacat 64740
tttagcataa ctcataaaat cttgagacca atgttaaatg gtgaccaaaa gtataataat 64800
cgtttgatcc ataaaagctc atatccaatg cattaaaata aaatcagata ctgaactaca 64860
ttttagcata actcataaaa tcttgagacc aatgttaaat ggtgaccaaa agtataataa 64920
ttcgattctc ttgtaatctc taacgacatt atggccagag tcaatatata ataatttgat 64980
ttccatgttg taatctctaa cgacattgaa aataatagtg gaataatgag tagctcagat 65040
gtgctatttt tgtcatctta acattcagac atggtgaaag acccaaagtt ttcacacttg 65100
cacggttatc ttcatggcac tcaaactatt gcatcagtcg gaaatcgaac ccaggtctgg 65160
accatggcag gatactgttc tatcactaga tcactagtgc ttacacatta aaatacttcc 65220
ttcgtttcta tttagaaacc aactaattat agcaggatgt catataaaaa ggaacggagg 65280
aagtatactt catcttttgt actagcagta aagtacaatc cctaaaatat tttatatcca 65340
ataaattgaa aatgcatgat catgtgtagt atctgctctt attagtataa tatcttatat 65400
taaacttttc aaaaaaaatt tatagtaatt aggggtgtgc atttcaattc gattttatgt 65460
attatcagtt tgatttatta gtttttgact tttaaatacg ctaaatcatt aaaaaaaatcg 65520
ataagatatt ctttatcagt tttcagttta cccaataaga aaatattcgt aaaatagatt 65580
tatgatttct cacttttcta acaatttggc acgagactgt gagacaagca aaacagatgt 65640
aaatgctttg atatagtgaa ataggaaata taatgaaaaa ttacatcaat aatagtagat 65700
gtagtatgaa ggctacaaca acatgttaca tagtatgaaa tttcggatgt gaactagaag 65760
tactatgacg tgtgaagtgt gtagactgta gtatagagta ctgacatagt gtctaattat 65820
gctaatttat taatatttaa tattcatgaa ggatatagta atatattact gtcgtcttaa 65880
cgagttatcg ttttacccat actaaaaatc gaaaccaaat cgataaccga ataagttttt 65940
cttataacac cattaaaaat ttgttaaccc aataaaatat aattttgtgt ttcttattag 66000
ttttcaatgt tattcataac taaggaatat gatgggaatg tcaattacgg tagcttgcta 66060
ccaaagacct ttcccactaa ttctaatttt aaaccttttt ttttttaatt ttttgttgaa 66120
```

```
ggaatttctt cgaggtctac gacaaagata ttaattctta cgatttttct gaagttatta  66180
ttaacctttt aacatttttg gagcaacgat ggatatgata ctgtgaaaaa tgttacgtag  66240
gcaacaaatt atacatcttt atagtcccac attgactaga aagagagatt ttatgcaaca  66300
agtgacatat aaaataatcc agaataacac atgaaaaatc ataccttttct cggccttttg  66360
gctaagatca agtgtagtat ctgttcttat cagtttaata tctgatatgt gagtcattga  66420
ctcacacgat attaactcta tttttttagg ggaaggttca tcatggtagc ttgctatcgg  66480
gatcttcaag tgtcgcctag gtgttgcact attgccttgg cctggcacac cccaccaatt  66540
ctagttccaa aaacctttttg tgttcataaa tgataattct atattatata taataatttg  66600
atttccatgt tgtaatttgt aacgacatta aaaataacga caaatatata ataatttgat  66660
tcccgtaatt tctaacgaca ataaaaaaat aatggaaaaa ggagtggctc agatgtgtta  66720
ttttgtcatc ttaacattca gacatggtgg tgaaagactc aagttttcac atttgcacaa  66780
ttatcttcat ggcactcaaa ctattgcacc agccgggaat cgaactcagg tctgtaccgt  66840
ggcaggatac ttccttcgtt tctattatat gtcatcctct agatttacgt gaacaagttt  66900
tactattcta ctcttattca ccccatatta gttttctttg ttggtcaaag gactattttt  66960
aagattagta actcataaag gtaaagagaa agaatgtagt tataatttat acattaattt  67020
taagaaatga caagtattac gaaccaacta attaattata aaaaggaata aagggagtat  67080
gcctcatctt ccgtacttag cagcaaggta ccacccctaa aatattttat atcaataaat  67140
tgaaaatgta tgatcaagtg tagtatctgc tcttataata tatcttatat ttcgatctga  67200
tttattgatc ggtccgattt ttgtacattc ctaatttcat attatatact tccaacaagg  67260
taccactcta aaatatctca ataaataaaa atgtaaaatc aagtatagta tttgctctta  67320
taagtataat atcttatatt aaattttagt taaattttcc aaaaaaaata tttatagtaa  67380
ctcgacacga tataatcact aataaaaaat tgttattttc tcccattgaa aaatattctg  67440
ctgcaaatat tttgattaga ctggtaataa gagaaaatat atatattaat acaaaaaaaa  67500
ttcattattt tagtgtgatt ttattttccc cctgtatttt ttcataaagt tgataaaatg  67560
aaaaatgaat agcaaaatca tactctatta cattattttt cactaaagaa aaactatttc  67620
taatagttac acgaacccac acggatcaaa gttaaccata aaaaacccaa accaatcgaa  67680
cagggtttcc caaaccctaa ccgaaacgaa acaaatcgtg ttatattttc aacccgcccc  67740
gacccgcccc aacaactaag tatctataaa aaggcccctt ctagttctag cctactcata  67800
aacttctcaa attaaatttt atttctccct tctctctcta aacttctctc tctctctaaa  67860
tatggggaac tcccttcgtt tgtttgcaac tttcttcctt gtagctatgc tgcttttggc  67920
cactggtttg tctttctttt attaatcaat ttattcgtat ttatttttat gttatcgaac  67980
tttgagaaaa aaagttatct atatcatttt ttttagaaaa aacttattca tgcatgtcgt  68040
taatttgtta acttaaatga tataaatgag taaaattttg aacaatagat gatatatatg  68100
agtttcttta aaaaaaaaaa actgcaatta catatttgaa tctttttctt ttttcaaaaa  68160
atatttaact cataacatga ttgaattata attgatcacg tatataaaat aactttgaaa  68220
agttaaaatt attttcaatt aataaatgat gacatgaatg agtcatttct caaatgaaac  68280
atgagtcaaa ttcttaacga ggatatagac agcttttttt ttaagtttga tgacatattt  68340
tagcacgcgt gatggaatta taattaacga tatgtaaaaa atgattttac aaaattaaaa  68400
ttatttttca ttaataaata attacgtata tgaactcttt ctcaaacaaa aataacagaa  68460
atgatctaaa tatttaagaa atgatatgaa tagacttttt ttctcaaaat tctatttaca  68520
```

```
atttttgtttt ccaaatcaaa cacccaaaat gaaactacaa tcaataaaca aacaaatctt  68580
tgtaaccaaa aaataaaaat gatctgataa tataaaaaat aatatttcga atttttcatt  68640
ttacaggacc aacaacaagt gtagaagcaa gaacttgtga gtcgcagagc caccatttca  68700
aagggaattg tcttagcgat accaattgtg gttccgtttg ccgcaccgaa gggttcaccg  68760
gtggcaactg tcgcggtttt cgtcgacgtt gcttttgcac ccggaattgt taatagaaga  68820
aaataatctt ttcataacga                                                68840
```

<210> SEQ ID NO 3
<211> LENGTH: 33008
<212> TYPE: DNA
<213> ORGANISM: Solanum pimpinellifolium

<400> SEQUENCE: 3

```
tctaacaata ttatgttgtc atttgataat cgatgggttg tgcagtttgg gtcaattagt    60
gtggcttgta catatctttt ttatttttac taaattaaaa actttatgaa attaaaaact   120
ttattaaatt tataattaat attgttattg aaaaaatgaa aaagtaagac acataataaa   180
ttgcaaagta gggagttatt actataacaa aaatattatt agcaataatt aatttttaat   240
tatcattaaa tatttatttt tagcgataat tatcactctt tgtatatatc tctaaagctt   300
ttagcgacat taattctaat gacacttaac taatgttgat aaaaacttta aaacttttat   360
gtcaatattt aatgtcgcta aaaattaatt ttattacggt gtatgtactt ttatgcttta   420
tgaaaacaat aatatatata cggttgcatt cttttgaata atttacacta tgattgttca   480
aagatatgta atattactaa ttttgtttgt aaaactaaac ttataatctt tatgtgtgta   540
tttcttgttt ttctaaaata ttatggataa aatctgtttt tggacctcta atttttacta   600
tctttatttc taacaattat tattattatt atgagaagtt tatttttttta aactccttta   660
ggagtttcta tcatttttttg ctcatttaat gactcgaatc tacaatttta aattagaaat   720
aaaaatattt attatctgat caatcccctc ttaacaaaca tatccttaac actagagaaa   780
tatgtagttt atttatttat ttaacaatat tcaaattctc aaaatcatct aataattaaa   840
taggaataac ttaataaata ataacttata tcttgttttt cttaatgaca ttagaaaaag   900
aagctaaaaa taaaacaata caaaagtgat aatattcttt ttaaaaataa atttaaaaag   960
tctaaattaa aacacatgtg atatatactt agtttaatcc aaactatgaa taaaaaagaa  1020
ttttttttttt atcttccaca agataagact ttagagctct ataaaaccac atgtatacta  1080
gtctaaatat ctctcacatt acattaaaaa aaaaatttat tatttcttct ctctcaaaaa  1140
aaaattgtga aaatggcaca atccattcgt ttctttgcta ctttgtttct tctagccatg  1200
cttgttatgg ctactggtta gacttctatc tttttttattt aggttacgtt caaaatttat  1260
tagcttttcg atattatgtc gataatgtta tagaataaat cactttctat caaaaatatc  1320
gacaattcaa gtcatctcct cacatttttt agttatttct agtaaaaaat ttaaatatcg  1380
taccataata ttgttatttt tttcctctaa agtttgggtg aggtgggggt gggggtgggg  1440
gtggggggac tattttgttt atatatattt tgactagggt taaaatttaa gaatataaga  1500
aagatttttt atttaaagta aaaatgtgta aatacattaa tcttacgcca ttatttagaa  1560
gttggttttt ataatattca aattaaaaat ttagtaacat tcatttcgaa acagattaaa  1620
aaaataataa tgcgtataaa ttgcaaagta gagagtatca cgctttgatt tgttgtttaa  1680
agtaactcgt acgtaactaa tatgatttta ttttcacaga gatgggacca acgagaatcg  1740
tagaggcaag acattgtgag tcgttgagcc atcgtttcaa gggaccatgt gtgagcgata  1800
```

```
agaattgtgc ctcggtttgc gagaccgaaa gattttccgg tggtaattgc cgtggattcc   1860
gtcgccgttg cttttgcacc aagccatgct aaataaataa ttttgatttt tatgtgtaaa   1920
agaagaagtt tgagaagaaa aaaaatatta tgtaattttg aataaagatg tattgtaatg   1980
ctagttttgt ttgtaaaaac tagttgtgat ctttgaattt gtatgcaatt atggtgcact   2040
agacttgtaa ttcttcatgt ggtgtatttt tatttttatt tttgaaatat tatggataaa   2100
atttgtcttt tagccttttt gttagtaagt tttaataaaa tattcttcga tgcggaatca   2160
agaatcgatc atttcttttt attaagtatt ttgaaatgtg aaagcaataa attgataatt   2220
ttatgaggaa gtttctgtgc ggaatcaaga atcgatcatt tttttttatt aagtattttt   2280
aactgtgaaa gcgataaatt gataatttta tgaggaagtt tctgtattct ttctgattca   2340
tgtctgagta attttttttt gctataagta aagtattttc ataagcatgg agtaaaaaaa   2400
aaatactttc tatcattttt gttgtagttg atcattcaca acgatatttt attagacata   2460
tttaatcttt aattaaagta ttaattaatt tttcttcttc tttaatataa gtttacaatt   2520
tttcgtaaat aggaatattg gttaaagtct aagctagggg ttatttgaat ggcaatggaa   2580
tggacaaatt attctacttc ataattttta gtagataaaa ttatttttgg cacaaatctt   2640
acgccatgcg ttcaatacga aatctgaaaa gctgcgggga tgacaaaaag agggcgcttt   2700
cctatgttgc accgaaaaaa gacttaagag acaagcgtct tctcttaagt ttttttctcc   2760
cgcgcccgtc accacttgac ccgcgttaga gggaaagatt agcaaaacga gaaaagaaag   2820
agggaagaaa agtagcatct tattatatta ttattattaa aaatacaaat agtaaaattt   2880
aaattcaaaa aaatttaata tttctcaatt aaatatgata ttttatttca aaattattac   2940
ttatcacttt attatttcac gaccctttag aaataaagga gatccatcaa gatatgttgg   3000
atagtaattc aattattggt caagtggttc ataaaatcac gacatataat aataattgtt   3060
catctttttg ttttttttta acgataaact caagattctt tttgataaat tattaatgat   3120
atatttaaag tcattaaatt aatttttttt atatatcaca taatttaaaa ttctttcaaa   3180
tatcataaac agacactaat tttgaattta tatttttaaa aaaaatatta tattgtatat   3240
ccttttgtag ttgactctcc ataagtttta gaatatttca aattcgattt gatcatttaa   3300
cggtgtatct tataaagtgt gcatgtaaat gacatatata gaaggaataa tttcaaaact   3360
caagctaaaa gttaaagtag agttcaaaaa gaagaggaag ccaaagtaaa attaaaagta   3420
aattagggga tgaagttaga caaagtaaaa taaacctttt ttttagaaaa atcttattca   3480
gtattcgata tttatattga agtctgatta atttaaattt gtgtcgaata aagtccattc   3540
caagagatat cactctctat cgagaacttt ttatatctaa aactcgaact caaaacctct   3600
atacaaaatt aacttttgta tctggctaat cgtcgccttt ttagtgtcat tttaattact   3660
ttttatgtgt ttttagtttc attgatttta aaaattaagg gagattttat aattttaaag   3720
taaagatata ttcaacatgt taaaatattc tttaaatttt tatagtttaa atatatcata   3780
tgagatattt aaattaaaga gtcatttata tacaaaataa tattcttttt taatatagaa   3840
aaagtaaaaa aataaattga ggtatattta ttcgcatagg ttatttaatt actttactaa   3900
acttataata tgatgtatat catagactta ttgggtaatc gaaatgagat aaataaaaat   3960
atcttacgag aacaaccatt atataaattc atttgatcat taattttaaa tattttttgt   4020
ttaattgaaa acttacggag tcaaagttaa aaattgagtt gtgattagtt atatttctta   4080
taaaatatat ttaaaaataa tgtccatact taaacgtact taaatataat ttcaaattaa   4140
ataatgagtc ataagttttt ttctaaagga aaaaagggtc taatataccc ctcaacttta   4200
```

-continued

```
tcatttggag ctgatatatt cctcgttata aaagtggctc atatatgccc ttacccttat   4260
acaaatggct cacatatacc cctgccgtta caaaatgact cacatatacc cttcatttaa   4320
cggaagttaa aaaattagtt ttaaatttat atttattaca tctaattttt tttacgaaat   4380
tatttagtgg tatatatgat tcttctatca aagttcaagg tatattttaa tttttccat    4440
gcatcaatta ttttttgact tcttttatta taattatttg agtttcttat tcttattttg   4500
ttttttcttt cattccttag tttaaagaaa aaaaattaaa ctattttttg tgtatgtgta   4560
ttgtaattta atttcgtatt caaagaaaaa atttggtcat ctacaataag ttttgcaaga   4620
atattagtga aatataaata aatttgatta tcaaaataat aattataaat tagtcattga   4680
aacaaaaaaa agtcaaaaaa aaatatgttt gacgatgatt aaatttactc atatgagatt   4740
atattttttt agaaaataaa aataaaaatg tagattaaaa ttattttttt ccatttccgt   4800
tagatgaaaa gggtatatat gagccattta tttacaagta gaggtatata tgaaccactt   4860
tcataataag ggtatatcag ctctaaatga caaagttggg ggttatatca gaccattttt   4920
ccttttctaa atctgatata caagaaaaaa aaaaagaata acaactttta tagccaaacc   4980
cccatcgtaa taaatctttt tagttaataa ttataactaa ataccaaata aatttcgaga   5040
ttattatttc ttatctcacc aatcaattta aatttgtcca tatatttata aattatatcg   5100
ataaacaaca aagtataaaa acgtgatttt acctaccaaa aatattccaa caaactttta   5160
gtacaagttc acgagacact cattttagca tcttttatct tattataaaa agccacacaa   5220
atattaggtc taacataata tcaaaaaata aaaattgaaa aaatttgttt gtgaaaatta   5280
atggcaaact ccatgcgttt atttgctact atgttacttc tagcaatgct tgtcatggct   5340
actggttcgg cttcttcttc cttataattt aatttttttt aacgattcga tatttgaaat   5400
cgaaccggtc tgactcttct cgcgtcatgt tatgtctgca aggacattta catgatctga   5460
ttcgagatct ctgattaaaa ccaagagaaa atattccgat catttcatca tgttccgtat   5520
agtaccataa tataatatga tactcctttc tccccaattt tcatgataca tttggaattt   5580
cgataaatta agttttattt tgactgaatt tttaaatatt ttaagttgtt agctatgatt   5640
tatagtagtt tttatgaatt tctatttaca tagataaaat tttttaaaat ttctatgttt   5700
gaatttacgc tcaaaattta gaagttttga atatccattc gtatcatttt tgtgtgtttt   5760
ttagttaact cgaaatttga gactgcaaaa agatttttga attttttttg ttctaattat   5820
aatagtgtgc atagtgtatc cttcaagtca acattttttt tttatttttt tttatttata   5880
attttaaatt ttggattcga ttttttcttt taacatgctt gtatgatatc atgaccttga   5940
taagcaactt ataacacttc gatgtatttt aggaccaatg aaaattgttg aggcaagaac   6000
ttgtgagtct cagagtcatc gtttcaaagg accatgtgtg agtgagaaga attgtgcctc   6060
ggtatgtgag accgaaggat tttccggtgg tgattgtcgt ggattccgtc gccgttgctt   6120
ttgcactagg ccatgctaaa ttaagagtat tttatattca cgatatgtat cggaaatact   6180
catgaatgaa taaaagacac tataattgtt caaagatgta tagtgctagt tttgtttgta   6240
aaaactagtc atggtctttg aattatatgc aattatggtg cactagactt ataattcatg   6300
tggtgtgttt cttgttttat gcaatattat gaataaaatt tttcattata tcactaatct   6360
tagtgtttgt attttggggt gatctaattt ttgccctaaa aatgattatc tcaaattaag   6420
agtaatattt agaatatgaa ttaataaaga tgaagtattt attatgatta tccaaacaac   6480
ttatgccaag tgaattacat ttattgccgc ataacctaat tattacaaat aggattttac   6540
tgtagaaata atgctatact ccattattcc accctgttat caacttatcg tcctattaat   6600
```

```
ctgaattatc gcggtataaa atagaattct aatagagtga taattttcac atatagcaaa   6660
cgtaaaaatc atatttgcat gctatagcta tagtttgtat aattgtgttt catagaaaac   6720
atatatatgt atatttcgct atacatatac aaagaaaata gttgtataat tcgctataca   6780
tatacaaaga aagcagttgt ataattcgct atatatatac aaaagaaaga agttgtatac   6840
aaaagatcag ttgtattgtg tatatataaa acgagaaaga aagaaagact gaagaaaaat   6900
gggcagggaa atattttgta ttgtataatt ataagtgtat aggacgaatg tatatgcatt   6960
tgtgtgtgta tatacaattt tctctcgctt tatacaaata aaaatacaat ttatacattt   7020
tttttctgtt tgtatacgtg atataggcga gggtggcgag ctagatctgg gacaataaca   7080
gctgagatct gggatagggg agagagggaa cgaaaatata tgtttatata caattttctc   7140
tcgatttata caaacacaaa cgcattttat acatttgtgt ttgtataaaa gtgagagagg   7200
caagcgagac ttccaccaaa caagagtagc aagcgagatt tcaccagacg aaaatagcaa   7260
gaattggcta tagggtacaa ttaaatcaaa ttaaaaatcg ttaaataagt ggtcaatttt   7320
gaaccaaaag gtggatgaca agggtatttt ggacccaata ggtgggtgag aagggaattt   7380
tggagccaat aggtggatgg agggtaattt tataccattt ccaataattt gaggatattt   7440
tgggcccttt tccgtacatt atatctgcat gcatacaaca tctcatccta actcaaagtt   7500
gcgcgaatac aatatttgat tgtaataatt atatatgtat gtatgtgttt caaagcagaa   7560
aatgaatgca tgtatgtatg gtcaattata tgtgtatgta tatatgaaag tagcagttga   7620
ctatgggttc tttttttatat tggagctctg actaaatttg gattgtgcat tataggacct   7680
atttgagggt gacgctccca aattctaaca agattttctc caaactcaag gctcgaaccc   7740
gaggcctcta gtcaagaatg caacagtctc atcattccac cataacctat gttggtaaca   7800
ttgttactaa tcgaatatga aaaagttgaa aaatagattt tgaaaaatat tttcctccat   7860
aacaaaaatt atcccatttt gatttcatac ttaaactatt gaagtgcaat tttataccta   7920
aattaccaca cattagcttg agaaacacac atcagtagta tgtgtaataa gagcgcgctc   7980
tctctctctc tcttttttttt taaaaacaaa ctaataaatat gacattttac atcaataaaa   8040
aatttcacct cgataaaaat taaatcaact attagtctta gttaaagtat cactatctca   8100
aaaaataaaa ctcatttttt taaaatttaa aaatttaatt tcttttcctt taattaagga   8160
atatctcaat ataaataaga ttttgactaa agtaattagg tttgacaaca gaaaactttt   8220
aaaactcctt gcatcatatc ttcatgtaat ttactttcat tttatctcca tttactttat   8280
aattaaaaat gaattaattg tgtctattat gagctaattg tttggctgac ttttgaaggg   8340
aaatatgtca tatatttatt ttataagaga tttttttatt ttttttactt tataagaggc   8400
cagcttgatg cttttcatta tcataaattt tatgcataag attaaaaaat attaagatgg   8460
aacatttgtt taaagttttt tttctcctcg tgttattttt cgttgaaaat tcaggtaaca   8520
attcttttaa ttacttacta gacttctaga ctatatatat aaactttttt caatcgaaaa   8580
attaatcaac tacattttaa ttcaaagcta gttgagattg attaatatat gaatcattta   8640
tatatgttat gatttattca tttcatgtat tacccttata attcttcata ttaagttaat   8700
tttgaggtat tttttatttt tcaaactgac ttaattgttt agtttcaaga ccatttttag   8760
agtgttcttc caattttacc cttcgttagt tagtattaga attaatgatt aattaatatt   8820
tagttatttt aatcataaat ttgacaataa ttaataaggg taagaacgga aaattgtgtt   8880
cagtttatgt cttaatttac ttttcttaaa agggtgtgaa acacctcaga aattaactta   8940
atatggaatg gagagactaa atgatactcc gtccgtccct atttacttgt ccatatttca   9000
```

-continued

```
tcttttagtt gtccctattt attggtccat tttgacaaat caagaaagca caatttattt   9060
tcctattata ccctcattta tactttttga aaattcttaa gttttaattc atgctttttg   9120
aaaccataat taataagggt aaaattgtaa ctccactatg cttattatcg ttaccttaat   9180
gtgtgtgtca tttctaaagc ggagaactaa tcaggggcgg aggagggagt accttttttat   9240
ttttcttata acttatggac ctatggacca ctatctaaat atatcttatg ggaatcgaa   9300
aatagtattg gaaaatgtta gatcgcaatc taaaaattat tataaacatt aagcgataat   9360
ctaatttttt ttataaatta gataaatata tgaacaaaca tcatacgtta cataatattg   9420
tttaaaatat cgttacgatc atagtaatat gtagatcgag atcgctaatt atcatcttat   9480
ttttattata acagaggcag ggaattgtgt tgaatggagc aaaacctatc agtggcaatg   9540
ttttgatact aataagtgta gagaggcttg cataagtgaa ggttttacag atggatggtg   9600
tgcttatttg ataagatata gacgatgtgc ttgtacaaag ccatgtcttt ttaataataa   9660
ttagtatttt tttgctaaaa tatgtgttaa attataaagt ttaacaaaca aacaaaaaat   9720
atagttaatt agcctctaat cttatgtaat cctttgatca taaattatga aatggcattt   9780
taatgatttt catattacat tctacctctt tgtgtttgtt tggaacgaaa ggaaataagt   9840
gaattttttt atttaaaaaa ttgtgttcga tatgtaagta aaaatatata ttatttttaa   9900
tatatttaag aaagtgtgtg tgcggggggg gggtggtgat taggagtggg gtgaggatta   9960
ggatgaagtc acaagtggcg aaatcagaaa tttagagctg atcaagattt aatatgtgca  10020
tatgaaaaat aatttttga tgaaaatgtt cgactgatca ttcgtcacta tacatgtcta  10080
caccagtaaa tatcacttgt gaaaattgtt ctcatgtgct tccatcacga atttttttta  10140
attcattttt aaagaacttg tttttcttaa atatttttgt caattaatca taaaaaaata  10200
aaaaaaaatg ttttccttcg taccaaaaac accctaaatt tctacctctt tctcccttgg  10260
ataatttgtg tttttaatac aactatacat gttggtaatt ataataaagt ttaagaagaa  10320
aattcaaatt aatactaata caaaaaggaa attcatgaaa ataatattaa atatttattt  10380
tttagtttta catagattta tataattaaa atacatgatc taattttact ttcttttaat  10440
atctagtcat gtaactgata cttactaaac ttattttagc atgatttagt actttaaatt  10500
atgatcaatt tcattttggc ttattaattt gcaatatttg ttttacgcga ttttattatt  10560
attgttattt ggatatatta gtgtcattaa ttatatatca tatttttgtt attttcttga  10620
gaaataactt agataattgc attttggtag gactaaagat atatttgaag tacaagtaaa  10680
ttatatgtat gtatgaatac tttatcgaaa aaaccgaaaa ccccgaaatt gaaaaatccg  10740
atttttattg gtttataagt tcaaaaaccc gacacaaatg gtttggtttt gtaacgaccc  10800
gtttagtcgt tttgagcagc agactttatt tctggaaaaa ctggcagaag cgacggaccc  10860
cacgacggac cgtcatgggc acgacggacc gtcgcagggt ctcgtttcaa aacacttaga  10920
aaatctgaaa ttgggtacta aaaatcgact ctctgaactt tgtgacggaa tggcaggacg  10980
gaccgtcaca ggtgtgacgg accgtcacag acccttggtg gaaatttggg tctctgaact  11040
ctgcgacgac ctgcaggacg gacagtcgca ggcacgacgg cccgtcacag gttgcgcaaa  11100
tcccaggcag aatcggattt ccttacacgt tttaaggaac gtttgggact attctttcct  11160
taattataga tttcgtgggt ttatattaat aactcaaatt cttgggggtt aaaagaggta  11220
accctaagtt aattagtggg gtattattgc catcttttat tcttaattat atgttaattt  11280
ggggtaaaag aaagagggtt ttgaataaga aaagagaaaa gaaaagtgag agatagattg  11340
atcgattgag agagaaagag tcgaacgagg aagaagaata tcaaagcctg ggagattgct  11400
```

```
tgttgattcc aattcttcgg tggaggtagg ttatggtttt catgctttca tcgtaaactc  11460
ttaatagaga atgatatgta ttggtagtat tgtaaaccct actatatgct taattgtatg  11520
tttgcgtgaa tatgattatg tgattgtgat aagataagca tgatgaaaat attgaatccc  11580
aaatcttgaa aggaaacttt aatatacatt attaatgatg atgtcttggt atagaagaag  11640
gcttgatgaa ttaaagtaat gggattgatg atgccttggt atagagaagg cctgatgatt  11700
tacagaatga tattagtgga tcggagtgtc acgtaccgac acatgtaggg gatcgggtgt  11760
cacgaaccga cacgtagaat taggggatcg ggtgtcacga accgacacgt agaattaggg  11820
gatcgggtgt cacgaaccga cacgtagaat taggggatcg ggtgtcacga accgacacgt  11880
agaattaggg gatcgggtgt cacgaaccga cacgtagaat tagggaatcg ggtgtcacga  11940
accgacacgt agatataggg gatcggagtg tcacgtaccg acacaagaga attaaagata  12000
atgaatcttg aaagatgtta atatactcaa tctaacgaac ataattccca aatgagtatg  12060
gtgttgaggc ttgagccctc atggatgaac ttgatggtac ttattgctga ttataatact  12120
tgttgtggct acatgttgag ttttatagtt gatttacgat aatattgata tatactgttc  12180
cctattttga gttggccgat gatatctact cagtacccgt gttttgtact gacccctact  12240
tttatgtttt cttcttgttt atttgtggag tacagcaaac gtgccatcgt cttcaactca  12300
acagtaattc aagccagtct tactacatcg gaaattcagg gtgagctaat gcttctagct  12360
tggactggat cttcttcttc aagtcttgat gccttgaact tccggcatgg actagcttct  12420
tatgtatttt tagcttttag aatactctta gtttagtcat ttgattgtag atgttcttgt  12480
gatgatgact tccagatttt ggggatgata ataatagttt tgaattgttt ttattaatga  12540
gtttaagtct tccgcattac tttctgttga tatacgttga aatgttaagg gttagattgg  12600
ttggttcgct cacataggag ggtaagtgtg ggtgccagtc gcggctcgga ttcaggtcgt  12660
gacaggtttg atatttgaaa aacccaaacc aatccgatca tatacacccc tagtcgtact  12720
tttctcttta gtgaatttat aaaaataaga ttttgattaa gcaaattagg ttttactgaa  12780
ccataggtaa ctttctaact gaactgtaga taatagataa ctttataact cgtgcgtgat  12840
taaaaagcct agtatgagtt ggttgatcgt ctgacctttc tattttctgg cccatatctt  12900
tttaaacaag gcccaaactc tcaaggccca atacccttca ccaatgtagt ggtattaacc  12960
ttatatttgt gtatttactt tcatctcatc tctattgaat ttataatcaa tatgaaattg  13020
acagtacatg caaaatgtta aaagagtatt caaaattgat taattgcgcg atcgaaagtc  13080
tacaatgaac ttaatcgttt gattgacttt taagagaaaa ttacaagtaa acatatattg  13140
tcacgtatct tctttatata ttaagaggcc tggatgcttc tcatcatcag aaatttttag  13200
tagaagatta aaacaaaata aaaataaaaa taaactaaag atggaacatt tttttaaagt  13260
catatttctc cttgtgttga tttccattgg caacgcaggt aataattctt taatttccta  13320
ctagactata tatatatata tatatgtata tattgtcaaa gtaccactat gaataataat  13380
acgtagatcg agatcgctaa ttatcatttt atttttattt ttataacaga ggcaaaggat  13440
tgtgttgagt ggagcaaaac atacaagggg ttttgtagag ctcaacagtg cagagatgct  13500
tgcataagtg aaggttttac aaatggatat tgtgtttctt tgagaagata cagaagatgt  13560
tcttgctcaa aaccatgtat tatcaataat tatctacaat aattaatatt tttctaaatt  13620
atgtgtttaa ttatgaggtt taacaacaaa tatatatata taaaagtcca taatcaatac  13680
tgtcttaatt ctatctcttt ttgtttttgt tttattatac aaaaaaaaat gtatgtaggt  13740
cgctctctct ttaaatatat atatatatat atatatatta tatatatgag ttcgaagttc  13800
```

-continued

```
aagttctaga ggatttgcaa tacattaaag aaagtcgaaa ctcaaatact aaaaatcgat  13860
ttgtcacaaa tgaactttat atcaagtgga taatatctca aaagaattga agcatcgaaa  13920
ggaattgaat cttaatttag aaggctattt ggatatgatt tgagttagtt ttaacttgaa  13980
attttagttg aagttcgaag ttacaattaa attgtattga agttggatta taattatatg  14040
ttgagatggt atgaaaatta ttttaaattt gcttgtgtgc tttatagttg tattaaattt  14100
atatggatat tatatgatgg ttgtatcaat gtattgtatt aaatttttgg aaatcaacat  14160
gaactttata caaaattggg aaaatgcact agtactcccc tacactatga tcaaaatcac  14220
agagacacac cttaactaat acaaaaatta tacagttata tacatatgta tatcaatttt  14280
atataaaaaa aattgtgacc caaaattcta agccttgacg agatatacat atatcatatc  14340
gatttcacac aatcttcata catgaaaaaa atatgagtga aattttaagg ctcgagtaaa  14400
attaattcat atatattttg aaaaaataac tcctactata ttttggtaaa taaaaatctc  14460
ctattacatg tgataacact ataaatctaa tttggtatat aaagaaaaat tcccaattgc  14520
caaatttatt tatatttcaa ttatcaattg attcaagaaa gaagacatgt caaagaatga  14580
aaataataca tgcctaattt catgctttta tatggatttt gacttgtaat aattattttt  14640
ttatatgcaa ttttatttca attttccttt tttttgttag acataacatg tgtaatagag  14700
tgtggcaaag gagtctcccc cctttcctca ttttcatgtt taaaacatat caactttcag  14760
cattattcat gttggctctc ttgttagcat aattttcttg accctatata cttaattatt  14820
attttttttt aaaaagaaag caaaataaat aattaagcac aattgtcgag actcgtctcg  14880
atatgcatac tcaaaattgg agtgttcact tgtcaactaa aaaggccaga ttcaaatgtt  14940
tgtttatata aatatctttt gaaaatcttc tttttttttcc ttaaatttca tactcaatca  15000
aacacagcgt aaaatgagag atgttatatg ttgtgtttag aatagtaaat cagaaatact  15060
gttaagatga aaagaaagaa aatatccaag tccacttaat tatttactgt gttcgtaaga  15120
aatttaatcc cctcactgta ttcgaggtcg agattgtaga ttatttcctt ataggataaa  15180
atagatatat ttattaaaga agtagtggta cctctcactt caataactta cgcaaactca  15240
aaagttagca atgaaaaatc acacagactc tactttgttc gtaagaaaat atatatgtag  15300
aagaaaaaga aaaacgatac aaaagattga gagggaacct ctctatttac atccaacgat  15360
aggtgtgaac tcacatgtac agaaatattt gttcggaagg aacatgccct tctgtaacaa  15420
tttacgttac tattttatat ttagtaataa tttaacttta aacttctctt tttatcttta  15480
ttgagatatt ccctccgttc acttttcctt ttggcaatat taaaaagtaa aatttcactt  15540
ttaacttttc tactttagca tctaaaaaat aaataaatta aaatgatctc ttttttttcat  15600
gttttatcct taacatttaa ctataaaagc ccccttacta tactcaattt cttaaattat  15660
atttcccttt ctctctctat aattttctct ctctaaaaag atgggacaat ctatgcattt  15720
gtttgcaact ttcttcattg taccaatgct gcttttgtct aatggtttgc cttctttctt  15780
cataatattt attttattat atagtttaat tttattctat gtgttaataa tgtgtaagaa  15840
tttttataag tataaatgtt taaatataac tctttaactt tgtgatttag tctaccttta  15900
aagtatgata actagcaaga acttgaatta ctgaaaaatc taactgatat atccttatta  15960
aaaaaaaatg gcttataacc tttgttgtta cacaaatgac ccacattgat agtttggtta  16020
tgtatataaa tgaaataaca aatcgttaaa atatgaaact cacgaagaaa ataatagttt  16080
caatgtgtca taaaatactt ttactaacat acgatgtata aatttaaata tttgtggtaa  16140
aaggtagtag taccacccga gactatatat gacccaaatt ttagaaacac accttatcta  16200
```

```
tactaaggtc ttattaccct ttcgaactaa attttttgta attttaattt gtacaccttt  16260
tcggcttatg tggcatttaa atatctccca cacgccacaa ctgcgtggag tcacgggtgt  16320
gccacataat ccaaaaggtg tataatatta tatatagggg caacttaatg caattggagc  16380
tgtgaaattt caatttgagg cctaaaatat aaatgtagga acaaacttcg tatacgtatt  16440
tattcaaaat taatttccct tacactattc aaatgaaaat tattagtact taatgttgtt  16500
ttttcagtta ttgattttag gtaagatttt atcaactcaa tattgaaaaa acatcctttc  16560
agtgagataa ttattatatg aattgctaac ataatcctat aagtagcgtt gataaatatt  16620
aaataaagat aagagttaga accacaaaat gagattcaag agaatgatga cttgatttac  16680
cccatttcta tatgtttgtt gtaatgcttg aaacaaacaa aaaagaatct gtaattttct  16740
ttgttcaaca ctataaattc ttatttttaa tgaaagacta catatgttaa actgagtaaa  16800
ataatatata cttcttaaaa gtaatacttt ttatcgtaac taatcaattt tttctataaa  16860
aatttaacac ataatttatt tatgataaaa atttgggccc cccaaattgc cttattttgc  16920
aaaggcaaga gccggcactg aatatatata aaataagttc acgagataat agattctgtt  16980
gagatttcga tcatagtcaa gggatactta tgtcttctcc caatatttat tgataatata  17040
tggttctcga tttttgatgt ttgcgtacat taattaatag atatgggacc tatgagctgt  17100
ggtgtagagg caagaacttg tgagtcacag agtcacagtt tcaaggggcc atgtagtagg  17160
gacagcaact gcgccaccgt ttgccagacg gaaggattca ttggcggcga ttggcgtggc  17220
cttcgccgcc aatgtttttg tactacagaa tgttagaaga aagtttctaa atgatctttt  17280
ttacagtcta tgtatttgtt tacttgttaa gatatctaat gataaataat gttgtttaat  17340
caacaaaaaa aagtgactga ttaacctcat ataaatatat aatacatatg gtgcttttgt  17400
tacgattcaa aatcttaggt catgattttc cctaagagtc acgatctagg cataccaaaa  17460
ttatttatcg aggaagaaaa aataagttca ggatagtaaa tttcatcatt aaagcgaacg  17520
atatatgtaa aaatattttt aactaggaga atatttattc tatatttgtc cttttccctt  17580
tgttttttaa taaaaaaaaa atctccttgt aataagaaat agaactaatt aattcattaa  17640
ttatgacggt tcaccagcct tttctgctca ctcgtagagg ttgggacctc ataaaggaat  17700
agcgagggag tccactgaac attttagcta ttggcgggaa attcgctctt gtcaggtgaa  17760
taacaatcgt ttcgtcatag tactacttat tcatactgga attactcaac ggattctttt  17820
aatgtatcat ttctgggtcc aacgaaattc attgatatag aaagaagccc tatcatataa  17880
agattttttt cttgtgagct actaggtcac actttggcca agcacgtact accattggcg  17940
gagccacatg tagttgacac cccttcatcg aaaaattaca ttgtgtagct agagtaagat  18000
atcttcacga atcgccttgg tgttgcacta ctgccttggc ttagcacacc cccaccaatt  18060
ctagtcctaa accattcacg ttacaagtga tgaggacaaa ctccctataa taatgtaatt  18120
tcttagtcaa ttccaagaga ataacatttt tgaaatttaa aaataattta agttaaactt  18180
ataatttttt aaaaatattt ttggtatgta ggctatcgac tcacgtggta ctttggccta  18240
acacacctct aaaaacttat gagaaaaaac attccctaaa tgatgtaact ttttagccaa  18300
ttccaagaaa catgataact ttttaaattt tcaaaaaaaa tatttaactt tgaactttta  18360
attttacgct taatgagaag ctttttagat gttcaatgta attgaatgat cttaagttta  18420
aaaaaaattc atttatttct taaattttca tttatattaa gatattgtca cataaattaa  18480
aataaaataa ctaatgtctt gcatgtgatt catatatttg atattttaca cattgcaatt  18540
aataattcca aaatgtttaa ttttatcttc aagcattgaa ctcaccaaca aattaagatc  18600
```

```
tataatattg gatcatgtga aggccaatgt attacatcaa actactatat aatgtacgtt  18660
gttaattgaa agaacatagg aagggaaaaa acacaaaaag aagaatggaa tgagaagcag  18720
aactcggaga aacgagataa aaagaaaatc ggacacttca taacaattag tataaacctt  18780
tttttttgtt aaaccctagt tctttttaac cggttttcaa ttaagcatga atctcaaaca  18840
aaatttgcta atattttact atgttcaata atctcaacta aatcggtatc gttaagatga  18900
agggcacaaa tacctaattt tggggcttcc atttaagtgg tagccacatt ttttatttta  18960
taaaattaca aatatatcca cttttgaacc acttcaaata cactcgattc aagtaaaaat  19020
aattttaaca aagctcgact tcagacatat aatgacttgt taagatcgat ttctgaatac  19080
atacctaact ttagaattag gaaagataac ttaaagcttt tatgtggatt ttgacttata  19140
acaattttta catctttata aaggagaaaa ttcctctcaa attcttcttt ttgttaggca  19200
taacatgtgt aatagagtgt gacatgagag gagacccctt tttctcattc tcaagttgta  19260
acacatatca ctctccgaca ttatttatgc tcgcggattc aaaatttaaa atttatacag  19320
aaaaaaatga tgaacggatg aagtagttaa tgttttagaa aattaatata taattagtta  19380
tttatgttca cctttattct tactctataa ctaaatggag agggaattaa atcaaagaga  19440
aaattagtaa tttaatcaaa ttatcctttt agttaatgtt tttattaagg gacgtgtaaa  19500
aaaaaatatg acaaataaga tgaaccaaaa gaatcacaaa tcttcaagtc ctactcccctt  19560
cttttcaaat atgtacttgt cacgatttta ttttgagaat caaacgatat gaaattagat  19620
cagttaatat gagaaaaatt acaattttta gcattttcta taaaaatttt aattttaaaa  19680
tattaaatta atttaagcta aaaattattc attatcaatc ttgaaaaatg aattatgaca  19740
actatttaaa aaatatttga aattaaattt cgtgtctaat caaatagtca ggtaaatgtg  19800
catgtataaa tacccccctt tgcttactcc ttgtcttaac caattctcaa tatatttctc  19860
aaattgcatt tttctttctc tatttgaaga tggcacactc tatccgtttg tttgcaactt  19920
tcttccttgt agcaatgcta ctgcttttat ccactggttt gtcttcttta tttatattat  19980
ttaattttat tatatagttt tataatatta gctctacgtc aaaatttagc tcaatgagag  20040
aaaattgtcc aatttatgtt aagaagtctt agtcctctca ttcaccttca atgtgagagt  20100
atcctttttt cataaccctc cacacacaaa tcgaaacata attctatact gaagtgtgaa  20160
cagtttattc gaaaactcaa tatcatattt ttttaaattt taatatcatg atgtatgaat  20220
tttagacttg agacaaccca aaattagttc aaagtacaat aacaaaagag acattatcca  20280
aacacaatat gatattgtag catgaacacc cgatatcata tgatttgatt ctaatatcat  20340
gatatatgaa ttttggactt aacaaaaccc aaaaatagct caaaacacta taacaaaaga  20400
gacattaccc aaacacgatc tgacactgag gcatgaacat tcgataatcc gttatcatat  20460
gttttgattc taatatcatg atatatatga attttggact tgacacgatc aaaaatcagc  20520
tcaaggcact ataacaaaag agacgttatc taaacacaat ttgctactga agcatgaaca  20580
ccccaaattt gggactcaac acaacccaaa attagctcaa ggcactatgt tttgattcta  20640
aatatatgaa tttcggactc aacacaattc aaaattagct caaggcacta taacaaaaga  20700
gacattactc aaacacgagc cgatactaaa tcatgaacaa ttctagacat tacccaaaca  20760
cgatccgata ctgaagcatg aacaattcta gacattaccc aaacacgatc caatactgaa  20820
gcacgaacaa ttcttgttgc tatacaatta tattaagtat atcctagtta tctcatccac  20880
gaccgatgtg ggagtcttgt ttcatcattc ataacatgtt tggctaaaat tgaacagaga  20940
tgggaccaat tagcagtgca gaggcaagaa cttgtgagtc acagagcaac agtttcaagg  21000
```

```
ggacatgtgt tagggacagc aactgcgcca ccgtttgcca gactgaaggc ttcatcggcg  21060
gcaactgtcg tggcttccgt cgccgttgct tttgcaccag aaactgttag aacatataga  21120
gtttctacat gaaatactca tcatgcattc atgataaata atgatgttct attctatcaa  21180
taaaaaagag agactagata tatatagtct catatttatt tatatataat atgtggttac  21240
gatcaaaaat cataggtcat gattggctaa tctagtatct gtttttatta gtttaatatg  21300
tgaatcatcg acgaatcacg tgatgtgttg ccttagcgtt gcacttattg ccttgacttg  21360
gctaatctag tacatgatcg atcctaacat cttttgaatt tatgatatta caagttcggg  21420
aggggtaaaa aaggaattta attacatgta ctttttagt taggagtatt tgcttacttt  21480
ttcttctctt aaatcgtttt attcgccgct ctttgatcaa ttatctagca cttctagtcc  21540
cacactgact agaaagagag attttatgta aaatattgcc atataaaata gcgcggtata  21600
gaatatgaaa aatcatacct ttctcggcct tttggctaag atcaagtgta gtatctgttc  21660
ttatcagttt aatatctgat atgtgagtca ttgactcaca cgatattaac tctatttttt  21720
tcgggtgaag gttcatcatg gtagcttgct attgagacct tcaagtgtcg tctaggcgtt  21780
gcactactgc cttggcctgg cacaccccac caattctagt tgtaagcctt tctttcaatt  21840
gttagttgag gacttcttag gatttttgtg tagttataat aacctctaca tttttggagc  21900
aaaatcgata caatatggtg gagaaggcaa tggacttggc caaacttgct ttgtctggat  21960
gattttaatt agacgtgtat gagagattaa agtgattgag aatatccatg atcaattgag  22020
gaggttacgg gttgagtcat gttggagggt gagtgagatc gtcactattg atcctcctcg  22080
gatggggtgg gggaaataac aaaacgaaat ttttctcaaa ggattttaga tgaatctcgt  22140
aagaacgaca aaaaatataa tgcaccagcc gggaatcgaa cccgggtctg taccgtggca  22200
gggtactatt ctaccactag accactggtg cttgatgact ttgtttattt attaaataac  22260
tacatatttg atatcaataa aattgcaaat gtaagatcaa gtgtagtata tgtggtgcat  22320
ttgtcacaat ttcaaaatta ttagtcatga ttaatgacca aaaatccact atctagatta  22380
gagagggatc gactacgatg ctaaagccag gtccgtaagg tcatcaatcc acttgatcgt  22440
catatccatg gagtaaatct cgataaggta ctaaagctac ggtttgtaca aagcaaatac  22500
aaacaatata catgacatgt gtgaaaataa attttgtgat ttagaaatga tatattaaaa  22560
cgtgatatat tatatgttag acaacaaggt atctatgtag ccatttgtta gactattgga  22620
attaagttat gattagtggt caagaagttg ttagtctgtt acataggtaa aaaaatgaaa  22680
aaaacaagtt agttaatagt tagttactta gtgttagaat gtagactcaa taatgcccct  22740
ggaaactata aaatttcact aaagaaaagg acaaatatga agaaaaaaaa aactataaat  22800
ttaattattt tgaaaaagta agactcaaaa aatcatttca tatggaaaat tgatggaaat  22860
gaaataaagt gttgagattt tatatgtgaa atccaactaa ttcagaaatg aggtattatt  22920
acagttgtta aatttctata tatgtattat tactatactg catactctta gaaaggaaaa  22980
agaaagataa cgtttctcat gtcagaagga accctcaaaa gtatttaaaa ttttcaacta  23040
aattcatacg cacacatatg caccatcaca cgcaagcaca aggacacgcg cacgcgcaca  23100
atatataaga taaagacatc attatacata taatacccct tctatttaaa tatatagtgt  23160
attatttata ttttgcatga tcttgcgaag cgagtatgag ttcacttgta taacatcaaa  23220
gaataaatat tattatcatt cttagtgttg aagtaacttt ttttagcact agtattgatt  23280
tgattttaat tcgagttttg ttagagttac taatatctat ggactataac cttaattaga  23340
ccattcaaaa ttcaagtctt agaaacaaga aataatatga taaaagataa aaactatgaa  23400
```

```
aaagtaaaag aaatattttt aaaaattatt caaagtaaat atttttatgc ataaaaagta  23460
ataattttaa aaaatatata tataatgtcg ggtccgtttg atctcaaatt gacatttttt  23520
taggtaaaac aaaactaatc aaccacattt gtggaaatgg accgaaaacc acaattgaca  23580
ttgaaaactg ccgatatccc ttctttttaa gtttaaatat ggactcatgg tccattttac  23640
ttaataaaaa tgggctcata aatgggtcca cacataaata taccaaaaaa agagttggtc  23700
ggccttgaag tggttagact aggtaagtat aaaagaaccc taaatgatag agttttctga  23760
ttagttgctc tccgcctctt cttctcattg ttctcatcgc ctctgcggag atgttgtctc  23820
ttgtgcccca caattgtagc ttcttccccc tttggttatg cgggattaac atattccacc  23880
ttgatcttgt tgctgtggag atcaattaaa aaggttcatt tttttagcca tctggcatct  23940
tcattgtctc gtttctgaac tgactcttct ttttgtttga aagtgtacta caaattatta  24000
agtattggaa aaaaattatg gagatggaat aaaattgata ttgagatttt atatgcaaaa  24060
tccaactaat tcaaaattga ggtattatta tacttgttaa attcctatat atgtattatt  24120
actatactgc atattcttag aacgaaaaaa aaacataata tttttcatgt tagaagaaac  24180
actcaaaaag tatttaaaat tttcaattaa aattcacacg cacgcacaca caaacgcgca  24240
cgtgcgcgca cacacaaaat ataagataaa gacattatta ttatatataa taccccttct  24300
atttaaataa tatatagtgt attatttata ttttgcagga tctccgaagt gaggatgaat  24360
tcacttgtgc aaaattaaag aacaaatatt attatcattc ttagtgttta aataacattt  24420
tctagcacta gtattgattt gattttaatt tgagttttgt tagagttact attatgtatg  24480
aactataacc tttattggac tgttcaaaat caagtcttag aaactggaaa taatatgata  24540
aaagataaaa actatgaaaa agtataagaa atatttttaa aaataataca aagtaaatat  24600
ttttatgtat aaaaaattat aatatcaaaa aatatatata taatgtcggg ttggtttgat  24660
ttcgaataga catttttttt tgggtaaaac caaaccaatc aagtatagtt gtggaaatgg  24720
atcgaaccac aattgacatt gaaaactacc aatatccctt ttttaaagtt taaatatgga  24780
ctcagtatag ctaaacttgt tctgtagaga tgacttttat aagcaatttg tataattaat  24840
atttagcaaa tttcagcaac attgttgaaa ctattttgca gccaactgta cataaattgt  24900
tttattcact actctttgat caatggaatt atttatgatt aatggaattg aatgaagatg  24960
attactagtt taatatataa aagctcttct agttccacac tgcctagaaa gagagatttt  25020
atgtaaccaa gtaacaaata aaatagcgcg gcataacaca tggaaaatca tacctttctc  25080
ggccttttgg ctaagatcaa gtgtagtatc tgttcttatc agtttaatat ttgatatgtg  25140
agtcattgat tcacacgata ttaactctat tttttagggg gaagattcag cacgatagct  25200
tgctattggg accttcaaga gtcgccttgg tgttgcacta ctgccttggc ctggctcacc  25260
ccaccaattc tacttctaaa aaaaccttct gattcatagc agtacataat tttgggcagt  25320
ttgatacaag ttgaacattt tatttaaaat cagatatgga ctaatgtttc aacctagtat  25380
ttggcacctt tttttttttt ttccagaaag atgtactgta caattactaa agataacagt  25440
aaccttataa tgtgtaattc tactgagttc gatctctcat cttgtatctc caacgatatt  25500
taataattaa tagcggaaaa agaaagagct cagattcgaa cccgggactg taccgtggca  25560
gggtactatt ctaccactag acaactggtg ctagatattt tatgaattcc attttgtata  25620
attagtgtca aagtaccacc cctaaaatct gtgatatcaa taaattgaaa tgtaagatta  25680
tgtgtagtat ttgttcttat caatataata atagtaataa aaaaactgtg gagaaatggc  25740
ctttttcgtc cctatatgaa atctatattc ttattttagt cattgtataa tctaacttag  25800
```

```
cacattaacc ttcaattata tcaagtgagt gattttgatc cttcaactaa catattcaca  25860
aaaaaattaa cagagagttc actgctaaaa gggatagttc ggatatttca ttttaattct  25920
gtctttttga aaaacaagct tagtcttcca tgtctctatc ttgaagaaca agctcatcaa  25980
attgagctac aatttcaaca aacccaactt gataggcatt aaccctccct ctcaaatcga  26040
cgaacgatag atttgcagcg aaaattattt ttgaaaattg tatgttttct caagcaataa  26100
ctttaaaaat attcgaatta ctccttttag cagtgaattc tctgttaact ttttcgaatc  26160
tgttagtcga aggattaaaa tcactcactt gatataattg aaggtcaata gtgctaagtt  26220
agataacaca aggactaaaa taagaaatta gctttaatat atggactaaa aatgttgttc  26280
tcccaaaacc tattgaggtc aatggggata aatattgctc ttgtgaatag tttccttact  26340
taaagtacat cgttgtacca tgcgacctgg agcaatgctc atttcatttc tatgatgcct  26400
agtattgttg actccaaaag ttctattaca atcaaaatga atggaaaatt gcagttctaa  26460
gagcaacttt ttttaaaaaa attatttgta tgaatttttc gtttaagatc taagagcatc  26520
actatatatg aaaaatgatt gagatgtcac atatttttaa aaatgcatat ccaattgaag  26580
ttcatgaaat aagccacaat ttttgttata aaatattatt agggtccgtc tctaatgagg  26640
caaactccaa ttgttttttt ttttttaaaa aaaaatgttg cgtttcatta gtatgtaggt  26700
ttttttttt ttttgttaaa ttaaccttta acatttatga agcaagatcg atgcgttacg  26760
tgtggaaaat gttatgtagg caacaaattg gtattttaca tttgttgttt tttccatctt  26820
attttggatt aatgaacctt aggaatagac aatgaatctc agtaaacttg ttatgttatc  26880
tgtataattt attaacctgt tgtaggatat ataaatgatt aaatgatgct tgctcaagtg  26940
gttgagcatc ttcgattcga gtcatgttgg agggtaagtg gcattaatat tgatactcct  27000
cggtggggtc ggaaaaataa cttctttgtt gaaactattt tgcagccatc aatacgttaa  27060
cagaacaaaa aattcattta ctgcactttg ataaaaaaaa atatactata gactattaat  27120
gggattgaat tattagttat atataaaagt atagagtcta ttcaagtccc acattgactg  27180
caaagagaga ttatatgtaa ccaagtaaca aataaagtag tgcggcataa gtcatggaaa  27240
atcatacctt tctcggcctt ttggctaaga tcaagtgtag tatctgttct tatcagttta  27300
atatctgata tgtgagtcat cgactcacac gatattaact ctattttttt agggggaagg  27360
ttcaccacga tagcttgcta tcgggacctt caagagtcgc cttggtgttg cattattgcc  27420
taggcctggc tcaccccacc aattctagtt ctaaaaacat gttgtttcat aatggtacac  27480
aataaaaatg ttatgtaggc aacaaattaa aactaaccgc atcacctctt aaacctaacc  27540
ttctgtttct tcatagtaga atgatagatt tttagcaaaa gaagaaaatt ttgatagaaa  27600
tatttgggaa gctctctatg aatctcaaag aattaaacta ttttgcagcc aacagaatgt  27660
aaattgtttc accccaccaa ttctacttct aaagaccttt tggttcacaa tagcacacaa  27720
tttgtccctt ctaatattgg gcagtttgat ccataaaagc tcatatccaa tgcattaaaa  27780
taaaatcaga tactgaacta cattttagca taactcataa aatcttgaga ccaatgttaa  27840
atggtgacca aaagtataat aattcgattc tcatgttgta atctctaacg acattatggc  27900
cagagtcaat atataataat ttgatttcca tgttgtaatc tctaacgaca ttgaaaataa  27960
tagtggaata atgagtagct cagatgtgct atttttgtca tcttaacatt cagacatggt  28020
gaaagaccca aagttttcac acttgcacgg ttatcttcat ggcactcaaa ctattgcatc  28080
agtcggaaat cgaacccagg tctgaaccat ggcaagatac tgttctatca ctagatcact  28140
agtgcttaga cattaaaata cttccttcgt ttctatttag aaaccaacta attatagcag  28200
```

```
gatgtcatat aaaaaggaac ggaggaagta tacttcatct tttgtactag cagtaaagta  28260
caatccctaa aatattttat atccaataaa ttgaaaatgc atgatcatgt gtagtatctg  28320
ctcttattag tataatatct tatattaaac ttttcaaaaa aaacttatag taattagggg  28380
tgtgcatttc aattcgattt tatgtattat cagtttgatt tattagtttt tgacttttaa  28440
atacgctaaa tcattaaaaa aaatcgataa gatattcttt atcagttttc agtttaccca  28500
ataagaaaat attcgtaaaa tagatttatg atttctcact tttctaacaa tttggcacga  28560
gactgtgaga caagcaaaac agatgtaaat gctttgatat agtgaaatag gaaatataat  28620
gaaaaattac atcaataata gtagatgtag tatgaaggct acaacaacat gttacatagt  28680
atgaaatttc ggatgtgaac tagaagtact atgacgtgtg aagtgtgtag actgtagtat  28740
agagtactga tatagtgtct aattatgcta acttattaat atttaatatt catgaaggat  28800
atagtaatat cttactgtcg tcttaacgag ttatcgtttt acccatacta aaaatcgaaa  28860
ccaaataagt tttcttata acaccattaa aaatttgtta acccaataaa atataatttt  28920
gtgtttctta ttagttttca atgttattca taactaagga atatgatggg aatgtcaatt  28980
acggtagctt gctaccaaag acctttccca ctaattctaa ttttaaacct tttttttaa  29040
ttttttgttg aaggaatttc ttcgaggtct acgacaaaga tattaattct tacgattttt  29100
ctgaagttat tattaacctt ttaacatttt tggagcaacg atggatatga tactgtgaaa  29160
aatgttacgt aggcaacaaa ttatacatct ttatagtccc acattgacta gaaagagaga  29220
ttttatgcaa caagtgacat ataaaataat ccagaataac acatgaaaaa tcataccttt  29280
ctcggccttt tggctaagat caagtgtagt atctgttctt atcagtttaa tatctgatat  29340
gtgagtcatc gactcacacg atattaactc tattttttga gggggaaggt tcatcacggt  29400
agcttgctat cgggatcttc aagtgtcgcc taggtgttgc actattgcct tggcctggca  29460
caccccacca attctagttc caaaaacctt ttgtgttcat aaatgataat tctatattat  29520
atataataat ttgatttcca tgttgtaatt tgtaacgaca ttaaaaataa cgacaaatat  29580
ataataattc gattcccata ttgcaatttc taacgacaat aaaaaaataa tggaaaaaag  29640
agtggctcag atgtgttatt ttgtcatctt aacattcaga catgatggtg aaagactcaa  29700
gttttcacat ttgcacaatt atcttcatgg cactcaaact attgcacagc cgggaatcga  29760
actcaggtct gtaccgtggc aggatacttc cttcgtttct attatatgtc atcctctaga  29820
tttacgtgaa caagttttac tattctactc ttattcaccc catattagtt ttctttgttg  29880
gtcaaaggac tattttcaag attagtctca taaaggtaaa gagaaagaat atagtaataa  29940
tttatacatt aattttaaga aatgacaagt attacgaacc aactaattaa ttataaaaag  30000
ggtctgatat accccacaac tttgtcattt agagctgata tactcctcgt tataaaagta  30060
gctcatatat gatttttcat ttctctaaaa aatgtggcat gagattgtga gacaagcaaa  30120
tcagctgtag tacaaaggct acaataacat gttacaatca aaacataata tggaacttct  30180
gatgtgaact aaaagtacta tgacatgtga agtgtaaata ctatgacgtg tgaagtgttt  30240
agattgttgt atacagtact gatatagtgt ctagttatgt taacttatta atatttaata  30300
tttatgaagg gcatagtagt acgtatctta ctatcgtctt aatggattat cgatttaccc  30360
aatactaaaa atcgacacca aattgataac gcgacaagtt ttttataaca ccattaaaaa  30420
tctattaatc taataaccca ataacaatga accagtaatt ttttttcgat ctgatttatt  30480
gatcggtctg atttttgtac attcctaatt tcatattata tacttccaac aaggtaccac  30540
tctaaaatat ctcaataaat aaaaatgtaa aatcaagtat agtatttgct cttataagta  30600
```

-continued

```
taatatctta tattaaattt tagttaaatt ttccaaaaaa aatatttata gtaactcgac  30660
acgatataat cactaataaa aaattgttat tttctcccat tgaaaaatat tctgctgcaa  30720
atattttgat tagactggta ataagagaaa atatatatat taatacaaaa aaattcatta  30780
ttttagtgtg attttatttt ccatcacccc tgtatttttt cataaagttg ataaaatgaa  30840
aaatgaatag caaaatcata ctctattaca ttatttttca ctaaagaaaa actatttcta  30900
atagttacac gaacccacac ggatcaaagt caaccatgaa taacccaaac caatcgaaca  30960
gggtttccca aaccctaacc gaaacgaaac aaatcgtgtt atattttcaa cccgccccga  31020
cccgccccaa caactaagta tctataaaaa ggccccttct agttctagcc tactcataaa  31080
cttctcaaat taaattttat ttctcccttc tctctctaaa cttctctctc tctctctaaa  31140
tatggggaac tcccttcgtt tgtttgcaac tttcttcctt gtagctatgc tgcttttggc  31200
cactggtttg tctttctttt tttaatcaat ttattcgtat ttattttat gttatcgaac  31260
tttgataaaa aaagttatct atatcatttt ttttagaaaa aacttattca tgcatgtcgt  31320
taatttgtta acttaaatga tataaatgag taaaattttg aacaatagat gatatatatg  31380
agtttcttta aaaaaagaaa gaaaactgca attacatatt tgaatctttt tctttttcaa  31440
aaaatattta actcataaca tgattgaatt ataattgatc acgtatataa aataactttg  31500
aaaagttaaa attattttca attaataaat gatgacatga atgagtctgt ttctcaaatg  31560
aaacatgagt caaattctta acgagggtat agacagcttt ttttttaagt ttgatgacat  31620
attttagcac gcgtgatgga attataatta acgatatgta aaaaatgatt ttgcaaaatt  31680
aaaattattt ttcattaata aataattacg tatatgaact ctttctcaaa caaaaaataac  31740
agaaatgatc taaatattta agaaatgata tgaatagact tttttctcaa aattctattt  31800
acaattttgt tttccaaatc aaacacccaa aatgaaacta caatcaataa acaaatcttt  31860
gtaaccaaaa aataaaaatg atctgataat ataaaaaata atatttcgaa tttttcattt  31920
tacaggacca acaacaagtg tagaagcaag aacttgtgag tcgcagagcc accatttcaa  31980
agggaattgt cttagcgata ccaattgtgg ttccgtttgc cgcaccgaag ggttcaccgg  32040
tggcaactgt cgcggttttc gtcgacgttg cttttgcacc cgtaattgtt aatagaagaa  32100
aataatcttt tcataacgat cgctttaatt tacccttaat gttaaattaa agtgtatgat  32160
ctatcaataa aacacgtact ctcatatatt atatatatat atatggttgt atgttttgtt  32220
atgttatgtt cttttaaata aatattttgc gtttaaaata tattgacttg ataaatttag  32280
attcgcgata ataataataa taatacgttt tgttgaatgt catttttatg gtcatgcatt  32340
ctatcctctt gccaaatgtt agaatcaaga tggacacgtg ttaatcaagg gaagagcctc  32400
aacctatgac caaaaaaaaa aaattataat tatttaaatt ttcgaaattc tcaatcgatc  32460
tttttggaat ttataagtaa tcatataaaa ttatcttaat taaattgaat aaatagacgg  32520
attattatat ataataatat atataacgta ggtgtttagt tattcaagtt aaataactat  32580
tttatatata agctagtctc ctattttcat tttcctcctt tttgagtttt tgcgcgcgtg  32640
tgtgtttctg gtgtcatgtt ttgatctgac ataaaatttt aaaaagaaat aaagcttttg  32700
aattttgtac ttttaaaata aaatttatat taaattatat caaacgtcct taaattttgt  32760
gattttaaat atattacgta aaaattaaaa tttaaaaatt atattagaat attcgattag  32820
tccattgtat gccacgtatt catgggaaat gtgagtggca atttttgtag gttttgtgtg  32880
aaccgaatgc cttcattgta agaagaagtt gcacgaaact cttttaagaa tactgccaat  32940
atatcttctt gaactcagtg attgctttcg tttgacgata actcggtgca taaagtatct  33000
```

```
cgagttga                                                            33008

<210> SEQ ID NO 4
<211> LENGTH: 421
<212> TYPE: PRT
<213> ORGANISM: Solanum lycopersicum

<400> SEQUENCE: 4

Met Gly Lys Arg Arg Asn Trp Phe Thr Phe Val Lys Arg Leu Phe Ile
1               5                   10                  15

Pro Glu Thr Glu Ser Thr Ala Asp Gln Lys Lys Pro Lys Arg Trp Arg
            20                  25                  30

Cys Cys Phe Leu Arg Lys Phe Lys Leu Arg Lys Cys Pro Ala Ile Thr
        35                  40                  45

Ser Ala Pro Gln Gln Thr Leu Pro Glu Ala Lys Gly Thr Pro Gln Gln
    50                  55                  60

Thr Leu Thr Glu Ala Lys Glu Gln Gln Arg Lys His Ala Phe Ala Val
65                  70                  75                  80

Ala Ile Ala Thr Ala Ala Ala Ala Glu Ala Ala Val Ala Ala Ala Asn
                85                  90                  95

Ala Ala Ala Asp Val Ile Arg Leu Thr Asp Ala Pro Ser Glu Phe Lys
            100                 105                 110

Arg Lys Arg Lys Gln Ala Ala Ile Arg Ile Gln Ser Ala Tyr Arg Ala
        115                 120                 125

His Leu Ala Gln Lys Ala Leu Arg Ala Leu Lys Gly Val Val Lys Leu
    130                 135                 140

Gln Ala Val Ile Arg Gly Glu Ile Val Arg Gly Arg Leu Ile Ala Lys
145                 150                 155                 160

Leu Lys Phe Met Leu Pro Leu His Gln Lys Ser Lys Thr Arg Val Asn
                165                 170                 175

Gln Ile Arg Val Pro Thr Phe Glu Asp His His Asp Lys Lys Leu Ile
            180                 185                 190

Asn Ser Pro Arg Glu Ile Met Lys Ala Lys Glu Leu Lys Leu Lys Cys
        195                 200                 205

Lys Ser Leu Ser Thr Trp Asn Phe Asn Leu Ala Ser Glu Gln Asp Ser
    210                 215                 220

Glu Ala Leu Trp Ser Arg Arg Glu Glu Ala Ile Asp Lys Arg Glu His
225                 230                 235                 240

Leu Met Lys Tyr Ser Phe Ser His Arg Glu Arg Arg Asn Asp Gln Thr
                245                 250                 255

Leu Gln Asp Leu Leu Asn Arg Lys Gln Asn Arg Arg Ser Tyr Arg Ile
            260                 265                 270

Asp Gln Leu Val Glu Leu Asp Ala Pro Arg Lys Ala Gly Leu Leu Glu
        275                 280                 285

Lys Leu Arg Ser Phe Thr Asp Ser Asn Val Pro Leu Thr Asp Met Asp
    290                 295                 300

Gly Met Thr Gln Leu Gln Val Arg Lys Met His Arg Ser Asp Cys Ile
305                 310                 315                 320

Glu Asp Leu His Ser Pro Ser Ser Leu Pro Arg Arg Ser Phe Ser Asn
                325                 330                 335

Ala Lys Arg Lys Ser Asn Val Asp Asp Asn Ser Leu Pro Ser Ser Pro
            340                 345                 350

Ile Phe Pro Thr Tyr Met Ala Ala Thr Glu Ser Ala Lys Ala Lys Thr
        355                 360                 365

Arg Ser Asn Ser Thr Ala Lys Gln His Leu Arg Leu His Glu Thr Leu
```

```
    370                 375                 380

Ser Gly Gln His Ser Pro Tyr Asn Leu Lys Ile Ser Ser Trp Arg Leu
385                 390                 395                 400

Ser Asn Gly Glu Met Tyr Asp Ser Ala Arg Thr Ser Arg Thr Ser Ser
                405                 410                 415

Ser Tyr Met Leu Ile
            420


<210> SEQ ID NO 5
<211> LENGTH: 2066
<212> TYPE: DNA
<213> ORGANISM: Solanum lycopersicum

<400> SEQUENCE: 5

ccacatggaa caacaaaaca acactattat tattattatt caagaatcac tagcaagact     60

ggttaattaa tgttaccaaa ttttgcatgt ccttcaaatt gatcattttt agtcaccctt    120

tcctacaatt gcactaggac tattgaatgg gaaagcgaag aaactggttt acctttgtca    180

agagactttt cattcctgaa acagaatcaa cagcagatca aaagaaacca aagagatgga    240

gatgttgttt tctgagaaag ttcaagttga ggaaatgtcc tgctataaca tcagcacctc    300

agcaaacgtt acctgaggcg aaaggaacac ctcagcaaac gttaactgag gcgaaagaac    360

agcaaagaaa acatgctttt gcagttgcta tagcaacggc agcagctgct gaggctgctg    420

tagctgctgc taatgctgct gctgatgtta ttcgtctaac agatgctcca agtgaattca    480

aaaggaaacg caaacaagct gctattagaa tccaaagtgc ttatcgcgct cacctggccc    540

agaaagcatt aagggctcta aagggtgttg tgaagcttca agcagtgatt agaggtgaaa    600

ttgtgagagg aagactcatt gccaaactga agttcatgtt gccacttcat caaaagtcaa    660

aaacaagagt taatcaaatt agagtcccta cttttgaaga tcatcatgac aagaaactca    720

tcaatagtcc aagggaaatt atgaaagcta aagaactaaa gcttaaatgc aagagcctta    780

gcacttggaa tttcaactta gcttcagaac aagacagtga agccttgtgg tcaagaagag    840

aagaagccat tgacaaaaga gagcatttga tgaaatactc gttttcacat cgggagagaa    900

gaaacgatca aactctacaa gacttactaa acagaaagca aaacagaaga agctacagga    960

ttgaccagtt agtagaactt gacgcaccaa gaaaagcagg gttgttagag aaattgagat   1020

catttacaga ctcaaatgtt cctctaactg atatggatgg aatgacacag cttcaagtga   1080

gaaaaatgca tagatcagat tgtatagagg acctacattc tccttcttca cttccaagaa   1140

gatcattttc taatgcaaaa cgaaaatcaa acgttgatga taactcatta ccaagttctc   1200

ctatatttcc tacttacatg gcagccacag aatctgcaaa ggcaaaaaca aggtcaaaca   1260

gcacagcgaa gcaacaccta aggttacacg agacattgtc aggtcaacat tctccttata   1320

acctcaagat ttcttcttgg agattgtcta atggtgaaat gtatgacagc gccagaacaa   1380

gcagaacttc tagcagttat atgttaatat agaaggtgtt ttacaaggat tgaagaacat   1440

gagtgttgta cattattact atctttgata acgaagtgtc caagccggtt tgctctcacc   1500

tctgctagtt caccgagtgt tgttaacttc tacaagtacc agtaccagta ctaggtaact   1560

ctgttcacca aagatgaatg tgtacattat caacctgttt atgcaagcaa gggagcgcag   1620

aaactcctag atttgcagca ttacttctgg acatgaaaac aatcagaaaa atggagctat   1680

tattggagct tcaaacttct tcagtaatct atctacagtt gattgatgaa agattactgg   1740

ttttaacact tttttatata gacttgccac aatgtgtata tatagttcaa gtttttttcc   1800

ctttccctgt ttgttttccc ttgtttcatt tatttattga tttgtaaagt tgtttccatg   1860
```

```
agaccaggag gtcacagggg taagattctg tacaatagac catatggtct cgagccttca   1920

ccagaccgca catagcgggg agcttagtgc actgggctgt tgttcttttt tttttttttt   1980

gcttctgagt tgatatactg gaggaagaat tgttgtttga tggccattca cctggaagca   2040

tttccaagtt tggtaattgc atagag                                         2066
```

<210> SEQ ID NO 6
<211> LENGTH: 14067
<212> TYPE: DNA
<213> ORGANISM: Solanum lycopersicum

<400> SEQUENCE: 6

```
gatcaaaact atttaggtcc caaaattgca ttttgtagtc tagtgcaatg tgcaatagtg     60

cttaattata aatgatattt gagatgtcaa ttttagaata atggagatat atatgctggt    120

ccaccatatc ttttatcttt tacctttgtg tttcagagtt cagaccaagt tgttgcaaag    180

ttttaatttg tttacgtatc gatatagatt gtgatatagt gattgaatta ttttattttt    240

aattagagat tttaaatttg agtaaatgta tattgaaaat atcttgttga aagcatatct    300

ttaaatagat cttgcagtgt gcgatttaaa tttaatcgag attttaatgt gactcgaaat    360

atcgagtata aagtcaaaaa aaaaaatact ttgcgtgaaa aaaatcacaa agttaaaggg    420

gctatctatg tatttggcct tttctatttt attgtgtcct tttttttttt taatttgatc    480

tagttttctc tttagctttt tatttatttt ttgttttaat ttttcacgta atatatttaa    540

gattatagaa ttaataaata ttttacttcc tccgccttaa aaagagtcac caagtttggc    600

ttgacacgag aagagtaaat cttgtgattc taaattcaaa ttattttata tatagaaaat    660

tgtcttttaa tcttgtggta ttaaacatgt cacatgaaaa actaaaaata aatgttacaa    720

attaaatttt cttttcagac aaactaaaaa gaaaaaaata ctattctttt taaaataaaa    780

aaataatata cttaacatat ttttaattta aaatcataac attttaattt attttattaa    840

ataccaaaca aaataaatta aaataacttt tatctttacc tccacttttt aagtagctta    900

aattcccacc aacctacacc gtagaccttt gtaccatgag tagtgatatt aatatatttt    960

tttcgttcgt tttatattat ttgatctctg ttaatttaat atatttttga agaaaatttt   1020

aattaaaaat atattttttt aaaattaaaa atgatattct gcattttaaa tttgaatact   1080

gctattcttt ccgttttaaa ataattatca tattttattt cttaaacatc aaattaagat   1140

ataaaattat atatttaaac gcataatata atttataaat ttaaaatttt aaacgttgcc   1200

gacatcgaaa tctctgaata ataataaaag ataaagacag catgatatat gtcagatgat   1260

aattcaatta ttggtcataa ataatgacag ataataattt tgcactttat taccttttttt  1320

tttttttttt tttttgcttt ttaatgatta tttttttcac caattcaata tcacacgtat   1380

acgaaatttg acaaatgttg aagtgttata ttagctaaat tacaaatata gtactaaggt   1440

gttattatca gctttaatca atcaactatt tcaataatta atcatattac tagctcaaat   1500

tcagacaaag tgtttggtga aatgaaatat cagttaaaca ctttaacaaa taaaatttaa   1560

catttagata catgttaaac tttcgaattt cacgaaaaat ataaagattc ttgagttaat   1620

gtgtttgaat gtgcatctct ctcaaaattc aaacgtttag tactgattaa ttgacatcaa   1680

atttgaacga aaaataaaca aaaatctcac caagaccccg tctccttttt aagtttttga   1740

ccaaactaag ccattattat aactatttat tttatttata taaaaaaatt aattttttta   1800

tagattattt aacttgatga tacaaaagat cttgtgatat aatgggatga cacataataa   1860

tgatctttat catgataaaa tttgaacttg tgatataatg acacatagtc tcaatctaga   1920
```

```
tttgtccata aagaaaaatt atttaaaatt gctttttact tggtgcagta gataaaatta   1980
ttttttaaaa aaaataaatt ttaattttaa attaaatgtt aaaattaaag tattatgtga   2040
tacaatttta tttttaaaaa atcttcttat tgtaatatga actaataaat aaacttataa   2100
gatattcaac ttattttttt attttatatc ttacttctaa atttatctaa ataagaataa   2160
aaattttgaa caatataagc ataggatata aatgtctttt aaattttatg atgttaaaaa   2220
tattacgtaa gatattgaaa tttaaaagtt aagtactgat tataataaac taacctcttc   2280
cacacgacca atatcttctc attttaactg ttattttggc ttttaaaaaa ttaccatttt   2340
agaaatttaa gatttaagct atccattttt tcgacttggt tttctaatat ttttatttat   2400
ttatcattat tattgaaaga ttaaattttt tttatccctt tctgaaagtt tttttatttt   2460
tttgtgattc gaaccacgat cttaagttga aggacggaag tgaacgatgt ttactattta   2520
tcatatatct gccttttctt aacgacataa aagagttaag atgataatta aaatactatg   2580
aatggaataa tattattttt aagataaatt aaaaaataaa gagtatgtat gtatgcacat   2640
atagtttaat tcaaacgatc gataaaaaag aaaaaaaata tgtatcattt acttaattgt   2700
atcatcttcc acaaggaaaa atccctataa aaagaaaatg acatactcca tgcgtttctt   2760
tattattgta tttgtttaat cagtagtgaa attaaaaatt ttaaaaaaaa tatatttaaa   2820
atttgaaaaa taaatatacg atctagtgaa aaagggttca acatctatta tatatatcta   2880
caaaataatt ttaaccacat ataaataata atattttcac cgaagagatg aaccctaaat   2940
atatgtcgcc tccgctcctg cttctagcca tgattgaaat agctacgggt tattactttt   3000
tttcctcaat tttttaattt aattatataa aaaataaaac actttctatc aaaaattact   3060
atcgctttcg aatcatttta aaatatcttt tatattttcc gttaaagttg tcaatattgt   3120
catgccatta tattttttct tagtagtcct cgttaaagtt gtcaatattg tcatactgta   3180
atattttttt aaatatattt ttaaatgtaa taaaaatatt tgatctaaca atattatgtt   3240
gtcatttgat aatcgatggg ttgtgcagtt tgggtcaatt agtgtggctt gtacattttt   3300
tttttatttt tactaaatta aaaactttat gaaattaaaa actttattaa atttataatt   3360
aatattgtta ttgaaaaaat gaaaaagtaa gacacataat aaattgcaaa gtagggagtt   3420
attactgtaa caaaaatatt attagcaata attaattttt aattatttat taaatattta   3480
tttttagcga caattatcac tctttgtata tgtctctaaa gcctttagcg acattaattc   3540
taatgacact taactaatgt tgataaaaac tttaaaactt ttatgtcaat atttaatgtc   3600
gctaaaaatt aattttatta cagtgaatgt acttttatgc tttatgaaaa caataatata   3660
tatacggttg cattcttttg aataatttac actatgattg ttcaaagata tgtaatatta   3720
ctaattttgt ttgtaaaact aaacttataa tctttatgtg tgtatttctt gtttttctaa   3780
aatattatgg ataaaatctg tttttggacc tctaattttt actatcttta tttctaacaa   3840
ttattattat tattactatt attattatta ttattattat tattatgaga agtttatttt   3900
tttaaactcc tttaggagct tctatcattt tttgctcatt taatgactcg aatctacaat   3960
tttaaattag aaataaaaat atttattatc tgatcaatcc cctcttaaca aacatatcct   4020
taacactaga gaaatatata gtttatttat ttatttaaca atattcaaat tctcaaaatc   4080
atctaataat taaataggaa taacttaata aataatacct tatatcttgt ttttcttaat   4140
gacattagaa aaagaagcta aaaataaaac aatacaaaag tgataatatt ctttttaaaa   4200
ataaatttaa aaagtctaaa ttaaaacaca tgtgatatat acttagttta atccaaacta   4260
tgaataaaaa agaatttttt ttttatcttc cacaagataa gactttagag ctctataaaa   4320
```

```
ccacatgtat actagtctaa atatctctca cattacatta aaaaaaataa attattattt   4380

cttctctctc tcaaaaaaat tgtgaaaatg gcacaatcca ttcgtttctt tgctactttg   4440

tttcttctag ccatgcttgt tatggctact ggttagactt ctatcttttt tatttaggtt   4500

acgttcaaaa tttattagct tttcgatatt atgtcgataa tgttatcgaa taaatcactt   4560

tctatcaaaa atatcgataa ttcaagtcat ctcctcacat tttttagtta tttctagtaa   4620

aaaatttaaa tatcgtacca taatatttgt tgtgcggaat ttgagataat acgagaaaat   4680

ataaacgcga aaaataagac aacagattta cgtggttcac caacaaattg gctacgtcca   4740

cgggaagaga gggagcagtt ttattatgga gaggcaaaaa cagaattaca gaatagggtt   4800

tcccatagcg tctatatata gtgctaagct acgccctaac aggcttgggc ccaacataca   4860

gaatcaacag aaaattaagg gcccaataca acaacattgt ataccgtcgg cccgggggcg   4920

tctccgcccc cccggacccc caggccaggg ggcgcgtcgc cccccctggac cccccgactc   4980

gctgaccggg cagcgagacc cccgtccttt ctgtttgtag cgggtccgat tcaaggcatt   5040

caacagacct aatttgactt aaaacggaat ttaagaaaag aaagaaattt ttttaatctt   5100

atggttctaa atcaaagttg tgtcaaatgt atcaaaatgc gttttaatct tgtggtcttt   5160

ttcatatcac gtggaaagtt aaaattaaaa tgttactgaa aaaagaaaag ggtcattctt   5220

ttttaaacag actaaaaaat gaaataaaat tattcttttt aaaacgaagg ggataataaa   5280

caataacaac aagaagtaaa atgtcgcaaa ttacccaaca tgttgcacaa aaatctgttc   5340

aattaatgtt ctcttcatga cttaattctt attaaagatg gatagctttg atagaaagcg   5400

ttttatccct gacattttaa gatgagactt ttcgatacga atctagattt aatcagatcc   5460

taacacgggt acgattcaca ggttaaatca gtaaataaat tcaaagcaga aagagacatt   5520

tgaaaaggtc aattcacagt taggaaaatg acagttagaa aataaggaca gagggccctt   5580

taataagaag tatatgatgt taaaagagac ttcccacaag tcacctccaa aagtagttaa   5640

aaataataga aagttgaaac atcaattctt ttttcccttt taataaccgc gatgttcaag   5700

tcagctttcg cgcgcctcaa cttataattc caagaaatat ctgtcattgg aatcgcttac   5760

tatttttgaa tttccaaaaa tagatcaaaa taactgggga tattatgtga tttattagta   5820

ttctaaatct tagtttcttt cgcgtgccgt accttaggat tcgtgctatt gctaggtaac   5880

tctgtccatc aagaccgaaa caaatgagaa aaatcaccta gtgtattttt ttgtctccgc   5940

aactgttgtc taaaggtacc ttttttcact cttcaatata tttcatatac tccacggcac   6000

atggtgtggt tctcaaagca taagtgaggt cagtgtttct tactggatat aaatagacat   6060

aaatttgggg agaaaatgaa accacatgga acaacaaaac aacactatta ttattattat   6120

tcaagaatca ctagcaagac tggttaatta atgttaccaa attttgcatg tccttcaaat   6180

tgatcatttt tagtcaccct ttcctacaat tgcactaggt atgtgtttta aattttgtga   6240

ttactcatat tattaatata tgattccaag attgtaagct catttagcca tcacatgaac   6300

aattttgctg atgtaagaca attgttgttt tctgctgtta tagtaggtta aagaatagac   6360

taatgaaacc cctctcgtga gatagttttt ggagttgagg tagacttaga taccttatag   6420

tttacatggt atcagagtta cgttgatccg agctcctagt ccatggtctt agagtggatt   6480

agagtcttac atggacttgg gaaatccttc cctcacgctc caatttgctt atattacgcg   6540

agatgctagc tgtcctattg aggcagtttt tgtttttata ttgtagctct gcagcatttt   6600

gttgtatatg gaatagaaat gcctctgaaa tacttttcta tatctgtttg attgctgaag   6660

gactattgaa tgggaaagcg aagaaactgg tttacctttg tcaagagact tttcattcct   6720
```

```
gaaacagaat caacagcaga tcaaaaggtt tgaatttcaa gatttctgtt gcttagtagt   6780
gtgagtgaat cttcggatat ctaaactgga aatttatgaa aaatatttca gaaaccaaag   6840
agatggagat gttgttttct gagaaagttc aagttgagga aatgtcctgc tataacatca   6900
gcacctcagc aaacgttacc tgaggcgaaa ggaacacctc agcaaacgtt aactgaggcg   6960
aaagaacagc aaagaaaaca tgcttttgca gttgctatag caacggcagc agctgctgag   7020
gctgctgtag ctgctgctaa tgctgctgct gatgttattc gtctaacaga tgctccaagt   7080
gaattcaaaa ggaaacgcaa acaagctgct attagaatcc aaagtgctta tcgcgctcac   7140
ctggtaaaac atcctctctg gtagctctag tactttcact catacaattt cactgtgaac   7200
ttgttgcaga gacgctttta aatgcagaaa gattgaaaat tagttagtca ttcaagacaa   7260
aacttaaagg atagtatggg aaaaggtagg ccagtttgga tatagcagga ttaaacgccc   7320
agtgctctac cagctgagct acacacctaa aaaatgataa tcaagtaaac aagtattgat   7380
acagaaaaaa ggcctgcccc tttactctca tcttattaaa ggagcacgac tatttattat   7440
gaggcttgta ctacagagca agtggaagct ccgaaggtca cacttttttt ttttttttgc   7500
cttttggctg ttaatcatat tagtcataag gtagtctatc acctcggttg gaaagaaaat   7560
cttattggtt ggaaaatccc tctccgctag taaaactctt ctcttatggc ggctactaat   7620
tctttttcct ttcatctctc aaaaaaactt tccgagattt ggtgaaatga actggtgtct   7680
gatctatgtc cctgtgaaat gttgtgcagg cccagaaagc attaagggct ctaaagggtg   7740
ttgtgaagct tcaagcagtg attagaggtg aaattgtgag aggaagactc attgccaaac   7800
tgaagttcat gttgccactt catcaaaagt caaaaacaag agttaatcaa attagagtcc   7860
ctacttttga agatcatcat gacaagaaac tcatcaatag tccaagggaa attatgaaag   7920
ctaaagaact aaaggtaaga tcaatcattc attctctttt gtttaattaa gtttccaaac   7980
attagttcaa ctatactaaa tctataaaag agacctacta acacatctta ttatgacttt   8040
tatggtttgg aactgtaata tggtttttg ttttttggc agcttaaatg caagagcctt   8100
agcacttgga atttcaactt agcttcagaa caagacagtg aagccttgtg gtcaagaaga   8160
gaagaagcca ttgacaaaag agagcatttg atgaaatact cgttttcaca tcgggtaaag   8220
tcattacttg ttatacagac actgcaatta cacttgtcaa tgtattataa aatgttgtag   8280
cagttaacct gccttatttt ctagaatact aatctcacat tttatgaacg attatttata   8340
atatattttt aggtaagctg atagtatatt gcttctttta ggagagaaga aacgatcaaa   8400
ctctacaaga cttactaaac agaaagcaaa acagaagaag ctacaggatt gaccagttag   8460
tagaacttga cgcaccaaga aaagcagggt tgttagagaa attgagatca tttacagact   8520
caaatgttcc tctaactgat atggatggaa tgacacagct tcaagtgaga aaaatgcata   8580
gatcagattg tatagaggac ctacattctc cttcttcact tccaagaaga tcattttcta   8640
atgcaaaacg aaaatcaaac gttgatgata actcattacc aagttctcct atatttccta   8700
cttacatggc agccacagaa tctgcaaagg caaaaacaag gtcaaacagc acagcgaagc   8760
aacacctaag gttacacgag acattgtcag gtcaacattc tccttataac ctcaagattt   8820
cttcttggag attgtctaat ggtgaaatgt atgacagcgc cagaacaagc agaacttcta   8880
gcagttatat gttaatatag aaggtgtttt acaaggattg aagaacatga gtgttgtaca   8940
ttattactat ctttgataac gaagtgtcca agccggtttg ctctcacctc tgctagttca   9000
ccgagtgttg ttaacttcta caagtaccag taccagtact aggtaactct gttcaccaaa   9060
gatgaatgtg tacattatca acctgtttat gcaagcaagg gagcgcagaa actcctagat   9120
```

```
ttgcagcatt acttctggac atgaaaacaa tcagaaaaat ggagctatta ttggagcttc   9180
aaacttcttc agtaatctat ctacagttga ttgatgaaag attactggtt ttaacacttt   9240
tttatataga cttgccacaa tgtgtatata tagttcaagt ttttttccct ttccctgttt   9300
gttttccctt gtttcattta tttattgatt tgtaaagttg tttccatgag accaggaggt   9360
cacaggggta agattctgta caatagacca tatggtctcg agccttcacc agaccgcaca   9420
tagcggggag cttagtgcac tgggctgttg ttcttttttt ttttttttgc ttctgagttg   9480
atatactgga ggaagaattg ttgtttgatg gccattcacc tggaagcatt tccaagtttg   9540
gtaattgcat agaggtttaa tctttgcctt ctgtatttac ataggtttat ttcttttgat   9600
ttcttccttc aaagttcaaa ccacctcttt attatttcat gtaaaatcct tcaaaaaaaa   9660
atgaacttac accaaaattt atgtcttacc tttcttacaa aaccattgat gttgaaacta   9720
aggaaaatgg attggaccaa ccatatgtag aagaaatata gcaagtttac tccaactttc   9780
actacttatg ttaacacatt gaacacttga gaaacaaaat ccattggaag ctcctcattt   9840
ctacaggctt aaaatgtcta tggtatatcc aatgtaacag aataacacat gtgaggcaca   9900
ctgttctcct caactgagat tgacagattt cacatactac aaatttgtaa acttttggaa   9960
cataacgcaa taggcaagat aatgacattt gacaagaagt atcaactgta atgctcaaat  10020
taccagataa gtgaatgaga tagtcggaaa tgtctgatcc acgacgataa aatctatacc  10080
agtaaaagta gccctcctgt atgttttgaa ctaatgataa cattcagtcc agcaacaact  10140
ctgctgacct caaatctaga agccaaataa aattacttga ccatgaggct tagatattgg  10200
ttgttcgagg tttagatatt ccatcttcta tacagcataa agtagtgaat agatttcctt  10260
ttaacttata cacgtattag ttgtaattga ttctaacttg ctaaccaaaa gttgtgttta  10320
gtgtgttgaa ttttatatat tagcaaaaaa ttactgcccc aaatatggta caaattctgc  10380
ggtgatttaa tacatgaatg actcacatcc taaccagcaa ccaaacatac atattttact  10440
gttggttttg gctctgttca tgcttttaat gagtgcagtt gggctggaga attagcacct  10500
catttttttcg catgttttc tctaaatgaa gaattgcaat cttatagttg gtcttcacta  10560
ttctttctcc ccccgccctc tttattttct tgtagttaaa ttattctata tcagtatcct  10620
aagagacttg ttacctttgc ttgatgttag atatcgatta ctacaagtac ttccgctggc  10680
ttagagcaga tcctgccatg gatgttttat cataaggtca ttggcgtgac aaactttttc  10740
ctgtttgtgg agggaaaagc tgcatctccc gatgtatcta aagtgctaaa atctattcca  10800
gtaagtgttc atatctcctt aatatttcca ttgtcgtgtt gaacattttg tttcatcact  10860
tctaccattt tgtgtatttg gacttgtcgt atttcttctg ttgattatat acaaaatgtg  10920
tgtgctctgc agggtgtaag agttatatat agaacaaaag aactagagaa tgtacaagcc  10980
aaaaggtaag cggtctttgc ctatatatac attttctgtg cctaaactat gaagatgagg  11040
tctttgttca gtagagtaga cgttatttcc tattgctttg agaaatgttt ttatcccttc  11100
cgtgggttta tgttctttat ttagcctcgt atgattcatt ttctttatgt tgctaatgga  11160
tgcaagtaat agtcgatgat agaaactatt tatccaaagc aaagcttatt gacgaacata  11220
tgttagcatg ggtcaacaag tttccaaaac ttgttgggag ttccttacat agcaacgtaa  11280
tatatatcag gagtaactac aatgcacggg tggagggggt tgatgtggac cgtctaattt  11340
acctattaat agcaagcagt aattaccttg ggtagtggtg acaacagatt ctctattcta  11400
tttgtcttga gactaataat agacttggtt cctagaaggg aaagagggaa ggttaaatga  11460
gagtgaagtt cattgattat ttaccctacg tggagcaccg agtatttaat tcactttatt  11520
```

```
tgatgtattg gaaggtaagt aaataagaca tacttctctc agtccccctt ggtaaacaag  11580

agaaataact ctttcacctc tcgtctccca accctttctc ctttcaaccc aagcgacatt  11640

gtatgacgta tgtttcaagt cattcatctt gagtaagctt ggatctgttt tgagtgtaat  11700

atgactaatg tagtgaaaaa tggtaataga ctttaatgaa gaagtgatta ttcaagttac  11760

taacttaaat agaactaaat ttggagagtg aaatttccat acaagctagt aaaaatgctc  11820

tgttccctat atttcatctc acgtctcaat taagtaagct tattatctga catactgatg  11880

atctataatg tgttgtgtcc tagtcggatt tggaatgaga cgtggctggc tggattcttt  11940

taccaaccat gcaaccatga gttatttgtc aagcagactc ttaacatgga aatggccatc  12000

gtcatggcaa gggtatgatt gcaataactt ccatctgttt ccagttatgg ttaccttttg  12060

atccactata ttgcctagta actctacagg aagctggcgt ggactggatc attcatctcg  12120

acaccgatga gctaatgcat ccagctggaa ctagtgagta ttctttacgg aaacttttgg  12180

cagatatacc tgaagatgtt gacatggtca tctttcctaa ctatgtaagt aattgagctc  12240

taggctgtct tttaactgtg tctaagcatg taattacatg ccgaatagtc aaaacgcatg  12300

catttgattc gttttcattt tctgcggtct tttttcatgt caatatcttc tctgatgatg  12360

acaaatattt caggagagca gtgttgagag agatgatgtg aaggaacctt ttagtgaagt  12420

aagatatctt tcactgtatc cttttttctt atctttcaag ttctagtatt aaaattcaat  12480

cgtttggcta ggaacatcct ccacctctat acatgaataa atttagattt tcttaaaata  12540

aatttggata attctattac ccaatacttg agaatggagc aacagctagt agtcaaagag  12600

tcaccgcttt ccagacgaat gaaaaagaag gttgcgttgg agttagacat tgtggaggca  12660

agaaaggaaa attgtaccta gcgaacacaa ggagcttgag tgttaaaatt ttttagagag  12720

agtttgcgta gtctgtaatt tattttaatt attgtgcaac taaagttctt ttagactgtt  12780

taccagcaat gcatctgtat catgtggtag gtctcgatgt tcaagaagaa ttatgaccat  12840

ctcacaaagg aaatgtactt tggaagctac aaggaagcaa ctcgtggtaa tcccaactac  12900

tttttgactt atggaaatgg caaatcagct gctcgagttc aagatcatct tcgtcctaat  12960

ggtgctcata gatggcacaa ctacatgaaa agcccaaagt atgcttgttc tgcatgttac  13020

ttgttttcct ttatctctat ttcgtttctt atttattccc agtcctatag aatcactgtt  13080

ttatcgaagt tgaaaacata cttgtaatgt tgtcatattt tttcacttct ttggtgtgat  13140

tgtcttcgct tgtataatga aaatgtattt tcttattatt gtagagagat caaactggga  13200

gaggctgctg ttttgcacta cacatacccc aaattttcag atttaacctc acgacgagat  13260

cgttgtggat gtaaacctac taaagaagat gtgaaaagat gcttcatgct agaattcgac  13320

agagctgtga gtaataggca gtctgttatt aaaacaacaa atgtttttgg ggtcaaaaag  13380

atggactgta tagtttgttt gttgataatt ttcatcttca cattgcaggc ttttataata  13440

gcttcgactc tgacagagga ggagatgctt gactggtagt aattctttta acttccattc  13500

catcgaattc atgctaatcc ttatactact tatttcgtga aatccttccc ttgttatact  13560

gtaaaatctt atttcatact gatctgtagt ccgcgtggtg cttgatttct ttttggtttg  13620

tatattatgc tgacagaacc tttattggat taggtaccgt gaacatgttg tttggacgga  13680

taaaacactc atccagaagc ttatcaagaa gggcatattg acgcgcatat atactcccat  13740

ggtaagatca acttatattt gattgcggaa gctccttttg agtttatatt gagggtcatg  13800

aatcctaaga agctgaactc atagtaactt ttgtttttcg gtctgtgtag gccattgtac  13860

agggtttgaa ggaatctggt gttttcgttt ctattattgc ttcagcacat agagatgtca  13920
```

```
taaaagacga gtctctatct tcttctgctg gaaacagaaa tgcttccgga tatcctcata  13980

ttactgatac ttttcccaga aagatgggtc gtatattgga atctcaatca actgcaagga  14040

aattcgtgga ctttagtaca actgatc                                      14067


<210> SEQ ID NO 7
<211> LENGTH: 327
<212> TYPE: PRT
<213> ORGANISM: Solanum lycopersicum

<400> SEQUENCE: 7

Met Ala Ile Glu Ser Pro Asp Ala Glu Phe Gly Val Arg Phe Arg Pro
1               5                   10                  15

Thr Asp Glu Gln Leu Ile Arg Tyr Leu Ile Lys Phe Val Val Ser Lys
            20                  25                  30

Asn Tyr Val Cys Lys Asp Ile Glu Phe Glu Glu Leu Tyr Gly Ser Lys
        35                  40                  45

Lys Pro Trp Glu Leu Leu Glu Asp Ser Ser Gly Thr Lys Tyr Phe Phe
    50                  55                  60

Thr Lys Leu Lys Lys Arg Asp Thr Arg Phe Ser Arg Thr Leu Val Gly
65                  70                  75                  80

Gly Gly Ser Trp Lys Gly Lys Ser Lys Gly Lys Ser Ile Gly Ala Lys
                85                  90                  95

Lys Ile Gly Met Lys Lys Thr Tyr Asn Tyr Glu Glu Asn Lys Lys Asp
            100                 105                 110

Val Val Asn Asp Val Ser Trp Ile Met Lys Glu Tyr Ser Leu Asp Asp
        115                 120                 125

Lys Val Ile Lys Leu Leu Ser Asn Arg Gly Val Met Lys His Lys Asp
    130                 135                 140

Val Val Leu Cys Tyr Ile Arg Cys Lys Val Lys Lys Ser Arg Asn His
145                 150                 155                 160

Met Pro Thr Thr Thr Gly Ser Gly Tyr Asp Asp Gly Asp Gly Asp Asp
                165                 170                 175

Thr Leu Leu Leu Pro Gln Gly Pro Asn Glu Phe Gly Tyr Gly Asp Gln
            180                 185                 190

Phe Pro Gln Gln Ile Val Asn Pro Met Gln Asn Val Gly Ser Gly Tyr
        195                 200                 205

Val Gly Cys Asp Asp Thr Leu Val Pro Gln Gly Pro Asn Glu Phe Gly
    210                 215                 220

Tyr Ser Asp Gln Leu Pro Gln Gln Ile Val Lys Pro Met Gln Asn Ile
225                 230                 235                 240

Glu Ser Gly Tyr Val Gly Cys Asp Asp Glu Asn Arg Asn Asp Met Thr
                245                 250                 255

Thr Gln Pro Gln Trp Pro Met Glu Asp His Gln Leu Ser Gln Leu Ile
            260                 265                 270

Val Thr Phe Pro Met Val Gln Gly Asn Asp Ala Ala Met Asn Glu Gly
        275                 280                 285

Asn Met Asn Gly Glu Leu Val Phe Pro Tyr Gln Glu Glu Gln Val Leu
    290                 295                 300

Gln Asn Val Glu Glu Thr Ala Gly Met Ala Ile Ser Val Ala Leu Leu
305                 310                 315                 320

Val Tyr Phe Leu Ser Thr Met
                325


<210> SEQ ID NO 8
```

<211> LENGTH: 486
<212> TYPE: PRT
<213> ORGANISM: Solanum lycopersicum

<400> SEQUENCE: 8

```
Met Glu Gly Gln Thr Gly Gln Gln Glu Glu Leu Phe Val Glu Ile Asp
1               5                   10                  15

Gln Lys Thr Asp Asp Gln Thr Tyr Ser Asp Gly Glu Ala Ala Ser Cys
            20                  25                  30

Thr Thr Asp Gly Asn Glu Ile Val Asn Val Ile Val Thr Ser Asp Pro
        35                  40                  45

Ile Leu Gln Gly Glu Ser Met Pro Arg Arg Tyr Thr Tyr Ser Trp Arg
    50                  55                  60

Arg Arg Ile Gln Lys Val Leu Pro Leu Leu Lys Thr Asp Glu Tyr Asn
65                  70                  75                  80

Arg His Glu Tyr Asp Pro Lys Val Val Ser Leu Gly Pro Tyr His His
                85                  90                  95

Gly Lys Thr Glu Leu Gln Leu Ala Glu Asp Phe Lys His Ile Ala Leu
            100                 105                 110

Glu Met Phe Val Ser Gly Ser Ser Arg Asp Val Ala Tyr Phe Tyr Asn
        115                 120                 125

Lys Ile Leu Glu Val Val Asp Asn Ala Arg Ser Cys Tyr Val Asp Gly
    130                 135                 140

Ser Thr Asp Lys Tyr Asn Asp His Glu Phe Ala Leu Met Met Leu Leu
145                 150                 155                 160

Asp Ala Cys Phe Ile Ile Asn His Ile Glu Leu Ser Thr Thr Asp Arg
                165                 170                 175

Tyr Asn Lys Leu Arg Thr Thr Arg His His Leu Gly Met Leu Ala Leu
            180                 185                 190

Ser Thr Thr Val Arg Asp Met Phe Leu Leu Glu Asn Gln Ile Pro Phe
        195                 200                 205

Trp Ile Leu Lys Leu Leu Ile Ser Leu Arg Tyr Asp Lys Asp Glu Gly
    210                 215                 220

Asp Glu Leu Leu Glu Met Phe Leu Asn Phe Thr Leu Phe Gly Glu Tyr
225                 230                 235                 240

Glu Gln Glu Gly Glu Met Ser His Asn His Val Glu Glu Pro Leu His
                245                 250                 255

Leu Leu Glu Ala Phe Arg Thr Arg Leu Val Ser Gln Gln Ser Glu Val
            260                 265                 270

Arg Ser Phe His Arg Thr Cys Thr Pro Gln Trp Leu Lys Arg Lys Lys
        275                 280                 285

Ser Ile Ser Asn Glu Arg Val Asn Met Lys Ser Tyr Ile His Ser Phe
    290                 295                 300

Arg Ser Val Thr Asp Leu Lys Ala Lys Gly Ile Gln Phe Lys Pro Ser
305                 310                 315                 320

Cys Thr His Ser Leu Lys Asp Ile Lys Phe Lys Ser Arg Tyr Phe Tyr
                325                 330                 335

Gly Gln Leu Val Leu Pro Thr Trp Tyr Val Ser Ile Tyr Thr Lys Ala
            340                 345                 350

Phe Phe Leu Asn Met Ile Ala Tyr Glu Met Cys Pro Asn Thr Val Thr
        355                 360                 365

Asp Arg Ala Val Thr Ser Tyr Val Tyr Phe Met Lys Ser Leu Ile Glu
    370                 375                 380

Ser Pro Arg Asp Val Lys Glu Leu Arg Glu Met Gln Ile Leu Phe Asn
385                 390                 395                 400
```

```
Met Leu Gly Ser Asp Glu Glu Val Ala Arg Met Tyr Lys Glu Ile Asn
                405                 410                 415

Thr Tyr Gly Val Asn Asn Ala His Ile Phe Tyr Asn Val Lys Glu Lys
            420                 425                 430

Ile Gln Glu His Tyr Asn Asn Lys Ala Lys Thr Trp Ile Ala Glu Leu
        435                 440                 445

Ile His Thr Tyr Phe Arg Ser Pro Trp Thr Ala Leu Ala Leu Leu Ala
    450                 455                 460

Ala Thr Phe Leu Leu Cys Leu Thr Phe Thr Gln Thr Tyr Phe Thr Ile
465                 470                 475                 480

Asn Pro Asn Pro Arg Leu
                485


<210> SEQ ID NO 9
<211> LENGTH: 1307
<212> TYPE: PRT
<213> ORGANISM: Solanum lycopersicum

<400> SEQUENCE: 9

Met Ser Ala Leu Asn Val Lys Ile Asp Lys Phe Thr Gly Arg Asn Ser
1               5                   10                  15

Phe Ser Leu Trp Gln Ile Lys Met Arg Ala Leu Leu Lys Gln Gln Gly
            20                  25                  30

Phe Trp Ala Pro Leu Ser Lys Asp Lys Asn Ala Val Val Thr Pro Glu
        35                  40                  45

Met Ala Ile Leu Glu Glu Lys Ala His Ser Thr Ile Met Leu Cys Leu
    50                  55                  60

Ala Asp Asp Val Ile Thr Glu Val Ser Asp Glu Glu Thr Ala Ala Gly
65                  70                  75                  80

Leu Trp Leu Lys Leu Glu Ser Leu Tyr Met Thr Lys Ser Leu Thr Asn
                85                  90                  95

Lys Leu Leu Leu Lys Gln Arg Leu Phe Gly Leu Arg Met Ala Glu Gly
            100                 105                 110

Thr Gln Leu Arg Glu His Leu Glu Gln Leu Asn Thr Leu Leu Leu Glu
        115                 120                 125

Leu Arg Asn Ile Asp Val Lys Ile Glu Asp Glu Asp Ala Ala Leu Ile
    130                 135                 140

Leu Leu Val Ser Leu Pro Met Ser Phe Glu Asn Phe Val Gln Ser Phe
145                 150                 155                 160

Ile Val Gly Lys Asp Thr Val Ser Leu Glu Glu Val Arg Ser Ala Leu
                165                 170                 175

His Ser Arg Glu Leu Arg His Lys Ala Asn Gly Thr Ser Thr Asp Ile
            180                 185                 190

Gln Pro Ser Gly Leu Phe Thr Ser Ser Arg Lys Gly Arg Lys Asn Gly
        195                 200                 205

Gly Lys Lys Asn Lys Pro Met Ser Lys Gly Ala Lys Pro Asp Asp Val
    210                 215                 220

Cys Asn Tyr Cys Lys Glu Lys Gly His Trp Lys Phe Asp Cys Pro Lys
225                 230                 235                 240

Lys Lys Lys Gln Ser Glu Lys Gln Ser Val Ser Ala Ala Val Ala Glu
                245                 250                 255

Glu Asp Thr Asn Ser Glu Glu Asp Ile Ala Leu Val Ala Asp Glu His
            260                 265                 270

Thr His His Ser Asp Val Trp Val Leu Asp Ser Gly Ala Ser Tyr His
        275                 280                 285
```

```
Ile Cys Pro Arg Arg Glu Trp Phe Thr Thr Tyr Glu Gln Val Asp Gly
    290                 295                 300

Gly Ser Ile Ser Met Ala Asn Ser Ser Val Cys Lys Val Val Gly Thr
305                 310                 315                 320

Gly Ser Ile Lys Ile Arg Thr His Asp Gly Ser Phe Cys Thr Leu Asn
                325                 330                 335

Glu Val Arg His Val Pro Leu Met Thr Lys Asn Leu Ile Ser Leu Ser
            340                 345                 350

Leu Leu Asp Ser Lys Gly Phe Ser Trp Ser Gly Lys Asp Gly Val Leu
        355                 360                 365

Arg Val Trp Lys Gly Ser Asn Leu Ile Leu Lys Gly Val Met Arg Gly
    370                 375                 380

Thr Leu Tyr Phe Leu Gln Gly Ser Thr Val Thr Gly Ser Ala His Val
385                 390                 395                 400

Ala Ser Ser Glu Phe His Gln Lys Asp Met Thr Lys Leu Trp His Ile
                405                 410                 415

Arg Leu Gly His Met Gly Glu Arg Gly Met Gln Ile Leu Ser Lys Glu
            420                 425                 430

Asp Leu Leu Ala Gly His Lys Val Lys Ser Leu Glu Phe Cys Glu His
        435                 440                 445

Cys Val Phe Gly Lys Leu His Arg Asn Lys Phe Pro Lys Ala Ile His
    450                 455                 460

Arg Thr Lys Gly Thr Leu Asp Tyr Ile His Ser Asp Cys Trp Gly Pro
465                 470                 475                 480

Cys Arg Val Glu Ser Leu Gly Gly Cys Arg Phe Phe Val Ser Ile Ile
                485                 490                 495

Asp Asp Tyr Ser Arg Met Thr Trp Val Tyr Met Met Lys His Lys Ser
            500                 505                 510

Glu Ala Phe Gln Lys Phe Lys Glu Trp Lys Ile Leu Met Glu Asn Gln
        515                 520                 525

Thr Gly Lys Lys Ile Lys Arg Leu Arg Thr Asp Asn Gly Leu Glu Phe
    530                 535                 540

Cys Trp Ser Glu Phe Asp Gln Phe Cys Lys Asp Glu Gly Ile Ala Arg
545                 550                 555                 560

His Arg Thr Val Arg Asn Thr Pro Gln Gln Asn Gly Val Ala Glu Arg
                565                 570                 575

Met Asn Gln Thr Leu Leu Glu Arg Ala Arg Cys Met Leu Ser Asn Ala
            580                 585                 590

Gly Leu Asp Arg Arg Phe Trp Ala Glu Ala Val Ser Thr Ala Cys Tyr
        595                 600                 605

Leu Ile Asn Arg Gly Pro His Thr Gly Ile Gln Cys Lys Thr Pro Met
    610                 615                 620

Glu Met Trp Ser Gly Lys Ala Ala Asp Tyr Ser Asn Leu Lys Ala Phe
625                 630                 635                 640

Gly Cys Thr Ala Tyr Tyr His Val Ser Glu Gly Lys Leu Glu Pro Arg
                645                 650                 655

Ala Lys Lys Gly Val Phe Val Gly Tyr Gly Asp Gly Val Lys Gly Phe
            660                 665                 670

Arg Ile Trp Ser Pro Ala Glu Lys Arg Val Ile Met Ser Arg Asn Val
        675                 680                 685

Val Phe Asp Glu Ser Pro Leu Leu Arg Thr Ile Val Lys Pro Thr Thr
    690                 695                 700

Thr Ser Glu Thr Gly Ser Leu Asp Lys Gln Val Glu Phe Gln Val Ile
```

```
705                 710                 715                 720

Gln Asn Glu Ser Asp Leu Lys Glu Pro Glu Glu Glu Asp Gln Glu Pro
                725                 730                 735

Gln Thr Glu Thr Asp Ile Pro Glu Ser Met Pro Ser Asp Ile His Gln
            740                 745                 750

Ser Ile Ala Gln Asp Arg Pro Arg Arg Val Gly Val Arg Pro Pro Thr
        755                 760                 765

Arg Tyr Gly Phe Glu Asp Met Val Gly Tyr Ala Leu Gln Val Ala Glu
    770                 775                 780

Glu Val Asp Thr Ser Glu Pro Ser Thr Tyr Lys Glu Ala Ile Leu Ser
785                 790                 795                 800

Ser Asp Ser Glu Lys Trp Phe Ala Ala Met Gly Asp Glu Met Glu Ser
                805                 810                 815

Leu His Lys Asn Gln Thr Trp Asp Leu Val Ile Gln Pro Ser Gly Arg
            820                 825                 830

Lys Ile Ile Thr Cys Lys Trp Val Phe Lys Lys Lys Glu Gly Ile Ser
        835                 840                 845

Pro Ala Glu Gly Val Lys Tyr Lys Ala Arg Val Val Ala Arg Gly Phe
    850                 855                 860

Asn Gln Arg Glu Gly Val Asp Tyr Asn Glu Ile Phe Ser Pro Val Val
865                 870                 875                 880

Arg His Thr Ser Ile Arg Val Leu Leu Ala Ile Val Ala His Gln Asn
                885                 890                 895

Leu Glu Leu Glu Gln Leu Asp Val Lys Thr Ala Phe Leu His Gly Glu
            900                 905                 910

Leu Glu Glu Glu Ile Tyr Met Thr Gln Pro Asp Gly Phe Gln Val Pro
        915                 920                 925

Gly Lys Glu Asn His Val Cys Lys Leu Lys Lys Ser Leu Tyr Gly Leu
    930                 935                 940

Lys Gln Ser Pro Arg Gln Trp Tyr Lys Arg Phe Asp Ser Tyr Met Val
945                 950                 955                 960

Lys Leu Gly Tyr Thr Arg Ser Ser Tyr Asp Cys Cys Val Tyr Tyr Asn
                965                 970                 975

Arg Leu Asn Asp Asp Ser Phe Ile Tyr Leu Val Leu Tyr Val Asp Asp
            980                 985                 990

Met Leu Ile Ala Ala Lys Lys Lys  Tyr Asp Ile Gln Lys  Leu Lys Gly
        995                 1000                1005

Leu Leu  Ser Ala Glu Phe Glu  Met Lys Asp Leu Gly  Ala Ala Arg
    1010                1015                1020

Lys Ile  Leu Gly Met Glu Ile  Ile Arg Asp Arg Glu  Arg Arg Lys
    1025                1030                1035

Leu Phe  Leu Ser Gln Arg Ser  Tyr Ile Gln Lys Val  Leu Ala Arg
    1040                1045                1050

Phe Gly  Met Ser Ser Ser Lys  Pro Ile Asp Thr Pro  Ser Ala Ala
    1055                1060                1065

Asn Ile  His Leu Thr Ala Met  Phe Ala Pro Gln Ser  Glu Glu Glu
    1070                1075                1080

Lys Glu  Tyr Met Ser Arg Val  Pro Tyr Ala Ser Ala  Val Gly Ser
    1085                1090                1095

Leu Met  Tyr Ala Met Val Cys  Thr Arg Pro Asp Leu  Ala His Ala
    1100                1105                1110

Val Ser  Val Val Ser Arg Phe  Met Gly Gln Pro Gly  Arg Glu His
    1115                1120                1125
```

```
Trp Gln  Ala Val Lys Arg Ile  Phe Arg Tyr Leu Arg  Gly Thr Ser
    1130                 1135                 1140

Asp Val  Gly Leu Ile Tyr Gly  Gly Asp Thr Gln Cys  Leu Val Thr
    1145                 1150                 1155

Gly Tyr  Ser Asp Ser Asp Tyr  Ala Gly Asp Val Asp  Thr Arg Arg
    1160                 1165                 1170

Ser Met  Thr Gly Tyr Val Phe  Thr Leu Gly Gly Ser  Val Val Ser
    1175                 1180                 1185

Trp Lys  Ala Thr Leu Gln Pro  Thr Val Thr Leu Ser  Thr Thr Glu
    1190                 1195                 1200

Ala Glu  Tyr Met Ala Leu Thr  Glu Ala Ala Lys Glu  Gly Ile Trp
    1205                 1210                 1215

Leu Lys  Gly Leu Val Ser Asp  Leu Gly Leu His His  Asp Gln Ala
    1220                 1225                 1230

Thr Val  Tyr Cys Asp Ser Leu  Ser Ala Ile Cys Leu  Ala Lys Asp
    1235                 1240                 1245

Gln Val  His His Glu Arg Thr  Lys His Ile Asp Val  Arg Tyr His
    1250                 1255                 1260

Phe Leu  Arg Ser Glu Lys Arg  Ile Lys Val Lys Lys  Val Gly Thr
    1265                 1270                 1275

Ala Asp  Asn Pro Ala Asp Met  Phe Thr Lys Pro Val  Pro Gln Ser
    1280                 1285                 1290

Lys Phe  Gln His Cys Leu Asp  Leu Leu Asn Ile Arg  Ser Cys
    1295                 1300                 1305


<210> SEQ ID NO 10
<211> LENGTH: 76
<212> TYPE: PRT
<213> ORGANISM: Solanum lycopersicum

<400> SEQUENCE: 10

Met Ala Asn Ser Met Arg Leu Phe Ala Thr Met Leu Leu Leu Ala Met
1               5                   10                  15

Leu Val Met Ala Thr Gly Pro Met Arg Ile Val Glu Ala Arg Thr Cys
            20                  25                  30

Glu Ser Gln Ser His Arg Phe Lys Gly Pro Cys Val Ser Glu Lys Asn
        35                  40                  45

Cys Ala Ser Val Cys Glu Thr Glu Gly Phe Ser Gly Gly Asp Cys Arg
    50                  55                  60

Gly Phe Arg Arg Arg Cys Phe Cys Thr Arg Pro Cys
65                  70                  75


<210> SEQ ID NO 11
<211> LENGTH: 79
<212> TYPE: PRT
<213> ORGANISM: Solanum sp.

<400> SEQUENCE: 11

Met Ala His Ser Ile Arg Leu Phe Ala Thr Phe Phe Leu Val Ala Met
1               5                   10                  15

Leu Leu Leu Leu Ser Thr Glu Met Gly Pro Ile Ser Ser Ala Glu Ala
            20                  25                  30

Arg Thr Cys Glu Ser Gln Ser Asn Ser Phe Lys Gly Thr Cys Val Arg
        35                  40                  45

Asp Ser Asn Cys Ala Thr Val Cys Gln Thr Glu Gly Phe Ile Gly Gly
    50                  55                  60

Asn Cys Arg Gly Phe Arg Arg Arg Cys Phe Cys Thr Arg Asn Cys
```

65 70 75

<210> SEQ ID NO 12
<211> LENGTH: 76
<212> TYPE: PRT
<213> ORGANISM: Solanum sp.

<400> SEQUENCE: 12

Met Gly Asn Ser Leu Arg Leu Phe Ala Thr Phe Phe Leu Val Ala Met
1 5 10 15

Leu Leu Leu Ala Thr Gly Pro Thr Thr Ser Val Glu Ala Arg Thr Cys
20 25 30

Glu Ser Gln Ser His His Phe Lys Gly Asn Cys Leu Ser Asp Thr Asn
35 40 45

Cys Gly Ser Val Cys Arg Thr Glu Gly Phe Thr Gly Gly Asn Cys Arg
50 55 60

Gly Phe Arg Arg Arg Cys Phe Cys Thr Arg Asn Cys
65 70 75

<210> SEQ ID NO 13
<211> LENGTH: 68840
<212> TYPE: DNA
<213> ORGANISM: Solanum lycopersicum

<400> SEQUENCE: 13
tcctgaaatt gatgcagaaa agattagccc agctagtaca ttatacttgt tttcctttct 60
aagaaaatgc agtataataa taatacaaaa aatagaaatt caacaactgc aataattcct 120
cagtcccgaa ttagttgaat attctatata aaatcccaac atcaatttta ttccatctcc 180
gtcatttttt ccaatactta ataatttgta gtacaccttt aaaaagaatc agagtgagtt 240
aagaaacgaa ataatgaaga agtcagatgg ctaaaaaatg aacctttgaa agttgatatc 300
aaacgcagac aacaaggtgg ggaatgttaa tcccccataa caaaaggtgg aagaatctac 360
agttgtggag cacaagagag aatatctccg cagaggcaat gataacaagg agagcataaa 420
tgagaaaacc ctatcattta gggttctttt atattcacat ggtctgacca cttttgggct 480
gaccaactcc tttttggtat atttatgtgt ggatccgttt aggagcccat ttttattaaa 540
taaaatggac catgagtcca tatttaaact ttcaaaaagg gatatcggta gttttcaatg 600
tcaattgtgg tgttcggtcc atttccacaa ctatacttga ttggtttggt tttacccaaa 660
aaaattgtca attcgagatc aaaccaaccc gatatcatat atataatttt gaaatttata 720 atttttata cataaaaata tttactttct attattttta aaaaaatttc ttacactttt 780
tcatagtttt tatcttttat catattattt ctagtttcta agacttgatt ttgaatagtc 840
caataaaggt tatagttcat agatattagt aactctaaca aaactcaaat taaaatcaaa 900
tcaatactag tgctaaaaaa tgttatttaa aaagtaagaa tgataataat atctgttctt 960
taattttgca caagtgaatt catcctcact tcgaagatca tgcaaaatat aaataataca 1020
ctatattatt taaatagaag ggatattata tataataata atgtctttat cttatatttt 1080
tgtgtgcacg cacgtgcgcg tttatgtgtg tgcatgtgat gtgtgaattt tagttgaaaa 1140
ttctaaatgc tttttgaggg tttcttctaa catgaaaaac attactattt ttcattctaa 1200
gaatatgcag tatagtaata atacataaat aggaatttaa caagtataat aaaatacctc 1260
aattctgaat tagttgaatt ttgcatataa aatctcaata tcaattttat tccatctcca 1320 ccatttttc caatacttaa taatttgtag tacaccttca aacaaaaaga agagtcagtt 1380
gagaaacaag acaatgaaga tgccagatgg ctaaaaaaat gaacctttga aagttgatct 1440

```
ccacagcaac aagatcaagg tggaatatgt taatcccgca taatcaaagg gggaagaagc   1500
tacagttgtg gagcacaaga gacaacatct ccgtagaggc gatgagaaca atgagaagaa   1560
gaggcggaga gcattaatca gaaaactcta tcatagaggg ttctttcata ctcacctagt   1620
ctgaccactt cagggccgac caactctttt tttggtatat ttatgtgtgg atccatttat   1680
gagcccattt ttattaagta aaatggccca tgagtccata tttaaactta aaaaggaggg   1740
atatcggttt tcaatgtcag ttgtggtttt cgtccatttc cacaatcatg gttgattagt   1800
ttggttttac ctaaaaaaat atcaattcga cattaaacca acccgacatt atatatataa   1860
tttttaaaat tataattttt tatgcataaa aatatttact ttgaataatt ttttagaata   1920
tttcttatac tttttcatag tttttatctt ttatgatatt atttcttgtt tctaagactt   1980
gaattttgaa tggtctaata aaggttatag tccacagata ttagtaactt taacaaaatc   2040
aaattaaaat caaatcaata ctagtgctaa aaaaagttac ttcaacacta agaatgataa   2100
taatatttat tctttgattt taaataatac actatatatt taaaaagaag ggtattata    2160
tgtataataa tgtctttatc ttatattttg tacgtgtgcg cgtacttgtg cgtgtgcgcg   2220
tgaatttaat tgaaaatttt aaatacttct gagggttcct tatgacatga gaaacattat   2280
ctttttttc ctttctaaga gtatgcagta tagtaataat atctatctat ctatctatct    2340
atctatatat atatatatat atatatatat atatatatat atatatatat atatatatat   2400
ataggaattt aacaattgta ataatacctc attcctgaat tagttggatt ttacatataa   2460
aatctcaaaa ttttatttca tctccatcaa tttttcaaat acttaataat ttgtagtaca   2520
ccttcaagca gaaagaagag tcagttgaga aacgaaacaa tgaagatgtc agatggctaa   2580
aaaaatgaac ctttgaaagt taacctcaaa agcaacaaca atagcaacaa catcaaggtg   2640
gggaatttaa tcctccataa ccaaaggggg aagaagctac agttgtggag cacaagagag   2700
aacatctcgg cagaggcgat tagaacaatg agaagaagag gtggagagca caaatcataa   2760
aaccctatca ttagggttct tttatattca cctggtttga ccacttctgg accgaccaac   2820
tctttttggg gatatttatg tgtgtattta tcttatcttt tgattatgca cgtacatgcg   2880
tgtgcgtgtg catgtgcgtg cgtgtacgtg tgattttagt tgaaaagttt aaattctttt   2940
ttgagggttt cttcttacat aaaaaaaata taaaataaat tatagtatac cttcctacaa   3000
atgggtagaa gtataatttg gttgcatagg gaaaaaaaaa cattattttt tacatgtaat   3060
catctttttt agaagtgaag gaatattctt gtaatttata atgatttcaa aataaataac   3120
ataaatatac tattttcaaa gtaaaaagaa gaagaagaaa taaataaata tactttgaag   3180
aattgattag atatattgag attgtttatt atcttatatt tttattgtaa ataaataatg   3240
gttacaatta aatagcgagt aatattttaa ttgtggaaat ttctacagac gtatttatcc   3300
atacaatata tatttgacta catatacata catcatcttc ttattttaaa tttttgtgat   3360
aagtctagca ctaattttgt aataatttat ataatttatt tgcgtaggta aatttgactt   3420
tattcatttc aatttttca ctattctcta accaaatatg aaccgtaatt atgtttacta    3480
aattaaattt tgttaaaata taataaacaa ttattatgga gtcatatgaa attaatacaa   3540
caaaaatatt ttatcgaaaa cattctaaat tgtagtatgc atgttttgtt atattgattg   3600
aggttcaacc aattatgata acaaaaatat tttatagatt catagagttc tttacaaaag   3660
aacattatta catatcaatt gagataatct aaattggaat aggattggtg gagtgcacca   3720
ggccaagaat atggtggaac atcatgggaa tgattgaaga tcccgatagt aagctaccgt   3780
aatggacctt ccccttaaa aaatagaatt aatatcgtgt gagtcaatga ttcatatatt    3840
```

```
aaatattaaa ttgataagaa catatactac acttgataat aaactcacat tcatttatga   3900
aagcttttat atttaatttg ttttaaataa aattccaaca taaatgacga aagaagactc   3960
ccgtggttgg ttatgaatgt cgctaatgac ttaagtgact ctagatgcat tggcattacc   4020
tcagttattt tgaatatttt tatgacatct attgtcacta aatgtctctt ttgttatagt   4080
gccttgaatc tgttaatgca aaatatttct tacatcaatc atatattata ttaaataaaa   4140
gctgctaaaa ttacacatct cacatttcga tgaagcttac ttgtaggtgc tccatctatt   4200
ccatatgaaa ttatttttg agtctttttc tttttcaaaa taattaaatt ttataggttt   4260
tttttttca tatttgtcct tttctttagt gaatttttat agtttccagg gcatttattg   4320
agtctacatt ctaacaccat gtaactaact attaactaag ttgttttttc ttttttttacc  4380
ttatgtaaca aactaacttc ttgaccacta atcataactt aattccaata gtctaacaaa   4440
tggctacata gataccttag ttgtctaaca tatatacatc acgtttcaat aaggatatat   4500
cagctctaaa tcacaaaaaa tatttttcac tcatgtcatg catattgttt gaatttgatt   4560
tgtacaaacc ctagctttag catgttatag agatttactc catgaatatg acgattaaat   4620
ggattgatga tcttactgac ctagctttta gtatatagtc gatccctctc taatcttaga   4680
tagtggattt ttgggtatta atcatgactt ttcattttga aattgtgaca aatgcaccac   4740
atatattata attgatctta catttgcaat tttattggat atcaaatatt taaaataaga   4800
tcttgttagt aaattgacag aatcattaag caccagtggt ctagtggtag aatagtaccc   4860
tgccacggta cagacccggg ttcgattccc ggctggtgca ttatattttt tgtctttctt   4920
acgagattca tctaaatcct tggagaaaaa tttcgttttg ttatttctcc caccccatcc   4980
gaggaggatc aatagtgatc tcactcaccc tctaacatga ctcaacccca taacctcttc   5040
gtttgatggt ggatattttc aaccacttga gctaatctca tactcgtcta attaaagtca   5100
tccagacaaa gcaagtttgg ccaagtccat tgccttttcc accatattgt atcgatttca   5160
atcaaaaaat gtagaggtta ttataacttc acaaaaatcc taaaaaattc ttcaactaac   5220
aatcaaaaga aaggcttaca actagaattg gtggggtgtg ccaagccaag gcaatagtgc   5280
aacgcctaga cgacacttga aggtaccaat agcaagctac catgatgaac cttcccctca   5340
aaaaatagag ttaatatcgt gtgagtcaat gactcacata tcagatatta aactgataag   5400
aacagatact acacttgatc ttagccaaaa ggccgagaaa ggtataattt ttaatgattt   5460
ggtaggactc attttgtatc ctatttgtca ataggagttc ttttgtccag tcaatgtggg   5520
actagaagag gaactattta aataagctat aggaaaatga agacaattag acaaataaca   5580
aaataatata tgctctttat tttaattttg tgtaggtaca tgttacattt gtaatatttc   5640
ttgacactag cttcaaacat cttggtaggc cttttgccaa cttaagattc ttatatatat   5700
ataagaatcg ataactcttg acacaagtta aaaaatttta atttaggcgt tgcaaaaatt   5760
ttctgaggtg atgtatgttc taatcctact agtctcatta ttaattttct tattacaatc   5820
attgaaactt cttataattt tttaatgaag aggtatcggg tgacactcct tagtcaagtg   5880
catctttatt tctatcacta tattataaag atgataacgt tattttcaat aaatttttaa   5940
gtcgaataaa ataacaaata atacgataac ctaaaagtaa tatgaacatg cctaatcttt   6000
tttgattttc agactggtga tgtccttttt ttcttttgac attgtaacac atatggaagt   6060
gcaataattt tcacaaaaag acaaattcaa tgacttatca tgactatagt ttccttattt   6120
tattttcttt tttttcaaat atataatgct ttccacacag gaatagaaat tattattatt   6180
attttttact gtgtcctcct tttttttacc tactgtaaaa ttagtggcca caagttaaat   6240
```

```
agttgaatat aatatctaca gactccacca accaaattat tacttccgcg tcttatatta   6300
gttattcata ttattaaaaa taattttctt tttgtatttg gtaaatgcta tttttaacca   6360
aacttagatc gtgactgttc attatttcta atcgtcttat tcaatcactc taaatctaaa   6420
gtaaaatcga taaaaatttc ttaattcttt gtgtattagc gaatttaaat gcaaattgtc   6480
tttttgcctg tggtagtttg gtgagctttc gcttttccaa gttacatatg aattaataaa   6540
atctaagata aaattaatta tatttttata gttaatcttt ttaaaaagtg taaataagtt   6600
tataaagttt caaaataaat tattactaag gggtaaatt agtaaaacta tcattcttat   6660
tcataatttc gtaagagaca tgtaaagaaa aagaagcaac taatatacgg gacaaaggga   6720
atacagtaat gatagttgtc actaaccata atttcactaa tttacatgta cataagccga   6780
tattcaaatt tggtctaaga taacaagtta atcagatgta tagatcggat ttgagctttg   6840
agtatggaga aaaaattgat tggaagcact atccctgaat ggttgcagtg cgtacttcag   6900
atttattcag agctctaaaa cggacctcaa acattgaatg aaaaataaaa aaatgaatat   6960
acacatctag acactttaat ttgatctcaa tttgtctcca acttatcccc attatatatg   7020
ttgtacaccc ttcactaatg tgatacataa atttagaagg tgtggcgata tacatacgat   7080
cttaatttat gtatacaccc gaccttaatt taggtataag tctgtatatc aacactagct   7140
acaagaccga aagttaaagt gaaaagtaag tatttcaata atcaaatatc tcgaattcga   7200
gatggtgcaa agtgctgcat tcgaacacta actacaagat caaaaagtta gagagaagag   7260
taaacattgt tataatctga tatctcaaat tcgaaataat ttttgatcaa aactatttag   7320
gtcccaaaat tgcattttgt agtctagtgc aatgtgcaat agtgcttaat tataaatgat   7380
atttgagatg tcaattttag aataatggag atatatatgc tggtccacca tatcttttat   7440
cttttacctt tgtgtttcag agttcagacc aagttgttgc aaagttttaa tttgtttacg   7500
tatcgatata gattgtgata tagtgattga attattttat ttttaattag agattttaaa   7560
tttgagtaaa tgtatattga aaatatcttg ttgaaagcat atctttaaat agatcttgca   7620
gtgtgcgatt taaatttaat cgagatttta atgtgactcg aaatatcgag tataaagtca   7680
aaaaaaaaaa tactttgcgt gaaaaaaatc acaaagttaa aggggctatc tatgtatttg   7740
gccttttcta ttttattgtg tccttttttt tttttaattt gatctagttt tctctttagc   7800
tttttattta ttttttgttt taatttttca cgtaatatat ttaagattat agaattaata   7860
aatattttac ttcctccgcc ttaaaaagag tcaccaagtt tggcttgaca cgagaagagt   7920
aaatcttgtg attctaaatt caaattattt tatatataga aaattgtctt ttaatcttgt   7980
ggtattaaac atgtcacatg aaaaactaaa aataaatgtt acaaattaaa ttttcttttc   8040
agacaaacta aaaagaaaaa aatactattc tttttaaaat aaaaaaataa tatacttaac   8100
atatttttaa tttaaaatca taacatttta atttatttta ttaaatacca aacaaaataa   8160
attaaaataa cttttatctt tacctccact ttttaagtag cttaaattcc caccaaccta   8220
caccgtagac ctttgtacca tgagtagtga tattaatata tttttttcgt tcgttttata   8280
ttatttgatc tctgttaatt taatatattt ttgaagaaaa ttttaattaa aaatatattt   8340
ttttaaaatt aaaaatgata ttctgcattt taaatttgaa tactgctatt ctttccgttt   8400
taaaataatt atcatatttt atttcttaaa catcaaatta agatataaaa ttatatattt   8460
aaacgcataa tataatttat aaatttaaaa ttttaaacgt tgccgacatc gaaatctctg   8520
aataataata aaagataaag acagcatgat atatgtcaga tgataattca attattggtc   8580
ataaataatg acagataata attttgcact ttattacctt tttttttttt ttttttttg    8640
```

```
cttttaatg attatttttt tcaccaattc aatatcacac gtatacgaaa tttgacaaat   8700
gttgaagtgt tatattagct aaattacaaa tatagtacta aggtgttatt atcagcttta   8760
atcaatcaac tatttcaata attaatcata ttactagctc aaattcagac aaagtgtttg   8820
gtgaaatgaa atatcagtta aacactttaa caaataaaat ttaacattta gatacatgtt   8880
aaactttcga atttcacgaa aaatataaag attcttgagt taatgtgttt gaatgtgcat   8940
ctctctcaaa attcaaacgt ttagtactga ttaattgaca tcaaatttga acgaaaaata   9000
aacaaaaatc tcaccaagac cccgtctcct ttttaagttt ttgaccaaac taagccatta   9060
ttataactat ttattttatt tatataaaaa aattaatttt tttatagatt atttaacttg   9120
atgatacaaa agatcttgtg atataatggg atgacacata ataatgatct ttatcatgat   9180
aaaatttgaa cttgtgatat aatgacacat agtctcaatc tagatttgtc cataaagaaa   9240
aattatttaa aattgctttt tacttggtgc agtagataaa attatttttt aaaaaaaata   9300
aattttaatt ttaaattaaa tgttaaaatt aaagtattat gtgatacaat tttattttta   9360
aaaaatcttc ttattgtaat atgaactaat aaataaactt ataagatatt caacttattt   9420
ttttatttta tatcttactt ctaaatttat ctaaataaga ataaaaattt tgaacaatat   9480
aagcatagga tataaatgtc ttttaaattt tatgatgtta aaaatattac gtaagatatt   9540
gaaatttaaa agttaagtac tgattataat aaactaacct cttccacacg accaatatct   9600
tctcatttta actgttattt tggcttttaa aaaattacca ttttagaaat ttaagattta   9660
agctatccat tttttcgact tggttttcta atatttttat ttatttatca ttattattga   9720
aagattaaat tttttttatc cctttctgaa agttttttta tttttttgtg attcgaacca   9780
cgatcttaag ttgaaggacg gaagtgaacg atgtttacta tttatcatat atctgccttt   9840
tcttaacgac ataaaagagt taagatgata attaaaatac tatgaatgga ataatattat   9900
ttttaagata aattaaaaaa taaagagtat gtatgtatgc acatatagtt taattcaaac   9960
gatcgataaa aaagaaaaaa aatatgtatc atttacttaa ttgtatcatc ttccacaagg  10020
aaaaatccct ataaaaagaa aatgacatac tccatgcgtt tctttattat tgtatttgtt  10080
taatcagtag tgaaattaaa aattttaaaa aaaatatatt taaaatttga aaaataaata  10140
tacgatctag tgaaaaaggg ttcaacatct attatatata tctacaaaat aattttaacc  10200
acatataaat aataatattt tcaccgaaga gatgaaccct aaatatatgt cgcctccgct  10260
cctgcttcta gccatgattg aaatagctac gggttattac tttttttcct caatttttta  10320
atttaattat ataaaaaata aaacactttc tatcaaaaat tactatcgct ttcgaatcat  10380
tttaaaatat cttttatatt ttccgttaaa gttgtcaata ttgtcatgcc attatatttt  10440
ttcttagtag tcctcgttaa agttgtcaat attgtcatac tgtaatattt ttttaaatat  10500
atttttaaat gtaataaaaa tatttgatct aacaatatta tgttgtcatt tgataatcga  10560
tgggttgtgc agtttgggtc aattagtgtg gcttgtacat ttttttttta tttttactaa  10620
attaaaaact ttatgaaatt aaaaacttta ttaaatttat aattaatatt gttattgaaa  10680
aaatgaaaaa gtaagacaca taataaattg caaagtaggg agttattact gtaacaaaaa  10740
tattattagc aataattaat ttttaattat ttattaaata tttattttta gcgacaatta  10800
tcactctttg tatatgtctc taaagccttt agcgacatta attctaatga cacttaacta  10860
atgttgataa aaactttaaa acttttatgt caatatttaa tgtcgctaaa aattaatttt  10920
attacagtga atgtactttt atgctttatg aaaacaataa tatatatacg gttgcattct  10980
tttgaataat ttacactatg attgttcaaa gatatgtaat attactaatt ttgtttgtaa  11040
```

```
aactaaactt ataatcttta tgtgtgtatt tcttgttttt ctaaaatatt atggataaaa  11100
tctgtttttg gacctctaat ttttactatc tttatttcta acaattatta ttattattac  11160
tattattatt attattatta ttattattat gagaagttta tttttttaaa ctcctttagg  11220
agcttctatc atttttgct catttaatga ctcgaatcta caattttaaa ttagaaataa  11280
aaatatttat tatctgatca atcccctctt aacaaacata tccttaacac tagagaaata  11340
tatagtttat ttatttattt aacaatattc aaattctcaa aatcatctaa taattaaata  11400
ggaataactt aataaataat accttatatc ttgtttttct taatgacatt agaaaaagaa  11460
gctaaaaata aaacaataca aaagtgataa tattcttttt aaaaataaat ttaaaaagtc  11520
taaattaaaa cacatgtgat atatacttag tttaatccaa actatgaata aaaaagaatt  11580
tttttttat cttccacaag ataagacttt agagctctat aaaaccacat gtatactagt  11640
ctaaatatct ctcacattac attaaaaaaa ataaattatt atttcttctc tctctcaaaa  11700
aaattgtgaa aatggcacaa tccattcgtt tctttgctac tttgtttctt ctagccatgc  11760
ttgttatggc tactggttag acttctatct tttttattta ggttacgttc aaaatttatt  11820
agcttttcga tattatgtcg ataatgttat cgaataaatc actttctatc aaaaatatcg  11880
ataattcaag tcatctcctc acattttta gttatttcta gtaaaaaatt taaatatcgt  11940
accataatat ttgttgtgcg gaatttgaga taatacgaga aaatataaac gcgaaaaata  12000
agacaacaga tttacgtggt tcaccaacaa attggctacg tccacgggaa gagagggagc  12060
agttttatta tggagaggca aaaacagaat tacagaatag ggtttcccat agcgtctata  12120
tatagtgcta agctacgccc taacaggctt gggcccaaca tacagaatca acagaaaatt  12180
aagggcccaa tacaacaaca ttgtataccg tcggcccggg ggcgtctccg cccccccgga  12240
cccccaggcc agggggcgcg tcgccccct ggaccccccg actcgctgac cgggcagcga  12300
gacccccgtc ctttctgttt gtagcgggtc cgattcaagg cattcaacag acctaatttg  12360
acttaaaacg gaatttaaga aaagaaagaa attttttaa tcttatggtt ctaaatcaaa  12420
gttgtgtcaa atgtatcaaa atgcgtttta atcttgtggt ctttttcata tcacgtggaa  12480
agttaaaatt aaaatgttac tgaaaaaaga aaagggtcat tcttttttaa acagactaaa  12540
aaatgaaata aaattattct ttttaaaacg aaggggataa taaacaataa caacaagaag  12600
taaaatgtcg caaattaccc aacatgttgc acaaaaatct gttcaattaa tgttctcttc  12660
atgacttaat tcttattaaa gatggatagc tttgatagaa agcgttttat ccctgacatt  12720
ttaagatgag acttttcgat acgaatctag atttaatcag atcctaacac gggtacgatt  12780
cacaggttaa atcagtaaat aaattcaaag cagaaagaga catttgaaaa ggtcaattca  12840
cagttaggaa aatgacagtt agaaaataag gacagagggc cctttaataa gaagtatatg  12900
atgttaaaag agacttccca caagtcacct ccaaaagtag ttaaaaataa tagaaagttg  12960
aaacatcaat tctttttcc cttttaataa ccgcgatgtt caagtcagct ttcgcgcgcc  13020
tcaacttata attccaagaa atatctgtca ttggaatcgc ttactatttt tgaatttcca  13080
aaaatagatc aaaataactg gggatattat gtgatttatt agtattctaa atcttagttt  13140
ctttcgcgtg ccgtacctta ggattcgtgc tattgctagg taactctgtc catcaagacc  13200
gaaacaaatg agaaaaatca cctagtgtat ttttttgtct ccgcaactgt tgtctaaagg  13260
tacctttttt cactcttcaa tatatttcat atactccacg gcacatggtg tggttctcaa  13320
agcataagtg aggtcagtgt ttcttactgg atataaatag acataaattt ggggagaaaa  13380
tgaaaccaca tggaacaaca aaacaacact attattatta ttattcaaga atcactagca  13440
```

```
agactggtta attaatgtta ccaaattttg catgtccttc aaattgatca tttttagtca  13500
ccctttccta caattgcact aggtatgtgt tttaaatttt gtgattactc atattattaa  13560
tatatgattc caagattgta agctcattta gccatcacat gaacaatttt gctgatgtaa  13620
gacaattgtt gttttctgct gttatagtag gttaaagaat agactaatga aacccctctc  13680
gtgagatagt ttttggagtt gaggtagact tagatacctt atagtttaca tggtatcaga  13740
gttacgttga tccgagctcc tagtccatgg tcttagagtg gattagagtc ttacatggac  13800
ttgggaaatc cttccctcac gctccaattt gcttatatta cgcgagatgc tagctgtcct  13860
attgaggcag tttttgtttt tatattgtag ctctgcagca ttttgttgta tatggaatag  13920
aaatgcctct gaaatacttt tctatatctg tttgattgct gaaggactat tgaatgggaa  13980
agcgaagaaa ctggtttacc tttgtcaaga gacttttcat tcctgaaaca gaatcaacag  14040
cagatcaaaa ggtttgaatt tcaagatttc tgttgcttag tagtgtgagt gaatcttcgg  14100
atatctaaac tggaaattta tgaaaaatat ttcagaaacc aaagagatgg agatgttgtt  14160
ttctgagaaa gttcaagttg aggaaatgtc ctgctataac atcagcacct cagcaaacgt  14220
tacctgaggc gaaaggaaca cctcagcaaa cgttaactga ggcgaaagaa cagcaaagaa  14280
aacatgcttt tgcagttgct atagcaacgg cagcagctgc tgaggctgct gtagctgctg  14340
ctaatgctgc tgctgatgtt attcgtctaa cagatgctcc aagtgaattc aaaaggaaac  14400
gcaaacaagc tgctattaga atccaaagtg cttatcgcgc tcacctggta aaacatcctc  14460
tctggtagct ctagtacttt cactcataca atttcactgt gaacttgttg cagagacgct  14520
tttaaatgca gaaagattga aaattagtta gtcattcaag acaaaactta aaggatagta  14580
tgggaaaagg taggccagtt tggatatagc aggattaaac gcccagtgct ctaccagctg  14640
agctacacac ctaaaaaatg ataatcaagt aaacaagtat tgatacagaa aaaaggcctg  14700
ccccttttact ctcatcttat taaaggagca cgactattta ttatgaggct tgtactacag  14760
agcaagtgga agctccgaag gtcacacttt tttttttttt ttgccttttg gctgttaatc  14820
atattagtca taaggtagtc tatcacctcg gttggaaaga aaatcttatt ggttggaaaa  14880
tccctctccg ctagtaaaac tcttctctta tggcggctac taattctttt tcctttcatc  14940
tctcaaaaaa actttccgag atttggtgaa atgaactggt gtctgatcta tgtccctgtg  15000
aaatgttgtg caggcccaga aagcattaag ggctctaaag ggtgttgtga agcttcaagc  15060
agtgattaga ggtgaaattg tgagaggaag actcattgcc aaactgaagt tcatgttgcc  15120
acttcatcaa aagtcaaaaa caagagttaa tcaaattaga gtccctactt ttgaagatca  15180
tcatgacaag aaactcatca atagtccaag ggaaattatg aaagctaaag aactaaaggt  15240
aagatcaatc attcattctc ttttgtttaa ttaagtttcc aaacattagt tcaactatac  15300
taaatctata aaagagacct actaacacat cttattatga cttttatggt ttggaactgt  15360
aatatggttt tttgtttttt tggcagctta aatgcaagag ccttagcact tggaatttca  15420
acttagcttc agaacaagac agtgaagcct tgtggtcaag aagagaagaa gccattgaca  15480
aaagagagca tttgatgaaa tactcgtttt cacatcgggt aaagtcatta cttgttatac  15540
agacactgca attacacttg tcaatgtatt ataaaatgtt gtagcagtta acctgcctta  15600
ttttctagaa tactaatctc acattttatg aacgattatt tataatatat ttttaggtaa  15660
gctgatagta tattgcttct tttaggagag aagaaacgat caaactctac aagacttact  15720
aaacagaaag caaaacagaa gaagctacag gattgaccag ttagtagaac ttgacgcacc  15780
aagaaaagca gggttgttag agaaattgag atcatttaca gactcaaatg ttcctctaac  15840
```

```
tgatatggat ggaatgacac agcttcaagt gagaaaaatg catagatcag attgtataga  15900
ggacctacat tctccttctt cacttccaag aagatcattt tctaatgcaa aacgaaaatc  15960
aaacgttgat gataactcat taccaagttc tcctatattt cctacttaca tggcagccac  16020
agaatctgca aaggcaaaaa caaggtcaaa cagcacagcg aagcaacacc taaggttaca  16080
cgagacattg tcaggtcaac attctcctta taacctcaag atttcttctt ggagattgtc  16140
taatggtgaa atgtatgaca gcgccagaac aagcagaact tctagcagtt atatgttaat  16200
atagaaggtg ttttacaagg attgaagaac atgagtgttg tacattatta ctatctttga  16260
taacgaagtg tccaagccgg tttgctctca cctctgctag ttcaccgagt gttgttaact  16320
tctacaagta ccagtaccag tactaggtaa ctctgttcac caaagatgaa tgtgtacatt  16380
atcaacctgt ttatgcaagc aagggagcgc agaaactcct agatttgcag cattacttct  16440
ggacatgaaa acaatcagaa aaatggagct attattggag cttcaaactt cttcagtaat  16500
ctatctacag ttgattgatg aaagattact ggttttaaca ctttttata tagacttgcc  16560
acaatgtgta tatatagttc aagttttttt cccttteccct gtttgttttc ccttgtttca  16620
tttatttatt gatttgtaaa gttgtttcca tgagaccagg aggtcacagg ggtaagattc  16680
tgtacaatag accatatggt ctcgagcctt caccagaccg cacatagcgg ggagcttagt  16740
gcactgggct gttgttcttt ttttttttt ttgcttctga gttgatatac tggaggaaga  16800
attgttgttt gatggccatt cacctggaag catttccaag tttggtaatt gcatagaggt  16860
ttaatctttg ccttctgtat ttacataggt ttatttcttt tgatttcttc cttcaaagtt  16920
caaaccacct ctttattatt tcatgtaaaa tccttcaaaa aaaaatgaac ttacaccaaa  16980
atttatgtct tacctttctt acaaaaccat tgatgttgaa actaaggaaa atggattgga  17040
ccaaccatat gtagaagaaa tatagcaagt ttactccaac tttcactact tatgttaaca  17100
cattgaacac ttgagaaaca aaatccattg gaagctcctc atttctacag gcttaaaatg  17160
tctatggtat atccaatgta acagaataac acatgtgagg cacactgttc tcctcaactg  17220
agattgacag atttcacata ctacaaattt gtaaactttt ggaacataac gcaataggca  17280
agataatgac atttgacaag aagtatcaac tgtaatgctc aaattaccag ataagtgaat  17340
gagatagtcg gaaatgtctg atccacgacg ataaaatcta taccagtaaa agtagccctc  17400
ctgtatgttt tgaactaatg ataacattca gtccagcaac aactctgctg acctcaaatc  17460
tagaagccaa ataaaattac ttgaccatga ggcttagata ttggttgttc gaggtttaga  17520
tattccatct tctatacagc ataaagtagt gaatagattt ccttttaact tatacacgta  17580
ttagttgtaa ttgattctaa cttgctaacc aaaagttgtg tttagtgtgt tgaattttat  17640
atattagcaa aaaattactg ccccaaatat ggtacaaatt ctgcggtgat ttaatacatg  17700
aatgactcac atcctaacca gcaaccaaac atacatattt tactgttggt tttggctctg  17760
ttcatgcttt taatgagtgc agttgggctg gagaattagc acctcatttt ttcgcatgtt  17820
tttctctaaa tgaagaattg caatcttata gttggtcttc actattcttt ctccccccgc  17880
cctctttatt ttcttgtagt taaattattc tatatcagta tcctaagaga cttgttacct  17940
ttgcttgatg ttagatatcg attactacaa gtacttccgc tggcttagag cagatcctgc  18000
catggatgtt ttatcataag gtcattggcg tgacaaactt tttcctgttt gtggagggaa  18060
aagctgcatc tcccgatgta tctaaagtgc taaaatctat tccagtaagt gttcatatct  18120
ccttaatatt tccattgtcg tgttgaacat tttgtttcat cacttctacc attttgtgta  18180
tttggacttg tcgtatttct tctgttgatt atatacaaaa tgtgtgtgct ctgcagggtg  18240
```

```
taagagttat atatagaaca aaagaactag agaatgtaca agccaaaagg taagcggtct  18300
ttgcctatat atacattttc tgtgcctaaa ctatgaagat gaggtctttg ttcagtagag  18360
tagacgttat ttcctattgc tttgagaaat gtttttatcc cttccgtggg tttatgttct  18420
ttatttagcc tcgtatgatt cattttcttt atgttgctaa tggatgcaag taatagtcga  18480
tgatagaaac tatttatcca aagcaaagct tattgacgaa catatgttag catgggtcaa  18540
caagtttcca aaacttgttg ggagttcctt acatagcaac gtaatatata tcaggagtaa  18600
ctacaatgca cgggtggagg gggttgatgt ggaccgtcta atttacctat taatagcaag  18660
cagtaattac cttgggtagt ggtgacaaca gattctctat tctatttgtc ttgagactaa  18720
taatagactt ggttcctaga agggaaagag ggaaggttaa atgagagtga agttcattga  18780
ttatttaccc tacgtggagc accgagtatt taattcactt tatttgatgt attggaaggt  18840
aagtaaataa gacatacttc tctcagtccc ccttggtaaa caagagaaat aactctttca  18900
cctctcgtct cccaaccctt tctcctttca acccaagcga cattgtatga cgtatgtttc  18960
aagtcattca tcttgagtaa gcttggatct gttttgagtg taatatgact aatgtagtga  19020
aaaatggtaa tagactttaa tgaagaagtg attattcaag ttactaactt aaatagaact  19080
aaatttggag agtgaaattt ccatacaagc tagtaaaaat gctctgttcc ctatatttca  19140
tctcacgtct caattaagta agcttattat ctgacatact gatgatctat aatgtgttgt  19200
gtcctagtcg gatttggaat gagacgtggc tggctggatt cttttaccaa ccatgcaacc  19260
atgagttatt tgtcaagcag actcttaaca tggaaatggc catcgtcatg gcaagggtat  19320
gattgcaata acttccatct gtttccagtt atggttacct tttgatccac tatattgcct  19380
agtaactcta caggaagctg gcgtggactg gatcattcat ctcgacaccg atgagctaat  19440
gcatccagct ggaactagtg agtattcttt acggaaactt ttggcagata tacctgaaga  19500
tgttgacatg gtcatctttc ctaactatgt aagtaattga gctctaggct gtcttttaac  19560
tgtgtctaag catgtaatta catgccgaat agtcaaaacg catgcatttg attcgttttc  19620
attttctgcg gtctttttc atgtcaatat cttctctgat gatgacaaat atttcaggag  19680
agcagtgttg agagagatga tgtgaaggaa ccttttagtg aagtaagata tctttcactg  19740
tatccttttt tcttatcttt caagttctag tattaaaatt caatcgtttg gctaggaaca  19800
tcctccacct ctatacatga ataaatttag attttcttaa aataaatttg gataattcta  19860
ttacccaata cttgagaatg gagcaacagc tagtagtcaa agagtcaccg ctttccagac  19920
gaatgaaaaa gaaggttgcg ttggagttag acattgtgga ggcaagaaag gaaaattgta  19980
cctagcgaac acaaggagct tgagtgttaa aattttttag agagagtttg cgtagtctgt  20040
aatttatttt aattattgtg caactaaagt tcttttagac tgtttaccag caatgcatct  20100
gtatcatgtg gtaggtctcg atgttcaaga agaattatga ccatctcaca aaggaaatgt  20160
actttggaag ctacaaggaa gcaactcgtg gtaatcccaa ctactttttg acttatggaa  20220
atggcaaatc agctgctcga gttcaagatc atcttcgtcc taatggtgct catagatggc  20280
acaactacat gaaaagccca aagtatgctt gttctgcatg ttacttgttt tcctttatct  20340
ctatttcgtt tcttatttat tcccagtcct atagaatcac tgttttatcg aagttgaaaa  20400
catacttgta atgttgtcat attttttcac ttctttggtg tgattgtctt cgcttgtata  20460
atgaaaatgt attttcttat tattgtagag agatcaaact gggagaggct gctgttttgc  20520
actacacata ccccaaattt tcagatttaa cctcacgacg agatcgttgt ggatgtaaac  20580
ctactaaaga agatgtgaaa agatgcttca tgctagaatt cgacagagct gtgagtaata  20640
```

```
ggcagtctgt tattaaaaca acaaatgttt ttggggtcaa aaagatggac tgtatagttt  20700
gtttgttgat aattttcatc ttcacattgc aggcttttat aatagcttcg actctgacag  20760
aggaggagat gcttgactgg tagtaattct tttaacttcc attccatcga attcatgcta  20820
atccttatac tacttatttc gtgaaatcct tcccttgtta tactgtaaaa tcttatttca  20880
tactgatctg tagtccgcgt ggtgcttgat ttctttttgg tttgtatatt atgctgacag  20940
aacctttatt ggattaggta ccgtgaacat gttgtttgga cggataaaac actcatccag  21000
aagcttatca agaagggcat attgacgcgc atatatactc ccatggtaag atcaacttat  21060
atttgattgc ggaagctcct tttgagttta tattgagggt catgaatcct aagaagctga  21120
actcatagta actttttgttt ttcggtctgt gtaggccatt gtacagggtt tgaaggaatc  21180
tggtgttttc gtttctatta ttgcttcagc acatagagat gtcataaaag acgagtctct  21240
atcttcttct gctggaaaca gaaatgcttc cggatatcct catattactg atacttttcc  21300
cagaaagatg ggtcgtatat tggaatctca atcaactgca aggaaattcg tggactttag  21360
tacaactgat catcaggcaa ttccacccga atcacctcct ggcatggatg gaattgatct  21420
cgcagataca aaataccttc tgaacaatag ctcttcttga agaagtatac ttacataccc  21480
ctcttgggaa aataggtgtg tacattagtt ctgtcatact ccatagagtt gttcgagtat  21540
catatcatag agaatgaagt attcttcatc ttttaaaagt tcgatatgta tacatgacag  21600
aatgctttgg agaatgacaa tcttatcgat atacaagaat agatctcttc catgcctcaa  21660
atctttcgat gatgttctaa ctattactcg tctgtttttt tctttattag aactgagtat  21720
gattcttaga ttgttgttaa gtaatttggt tctgaatcca gtagttctgg tccagaaatt  21780
atacaagtgc ttgtgcataa agggtgatgt tacatttgtt gtaatgctta tttgttatgt  21840
tttagataca ctacttttga actagcaatc agatgaagta gagatttaag aaataaaagt  21900
atattcattg atttgattat atgaaacaat ttcactaaac aaaactacat tgttgacaag  21960
aagtagacta agagagcaac tgagatagcc attccttgtt ttgtcccata aatttatcaa  22020
aatcacttaa ttcatctaat aaacactcgt cgttgtttgt tggttcgact tgataagcat  22080
tacctgctgt ctcttcaaca ttctgcagca cttgctcttc ctgataagga aaaactaatt  22140
caccattcat attcccttca ttcattgcag catcgttccc ttgaaccatt ggaaacgtga  22200
cgattagctg agaaagttga tgatcctcca taggccactg cggttgtgtt gtcatatcgt  22260
tcctattctc atcatcacat ccaacatacc ctgattcaat attttgcatt ggcttcacaa  22320
tctgttgagg aagttgatca ctatatccaa attcattagg cccttggggt actagtgtat  22380
catcacatcc aacataccc gatccaacat tttgcattgg attcacaatc tgttgaggaa  22440
attgatcacc atatccaaat tcattaggcc cttggggtag tagtagtgta tcatcaccat  22500
caccatcatc atatccactg ccagttgttg taggcatatg atttcttgat tttttaactt  22560
tacacctaat gtagcacaaa acaacatcct tgtgcttcat cacacctctg ttactcaaca  22620
actttattac cttgtcgtca agactatact ctttcatgat ccaagaaacg tcgttaacta  22680
catccttttt attttcttca tagttataag ttttttttcat cccaatttc ttcgcaccta  22740
ttgactttcc tttgctcttc cctttccaac ttcctcctcc caccaaagtc cgactaaacc  22800
ttgtatcgcg tttctttaat ttagtaaaaa aatatttagt accggatgag tcttccagta  22860
actcccatgg cttcttactt ccgtaaagtt cttcaaattc aatatcttta caaacgtagt  22920
ttttagaaac aacaaattta atcaagtagc gaatgagctg ttcatcagtg ggtcgaaacc  22980
tgactccaaa ttcagcgtct ggagattcaa ttgccataac tattgatgag agtagaaaca  23040
```

```
aactttatta gttttaggca atggctctaa ataacgatat atgattaacg tacgtgatgt  23100
attattagca agaactgtat tgatgcccaa agccctatat attatattat gacgttaagg  23160
ttagttaaaa aatggaaacc aaatttaaga ataattagga aacgtaaatg caaaaacttt  23220
ccttttatat ttcaagatta gttacttaaa atcattctaa tacaaacgta atgcaaaaac  23280
tttccatata taataaattt aaagtctcct tttttttgtt tcattatata aatcagttat  23340
taactgtaat gcaaatattt ttttttattt ttttttctat tttattcccg tacttcaact  23400
ttagtttgac cataaaagtt tgggtcaatt gtttttttctg atatattgct tattttttta  23460
tatagtttca ttaattgtta atataattta aattgtttgt tttaatatta tcagtattat  23520
gtagttaatt aggttttgcc acttttattg ccgcaaaatc ctatttagaa taggtaatgg  23580
aaaagcaaaa acttgtctta gataataaat ttaaaatttg atgaataaat aaataatcaa  23640
taattatatg ataagtacgg gtgtttataa gttgattaca attggaaatt ggaacttcga  23700
aacgtaagca ctgttttgca ttttcgattg agaaatgaaa gcattttttta tgacataata  23760
cataaataga ttcttttaac ttgatttcaa ttaatattta tattttttag aattttgagt  23820
gtgcacaaat aaatatttat acttttataa aactgagcaa attaacatat tcgataggga  23880
taattgtata taataaatag caaactaata acccaaaata aatggagtag ctacggtttg  23940
atttaattgt gctccatagc aaacgttagc caaagtttgt cagtcgcctc tctcccaaaa  24000
atctcgctcg ccactctcca attctcgctt gccactctcc ctatgcttgc ctctctcgct  24060
ttgtacacag aagtgtgtaa attgtgtttc tgttttgtat aaagcgagag aaaattgtat  24120
atacacatgc aaaaacatat atcttcgtgc tatacactta attatgcaat ttataaacat  24180
tttactttga ttcaattgta gacaaatgca aattttatac aaatacttca atgaaaaagg  24240
ccaacaaatt atataattgc gaattataca attgcagtga aatacaattt tctctcgctt  24300
tatacaacag aagtgtatat attgtgtttc tgtttttgta taaagcgaga gaaaaacata  24360
tatcttcttc ctatacactt ataattatgc aatatacata cattttactt cgattcaatt  24420
gtatacaaag caaattttat gcaaatattg cagcgaaata ggcagcgaat tatacaattg  24480
cagtgaaatt ggataacgaa ttatacaatt gcagcgaaat aggccagcga attatacaat  24540
ttaggccaac gaattataca attgtatatg tatagcgaat tatacagttt atgtttgcta  24600
tggagcgtaa ttattcaaac tttgatatag catacaaata tgaatttttt atttgctata  24660
tgtgaaagtt gccctattta atatcctatg tgtaaaaaaa taatgttatg gggtgataac  24720
gtcaaaattt tgaaaatagt ataattatcg ttgcattata tttaacaata ataataaata  24780
aaaatattta gcgacatgtc acatgttgat attttacata aattttcttt gtttagagca  24840
acaattacat aaacatggtt tgttcatatt gaatatctca acttcattat ttaggaaggg  24900
taaaatagta aattattacc tttttattaa gctatcgatt tatccaataa ttcaatagta  24960
aaattaacat cgaaccaata actcaaaaac atacaaaacg gactccttga tagcaatttg  25020
ttgatgtagg taacttattt tgacataata ttatagctaa tttcacgatt taaatccatg  25080
atgatacatc atatatatat atagtgtctt aatttttggc ctctaatatg tagtgtctta  25140
atttttggcc tctaatattt tgctggacca cttaattctt taggagtggc aaaaatatag  25200
tggtttgcct gtaatacaat tttgtaatat taactggact tcctctaaac tacattgtca  25260
aatgaaaagg ttgtgtggag ctttctgatt gggtagaata ttaatttttt tttcaaaata  25320
aataattaat ctgacctagt aaacaaatat acatcatttt taaatatata aatcagccta  25380
aactattgaa aactcaggtt tgcttcatgt gaacattgtc caattttttt taattacttt  25440
```

```
attattatta ttattattat tttattttta ttattaatag aaaaggacta cttctccatg  25500
tttatactgc cacatcaatc agaatttttt ttttgtttaa tgagttacta ctattagaaa  25560
aaaaataaaa tatataatta aaaggaaatc acttaagttg gcaattttca tgctttaaac  25620
tttgaatctc atgaatcatg atcaagaact gggataaaga ctccatatat aaacaaatga  25680
ttagatgaag tcataaaagg aacaggagac atgacggagt ggtaagtact caatcattaa  25740
aaaaaattta tagcgcgtat acaagcaaat ggtaagataa cgtattctgg atagtcttga  25800
cacaataacg tgttgtagcc ggtgatttca aggctcttaa aagagccaag acacgcaaat  25860
ttttagtgtt cacatgttcg caacgatcca aatttagtca gccctaatat gaataacgga  25920
cactgggtgg cgattcaaat ttagtcagcc ctaatctcac taccagtatt aatgaagaag  25980
gatttctcgc ggcgatctaa ctttaatcag ccctaatatg gatagcgaac actgggtggt  26040
gatccaaatt tagtcagccc taatctcact atcagtataa atgaactatg attctagcag  26100
cgatccaaat ttaatcaatc ctaatatgga tagcagacac tgagtggcga tccaagttta  26160
gtcagaccta atatggatat cggacgctag gcggaaaatt aaaccttata taaacaattg  26220
gttatagaaa gttttaaaag gaacatgaga gttgacaagt gagaaaacag aacaaaagca  26280
gatagatgaa gtgctgactt tgacaactac taaatctctt catttaatat tcttatgaat  26340
tttataacaa cttcatggta ggcaactttt tagtttgaca ttctttgatt ccttaagact  26400
ttttcaagta aatagatttg attatgaagt ttatatatat gaagttccac actcactagc  26460
aaaaaacccca caaaaacaca aaacaaagtc tttttacaac ttcaaaaaaa aaatggaagg  26520
acaaacagga caacaagagg agttatttgt agaaattgat caaaaaacag atgatcaaac  26580
atatagcgat ggtgaagcag catcatgtac aacagatggt aacgaaatag ttaatgttat  26640
tgtcacgtct gatccgatct tgcaaggaga atctatgcca agaaggtata catactcgtg  26700
gagaaggcga atacagaaag ttttacctct attgaagacg gatgaataca acagacacga  26760
gtatgatccg aaagtagttt cattaggacc ttaccatcat ggtaagacag agctacagct  26820
agcagaggat ttcaagcata tagcccttga aatgtttgta tcgggtagca gcagagacgt  26880
agcttatttc tataacaaga tacttgaagt tgttgacaat gcaagaagtt gttatgtcga  26940
tggctccacg gacaagtaca atgatcatga atttgcctta atgatgcttc ttgatgcttg  27000
ctttattatc aaccatatcg agctaagcac aacggatagg tataacaaac tcagaaccac  27060
gaggcaccat cttggaatgt tggcgttatc aacaacagtt cgtgatatgt ttttgcttga  27120
gaatcaaatc ccattttgga tactgaagct cttgattagc ttacgatatg acaaagatga  27180
aggagatgaa ttgctcgaga tgttcttgaa tttcaccctt ttcggtgaat atgaacaaga  27240
aggggaaatg agtcacaacc atgtagaaga gccactccat cttcttgaag catttagaac  27300
aagacttgtt tcacaacaga gtgaagtacg gagctttcac cgtacttgca cacctcaatg  27360
gctaaaaagg aagaaaagta taagcaatga acgcgttaac atgaaaagct acattcactc  27420
ttttcgttca gtaaccgatc ttaaagcaaa aggtattcaa ttcaagccta gctgcactca  27480
ttcactcaag gacataaagt tcaaatcaag atacttctat ggacagcttg tacttccaac  27540
ttggtatgtt tctatctaca ctaaggcgtt cttcttaaac atgatagcct acgagatgtg  27600
tccaaataca gttactgatc gcgctgtgac atcatacgta tacttcatga aatcactaat  27660
agagagtcca agggatgtca aggaactacg cgaaatgcaa atactattca acatgcttgg  27720
tagcgacgag gaagtggcaa gaatgtacaa agagatcaat acgtatggag tgaacaacgc  27780
gcacattttc tacaatgtga aagaaaagat tcaagaacac tataataaca aggcgaaaac  27840
```

```
atggatagca gagcttatac acacttactt taggagtcca tggactgctt tagcattact  27900
tgcagctact ttcttgcttt gcttgacttt tacacaaact tattttacaa taaatcccaa  27960
tcctagatta tgagaaaata tttgtaacta tttgagaaat tttgtggtag agtactagtt  28020
tcttatcttg tttgctgtta caagaaaata aagatgcttt tgtgatatag atatctctca  28080
taaaattatt tttcacgtat actttataga tgttgaactt cgatccttgg attagttctt  28140
gtatttattt tttcatattt tgaactaaaa ttaagagggt taattgggcc gggtcacttc  28200
accttgaaga ccaagaacca atcgggttca aaatccacct cggtaatcgg aaccagcact  28260
atttgtgatt tgatagtata gggttaacca actagcccag cccggaatgc ccaattgtta  28320
agtctaaaat ttaaaattat atttcaaaat cgttaagtat ttaaaaaaac actacaatat  28380
aaaaagttat ttttaaatta aaacccgacc ctatatggcc caaaattatg cgggttacat  28440
caaacccaaa ccgattggat tcgatatctg atcgggttcc ataatcagtg aaccagcccg  28500
ggccaactca atgccaccct cggtgaaaat tttcactttt tcacgggttc aatcaaaata  28560
gaaggaaaaa aactgaaata cacgtcttat gttttttttt tttcaatgtc tcctatttct  28620
aaaaacctct taaataattt atttttctcc caatgtattt aatgtatccg agttacatat  28680
taatgtatcc taactatata ttatgtattc gatttatttt ataatgtatt cgagctacat  28740
attatgtatt tgggctaatt tttaatatat ccaagctaca tattatgtat tcaatttatg  28800
ttataatgta ttcgagatac tctttaatgt attcaaaagg tataaagtat aaggaattat  28860
tataattaaa aaaaatagag ataaaatgaa atatattttt gcactatgaa atttaagtga  28920
attatacaaa atagaatatt acgatagaag ggcctaaagt tgaactgaga gtaggttctt  28980
ttgaaatgta ttgggcctca tcttggccct tactctggta acaaacattc cattttaatt  29040
ttttttttt atcacttggc tttttcatc atttaacatt gtattatgaa acaaaatata  29100
tttagtaata aatactcaaa caatattgat gagtgtatat acatctctaa tccatagtta  29160
tagcttatag gctgaatcca tcggtagctt tctaaagttg acattaattt tcatttaaat  29220
tagactttgt tcatcttaca cacctcatgt tgagttccgc tgtgtcattt gacacttttt  29280
gatgacttga tatattgtgt gtgttgcatc cattttgagt gcgtgagggg tctttttttg  29340
tgtggatatt tttaattttt ttccttcttc actttttagc cttaccactt attccacatt  29400
tcccaatgaa aattcatgat aaaaaacttt acaaaatatg aaaagatttt ttagaacaag  29460
acatacattt ttttcaaaaa aaaattggaa aaatgtcata tataattttc aaaatcaatt  29520
aaaaaaaacc taaaatctaa tgatttttta aaaaaaattg gaagaagaat caagaaaatg  29580
attgtagagt tgaggaggca aaagggacgc aagacagatg ggcttagggt gggatgatat  29640
aaggtggggt ggagtggtac aaactaggta attttattta tttatttttg ctaaaaaatt  29700
agttattttt tgatacttta ttttaaaatt attattttta catttaaatg tcaaatatca  29760
gcttttatag tcatcatgtc atgttatccg caagtgtgtt acacactctt tgtaatttta  29820
gctgattggc aaaaaggtgc caaaataaca tagcggtccc ctacttgagg tgtttaaaat  29880
gactacttga agtgtctaat tgaaaattga tgtcatattt aaggggttgc cgatgggttc  29940
aacctatctt ttatatatac gattatatac aatttataca atgtcaatac attacctaaa  30000
agtaaattta tgtgtatttt tgtttctttt cgctcagggt gcaccaagtt cgaaaagaat  30060
gaggatacaa cgtaagcatt agtgattgat tctactattt aaagttgaat ttataagtta  30120
cttgaagaca attatatcgt caaataggat cataaacaaa ctatcttaac acaagtatta  30180
gttattgtct agatttgctt tcatcaaact caaataaata ttaattaatg agaattatta  30240
```

```
taccttttta tattaaaata aactatactc ggagtttact taaaacaata aagaatattt  30300
gctgctctgg acagactcaa ataggggacc tatcataagt acaaccacaa cttataagta  30360
atcatatttt ttttaaaaaa attaaaatat tagtaatctt atatttaatg tttaaaataa  30420
ctgtgtattt gaaactttct gctattcatt ccatgcttaa attcttttta tcattacact  30480
aattaatttc ccaaattgtt tttgcatgta atgatccttc atggattggt cccattttta  30540
ttttttttta aaactcaaat gttgataatc tccaatcaga catatgatta gtggaacatg  30600
tgatcttcta gctagtgaca actctgcata tgtgagttta tttattttat cgagtttcaa  30660
tcgaaataga gtataacgat atatttataa attatgttaa ttttcaagta aaaataattc  30720
tgaaatgaaa atgaagaagt atagagaatc gatattactt ttcatttgta ttttgtataa  30780
tattactata tgtgtactgt ttaaatagtt aatctcgatt tatttgagat cgaagcacaa  30840
tggttagata gtttatcatt atagcctttt tgtattgaat aattgaaaga agcattaaaa  30900
aaatcaattt aagggctttt gcaattatga cctttcacat ttttcactaa gatatatata  30960
attaacatgc atgaagaaaa gtgttacctt ttctctatct ttcatttgtc aaatggaaac  31020
tttattattt aaagaacaca tataattccc aaaaaagatt taaaaaatat aaaggctaaa  31080
aattcaatta ttttggatta tatccttgat taccaaaatt gagtccatta aataactcaa  31140
aaagataaat gctactttcc aaaaggtgga tagatattca catggtttat ctatgaccca  31200
aaaatatatg ggactagtga tatagataca aaagcggctc aattaaatta atggcctaaa  31260
tttttttttt tttttaatct aacgatttta aaaagtaaac taacctaaaa tgtattatag  31320
gtaaaaataa aactccatcc tcccttaacc ttccctagag atattggttc gaaaatctcg  31380
ctagaaagtg ctttcctcga tcttacatgt ctcaaaacca aacaaaaaaa aattgaaagc  31440
ctaaagttct ctctttagtg acttgactgc atatacaata taattttta acgaaggatt  31500
ttaattgcat tctatatcag tggtctcttc acctctgacc aagtgatgat gatgagtatt  31560
acttggaagc tgaaagtata ctgttggatt tgctaggtga aaaaaacaaa agagaatata  31620
ctaaaatagt tttaacacat tgtgaaaatt ttcaaatttt ggtatcattt ttatacagct  31680
accaaaaaat aatcataagt tgtactacta attaaaactt tatatttctt ccgtttaaaa  31740
aagaatgacc ttgttgtgcg gaatttgaga taatacgaga aaatataaac gcgaaaaata  31800
agacaacaga tttacgtggt tcaccaacaa attggctacg tccacgggaa gagagggagc  31860
agttttatta tggagaggca aaaacagaat tacagaatag ggtttcccat agcgtctata  31920
tatagtgcta agctacgccc taacaggctt gggcccaaca tacagaatca acagaaaatt  31980
aagggcccaa tacaacaaca ttgtataccg tcggcccggg ggcgtctccg cccccccgga  32040
cccccaggcc agggggcgcg tcgccccccct ggaccccccg actcgctgac cgggcagcga  32100
gacccccgtc ctttctgttt gtagcgggtc cgattcaagg cattcaacaa atctccacct  32160
tgacttgaat tctccgaaca gattcttcag acgcactatg atagtgccaa gcctccccct  32220
cttcctcaga gttgccccgc agggcaatta acagcttctg atgttgagca agtccaaaca  32280
gtgttgaaac ttgctctgtg gaaccggctt tgtgaacata tcagcaggat tatcagcagt  32340
tcctactttc ttcaccttga ttctcttctc acttcttaga aaatgatacc ttacgtcaat  32400
atgcttggtt ctctcatgat ggacttgatc cttggctaga caaattgcgc tcaaactgtc  32460
acaatacacc gtagcctgat catgatgcag accaagatca ctaaccagcc ctttcaacca  32520
aatcccttct tttgcagcct ctgtcaaggc catgtactcc gcttccgtag tagacaaagt  32580
cactgtaggt tgcaaagttg ccttccaact gacgacagat cctccaaggg taaacacata  32640
```

```
gccagtcatc gatcttcttg tgtcaacatc tccagcatag tctgaatcag aatagccagt  32700

aaccaagcac tgagtatcac ctccataaat gagaccaacg tcagatgtac ctctaaggta  32760

ccggaaaatt ctcttcacag cctgccaatg ttctctccct ggttgtccca tgaatctgct  32820

cactacactg actgcatgtg ctaaatctgg ccttgtacag accatagcat acatcaaact  32880

tcctacggca ctggcataag ggactcgtga catatactcc ttctcttctt ctgactgtgg  32940

agcgaacatg gcagtgagat ggatattggc agcactgggg gtatcaatgg gcttagatga  33000

agacatgcca aacctcgcca agaccttctg aatgtagctt ctctgtgaca agaaaagttt  33060

ccttctctct ctgtctctaa tgatctccat ccctaaaatc ttccgagcgg ctcccagatc  33120

cttcatctca aactcagcac taagtaaacc cttcagcttc tgaatgtcat acttcttctt  33180

tgcagctatc aacatatcat ctacataaag caccagatag atgaatgaat catcattgag  33240

cctattgtag tagacacaac aatcatatga gctccgagta tagcccaact tcaccatata  33300

gctgtcaaac cttttatacc actgccttgg agactgctta agtccatata aggacttctt  33360

caacttgcag acgtgatttt ccttccctgg aacttggaaa ccatccggct gagtcatgta  33420

tatctcttcc tccaactctc catgtagaaa cgctgtcttc acatcaagtt gttcaagctc  33480

cagattctga tgtgcaacta tcgctagtaa cactcggatg gaagtatgtc tgaccactgg  33540

tgagaagatc tcattatagt ccactccctc tctttggttg aaacctctgg caacaaccct  33600

ggctttatac ttgactcctt ctgctggtga tatcccttcc ttcttcttga aaacccattt  33660

gcaagtaata atctttctcc ccgaaggctg tatgaccaga tcccatgtct gattcttgtg  33720

tagggactcc atctcatctc ccatagcggc aaaccatttt tcagaatcag aacttaaaat  33780

ggcttctttg taagtagacg gctcagatgt atctacctct tcagcaacct gcagtgcata  33840

acccaccatg tcctcaaaac catacctcgt aggtggccga actccaaccc tccttggccg  33900

atcttgagct atactctgat ggatatctga tggcatagat tctggaatat cagtttcagt  33960

ctgtggctct tgatcctcct cttcaggttc ctttaaatcg ctctcgttct gaatgacttg  34020

aaactccacc tgtttgtcaa gactcccagt ttctgacgta gttgtaggct tcacaatggt  34080

tctaagcaga ggactttcat caaagacaac gttcctgctc ataataaccc tcttttctgc  34140

tggagaccag attctgaaac ctttcactcc atctccgtag cccacaaata ctcccttttt  34200

agctcttggt tctaacttac cttcactgac gtgatagtaa gccgtacaac caaaagcttt  34260

cagatttgaa taatcagcag cttttccaga ccacatctcc ataggtgtct tgcactgtat  34320

acctgtatgt ggtccgcggt taatcaagta gcaagctgta ctaaccgctt ctgcccagaa  34380

tcttctatct agcccagcat tagagagcat gcaccttgct ctctccagaa gtgtttgatt  34440

catccgctca gctacaccgt tctgctgtgg tgtatttctg actgtgcgat gtcgagcaat  34500

cccttcatcc ttacagaatt gatcaaattc agaccaacag aattccagcc cattatcagt  34560

tcgcaacctc ttgatcttct tccctgtttg attttccatc aaaattttcc actccttgaa  34620

cttctggaag gcttcacttt tatgcttcat catgtacacc caagtcatcc ttgagtagtc  34680

atcaataatg gacacaaaaa atctgcagcc tcccaaagac tcaacacggc atggacccca  34740

gcaatcagaa tggatataat caagtgtgcc ttttgttcta tgaatggcct ttggaaactt  34800

gttgcgatgt agttttccaa aaacacaatg ttcacaaaac tctaggctct taaccttatg  34860

accagcaagt aaatcctcct ttgacagaat ttgcatccct ctttcaccca tatgaccaag  34920

tcttatgtgc cataacttag tcatatcctt ctggtgaaat tctgacgatg caacatgggc  34980

tgaacctgta accgtggaac cttgtagaaa atacaaagta ccacgcatga cacctttcag  35040
```

-continued

```
aatcaaattt gaacccttcc agacccgcaa gactccatct tttcccgacc agctgaatcc  35100
cttgctgtcc aaaagactga gagatatcag atttttcgtc atcaatggaa cgtgcctgac  35160
ctcgttcaat gtgcagaagc taccgtcatg tgtccttatc ttgatcgagc ctgtcccaac  35220
caccttgcag acagaactgt tggccatcga gatgctgcct ccgtctacct gctcataagt  35280
cgtgaaccac tctctcctag gacagatgtg ataggatgcc ccagaatcaa gaacccacac  35340
atctgaatga tgagtgtgct catccgcaac tagggcaata tcttcttcag aattggtgtc  35400
ttcttcagca acagcagcag acactgattg tttttccgat tgcttcttct tcttcggaca  35460
atcaaatttc caatgtccct tctccttgca gtaattacaa acatcatccg gctttgcacc  35520
cttcgacatc ggcttatttt tctttccgcc gtttttcctt ccctttctgc tactggtgaa  35580
cagaccggaa ggctgtatgt ccgtacttgt gccgttagcc ttatgccgta attccctgct  35640
atgaagggct gatctgactt cttccagtga cacagtatct ttcccaacaa tgaacgattg  35700
aacaaaattc tcaaacgaca ttgggagaga tactaacaga atcagggcag catcttcatc  35760
ctcgatcttc acatcgatat tacgcaattc taataacaaa gtattcaatt gctctaagtg  35820
ttccctgagt tgtgtacctt cagccattcg taaaccgaat agacgttgtt tcagaagcag  35880
cttgttggtt agagattttg tcatgtacaa actctccagc ttcaaccaca gaccagcagc  35940
agtctcttca tccgagacct ccgtgatgac gtcatccgcg agacacagca tgatcgtcga  36000
gtgcgccttt tcctccagaa tcgccatctc aggagtaacg acggcgttct tgtctttcga  36060
caacggcgcc cagaagcctt gctgtttcaa caaggcccgc atcttgatct gccataaact  36120
gaaactgttc ctccctgtga atttgtcgat tttcacgttc aaagcagaca tctcgaattc  36180
tccaagaaca ccgattaacc gagaggctct gataccaatt tgttgtgcgg aatttgagat  36240
aatacgagaa aatataaacg cgaaaaataa gacaacagat ttacgtggtt caccaacaaa  36300
ttggctacgt ccacgggaag agagggagca gttttattat ggagaggcaa aaacagaatt  36360
acagaatagg gtttcccata gcgtctatat atagtgctaa gctacgccct aacaggcttg  36420
ggcccaacat acagaatcaa cagaaaatta agggcccaat acaacaacat tgtataccgt  36480
cggcccgggg gcgtctccgc ccccccggac ccccaggcca gggggcgcgt cgccccccctg  36540
gacccccccga ctcgctgacc gggcagcgag acccccgtcc tttctgtttg tagcgggtcc  36600
gattcaaggc attcaacaat attgttattt ttttcctcta aagtttgggt gaggtggggg  36660
tgggggtggg ggtgggggga ctattttgtt tatatatatt ttgactaggg ttaaaattta  36720
agaatataag aaagattttt tatttaaagt aaaaatgtgt aaatacatta atcttacgcc  36780
attatttaga agttggtttt tataatattc aaattaaaaa tttagtaaca ttcatttcga  36840
aacagattaa aaaaataata atgcgtataa attgcaaagt agagagtatc acgctttgat  36900
ttgttgttta aagtaactcg tacgtaacta atatgatttt attttcacag aaatgggacc  36960
aacgagaatc gtagaggcaa gacattgtga gtcgttgagc catcgtttca agggaccatg  37020
tgtgagcgat aagaattgtg cctcggtttg cgagaccgaa agattttccg gtggtaattg  37080
ccgtggattc cgtcgccgtt gcttttgcac caagccatgc taaataaata attttgattt  37140
ttatgtgtaa aagaagaagt ttgagaagaa aaaaaatatt atgtaatttt gaataaagat  37200
gtattgtaat gctagttttg tttgtaaaaa ctagttgtga tctttgaatt tgtatgcaat  37260
tatggtgcac tagacttgta attcttcatg tggtgtattt ttatttttat ttttgaaata  37320
ttatagataa aatttgtctt ttagcctttt tgttagtaag ttttaataaa atattcttcg  37380
atgcggaatc aagaatcgat catttctttt tattaagtat tttgaaatgt gaaagcgata  37440
```

```
aattgataat tttatgagga agtttctgtg cggaatcaag aatcgatcat ttcttttaat  37500

taagtatttt taactgtgaa agcgataaat tgataatttt atgaggaagt ttctgtattc  37560

tttctgattc atgtctgagt aatttttttt ttgctataag tacagtattt tcataagcat  37620

ggagtaaaaa aaaaatacct tctatcattt ttgttgtagt tgatcattca caacgatatt  37680

ttattagaca tatttaatct ttaattaaag tattaattaa tttttcttct tctttaatat  37740

aagtttacaa tttttcgtaa ataggaatat tggttaaagt ctaagctagg ggttatttga  37800

atggcaatgg aatggacaaa ttattctact tcataatttt tagtagataa aattattttt  37860

ggcacaaatc ttacgccatg cgttcaatac gaaatctgaa aagctgcggg gatgacaaaa  37920

agagggcact ttcctatgtt gcaccggaaa aagacttaag agacaagcgt cttctcttag  37980

gtttttttct ctcgcgcccg tcaccacttg acccgcatta gaggggaaaa ttaacaaaac  38040

gagaaaagaa agagggaaga aaagtagcat cttattatat tattattatt agaaatacaa  38100

atagtaaaat ttaaattcaa aaaaatttaa tatttctcaa ttaaatatga tattttattt  38160

caaaattatt acttatcact ttattatttc acgacccttt agaaataaag gagatccatc  38220

aagatatgtt ggatagtaat tcaattattg gtcaagtggt tcataaaatc acgacatata  38280

ataataattg ttcatctttt tttttttcg ataaactcaa gattcttttt gataaattat  38340

taatgatata tttaaagtca ttaaattaat ttttttata tatcacagaa tttaaaattc  38400

tttcaaatat cataaacaga cactaatttt gaatttatat tttaaaaaaa atactatatt  38460

gtatatcttt ttgtagttga atctccataa gttttagaat atttcaaatt cgatttgatc  38520

atttaacggt gtatcttata aagtgtgcat gtaaatgaca tatatagaag gaataatttt  38580

aaaactcaag ctaaaagtta aaatagagtt caaaaagaag agaaactaaa gtaaaattaa  38640

aagtaaatta ggggatgaag ttagacaaag taaaaataaa tctttttaa aaaatattgt  38700

tatttcaata ttcgatattt atattgaaat ctgattaatt taaatttgtg tcgaatagag  38760

tccatttcga gagatatcac tctctgaact tttttatct aaaactcgaa ctcaaacttc  38820

tatacaaaat aaatttttgt atctaactaa tcgtcgtctt tttaacgtca ttttaattac  38880

tttgatgtgt ttttagtttc attgatttta aaaattatgg gagatttttt aattttaaag  38940

taaaagatat attcaatatg ttaaaatatt ctttaaattt ttatatttta aatatatcat  39000

atgagatatt taaattatag agtcatttgt atacaaaata atattctttt ttaatataga  39060

aaaagtaaat aaataaattg aggtatattt attcacatag gttgtttaat tactttacta  39120

aacttataat atgatgtaca tcatagactt atttggtaat cgaaatgaga taaataaaaa  39180

tatcttatga gaacaaccat tatataaatt catttgatca ttaattttaa atattttttg  39240

tttaattgaa aatttacgga gtcaaagtta aaaattgagt tgtgattagt tatatttctt  39300

ataaaatata tttaaaaata atgtccatac ttaaacgtac ttaaatataa tttcaaatta  39360

aataatgagt cataagtttt tttctaaagg aaaaaagggt ctgatatacc cctcaacttt  39420

atcatttgga gctgatatat tcctcgttat aaaagtggct catatatgtc cttaccctta  39480

tacaaatggc tcacatatac ccctgccgtt acaaaatggc tcatatatac ccttcattta  39540

acggaagtta aaaaattagt tttaaattta tatttattac ttctaatttt tttaaagaaa  39600

ttatttagtg gtatatatga ttcttctatc aaagttcaag gtatattttc atttttttca  39660

tgcatcaatt attttttgac ttcttttatt ataattattt gagtttctta ttcttatttt  39720

gtttttttctt tcattcctta gtttaaagaa aaaaaattaa actatttttt ttgtgtgtgt  39780

attataattt aatttcgtat tcaaagaaaa aatttggtca tctacaataa gttttgcaag  39840
```

```
aatattagtg aaatataaat aaatttgatt atcaaaataa taattataaa ttagtcattg  39900
aaacaaaaaa aagtcaaaaa aaaatatgtt tgacgatgat taaatttact catatgagat  39960
tatatttttt tagaaaataa aaataaaaat gtagattaaa attatttttt tccatttccg  40020
ttagatgaaa agggtatata tgagccattt atttacaaat agaggtatat atgaaccact  40080
ctcataataa gggtatatca gctctaaatg acaaagttgg gggtatatca gaccattttt  40140
ccttttctaa atttgatata caagaaaaaa aaaagaataa caacttttat agccaaaccc  40200
cgatcgtaat aaatcttttt agttaataat tataactaaa taccaaataa atatcgagat  40260
tattatttct tatctcacca atcaatttaa attagtccat atatttataa attatatcga  40320
taaacaacaa agtataaaaa cgtgatttta cctaccaaaa atattccaac aaacttttag  40380
tacaagttca cgagacactc attttagcat cttttatctt attataaaaa gccacacaaa  40440
tattaggtct aacataatat caaaaaataa aaattgaaaa aatttgtttg tgaaaattaa  40500
tggcaaactc catgcgttta tttgctacta tgttacttct agcaatgctt gtcatggcta  40560
ctggttcggc ttcttcttcc ttataattta attttttta acgattcgat atttgaaatc  40620
gaaccggtct gactcttctc gcgtcatgtt atgtctgcaa ggacatttac atgatctgat  40680
tcgagatttc tgattaaaac caagagaaaa tattccgatc atttcatcat gttccgtata  40740
gtaccataat ataatatgat actcctttct ccccaatttt catgatacat ttggaatttc  40800
gataaattaa gttttatttt gactgaattt ttaaatattt taagttgtta gctatgattt  40860
ataatagttt ttatgaattt ctatttacat atataaattt ttttaaaatt tctatgtttg  40920
aatttacgct caaaatttag aagttttgaa tatccattcg tatcattttt gtgtgttttt  40980
tagttaactc gaaatttgag actgcaaaaa gatttttgaa ttttttttgt tctaattata  41040
atagtgtgca tagtgtatcc ttcaagtcta atcctatagc taacatggtc aacatttttt  41100
tttttataat tttaaatttt ggattcgatt ttttctttta acatgcttgt atgatatcat  41160
gaccttgata agcaacttat aacacttcga tgtattttag gaccaatgag aattgttgag  41220
gcaagaactt gtgagtctca gagtcatcgt ttcaaaggac catgtgtgag tgagaagaat  41280
tgtgcctcgg tatgtgagac cgaaggattt tccggtggtg attgtcgtgg attccgtcgc  41340
cgttgctttt gcactaggcc atgctaaatt aagagtattt tatattcacc atatgtatcg  41400
gaaatactca tgaatgaata aaagacacta taattgttca aagatgtata gtgctagttt  41460
tgtttgtaaa aactagtcat ggtctttgaa ttatatgcaa ttatggtgca ctagacttat  41520
aattcatgtg gtgtgtttct tgttttatgc aatattatga ataaaatttt tcattatatc  41580
actaatctta gtgtttgtat tttggggtga tctaattttt gccctaaaaa tgattatctc  41640
aaattaagag taatatttag aatatgaatt aataaagatg aagtatttat tatgattatc  41700
caaacaactt atgcgaggtg aattacattt attgccgcat aacctaatta ttacaaatag  41760
gattttactg tagaaataat gctatactcc attattccac cctgttatca acttatcgtc  41820
ctattaatct gaattatcgc ggtataaaat aggattctaa tagagtgata acttttacat  41880
atagcaaacg taaaaatcat atttgcatgc tatagctata gtttgcataa ttgtgtttca  41940
tagaaaacat atatatgtat atttcgctat acatatacaa agaaaatagt tgtataattc  42000
gctatacata tacaaagaaa gcagttgtat aattcgctat atatatacaa aagaaagaag  42060
ttgtatacaa aagatcagtt gtattgtgta tgtataaaac gagaaagaaa gaaagactga  42120
agaaaaatgg gcagggaaat attttgtatt gtataattat aagtgtatag gacgaatgta  42180
tatgcatttg tgtgtgtata tacaattttc tctcgcttta tacaaataaa aatacaattt  42240
```

```
atacatttct tttctgtttg tatacgtgat ataggcgagg gtggcgagct agatctggga  42300
caataacaac tgagatctgg gataggggag agagggaacg aaaatatatg tttatataca  42360
attttctctc tatttataca aacacaaaca cattttatac atttgtgttt gtataaaagt  42420
gagagaggca agcgagactt ccaccaaaca agagtagcaa gcgagatttc accagacgaa  42480
aatagcaaga attggctata gggtacaatt aaatcaaatt aaaaaccgtt aaataagtgg  42540
tcaattttga accaaaaggt ggatgacaag ggtattttgg acccaatagg tgggtgagaa  42600
gggaatttg gagccaatag gtggatggag ggtaatttta taccatttcc aatactttga  42660
ggatattttg ggccctttc cgtacattat atctgcatgc atacaacatc tcatcctaac  42720
tcaaagttgc gcgaatacaa tatttgattg taataattat atatatatgt atgtgtttca  42780
aagcagaaaa tgaatgcatg tatgtatggt caattatatg tgtatgtata tatgaaagta  42840
gcagttgact atgggttctt ttttatattg gatctctgat taaatttgga ttgtgcatta  42900
taggacccat ttgagggtgg cgctcccaaa ttctaacaag attttctcca aactcaaggc  42960
tcgaacccga gacctctagt caagaatgca acagtctcat cattccacca taacctatgt  43020
tggtaacatt gttaccaatc gaatatgaaa aagttgaaaa atagattttg aaaaatattt  43080
tcctccataa caaaaattat cccgttttga tttcatactt aaactattga agtgcaattt  43140
tatacctaaa ttatcacaca ttagcttgag aaacacacat cagtagtgtg taataagagc  43200
gctctctctc ttcttttttt tttttttaaa aaaaatgaac taataatatg acattttaca  43260
tcaataaaaa atttcacctc gataaaaatt aaatcaacta ttaaatctta gttaaagtca  43320
aaattaaagt atcaccatct caaaaaataa aactcatttt tttaaaattt aaaaatttaa  43380
tttcttttcc tttaattaag gaatatctca atataaataa gattttgact aaagtaatta  43440
ggtttgacaa cagaaaactt ttaaaactcc ttgcatcata tcttcatgta atttactttc  43500
attttatctc catttacttt ataattaaaa atgaattaat tgtgtctatt atgagctaat  43560
tgtttggctg acttttgaag ggaaatatgt catatattta ttttataaga gatttttttt  43620
tttttttttt actttataag aggccagctt gatgcttttc attatcataa attttatgca  43680
taagattaaa aaatattaag atggaacatt tgtttaaagt ttttttctc ctcgtgttat  43740
ttttcgttga aaattcaggt aacaattctt ttaattactt actagacttc tagactatat  43800
atataaactt ttttcaatcg aaaaattaat caactacatt ttaattcaaa gctagttgag  43860
attgattaat atatgaatca tttatatatg ttatgattta ttcatttcat gtattaccct  43920
tataattctt catattaagt taattttgag gtatttttta tttttcaaac tgacttaatt  43980
gtttagtttc aagacccatt tttagagtgt tcttccaatt ttacccttcg ttagttagta  44040
ttagaattaa tgattaatta atatttagtt attttaatta taaatttgac aataattaat  44100
aagggtaaga acggaaaatt gtgttcagtt tatgtcttaa tttacttttc ttaaaagggt  44160
gtaaaacacc tcagaaatta acttaatatg gaatggagag actaaatgat actccgtccg  44220
tccctattta cttgtccata tttcatcttt tagttgtccc tatttatttg tccattttga  44280
caaatcaaga aagcacaatt tattttccta ttataccctc atttatactt tttgaaaatt  44340
cttaagtttt aattcatgct ttttgaaacc ataattaata agggtaaaat tgtaactcta  44400
ctatgcttat tatcgttacc ttaatgtgtg tgtcatttct aaagcggaaa actaaacagg  44460
ggcggaggga gtaccttttt atttttctta taacttatgg acctatggac cactatctaa  44520
atatatctta tggggaatcg aaaatagtat tggaaaatgt tagatgacaa tctaaaaatt  44580
attataaaca ttaagcgata atctaaattt tttttataaa ttagataaat atatgaacaa  44640
```

```
acatcatacg ttacataata ttgtttaaaa tatcgctacg atcatagtaa tatgtagatc  44700
gagatcgcta attatcatct tatttttatt ataacagagg cagggaattg tgttgaatgg  44760
agcaaaacct atcagtggca atgttttgat actaataagt gtagagaggc ttgcataagt  44820
gaaggtttta cagatggatg gtgtgcttat ttgataagat atagacgatg tgcttgtaca  44880
aagccatgtc tttttaataa taattagtat ttttttgcta aaatatgtgt taaattataa  44940
agtttaacaa acaaacaaaa aaatatagtt aattagcctc taatcttatg taatcctttg  45000
atcataaatt atgaaatggc attttaatga ttttcatatt acattctacc tctttgtgtt  45060
tgtttggaac gaagggaaat aagtgaattt ttttatttaa aaaattgtgt tcgatatgta  45120
agtaaaaata tatattattt ttaatatatt taagaaagtg tgtgtgcggg gggggggggg  45180
gggggggggt gattaggagt ggagtgagga tgaggatgaa gtcacaagtg gcgaaatcag  45240
aaatttagtg ctgatcaaga tttaatatat gcatatgaaa aataattttt tgatgaaaat  45300
gttcgactga tcatccgtca ctatacatgt ctacaccagt aaatatcact tgtgaaaatt  45360
gttctcatgt gcttccatca ggaatttttt ttaattcatt ttttaaagaa cttatttttc  45420
ttaaatattt ttgtcaatta atcataaaaa aataaaaaaa aatgttttcc ttcgtaccaa  45480
aaacacccta aatttctacc tctttctccc ttggataatt tgtgttttta atacaactag  45540
acaagcttat tatatctttt taaattaaat ccaatttgta gtgaagtgag taaagttttg  45600
attagtttat ctaacattat atccacaatc tttgcataat caaacttatt tttgcatcaa  45660
ctagctgacc cttaatgttt aagcataatt atctgatgtt gaaaatctat tactccctcc  45720
gtccagaatt atttgttatg atttttattt ttagagttaa attataaaaa ctttgactaa  45780
tgttttaaga tgtatttttt catcatatta atatgcaaaa aattgtaatt tatagtactt  45840
ttcatgtagt tttaaaatat ttattttttg gtttacaata tcgaattaat gtgatttaat  45900
ttacctttaa aattaatcaa attaactttc gataagcgca atatgacaaa caattctaaa  45960
tggaaagagt atatattttg aggcagagct agaacatgca accttataag ttctaaatat  46020
gggctgattg taaagcaact agtaagtaac tttctaactc tatgcatagt agaaagtcta  46080
atattgaccg attgtttgtc gtatctaggg gtgtacaaaa tcgaatcaaa ttgcaaattg  46140
agtcaaataa aaaaaatctg attagtgatt tggtttgatt tggtttggcg ttgaaaaaaa  46200
aacccccgac tatatttggg tttgtttgat atcaactaaa aaaaaaaacc cgagataaaa  46260
ccaaccagac attatatata taattttaaa atttttattt tatgcgtaaa aatacttact  46320
ttgatataat ttttaaatat ctcttatact ttttcatagt ttttatattt taatataatt  46380
atttcatgtt tggaagttag aattcttaac gatttaataa gattatagac tatacatgtt  46440
gataattata ataaagttta agaaaaaatc aaattaatac taatgcaaaa aggaaattca  46500
tgacaataat attgaatatt tgttttttag ttttacatag atttagataa ttaaaataca  46560
tgatgtaatt tttttttaat atttagtcat gtaaaaaaaa tttaatatgc aaaaaaatgt  46620
aatttataat actttttatg tagttttaga ttatctgttt tttggtttaa aatatcgaat  46680
taatgtgatc taatttataa aattaatcaa attaactttc gataagcgta acatgacaaa  46740
ttattctgaa cgaaggaaat atatattttg aggcagagct agaatgtgca accttataag  46800
ttctaacgag gaaaagggta tatgtgagcc atttgtttac aagtaagggt atatatgagc  46860
cacttttata acgaggggta tatcagctcc aaatgacaaa gttgaggggt atatcagact  46920
cttttcctta aaatatataa tacaaataaa gtttttggtt aaagcaacta gaaagtaact  46980
ttctaactct atgcatcata gaaagtctaa tattgaccga ttgtcgaaaa tttaattaaa  47040
```

```
tcgtaaattg agtcaaattg aaaaaaaatc tgactagtga tttggtgttg gaaaattttt  47100
tttgactatg tttgggttgg attggtttca actataaaaa tcaacccgac attatatata  47160
taattttaaa attttatttt atacgtaaaa atatttactt tgatataatt tttaaatatt  47220
tcttatattt ttttcatagt ttttatgttt gaatataatt atttcatgtt tggaaattag  47280
aattcttaat gatttaataa gattatagtc tatacatgtt ggtaattata ataaagttta  47340
agaagaaaat tcaaattaat actaatacaa aaaggaaatt catgaaaata atattaaata  47400
tttatttttt agttttacat agatttagat aattaaaaca catgatctaa ttttactttc  47460
ttttaatatc tagtcatgta agtgatactt actaaactta ttttagcatg atttagtact  47520
ttaaattatg atcaatttca ttttggctta ttaatttgca atatttgttt tacgcgattt  47580
tattattatt attatttgga tatattagtg tcattaatta tatatcatat ttttgttatt  47640
ttcttgagaa ataacttaga tagttgcatt ttggtaggac taaagatata tttgaagtac  47700
aagtaaatta tatgtatgta tgaatacttt atcgaaaaaa ccgaaaaccc cgaaattgaa  47760
aaatccaatt tttattggtt tataagttca aaaacccgac acaaatggtt tggtttgata  47820
tttgaaaaac tcaaaccaat ccgatcatat acaccccctag tcgtactttt ctctttagtg  47880
aatttataaa aataagattt tgatttaagc aaattaggtt ttactgaacc ataggtaact  47940
ttctaactga actgtagata atagataact ttataacttg tgcgtgatta aaaagcctag  48000
tatgagttgg ttgatcgtct gacctttcta ttttctggcc catatctttt taaacaaggc  48060
ccaataccct tcaccaatgt agtggtatta accttatatt tgtgtattta ctttcatctc  48120
atctctattg aatttataat caatatgaaa ttgacagtac atgcaaaatg ttaaaagagt  48180
attcaaaatt gattaattgc gcgatcgaaa gtctacaatg aacttaatcg tttgattgac  48240
ttttaagaga aaattacaag caaacatata ttgtcacgta tcttctttat atattaagag  48300
gcctggatgc ttttcatcat caaaaatttt tagtagaaga ttaaaacaaa ataaaaataa  48360
aaataaacta aagatggaac attttttaa agtcatattt ctccttgtgt tgatttccat  48420
tggatacgca ggtaataatt ctttaatttc ctactagact atatatatat atatatataa  48480
gtaccactat gaataataat acgtagatcg agatcgctaa ttatcatttt atttttattt  48540
ttataacaga ggcaaaggat tgtgttgagt ggagcaaaac atacaagggg ttttgtagag  48600
ctcaaaagtg cagagatgct tgcataagtg aaggttttac aaatggatat tgtgtttctt  48660
tgagaagata cagaagatgt tcttgctcaa aaccatgtat tttcaataat tatctaccat  48720
aattaatatt tttctaaatt atgtgtttaa ttatgaggtt taacaacaaa aaaatatata  48780
taaaagtcca taatcaatat ttacttgtct taattctatc tctttttgtt tttgttttat  48840
tatacaaaaa taaatgtatg taggtcgctc tctctttaaa tatatatata tatatatata  48900
tatatgagtt cgaagttcaa gttctagagg atttgcaata cattaaagaa agtcgaaact  48960
caaatactaa aaattgattt gtcacaaatg aactttatat caagtggata atatctcaaa  49020
agaattgaag catcgaaagg aattgaatct taatttagaa ggctatttgg atatgatttg  49080
agttagtttt aacttgaaat tttagttgaa gttcgaagtt acaattaaat tgtattgaag  49140
ttggattata attatatgtt gagatggtat gaaaattatt ttaaatttgc ttgtgtgctt  49200
tatagttgtg ttaaatttat atggatatta tatgatggtt ctatcaatgt attgtattaa  49260
atttttggaa atcaacatga actttataca aaattgggaa aatgcactag tactccccta  49320
cactatgatc aaaatcacag agacacacct taactaacac aaaaattata cagttatata  49380
catatgtata tcaattttat ataaaaaaaa ttgtgaccca aaattctaag ccttgacgag  49440
```

```
atatacatat atcatatcga tttcacacaa tcttcataca tgaaaaaaat atgagtgaaa  49500
ttttaaggct cgagtaaaat taattcatat atattttgaa aaaataactc ctactatatt  49560
ttggtaaata aaaatctcct attacatgtg ataacactat aaatctaatt tggtatataa  49620
agaaaaattc ccaattgcca aatttattca tatttcaatt atcaattgat tcaagaaaga  49680
agacatgtca aagaatgaaa ataatacatg cctaatttca tgcttttata tggattttga  49740
cttgtaataa ttattttttt atatgcaatt ttatttcaat tttccttttt tttgttagac  49800
ataacatgtg taatagagtg tggcaaagga gtctcccccc tttcctcatt ttcatgttta  49860
aaacatatca actttcagca ttattcatgt tggctctctt gttagcataa ttttcttgac  49920
cctatatact taattattat tttttaaaaa aaagaaagca aaataaataa ttaagcacaa  49980
ttatcgagac tcgtctcgat atgcatactc aaaattggag tgttcacttg tcaactaaaa  50040
aggccagatt caaatgcttg tttatataaa tatcttttga aaatcttctt ttttttttct  50100
taaatttcat actcaatcaa acacaacgta aaatgagaga tgttatatgt tgtgtttaga  50160
atagtaaatc agaaatactg ttaagatgaa aagaaagaaa atatccaagt ccacttaatt  50220
atttactgtg ttcataagaa atttaatccc ttcactgtat tcgaggtcga gattgtagat  50280
tatttcctta taggataaaa tagatatatt tattaaagaa gtagtggtac ctctcacttc  50340
aataacttat gcaaactcaa aagttagcaa tgaaaaatca cacagactct actttgttcg  50400
taagaaaata tatatgtaga agaaaaagaa aaacgataca aaagactgag agggaacctc  50460
tctatttaca tccaacgata ggtgtgaact cacatgtaca gaaatatttg ttcggaagga  50520
acatgccctt ctgtaacaat ttacgttact attttatatt tagtaataat ttaactttaa  50580
acttctcttt ttatctttat tgagatattc cctccgttca cttttccttt tggcaatatt  50640
aaaaagtaaa atttcacttt taacttttcc actttagcat ctaaaaaata attaaattaa  50700
aacgatctct tattttcatg ttttatcctt aacatttaac tataaaagcc cccttactat  50760
actcaatttc tcaaaatata tttccctttc tctctctata attttctctc tctaaaaaga  50820
ttggacaatc tatgcatttg tttgcaactt tcttcattgt accaatgctg cttttgtcta  50880
atggtttgcc ttctttcttc gtaatattta ttttattata tagtttaatt ttattctatg  50940
tgttaataat gtataagaat ttttataagt ataaatgttt aaatataact ctttaacttt  51000
ttgatttagt ctacctttaa agtttgataa ctagcaagaa cttggattac tgaaaaatct  51060
aattgatata taaaaaaatg gcttataacc tctgttgtta cacaaatgac ccacattgat  51120
agtttggtta tgtatataaa tgaaataaca aatcgttaaa atatgaaact cacgaagaaa  51180
ataatagttt caatgtgtca taaaatactt ttactaacat acgatgtata aatttaaata  51240
tttgtggtaa aaggtagtag taccacccga gactatatat gactcaaatt ttagaaacac  51300
accttatcta tactaaggtc ttattaccct tccgaactaa attttttgta attttaattt  51360
gtacaccttt tcggcttatg tggcatttaa atatctccca cacgccacaa ctgcgtggag  51420
tcacgggtgt gccacataat ccaaaaggtg tataatatta tatataaggg caacttaatg  51480
caattggagc tctgaaattt caatttgagg cctaaaatat aaatgtagga acaaacttcg  51540
tatacgtatt tattcaaaat taatttccct tacactattc aaatgaaaat tattagtact  51600
taatgttgtt ttttcagtta ttgattttag gtaagatttt atcaactcaa tattgaaaaa  51660
acatcctttc agtgagataa ttattatatg aattgctaac ataatcctat aagtagcgtt  51720
gataaatatt aaataaagat aagagttaga accacaaaat gagattcaag aaaatgatga  51780
cttgatttac cccatttcta tatgtttgct gtaatgcttg aaacaaacaa aaaagaatct  51840
```

gtaattctct ttgttcaaca ctataaattc ttatttttaa tgaaagacta catatgttaa 51900
actgagtaaa ataatatata cttcttaaaa gtaatacttt ttatcgtaac taatcaattt 51960
tttctataaa aatttaacac atatttattt atgataaaaa tttgggcccc ccaaattgcc 52020
ttattttgca aaggcaagag ccggcactga atatatataa aataagttca cgagataata 52080
gattctgttg agatttcgat catagtcaag ggatacttat gtcttctccc aatatttatt 52140
gataatatat ggttctcgat ttttgatgtt tgcgtacatt aattgataga tatgggacct 52200
atgagctgtg gtgtagaggc aagaacttgt gagccacaga gtcacagttt caaggggcca 52260
tgtagtaggg acagcaactg cgccaccgtt tgccagacgg aaggattcat tggcggcgat 52320
tgccgtggcc ttcgccgcca atgtttttgt actacagaat gttagaagaa agtttctaaa 52380
tgatcttttt tacagtctat gtatttgttt acttgttaag atatctaatg ataaataatg 52440
ttgtttaatc aacaaaaaaa agtgactgac taacctcata taaatatata atacatatgg 52500
tgcttttgtt acgattcaaa atcttaggtc atgattttcc ctaagagtca cgatctaggc 52560
ataccaaaat tatttatcga ggaagaaaaa ataagttcag gatagtaaat ttcatcatta 52620
aagcgaacga tacatgtaag aatattttta actaggagaa tatttattct atatttgtcc 52680
ttttcccttt gtttttaat aataaaaaat aaaatctcct tgtaataaga aatagaacta 52740
attaatttat taattatgac ggttcaccgg ccttttctgc tcactcgtag aggttgggac 52800
ctcataaagg aatagcgagg gagtccactg aacattttag ctattggcgg gaaattcgct 52860
cttgtcaggt gaataacaat cgtttcgtca tagtactact tattcatact ggaattactc 52920
aacggattct tttaatgtat catttctggg tccaacgaaa ttcattgata tagaaagaag 52980
ccctatcata taaagatttt tttcttgtga gctactaggt cacactttgg ccaagcacgt 53040
actaccattg gcagagccac atgtagttga cacccccttca tcgaaaaatt acattgtgta 53100
gctagagtaa gatatcttca cgaatcgcct tggtgttgca ctactgcctt gacttagcac 53160
acccccacca attctagtcc taaaccattc acgttacaag tgatgaggac aaactcccta 53220
taataatgta atttcttagt caattctaac atttttgaaa tttaaaaata atttaagtta 53280
aacttataat ttttttaaaa tatttttggt atgtaggcta tcgactcacg tggtactttg 53340
gcctaacaca cctctaaaaa cttatgagaa aaaacattcc ctaaatgatg taacttttta 53400
gccaattcca agaaacatga taacttttta aattttcaaa aaaaatattt aactttgaac 53460
ttttaatttt acgcttaatg agaagctttt tagatattca atgtaattga atgatcttaa 53520
gtttaaaaaa aattcattta tttcttaaat tttcgtttat attaagatat tgtcacataa 53580
attaaaataa aataactaat gtcttgcatg tgattcatat atttgatatt ttacacatat 53640
gcaattaata attccaaaat gtttaatttt atcttcaagc attgaactca ccaacaaatt 53700
aagatctata atattggatc atgtgaaggc caatgtatta catcaaacta ctatataatg 53760
tacgttgtta attgaaagaa cataggaagg gaaaaaacac aaaaagaaga atggaatgag 53820
aagcagaact cggagaaacg agataaaaaa aaaatcggac acttcataac aattagtata 53880 aaccttttt tttgttaaac cctagttctt tttaaccggt tttcaattaa gcatgaatct 53940
caaacaaaat ttgctaatat tttactatgt tcaataatct caactaaatc agtatcgtta 54000
agatgaaggg cacaaatacc taattttggg gcttccattt aagtggtagc cacatttttt 54060
attttataaa attacaaata tatccacttt tgaaccactt caaatatact cgatttaagt 54120
aaaaataatt ttaacaaagc tcgacttcag acatataatg acttgttaag atcgatttct 54180
gaatacatac ctaactttag aattaggaaa gataacttaa agcttttatg tggattttga 54240

```
cttataacaa tttttacatc tttataaagg agaaaattcc tctcaaattc ttctttttgt  54300
taggcataac atgtgtaata gagtgtgaca tgagaggaga cccctttttc tcattctcaa  54360
gttgtaacac atatcactct tcgacattat ttatgctcgc ggattcaaaa tttaaaattt  54420
atacagaaaa aaatgataaa cggatgaagt agttaatgtt ttagaaaatt aatatataat  54480
tagttattta tgttcacctt tattcttact ctataactaa atggagaggg aattaaatca  54540
aagagaaaat tagtaattta atcaaattat ccttttagtt aatgttttta ttaagggacg  54600
tgtaaaaaaa aatatgacaa ataagatgaa ccaaaagaat cacaaatctt caagtcctac  54660
tcccttcttt tcaaatatgt acttgtcacg attttatttt gagaatcaaa cgatatgaaa  54720
ttagatcagt taatatgaga aaaattacaa tttttagcat tttctataaa aattttaatt  54780
ttaaaatatt aaattaattt aagctaaaaa ttattcatta tcaatcttga aaaatgaatt  54840
atgacaacta tttaaaaaat atttgaaatt aaatttcgtg tctaatcaaa tagtcaggta  54900
aatgtgcatg tataaatacc ccccttttgct tactccttgt cttaaccaat tctcaatata  54960
tttctcaaat tgcatttttc tttctctatt tgaagatggc acactctatc cgtttgtttg  55020
caactttctt ccttgtagca atgctactgc ttttatccac tggtttgtct tctttattta  55080
tattatttaa ttttattata tagttttata atattagctc tacgtcaaaa tttagctcaa  55140
tgagagaaaa ttgtccaatt tatgttaaga agtcttagtc ctctcattca ccttcaatgt  55200
gagagtatcc ttttttcata accctccaca cacaaatcga aacataattc tatactgaag  55260
tgtgaacagt ttattcgaaa actcaatatc atatttttta aaattttaat atcatgatgt  55320
atgaatttta gacttgagac aacccaaaat tagttcaaag tacaataaca aaagagacat  55380
tatccaaaca caatatgata ttgtagcatg aacacccgat atcatatgat ttgattctaa  55440
tatcatgata tatgaatttt ggacttaaca aaacccaaaa atagctcaaa acactataac  55500
aaaagagaca ttacccaaac acgatctgac actgaggcat gaacattcga taatccgtta  55560
tcatatgttt tgattctaat atcatgatat atatgaattt tggacttgac acaatcaaaa  55620
atcagctcaa ggcactataa caaaagagac gttatctaaa cacaatttgc tactgaagca  55680
tgaacacccc aaatttggga ctcaacacaa cccaaaatta gctcaaggca ctatgttttg  55740
attctaatat catgatatat gaatttcgga ctcaacacaa ttcaaaatta gctcaaggca  55800
ctataacaaa agagacatta ctcaaacacg agccgatact gaagcatgaa caattctaca  55860
attctagaca ttacccaaac acgatccgat actgaagcat gaacaattct agacattacc  55920
caaacacgat ccaatactga agcacgaaca attcttgttg ctatacaatt atattaaata  55980
tatcctagtt atcttatcca cgaccgatgt gggagtcttg tttcatcatt cataacatgt  56040
ttggctaaaa ttgaacagag atgggaccaa ttagcagtgc agaggcaaga acttgtgagt  56100
cacagagcaa cagtttcaag ggacatgtg ttagggacag caactgcgcc accgtttgcc  56160
agactgaagg cttcatcggc ggcaactgtc gtggcttccg tcgccgttgc ttttgcacca  56220
gaaactgtta gaacatatag agtttctaca tgaaatactc atcatgcatt catgataaat  56280
aatgatgttc tattctatca ataaaaaaga gagactagat atatatagtc tcatatttat  56340
ttatatataa tatgtggtta cgatcaaaaa tcataggtca tgattggcta atctagtatc  56400
tgtttttatt agtttaatat gtgaatcatc gacgaagcac atgatgtgtt gccttagcgt  56460
tgcacttact gccttgactt ggctaatcta gtacatgatc gatcctaaca tcttttgaat  56520
ttatgatatt acaagttcgg gaggggtaaa aaaggaattt aattacatgt actttttttag  56580
ttaggagtat ttgcttactt tttcttctct taaatcgttt tattcgccgc tctttgatca  56640
```

```
attatctagc acttctagtc ccacactgac tagaaagaga gattttatgt aaaatattgc  56700
catataaaat agcgcggtat agaatatgaa aaatcatacc tttctcggcc ttttggctaa  56760
gatcaagtgt agtatctgtt cttatcagtt taatatctga tatgtgagtc attgactcac  56820
acgatattaa ctctattttt tttgggtgaa ggttcatcat ggtagcttgc tattgggacc  56880
ttcaagtgtc gtctaggcgt tgcactactg ccttggcctg gcacacccca ccaattctag  56940
ttgtaagcct ttctttcaat tgttagttga ggacttctta ggatttttgt gtagttataa  57000
aaacctctac atttttggag caaaatcgat acaatatggt ggagaaggca atggacttgg  57060
ccaaacttgc tttgtctgga tgattttaat tagacgtgta tgtgagatta aagtgattga  57120
gaatatccat gatcaattga ggaggttacg ggttgagtca tgttggaggg tgagtgagat  57180
cgtcactatt gatcctcctc ggatggggtg ggggaaataa caaaacgaaa tttttctcaa  57240
aggattttag atgaatctcg taagaacgac aaaaaatata atgcaccagc cgggaatcga  57300
acccgggtct gtaccgtggc agggtactat tctaccacta gaccactggt gcttgatgac  57360
tttgtttatt tattaaataa ctacatattt gatatcaata aaattgcaaa tgtaagatca  57420
agtgtagtat atgtggtgca tttgtcacaa tttcaaaatt attagtcatg attaatgacc  57480
aaaaatccac tatctagatt agagagggat cgactacgat gctaaagcca ggtccgtaag  57540
atcatcaatc cacttgatcg tcatatccat ggagtaaatc tcgataaggt actaaagcta  57600
cggtttgtac aaagcaaata caaacaatat acatgacatg tgtgaaaata aattttgtga  57660
tttagaaatg atatattaaa acgtgatata ttatatgtta gacaacaagg tatctatgta  57720
gccatttgtt agactattgg aattaagtta tgattagtgg tcaagaagtt gttagtctgt  57780
tacataggta aaaaaaagaa aaaaacaagt tagttaatag ttagttactt agtgttagaa  57840
tgtagactca ataatgcccc tggaaactat aaaatttcac taaagaaaag gacaaatatg  57900
aagaaaaaaa aactataaat ttaattattt tgaaaaagta agactcaaaa aatcatttca  57960
tatggaaaat tgatcgaaat gaaataaagt gttgagattt tatatgtaaa atccaactaa  58020
ttcagaaatg ggtattatta cagttgttaa atttctatat atgtattatt actatactgc  58080
atactcttag aaaggaaaaa gaaagataac gtttctcatg tcagaaggaa ccctcaaaag  58140
tatttaaaat tttcaactaa attcatacgc acacatatgc accatcacac gcaatcacaa  58200
ggacacgcgc acgcgcacaa tatataagat aaagacatca ttatacatat aataccccttt  58260
ctatttaaat atatagtgta ttatttatat tttgcatgat cttgcgaagc gaggatgagt  58320
tcacttgtat aacatcaaag aataaatatt attatcattc ttagtgttga agtaactttg  58380
tttagcacta gtattgattt gattttaatt cgagttttgt tagagttact aatatctatg  58440
gactataacc ttaattagac cattcaaaat tcaagtctta gaaacaagaa ataatatgat  58500
aaaagataaa aactatgaaa aagtataaga aatattttta aaaattattc aaagtaaata  58560
tttttatgca taaaaaataa tagttttaaa aaatatatat ataatgtcgg gtccgtttga  58620
tctcgaattg acattttttt aggtaaaaca aaactaatca accacatttg tggaaatgga  58680
ccgaaaacca caattgacat tgaaaactgc cgatatccct tctttttaag tttaaatatg  58740
aactcatggt ccattttact taataaaaat gggctcataa atgggtccac acatattcca  58800
ccttgatctt gttgctgtgg agatcaatta gaaaggttca tttttttagc catctggcat  58860
cttcattgtc tcgtttctga actgactctt ctttttgttt gaaagtgtac tacaaattat  58920
taagtattgg aaaaaatgat ggagatggaa taaaattgat attgagattt tatctgcaaa  58980
atccaactaa ttcaaaattg aggtattatt atacttgtta aattcctgta tatgtattat  59040
```

```
tactatactg catattctta gaacgaaaaa aaaacataat atttttcatg ttagaagaaa  59100
ccctcaaaaa gtatttaaaa ttttcaatta aaattcatac gcacgcacac gcaaacgcgc  59160
acgtgcgcgc gcacacaaaa tataagataa aggcattatt attatatata ataccccttc  59220
tatttaaata atatatagtg cattatttat attttgcagg atctccgaag tgaggatgaa  59280
ttcacttgtg caaaattaaa gaacagatag tattatcatt cttagtgttt aaataacatt  59340
ttctaacact agtattgatt tgattttaat ttgagttttg ttagagttac tattatctat  59400
gaactataac ctttattgga ttattcaaaa tcaagtctta gaaactggaa ataatatgat  59460
aaaagataaa aactatgaaa aagtataaga aatattttta aaaataatac aaagtaaata  59520
tttttatgta taaaaaatta taatttcaaa aaatatatgt ataatgtcga attggtttga  59580
tctcaaattg acattttttt tgggtaaaac caaaccaatc aagtatagtt gtgaaaatgg  59640
accgaaccac aattgacatt gaaaactacc tatattcctt ttttaaagtt taaatatgga  59700
ctcattattt aataaaaatg ggctcctaaa cagatccaca tataaatata ccaaaaaaga  59760
gttggtcggc ccaaaagtgg tcagaccacg tgaatataaa agaaccctaa atgatagggt  59820
tttctcattt gtgctctcct tgttatcatc gcctccgcgg agatgttcta tcttgtgctc  59880
cacaattgta gcttcttccc cctttagtta tgggggatta acattcccca ccttgatgtt  59940
gttgagtttg atatcaaatt tcaaaggttc attttttagc catctgactt cttcattgtt  60000
tcgtttctca actcactctg attcttgttt gaaggtgtac tacaaattat taagttttgg  60060
agaaaatggc agagatggaa taaaattgat gttgggattt tatatagaat attcaactaa  60120
ttcgagattg aggtattatt gcagtttttg aatttctatt tgtttgtatt attactatac  60180
tgcattttct tagaaaggaa aacaaaagta taatgtacta gctgggctaa tcttatctgc  60240
atcaatttca ggatccaaaa tagagtagaa aatcctacaa ttatcagcag cattacgtgt  60300
gaaaaagtat tcagactctc ttgttctagt ctaatctcaa ttctggaacc ttctatttca  60360
ggagacagtt gcaactcttg gatagctaca aacgtttaac tacggatggt aataatacta  60420
atacttcgtt tcattatatt ttcttctcct atttataatt atgatgatat atgttgaatt  60480
cgatgtgtta tgtttccact ctttcaacaa aattatttct acgcctatag gaagaaggta  60540
gtcgaattag ccttatataa atgataaaga aaagacattt cataagattt gtttaactga  60600
aaattataag agattcataa aaaataggtg acacactttc ttatacgatc attgtagtaa  60660
ttgttcatgg actaaaaaga ttttgtcaag acattacatt ggctgaagaa cttaatgttg  60720
tcattaccaa tatacttcca tccccctgcc ccccgccctc caaaaattat aataataata  60780
ataataataa taacaataat atatacatat atatatcaat taaatcttga ctaatgaaac  60840
ttaagattca aggagcaaag tatcatctgt tgtttggcga atctcacgaa attataaatt  60900
ggaaaaccta catgaggacc tatttggtgg aaagtaatac agagttgtga gattcaacct  60960
cttccgtttc tatcgctaat cctagtgaaa attatttaac tactacattg actcagacaa  61020
atgttaatca gtcaccttat tgctcttgat ctcctttacc acttaaagaa ttagaaggct  61080
tgaattaaca aaaatacaaa agagcaggtg aagattagga gaaaagtatc gattgattag  61140
gtggttgagt gtctcggatg taaacagatt tttggcagag attttgaagg ttgggcaaaa  61200
tggacaacat tgatcaaaag gaagaagtgg ttgtccaatt tgcccaagca tcaaaacctt  61260
tgccaaattc tctaaattcc tagcattcaa ctaccgaatc aaacaatact cttctcctaa  61320
tcttcagctg ctcttctgca ttattagtgc gagccttctg atctccaact ggtcaaagag  61380
atcaagaaca ataatactat gagtctcact caacatagat tttctccttg ccaagtctgg  61440
```

```
cttctaatta tatctcttat atatctaatc tttcactaag gtgattcatt gaaattttgt  61500
gaaagtcgat ttagtagttg gattcttttc acaatcatca acaagagaaa caaaagaggc  61560
tgagtccaac atctcttcat caccttttac caaatgggtc ctcatgtagg ttttttaatt  61620
cacgatttcg tgagattcac cgaacaaatg acacttgctc ccttaatcat aagtttcatc  61680
aatcaaaatt taattaatag ttgtttaagg aaaaaatgga agtatactga tatcatcaca  61740
atctgaaatg gcagagaaaa aaaagaatga aactaaatat caatattatt accatcatta  61800
gttaaacttc tacaatctaa agagttgtaa cctagtgttt tcaaagacct tttttgggca  61860
aatctcaggg tggccatacc aaaaaccttc gggcacaaat tgataagtcc tagaattggg  61920
cataagcact aagcataaaa caataagttc tggtgtaaaa acgtgtgccc taagtgtttc  61980
ttaagtattt tttttaatct tttttttttg ctttaaatca attctttttg taattattgg  62040
cgtagtgata tttctcaaat agtaattatt atactttttt ttctttatct caaataaaaa  62100
tcataataat ttccctatat attataataa aaaaaattac tagtaaagtc attgaaagtt  62160
taattttact tttgattatt ttcttagtaa taaaattata aaattaaata tacatgagat  62220
tatgccccat agatccatta gattactccc catgtctcaa gacttacgcc tcatcccgta  62280
ctacataaaa cgtctcgtct catgccccta cctttcaaaa ctctagttat tgtctcgtga  62340
gatagaaggt tccaaactta agtccagact agaacaaagg agactaaata ctctttcaca  62400
tgtaatttta ctgatatcct attagatctt gaaattgatg cagataagat cggtacaata  62460
caaaaacagc aattcaacaa ttgcaataat gtctcaatcc tgaattagtt gggtttcaca  62520
tgtaaattct caacatcaat tttattccat cttcaccaaa aaaaatctag agtaaataat  62580
ttgtacaatt aaacaaacta gagatactgg tgtttttcaa tatcgattat gattttcggt  62640
ccattccata atcatgaaac tctactaacc acgtagatat tggataacct aatgaaatac  62700
ttttcgtatt agaagatatt gaacttaatc atcgatgact tttatcaatc aataaacaaa  62760
atccttcaac gaatcaaaaa ataaatcaaa aactttgttt caatacctta attttgatat  62820
atgaacttct tagagtccat ctaattggcc aggcacacac ttttatccca cactgcttag  62880
aaagagagat ttaatttaac aagtgatata tgaaatagcc cggcataaca aatggaaacc  62940
catacctttc tcggcctttt ggctaagatc aagtgtagta tctgttctta tcagtttaat  63000
atctgatatg tgagtcaatg actcgcacga tattaactct atttttttag gggaaaggtt  63060
catcacgata gcttgctatt ggtaccttca agtgtcgcct aggcgttgca ctactgcctt  63120
ggcctggcac atcccaccaa ttctaattct aaaatctttt gtttcaaaat agtacacagt  63180
ttgtcccttc taatatttgg atatttgata cataacagct ctctctatgc cccattccaa  63240
gtaacacttt ttaactaaac ctatataaac tataaagttt tagcagagtc aattttagta  63300
tgatccgata tataatcaga ccgaattcga tttctcatct ggtaacctcc aacaacatta  63360
aaaaataata atggaaaaag ataggctcag atgcactatt ttatagtcta ttaatatcag  63420
acaaggtgag gacccaaagt tctcactaac tgtgcaattt tatcttcact gcactcacat  63480
agaatgtatc agaggggagt tgaacctggg tctgtactgt gacagggtat tactctacca  63540
ctagaccatt cgcgcttgac atttaaagaa tacactcgca aagtatcacc cctaatgtaa  63600
gatcaagtgt agtatctgtt cgtattaata tatacattaa actctatttt tgaggaggat  63660
atccatagga tagcttgcta ttgggatttg ggaccttcaa gtgtcctttg gcgttgcact  63720
ttgtttatcg attttttgga actataaaag gtcattctca acattatcaa aagatttaat  63780
gtgtgttact aatcgacaaa tctttaatga ttcatgaaaa ataatttgtg tttcttatta  63840
```

gttttcaata tttattcaca acaaaggaat atgaggggaa ggttcattac ggtagctttg 63900
ctaacgtagc ctaggtgttg cactactact tggcttggtg cactgttttt caaggttctg 63960
gacaaagata attagtactt gggatttttg ttcaagttat tatcaacctt ttaacattta 64020
tgaagcaaga tcgatacgtt acgtggaaaa tgttatgtag tcaacaaatt gtaatttaca 64080
tttgttgttt tctatcttat tttggattaa atgaaaacct taataagata acctttgttt 64140
cttcatagca gaatgttaga ttataagaaa aagtagttaa atttgatgac atctttgatc 64200
aactgttaat ttcagcaaaa ttgttgaaac tagtttgcag ccaacaaaac tttaacagaa 64260
aaaaaatttc atttactttg atttaaaatc atattataga tgattactgt gattatatac 64320
aaaaatatag aggatattca agtcccacac tgactgcaaa gagagatttt atgtaacaac 64380
taacatataa aatagtgtgg cataagacat agaaaatcat acctttctcg gccttttggc 64440
taagatcaag tgtagtatct gttcttatca gtttaatatc tgatacgtga gtcattgatt 64500
cacacgatat taactctatt ttttgagggg aaaggttcac cacggtagct tgctattggg 64560
accttcaaga gttgccttgg tgttgcgcta ctgccttggc ctggctcacc ccaccaattc 64620
tacttctaaa gaccttttgg ttcacaatag cacacaattt gtcccttcta atattgggca 64680
gtttgatcca taaaagctca tatccaatgc attaaaataa aatcagatac tgaactacat 64740
tttagcataa ctcataaaat cttgagacca atgttaaatg gtgaccaaaa gtataataat 64800
cgtttgatcc ataaaagctc atatccaatg cattaaaata aaatcagata ctgaactaca 64860
ttttagcata actcataaaa tcttgagacc aatgttaaat ggtgaccaaa agtataataa 64920
ttcgattctc ttgtaatctc taacgacatt atggccagag tcaatatata ataatttgat 64980
ttccatgttg taatctctaa cgacattgaa aataatagtg gaataatgag tagctcagat 65040
gtgctatttt tgtcatctta acattcagac atggtgaaag acccaaagtt ttcacacttg 65100
cacggttatc ttcatggcac tcaaactatt gcatcagtcg gaaatcgaac ccaggtctgg 65160
accatggcag gatactgttc tatcactaga tcactagtgc ttacacatta aaatacttcc 65220
ttcgtttcta tttagaaacc aactaattat agcaggatgt catataaaaa ggaacggagg 65280
aagtatactt catcttttgt actagcagta aagtacaatc cctaaaatat tttatatcca 65340
ataaattgaa aatgcatgat catgtgtagt atctgctctt attagtataa tatcttatat 65400
taaacttttc aaaaaaaatt tatagtaatt aggggtgtgc atttcaattc gattttatgt 65460
attatcagtt tgatttatta gtttttgact tttaaatacg ctaaatcatt aaaaaaatcg 65520
ataagatatt ctttatcagt tttcagttta cccaataaga aaatattcgt aaaatagatt 65580
tatgatttct cacttttcta acaatttggc acgagactgt gagacaagca aaacagatgt 65640
aaatgctttg atatagtgaa ataggaaata taatgaaaaa ttacatcaat aatagtagat 65700
gtagtatgaa ggctacaaca acatgttaca tagtatgaaa tttcggatgt gaactagaag 65760
tactatgacg tgtgaagtgt gtagactgta gtatagagta ctgacatagt gtctaattat 65820
gctaatttat taatatttaa tattcatgaa ggatatagta atatattact gtcgtcttaa 65880
cgagttatcg ttttacccat actaaaaatc gaaaccaaat cgataaccga ataagttttt 65940
cttataacac cattaaaaat ttgttaaccc aataaaatat aattttgtgt ttcttattag 66000
ttttcaatgt tattcataac taaggaatat gatgggaatg tcaattacgg tagcttgcta 66060
ccaaagacct ttcccactaa ttctaatttt aaaccttttt ttttttaatt ttttgttgaa 66120
ggaatttctt cgaggtctac gacaaagata ttaattctta cgatttttct gaagttatta 66180
ttaacctttt aacattttg gagcaacgat ggatatgata ctgtgaaaaa tgttacgtag 66240

```
gcaacaaatt atacatcttt atagtcccac attgactaga aagagagatt ttatgcaaca  66300
agtgacatat aaaataatcc agaataacac atgaaaaatc atacctttct cggccttttg  66360
gctaagatca agtgtagtat ctgttcttat cagtttaata tctgatatgt gagtcattga  66420
ctcacacgat attaactcta tttttttagg ggaaggttca tcatggtagc ttgctatcgg  66480
gatcttcaag tgtcgcctag gtgttgcact attgccttgg cctggcacac cccaccaatt  66540
ctagttccaa aaaccttttg tgttcataaa tgataattct atattatata taataatttg  66600
atttccatgt tgtaatttgt aacgacatta aaaataacga caaatatata ataatttgat  66660
tcccgtaatt tctaacgaca ataaaaaaat aatggaaaaa ggagtggctc agatgtgtta  66720
ttttgtcatc ttaacattca gacatggtgg tgaaagactc aagttttcac atttgcacaa  66780
ttatcttcat ggcactcaaa ctattgcacc agccgggaat cgaactcagg tctgtaccgt  66840
ggcaggatac ttccttcgtt tctattatat gtcatcctct agatttacgt gaacaagttt  66900
tactattcta ctcttattca ccccatatta gttttctttg ttggtcaaag gactattttt  66960
aagattagta actcataaag gtaaagagaa agaatgtagt tataatttat acattaattt  67020
taagaaatga caagtattac gaaccaacta attaattata aaaaggaata aagggagtat  67080
gcctcatctt ccgtacttag cagcaaggta ccacccctaa aatattttat atcaataaat  67140
tgaaaatgta tgatcaagtg tagtatctgc tcttataata tatcttatat ttcgatctga  67200
tttattgatc ggtccgattt ttgtacattc ctaatttcat attatatact tccaacaagg  67260
taccactcta aaatatctca ataaataaaa atgtaaaatc aagtatagta tttgctctta  67320
taagtataat atcttatatt aaattttagt taaattttcc aaaaaaaata tttatagtaa  67380
ctcgacacga tataatcact aataaaaaat tgttattttc tcccattgaa aaatattctg  67440
ctgcaaatat tttgattaga ctggtaataa gagaaaatat atatattaat acaaaaaaaa  67500
ttcattattt tagtgtgatt ttattttccc cctgtatttt ttcataaagt tgataaaatg  67560
aaaaatgaat agcaaaatca tactctatta cattattttt cactaaagaa aaactatttc  67620
taatagttac acgaacccac acggatcaaa gttaaccata aaaaacccaa accaatcgaa  67680
cagggtttcc caaaccctaa ccgaaacgaa acaaatcgtg ttatattttc aacccgcccc  67740
gacccgcccc aacaactaag tatctataaa aaggcccctt ctagttctag cctactcata  67800
aacttctcaa attaaatttt atttctccct tctctctcta aacttctctc tctctctaaa  67860
tatggggaac tcccttcgtt tgtttgcaac tttcttcctt gtagctatgc tgcttttggc  67920
cactggtttg tctttctttt attaatcaat ttattcgtat ttatttttat gttatcgaac  67980
tttgagaaaa aaagttatct atatcatttt ttttagaaaa aacttattca tgcatgtcgt  68040
taatttgtta acttaaatga tataaatgag taaaattttg aacaatagat gatatatatg  68100
agtttcttta aaaaaaaaaa actgcaatta catatttgaa tctttttctt ttttcaaaaa  68160
atatttaact cataacatga ttgaattata attgatcacg tatataaaat aactttgaaa  68220
agttaaaatt attttcaatt aataaatgat gacatgaatg agtcatttct caaatgaaac  68280
atgagtcaaa ttcttaacga ggatatagac agcttttttt ttaagtttga tgacatattt  68340
tagcacgcgt gatggaatta taattaacga tatgtaaaaa atgattttac aaaattaaaa  68400
ttatttttca ttaataaata attacgtata tgaactcttt ctcaaacaaa aataacagaa  68460
atgatctaaa tatttaagaa atgatatgaa tagacttttt ttctcaaaat tctatttaca  68520
attttgtttt ccaaatcaaa cacccaaaat gaaactacaa tcaataaaca aacaaatctt  68580
tgtaaccaaa aaataaaaat gatctgataa tataaaaaat aatatttcga atttttcatt  68640
```

ttacaggacc aacaacaagt gtagaagcaa gaacttgtga gtcgcagagc caccatttca 68700
aagggaattg tcttagcgat accaattgtg gttccgtttg ccgcaccgaa gggttcaccg 68760
gtggcaactg tcgcggtttt cgtcgacgtt gcttttgcac ccggaattgt taatagaaga 68820
aaataatctt ttcataacga 68840

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
cgaaagattt tccggtggta 20

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tttttacaaa caaaactagc attacaa 27

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gcggttgtgt tgtcatatcg 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gcgaagaaaa ttgggatgaa 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gaggcaccat cttggaatgt 20

<210> SEQ ID NO 19
<211> LENGTH: 20
<212> TYPE: DNA
<213> ORGANISM: Artificial Sequence
<220> FEATURE:

<223> OTHER INFORMATION: Description of Artificial Sequence: Synthetic primer

<400> SEQUENCE: 19
tgagtgcagc taggcttgaa 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
cagggtttga aggaatctgg 20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ccacgaattt ccttgcagtt 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
caccaagaaa agcagggttg 20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gattctgtgg ctgccatgta 20

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
tacaaggatc caaattttgc atgtccttca 30

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
acaaggatcc ggcttggaca cttcgttat 29

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tttggatcca tttaaattat gacagcgcca gaacaag 37

<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tttggcgcgc ctctagagac ctcctggtct catggaa 37

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
cagcttttgc caccaaaaat 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
tctgatccat gtctccgtga 20

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
cacgacgttg taaaacgaca atgctttccg ttcaacgac 39

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
cgtcggtttc tacgtcatca 20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tgaatgaact gcaggacgag 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
atactttctc ggcaggagca 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
agcgagctag caaaattcca 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
agcatgcaaa aaccctcaat 20

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gcagcacttt gcaccatct 19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
tgaatggttg cagtgcgta 19

```
<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

tttacccgat gtgaaaacga                                                20


<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

catcaatagt ccaaggggaa a                                              21


<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

catcttggcc cttactctgg                                                20


<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

aatgacacag cggaactcaa                                                20
```

COMPOSITIONS AND METHODS FOR ALTERING THE MORPHOLOGY OF PLANTS

CROSS-REFERENCE TO RELATED APPLICATIONS

This application claims the benefit of PCT application No. PCT/US2008/076936 filed Sep. 18, 2008 which claims priority to U.S. Provisional Application No. 60/994,349, filed Sep. 19, 2007, the disclosure of which is incorporated herein by reference.

STATEMENT REGARDING FEDERALLY SPONSORED RESEARCH

This invention was made with Government support and the Government has rights in this invention under the National Science Foundation Grants DBI 0227541 and DBI 0400811.

TECHNICAL FIELD AND INDUSTRIAL APPLICABILITY OF THE INVENTION

This invention relates to the field of plant biology, and to compositions and methods for modifying the phenotype of a plant.

BACKGROUND OF THE INVENTION

Altering a trait in a plant has long been a desired goal. For example, elongated fruit is an important property in tomato from cultural and agronomical points of view. Tomatoes that are mechanically harvested and used for canning as well as the preparation of sauces typically feature elongated and blocky fruits. These shape characters are important to prevent the tomatoes to roll of conveyer belts during machine harvesting. Whole rectangular shaped tomatoes fit better in a can than when they are round in shape. Furthermore, the recent development of new varieties for fresh consumption resulted in an expansion of novel fruit shapes in this class of tomatoes. Perhaps most notable of these are the grape tomatoes which feature the size of a cherry tomato but the fruits are oval instead of round shaped. In addition to other improved qualities such as flavor and aroma, the distinct shape of the fruit makes it easy for consumers to separate the cherry and the grape tomatoes. The elongated fruit shape features undoubtedly led to the rapid increase in popularity of grape tomato in the last five years.

The molecular bases underlying fruit shape variation in plant species are largely unknown. Fruit crops display tremendous diversity in the morphology of the reproductive organ in comparison to their wild relatives. Wild relatives of tomato bear small and round fruit, while cultivated types bear fruit of increased size and many diverse shapes including flattened, rectangular and blocky, oxheart, bell pepper, long pepper and pear forms. This morphological variation is controlled by genetic loci that have major as well as minor effects[1-5].

A prevalent morphological feature that distinguishes many cultivated tomatoes from undomesticated accessions is elongated fruit shape. Three major loci affect this feature: ovate, fs8.1, and sun, residing on chromosomes 2, 8, and 7, respectively. OVATE, which confers an elongated pear shape to fruit encodes a protein that negatively regulates plant growth[6]. The locus fs8.1 imparts an elongated blocky shape to fruit, while sun imparts an elongated and tapered shape to fruit[1, 4, 8].

The locus sun comprises a major QTL and explains 58% of the phenotypic variation associated with elongated fruit shape in an $F_2$ population derived from elongated-fruited *S. lycopersicum* variety ‘Sun1642’ and the small round-fruited wild relative *S. pimpinellifolium*, accession LA1589[8]. Fine mapping indicates that sun resides in a dynamic region of the tomato genome where a large inversion comprising half of the short arm of chromosome 7, and small-scale insertions, deletions and tandem duplications distinguish the species in the tomato clade[9]. One insertion, estimated to be 30 kb, is particularly noteworthy because it is present in Sun1642 but not in LA1589, and is linked to fruit shape[9].

Structural variations of genomes, such as duplications, deletions, inversions, and translocations, are prevalent in man and some of these variants underlie diseases[10-12]. The structural variants are named copy number variants if they comprise a region larger than 500 bp-1 kb but smaller than 3-5 Mb[10, 11]. Although the molecular mechanisms facilitating genome rearrangements resulting in copy number variants are often unknown, non-allelic homologous recombination is most commonly proposed.

In plants, the occurrence and extent of copy number variants and the role this type of structural variation plays in affecting phenotypic diversity within a species are largely unknown. The lack of information about structural variation within plant species is due to the lack of complete whole genome sequence information of accessions within the same species.

In addition to non-allelic homologous recombination, transposing elements can also create structural variations of genomes[13, 14]. Most notably, the transposition can lead to dramatic changes in phenotype when these elements land in the gene thereby inactivating its function. In fact, the ability of transposable elements to knock out host gene activity has been used extensively in functional analyses studies in many species.

An unusual group of transposable elements was discovered recently which were found to harbor segments of the host's genome. Of particular note are the Helitron and Pack-MULE DNA transposable elements found in maize, rice, and many other species[15-20]. These elements are unusual in that they ferry host gene and gene fragments around and have the potential to create novel proteins and protein functions through domain shuffling. Also, certain types of retroelements have the potential to create novel genes by read-through transcription into host genes followed by transposition of the element and its transduced segment elsewhere in the genome. Although this type of transposition is not often described in plants, the L1 retroelement is thought to be responsible for transducing up to 1% of the human genome[21]. Another transposon-like mechanism with the ability to generate novel functions is through the fortuitous reverse transcription of host mRNAs and the subsequent random insertion of these cDNA molecules into the genome. Although it is generally thought that most of these so-called retrogenes are non-functional, they have the potential to generate considerable phenotypic diversity in both plant and animals[22] and provide one of the mechanisms for gene family expansion over evolutionary time[23].

However, despite the potential of these latter types of transposable elements to underlie phenotypic variation via either the creation of novel genes, altering their expression through repositioning them in different chromosomal contexts, or by generating small interfering RNA that participate in silencing of host genes[13, 14, 24], documented examples of a change in phenotype as a direct result of these types of transposition do not exist.

SUMMARY OF THE INVENTION

In one broad aspect, there is provided herein certain novel compounds, methods for producing them and methods for varying the morphology of plants. In a particular aspect, there is provided herein an unusual and complex retrotransposition-mediated event in which the duplication and repositioning of a gene at once resulted in a novel fruit shape phenotype found in tomato.

In a broad aspect, there is provided herein a transgenic plant that expresses at least one polynucleotide described herein, where at least a part of the transgenic plant has an altered trait as compared to a non-transgenic plant or wild-type plant.

In another broad aspect, the altered trait is one or more of: sensitivity to hormone levels, altered shape of at least part of the plant, altered plant size; altered leaf shape; altered vegetable shape, altered fruit shape; at least partially parthenocarpic fruit, increased SUN levels, and decreased SUN levels. Also, in certain embodiments, the altered trait is an overexpression of at least a portion of one of the isolated polynucleotides wherein the altered trait comprised a parthenocarpic fruit. Also, in certain embodiments, the altered trait is an expression of at least a portion of one of the isolated polynucleotides wherein the altered trait comprises an elongated fruit shape.

In another broad aspect, there is provided herein a method for producing a transgenic plant having an altered trait as compared to a non-transgenic or wild-type.

In another broad aspect, there is provided herein a method for making a plant having at least one fruit having a shape that is different from a naturally occurring fruit, comprising transforming a SUN inverted repeat construct into a near isogenic line of the fruit, and growing the plant.

In another broad aspect, there is provided herein food and food products comprising the fruit of the plants described herein. In another aspect, there is provided herein a near isogenic line (NIL) comprising a Sun1642 background. In another aspect, there is provided herein a near isogenic line (NIL) comprising a LA1589 background. In another aspect, there is provided herein a 17.2 kb pHX2 construct containing IQD12, SDL1-like, HYP1 and nucleotides encoding the first 415 amino acids of HYP2. In another aspect, there is provided herein a 14 kb pHX4 construct containing IQD12 and terminating 180 nucleotides upstream of the SDL1-like stop codon.

In another broad aspect, there is provided herein a method for altering at least one of a leaf and fruit shape of a plant, comprising introducing and expressing the polypeptide in the plant wherein the expressing the polypeptide alters the shape of the leaf and/or fruit, as compared to a plant that does not express at least one of the polypeptides described herein.

In another broad aspect, there is provided herein an isolated host cell transformed with a vector comprising at least one polypeptide described herein.

In another broad aspect, there is provided herein a method for increasing the regeneration ability of a plant, wherein the method comprises the step of expressing at least one polypeptide described herein in a cell of a plant.

In another broad aspect, there is provided herein an agent for altering at least one trait of a plant, wherein the agent comprises at least one polypeptide described herein, or a vector thereof as an active ingredient.

In another broad aspect, there is provided herein a method for determining the ability of a plant cell to produce a fruit with an altered shape, wherein the method comprises detecting the expression of at least one polypeptide described herein or a protein expressed thereby in the plant cell.

In another broad aspect, there is provided herein a method for determining the ability of a plant cell to produce a fruit with an altered shape, comprising detecting the expression of the polypeptide in the plant cell.

In another broad aspect, there is provided herein a method for improving the ability of a plant to produce a fruit with an altered shape, comprising regulating the activity of at least one protein produced by expression of at least one polypeptide described herein in the plant.

Various objects and advantages of this invention will become apparent to those skilled in the art from the following detailed description of the preferred embodiment, when read in light of the accompanying drawings.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

In this regard, no attempt is made to show the various aspects of the invention in more detail than is necessary for a fundamental understanding of the invention, the description taken with the drawings making apparent to those skilled in the art how the several forms of the invention may be embodied in practice.

This application patent may contain at least one drawing executed in color. Copies of this patent with color drawing(s) will be provided by the Patent and Trademark Office upon request and payment of the necessary fee.

The Sequence Listing provides exemplary polynucleotide and polypeptide sequences of the invention. The traits associated with the use of the sequences are included in the Examples.

Figures 1A, 1B:
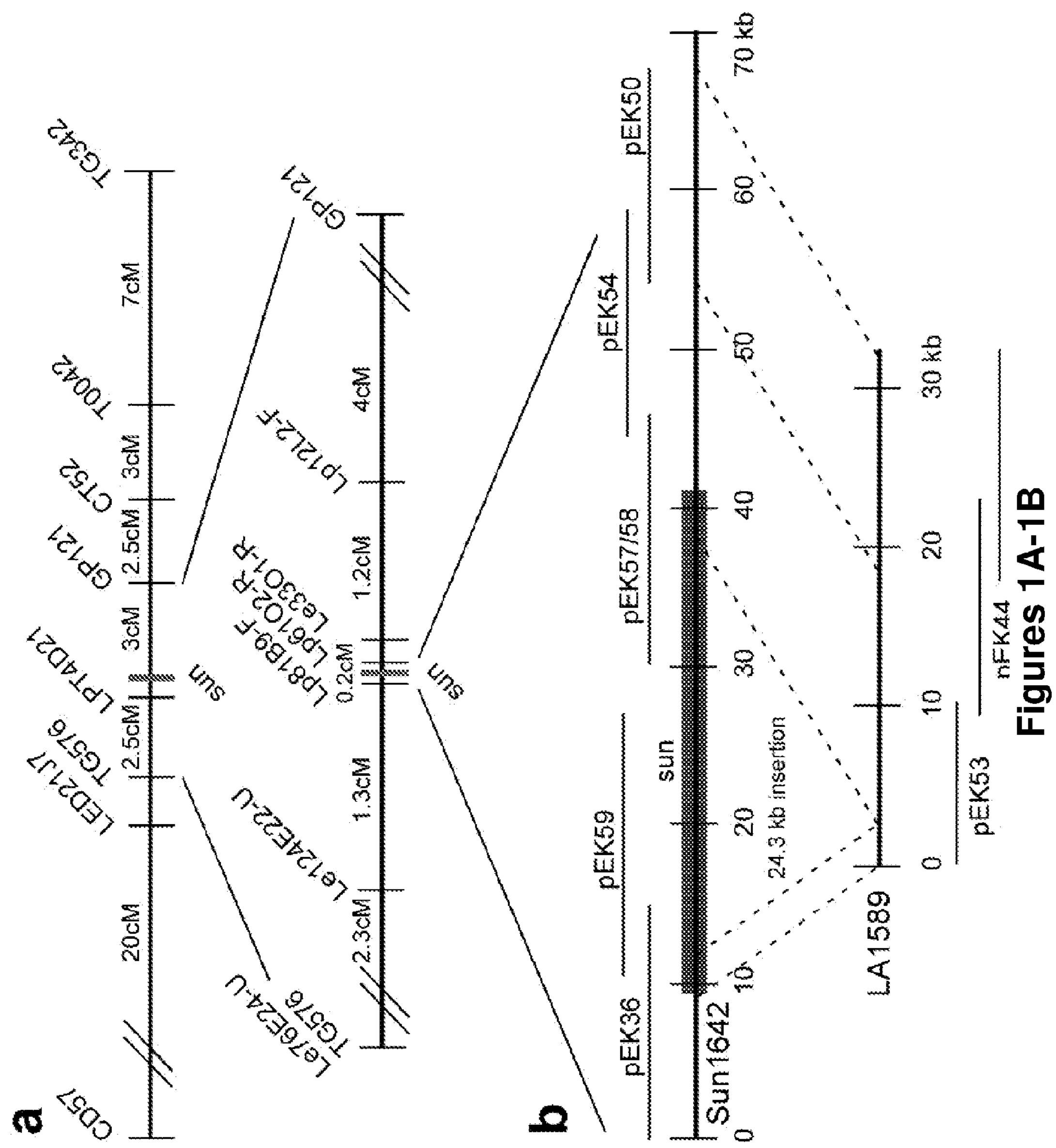
Figure 1C:
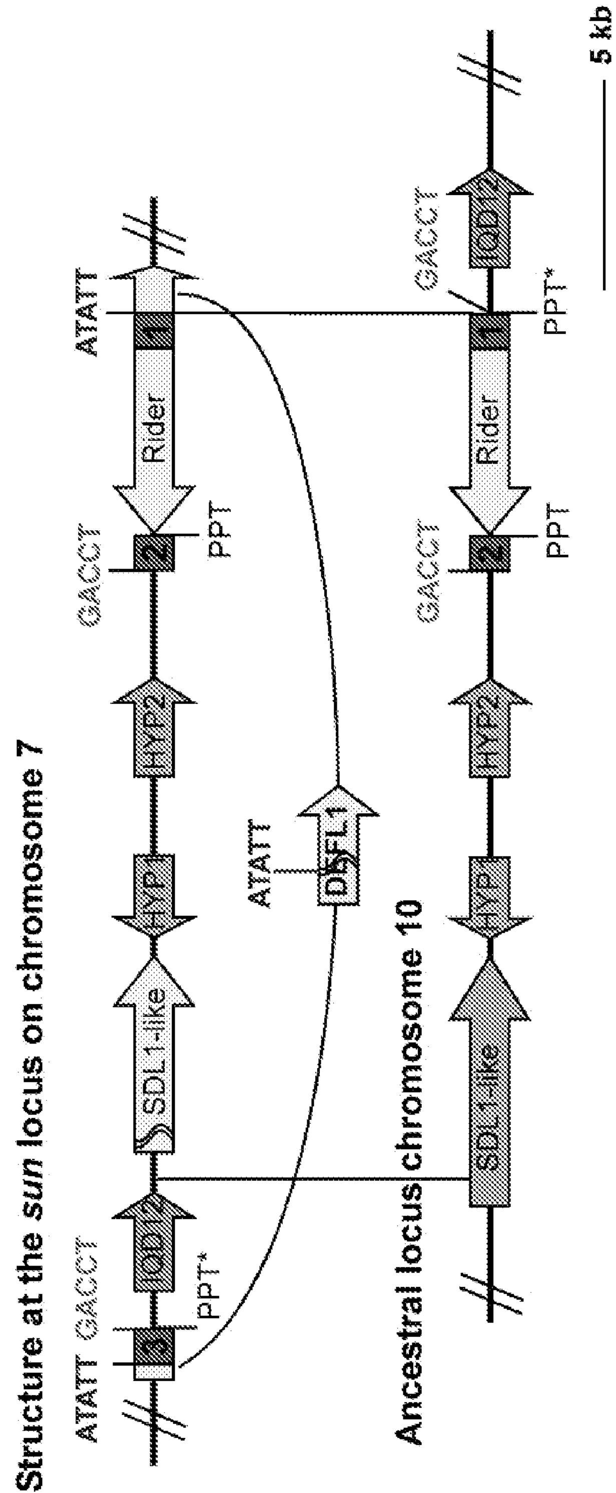

FIGS. 1A-1C show the high resolution fine-mapping positions sun to a 30 kb region on chromosome 7:

FIG. 1A shows the genetic mapping and fine mapping placed sun to a 0.2 cM interval between two markers Lp81B9-F and Lp61O2-F. The vertical red (thick) bar defined the sun locus.

FIG. 1B shows the physical map of the sun locus using bacteriophage λ clones spanning the region. The upper portion displays the physical map of the *S. lycopersicum* Sun1642 genome and the lower portion displays the physical map of the *S. pimpinellifolium* LA1589 genome. The thin lines above and below the physical maps represent the phage clones. The diagonal dashed lines between Sun1642 and LA1589 physical maps indicate the colinearity between Sun1642 and LA1589 and also show where the 24.3 kb insertion occurs relative to the LA1589 physical map. The smallest region encompassing sun is indicated by the red bar and was defined by the recombination breakpoints flanking the locus. Thus, the sun locus maps to the short arm of tomato chromosome 7 between markers Lp81B9-F and Lp61O2-R and the recombination breakpoints delineate the locus (shown in red (thick line)) which is tightly associated with a 24.3 kb duplication.

FIG. 1C shows the structural organization the chromosome 7 sun locus (upper) and the chromosome 10 ancestral locus (lower). IQD12 (also referred to herein as SUN) is located 20 kb downstream of Rider in the transposed copy as opposed to 1 kb upstream of Rider at its ancestral position. The transposed 24.3 kb segment landed in the intron of DEFL1. Arrows show directionality of the predicted genes and pseudo-genes.

Dark green arrows (HYP1, HYP2, SDL1-like) indicate ab initio predicted genes, purple arrows indicate the rearranged IQD12 gene, light green arrows indicate the retroelement Rider, and the yellow arrows (upper first box, second arrow, last arrow) indicate pseudo-genes. Red numbered boxes identify Rider's Long Terminal Repeats (LTR) and are numbered according to the order of transcription. The target site duplication (TSD) caused by Rider's original insertion into chromosome 10 is in green text (GACCT); the TSD resulting from the transposed duplication into chromosome 7 is in blue text (ATATT). PPT and PPT* indicate the position of the polypurine tract required for second strand synthesis of the retroelement.

Figure 2A:
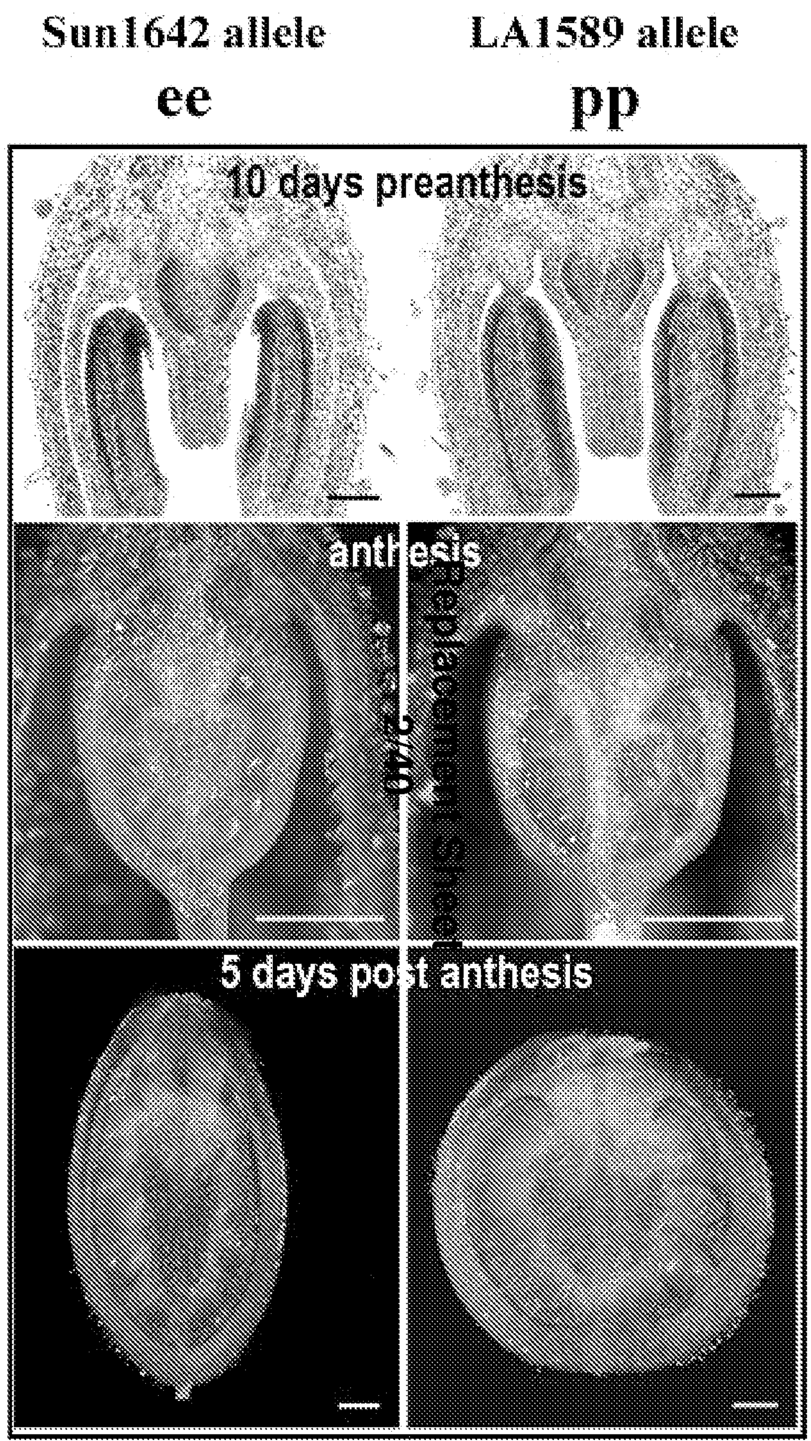
Figure 2B:
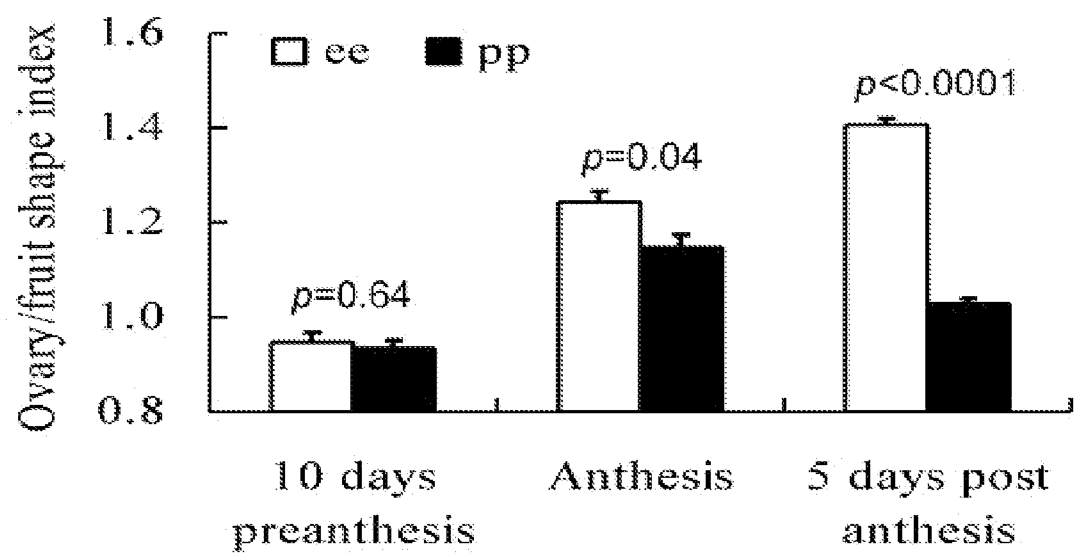
Figure 2C:
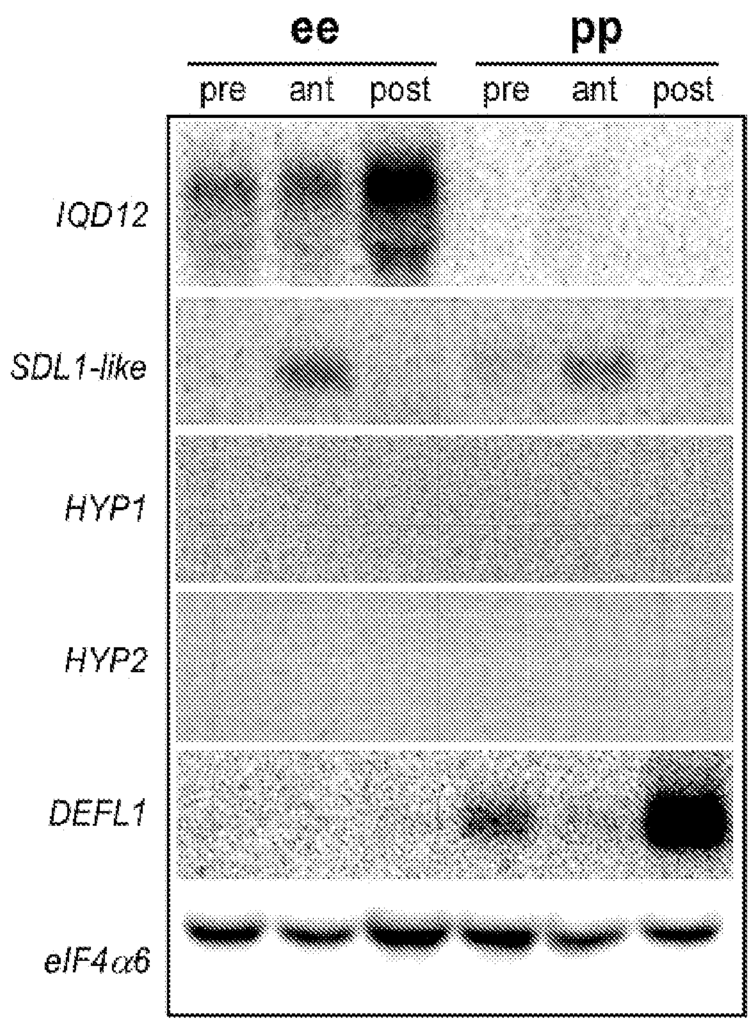

FIGS. 2A-2C show that sun affects fruit shape post anthesis and in a dosage dependent manner. The effect of sun and candidate gene expression was determined using Near Isogenic Lines (NIL) differing for the presence and absence of the Sun1642 allele in the LA1589 background. The nearly Isogenic Lines (NILs) differing at sun display a large difference in fruit shape in young developing fruit 5 days after pollination. In those fruit, IQD12 is expressed at higher levels in oval shaped fruit due to increased expression at its new location on chromosome 7.

FIG. 2A shows that representative ovaries at 10 days pre anthesis, at anthesis, and at 5 days post anthesis from elongate-shaped, homozygous Sun1642 (ee) genotypes, and round-shaped homozygous LA1589 (pp) genotypes. Scale bar, 100 μm, 500 μm and 500 μm for images at pre anthesis, anthesis and post anthesis, respectively.

FIG. 2B shows that ovary shape index determined by calculating the ratio of organ length to organ width, were similar at 10 days pre anthesis ($p=0.64$, $n=10$ of ovaries per genotype). At anthesis, ovary shape index of the NILs was significantly different albeit small ($p=0.04$, $n=5$ plants of 8 ovaries per plant per genotype), whereas fruit shape index was highly significantly different at 5 days post anthesis ($p<0.0001$, $n=5$ plants comprising 6 to 8 fruits per plant per genotype).

FIG. 2C shows the Northern blot analyses of the five candidate genes at sun. Total RNA was isolated from pooled tissues from 5 plants of each genotype at the same developmental stages shown in FIG. 2A. Fragments of the candidate genes were sequentially hybridized to the Northern blot. The signal for eIF4α6 served as an RNA loading control. "pre", tissue harvested 10 days pre anthesis; "ant", tissue harvested at anthesis; "post", tissue harvested 5 days post anthesis.

Figure 2D:
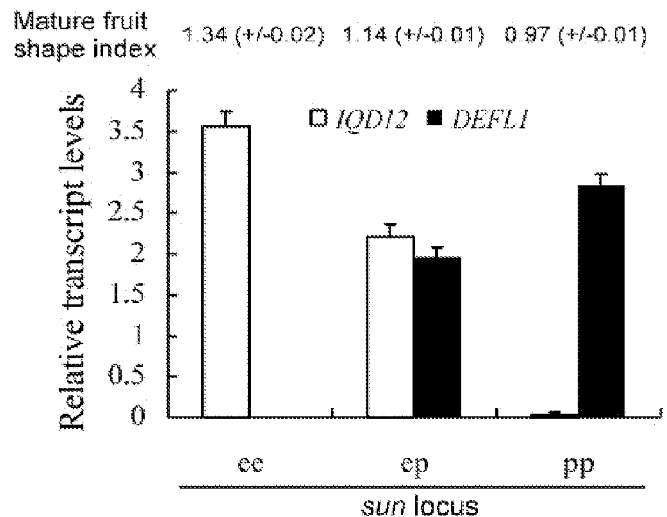
Figure 9A:
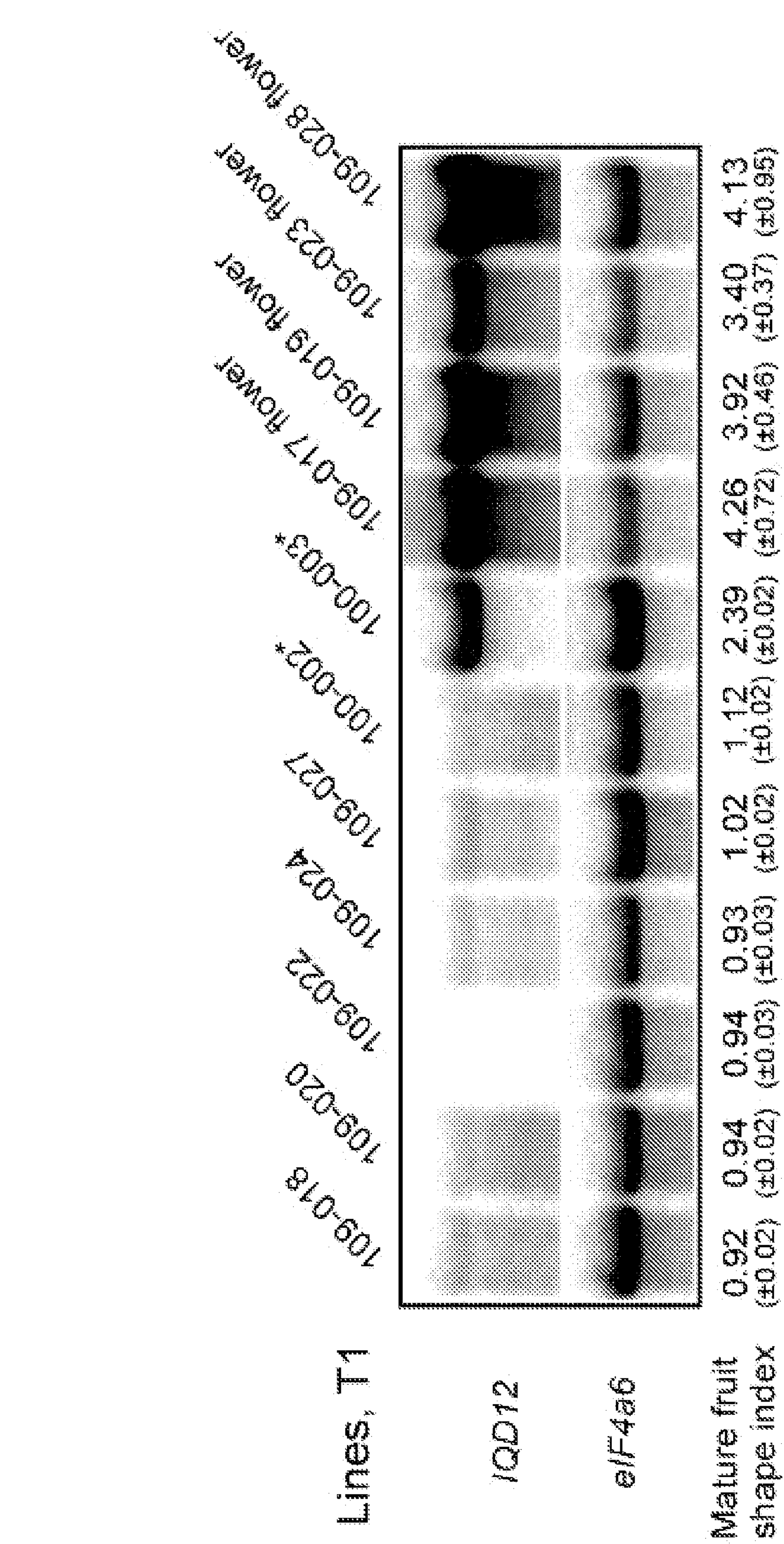

FIG. 2D shows that IQD12 and DEFL1 transcript levels are allele-specific, and dosage-dependent, and correlate with mature-stage fruit shape index. The fruit shape index of mature LA1589 fruit harboring 0, 1 or 2 copies of the Sun1642 allele is indicated above the graph bars. The average relative transcript levels of IQD12 and DEFL1 per genotype was determined by normalizing to eIF4α6 expression levels and was calculated for fruit harvested 5 days post pollination from 5 individual plants of each genotype (the Northern blot is shown in FIG. 9A). Error bars denote the standard deviation. Designations "ee" denote homozygous Sun1642; "pp" homozygous LA1589; "ep" heterozygous.

Figure 3A:
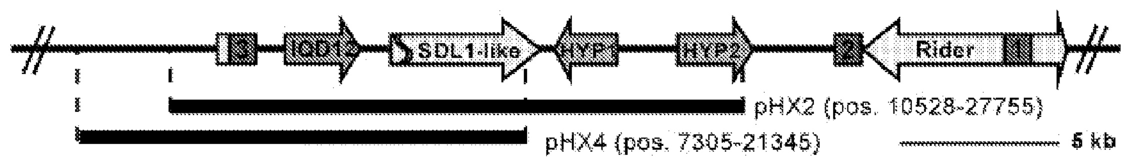

FIGS. 3A-3F show that tomato fruit shape is controlled by increased transcription of IQD12:

FIG. 3A shows the physical relationship between the two genomic constructs used to complement sun. Features of the genomic region are described in FIG. 1C. The 17.2 kb pHX2 construct contains IQD12, SDL1-like, HYP1 and nucleotides encoding the first 415 amino acids of HYP2 (residues 416-487 are deleted from this construct). The 14 kb pHX4 construct contains IQD12 and terminates 180 nucleotides upstream of the SDL1-like stop codon. Construct pHX2 extends to −1184 of the DELF1 methionine initiator codon, whereas pHX4 extends to −4407 of the DELF1 methionine initiator codon.

Figure 3B:
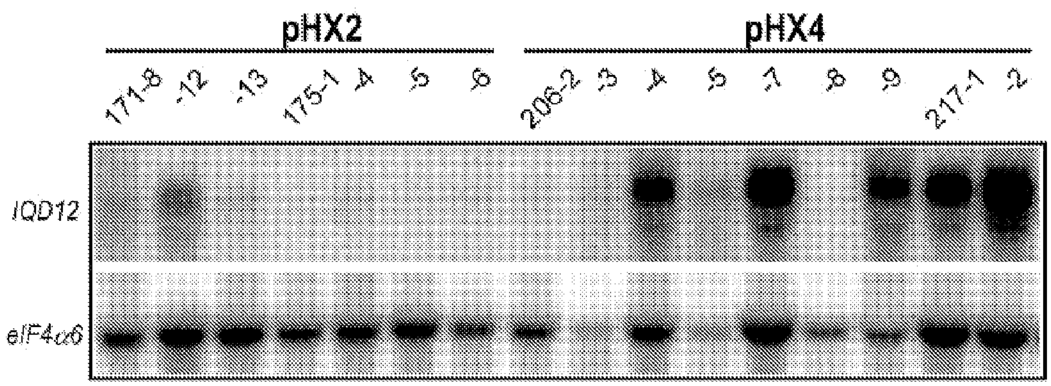

FIG. 3B shows that transformation of the genomic constructs into the round-fruited LA1589 genotype showed that IQD12 was expressed to higher levels in $T_1$ plants transformed with pHX4 in comparison to lines transformed with pHX2. Total RNA was isolated from several fruits that were collected 5 dpa from the individual transformed plants. Northern blot filters were hybridized with $^{32}P$-labeled probes of IQD12 and eIF4α6 for normalizing of loading.

Figure 3C:
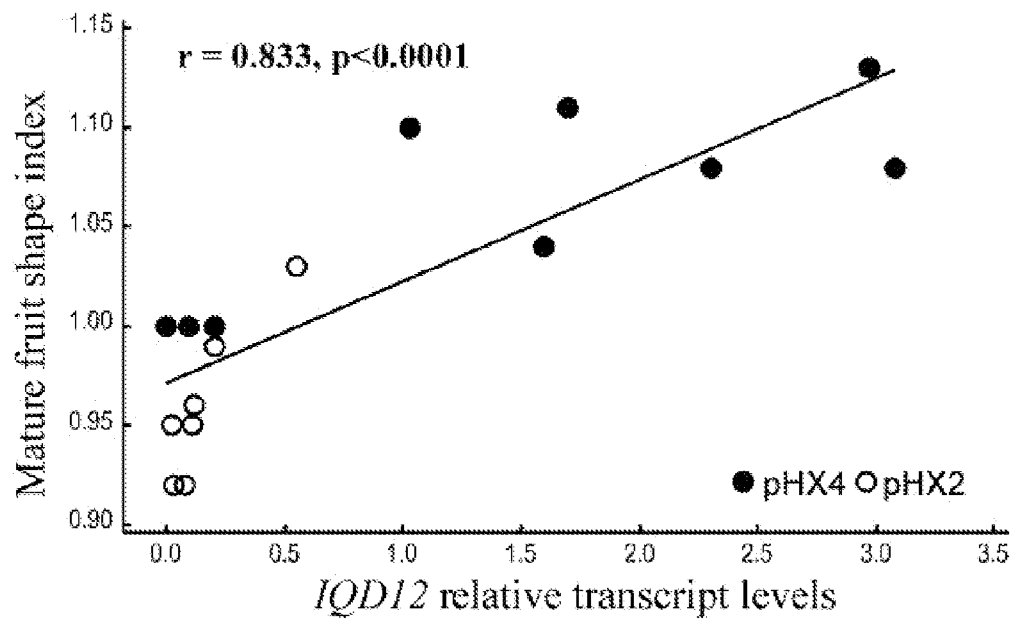

FIG. 3C shows that fruit shape index of $T_1$ lines significantly correlates with IQD12 transcript levels (Pearson coefficient $r=0.833$, $p<0.0001$).

Figure 3D:
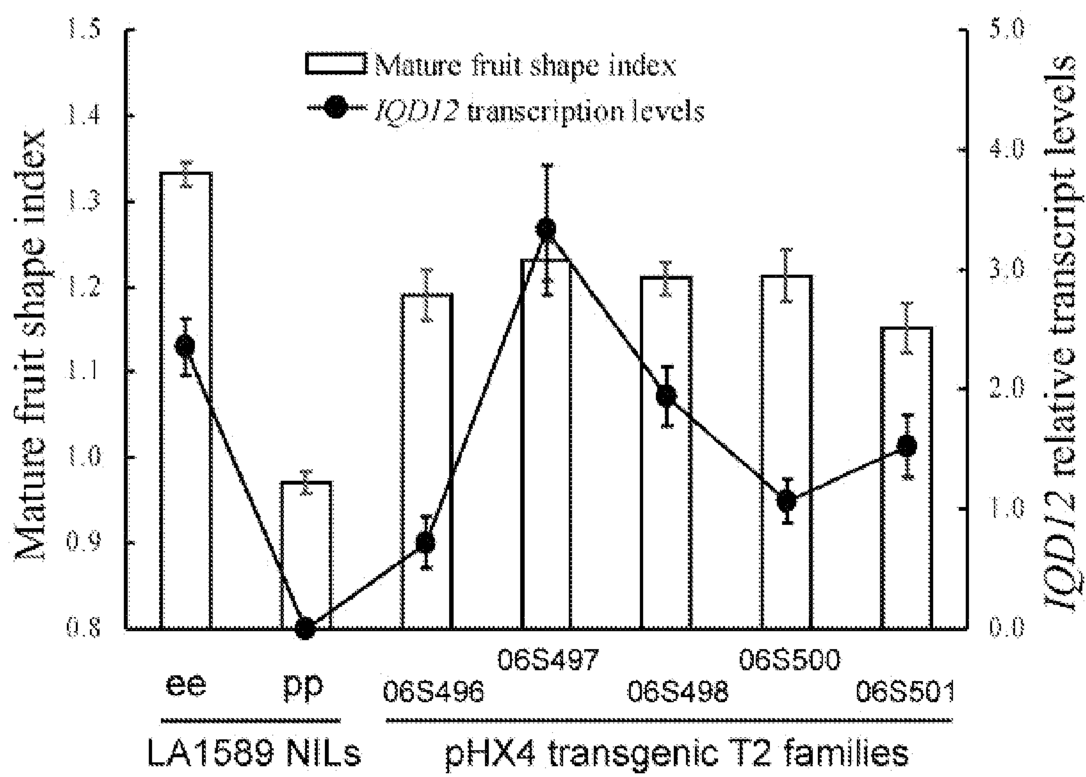

FIG. 3D shows that fruit shape index and IQD12 transcript levels of homozygous $T_2$ plants derived from five independent pHX4 primary transformants. Two to five homozygous $T_2$ plants were identified from selfed pHX4 primary transformants. Homozygosity was confirmed by progeny testing the T3 seed for the presence of the kanamycin resistance gene. The average fruit shape index (columns) and IQD12 transcript levels (line) were determined from the Northern blot data shown in FIG. 10B. Bars denote standard deviations. For comparison, four plants of each reciprocal NIL in the LA1589 background were included to determine IQD12 transcript level and fruit shape index comparisons to the $T_2$ transgene families. Constitutive expression of IQD12 in lines that normally carry round fruit leads to extremely elongated fruit. Conversely, down regulation of IQD12 expression in lines that normally carry elongated fruit leads to round fruit. These results conclusively show that IQD12 is necessary and sufficient to regulate tomato fruit shape and therefore underlies SUN.

Figure 3E:
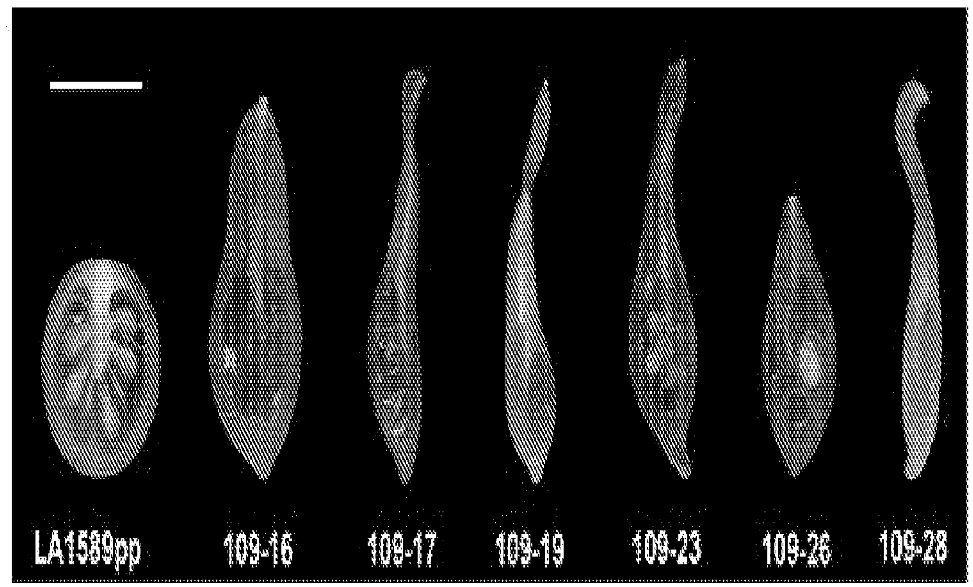

FIG. 3E shows that constitutive overexpression of IQD12 in the round-fruited LA1589 background results in extremely elongated fruit. Each fruit was taken from a plant that was independently transformed with the P35S:IQD12 construct. Fruit from the non-transformed round-fruited NIL (LA1589pp) is shown for comparison.

Figure 3F:
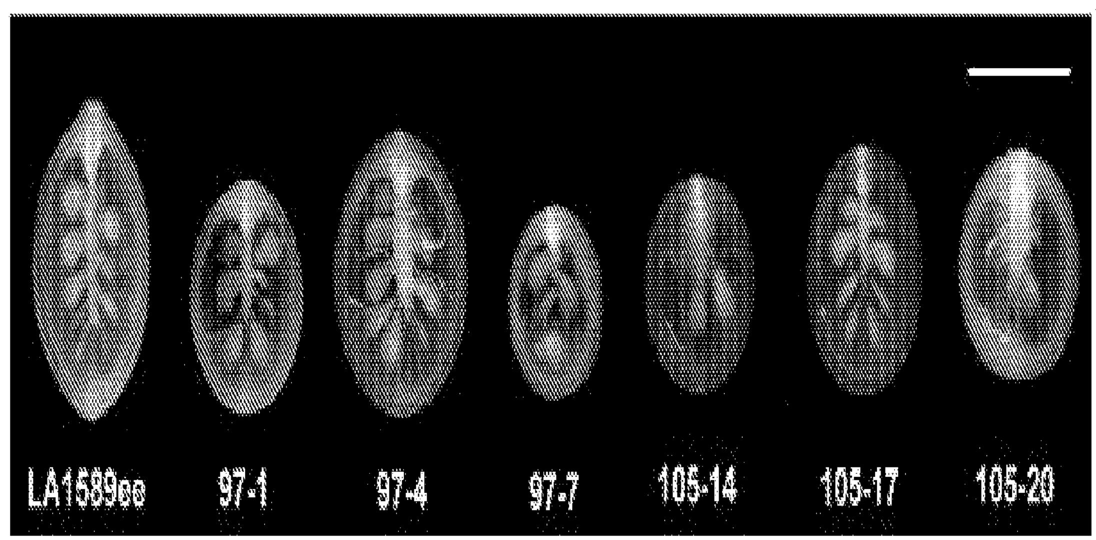

FIG. 3F shows that RNAi-mediated knock-down of IQD12 in the elongate-fruited NIL (LA1589ee) resulting in a significant reduction in fruit elongation. Each fruit represents an independent primary transformed RNAi line. The fruit from the non-transformed NIL (LA1589ee), is shown for comparison. Scale bar in (FIG. 3E) and (FIG. 3F) represents 1

Figure 4A:
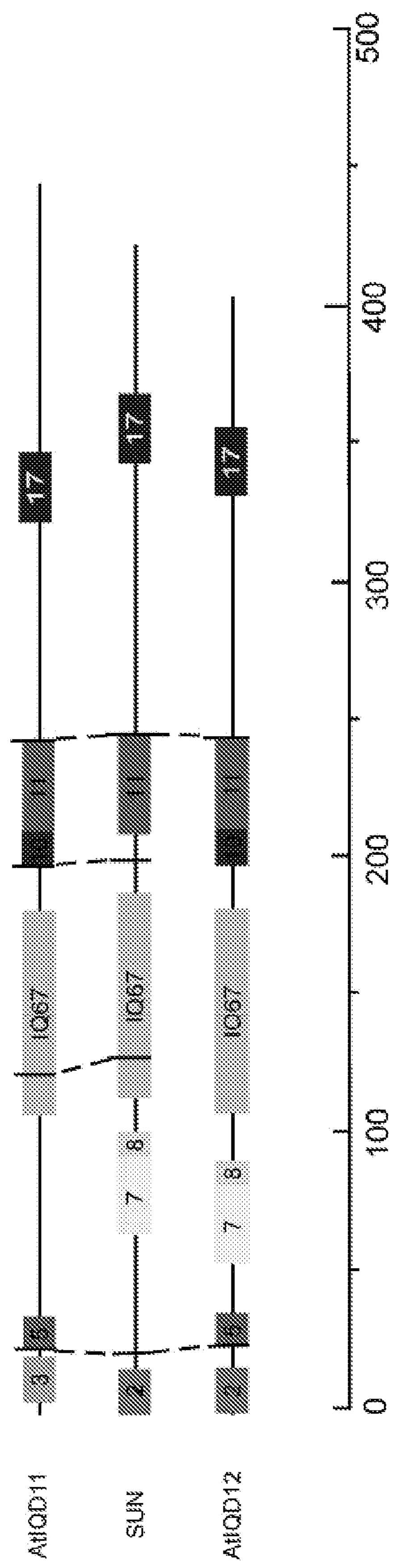
Figure 4B:
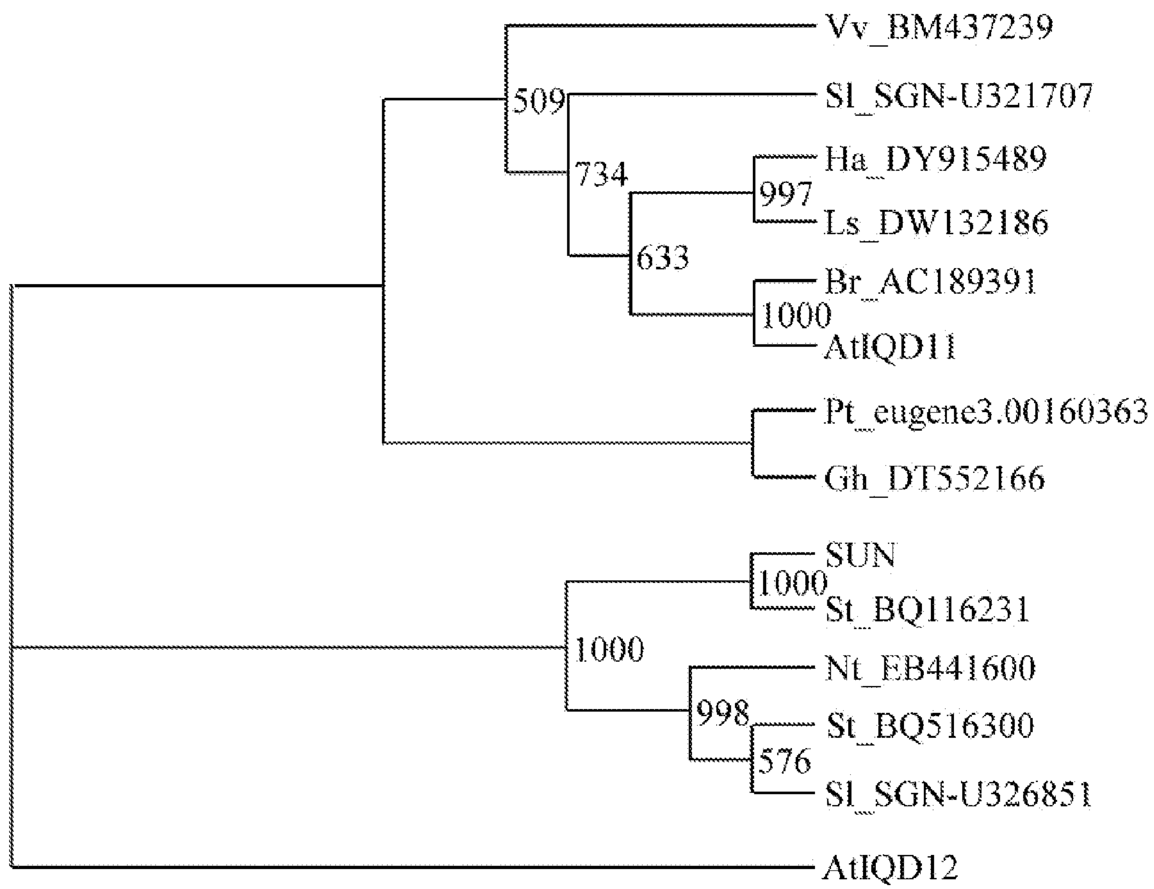

FIGS. 4A-4B show that SUN is a member of the plant specific IQD family:

FIG. 4A shows that motifs predicted in SUN, IQD11 and AtIQD12 proteins. The entire IQD family was run through the MEME[48] motif prediction program to identify conserved regions. Only the motifs with p<1.0e-5 are shown here. Motifs are numbered the same as previously reported[26]. Intron position conservation is indicated via broken connector lines.

FIG. 4B shows the phylogenetic relationships of SUN and its closest relatives. Bootstrapped phylogenetic tree (unrooted) of the IQ67 motif was generated after a complete sequence alignment using Clustal X (1.83) and the neighbor-joining method. The *Arabidopsis* proteins AtIQD11 and AtIQD12 were identified as At5G03960 and At5G13460, respectively. Other accessions were identified by their GenBank, SGN (Solanaceae Genomics Network), or JGI ("eugene3.00160363" (http://genome.jgi-psf.org/Poptr1__1/Poptr1__1.home.html)) numbers and a prefix denoting the genus and species. Br, *Brassica rapa* subsp. *chinensis* (bok choy); Gh, *Gossypium hirsutum* (upland cotton); Ha, *Helianthus annuus* (sunflower); Ls, *Lactuca sativa* (garden lettuce);

Nt, *Nicotiana tabacum* (tobacco); Pt, *Populus trichocarpa* (black cottonwood); Sl, *Solanum lycopersicum* (tomato); St, *Solanum tuberosum* (potato); Vv, *Vitis vinifera* (vine grape). Numbers at nodes represent bootstrap values from 1000 trials. Values below 500 are not reported. IQD containing proteins that are closely related to SUN were not identified in monocots.

Figures 5A, 5B:
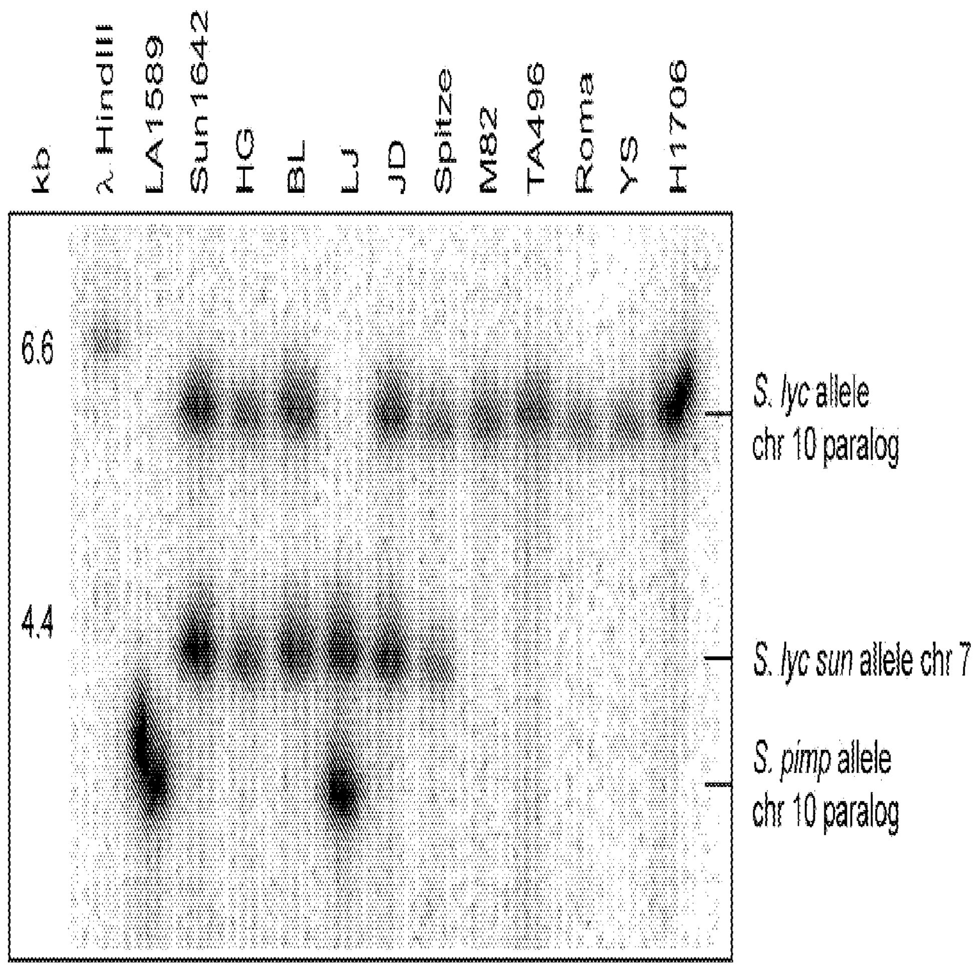
Figure 5C:
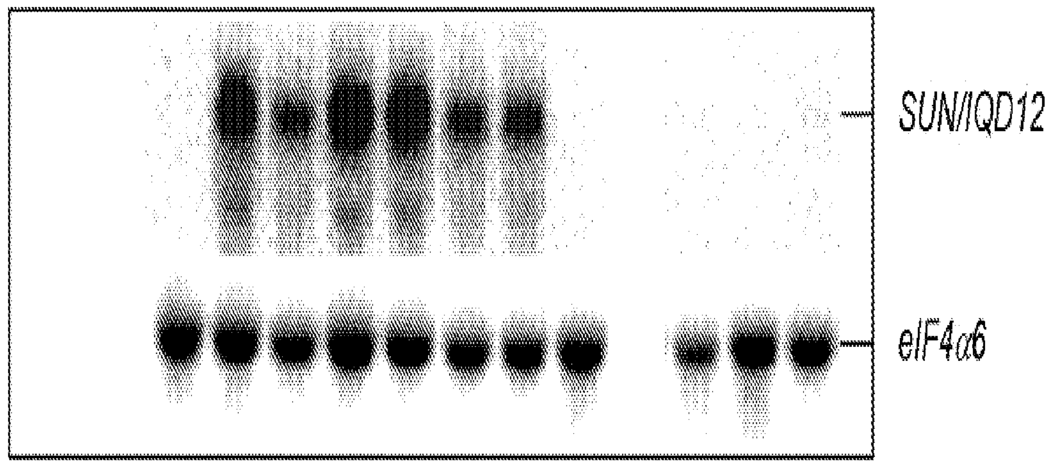

FIGS. 5A-5C show that the presence of the sun locus in other tomato varieties:

FIG. 5A shows that genetic analysis of segregation at sun in other cultivars. $F_2$ populations were derived from crosses between LA1589 and the cultivars indicated above the lanes of the Southern blot shown in FIG. 5B. Via marker-assisted selection using marker cos103R (see FIG. 13—Table 4), 10 homozygous *lycopersicum,* 10 homozygous *pimpinellifolium and* 10 heterozygous seedlings were identified and grown to maturity. Average fruit shape index of eight fruit per plant was determined and significant association of shape and genotype was determined by Duncan's multiple range test at $\alpha$ of 0.01 and ANOVA. A "+" denotes significant association between fruit shape and genotype at sun; a "−" denotes the lack of association. The ovate allele was amplified from genomic DNA and analyzed as a dCAPS marker (FIG. 13—Table 4). A "+" denotes the presence of the pear-shaped allele of ovate; a "−" denotes the presence of the round allele of ovate (i.e. wild-type). The average fruit shape indices are shown below the marker scores and above the Southern blot lanes.

FIG. 5B shows that all *S. lycopersicum* lines that segregate at sun harbor the 4.3 kb EcoRV restriction fragment. The Southern blot was hybridized to a $P^{32}$ labeled fragment that was amplified from phage clone EK36 using EP45 and EP46 primers (See FIG. 13—Table 4). This 4.3 kb EcoRV fragment signifies the presence of the duplication and hence sun. HG, Howard German; BL, Banana Legs; LJ, Long John; JD, Jersey Devil; Roma, RomaVF; YS, Yellow Stuffer; H1706, Heinz 1706.

FIG. 5C shows that the SUN gene was highly expressed in tomato varieties containing the transposed segment on chromosome 7. All *S. lycopersicum* varieties that harbor the 4.3 kb fragment express SUN to a high level, while expression is undetectable in the varieties without the transposed duplication.

Figure 6A:
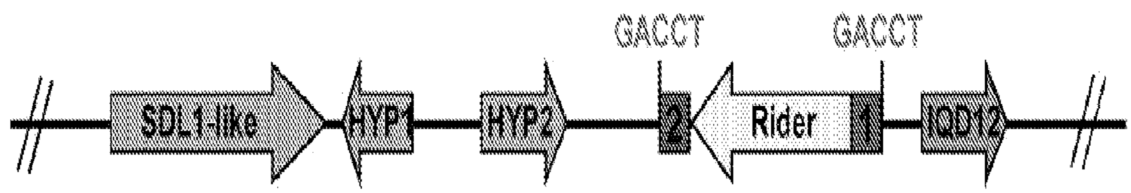

FIGS. 6A-6E show a model for the segmental duplication and rearrangement at the sun locus:

FIG. 6A shows that the genome structure of the ancestral locus on chromosome 10. The nucleotide sequences in light green (GACCT) represent the target site duplication flanking Rider.

Figure 6B:
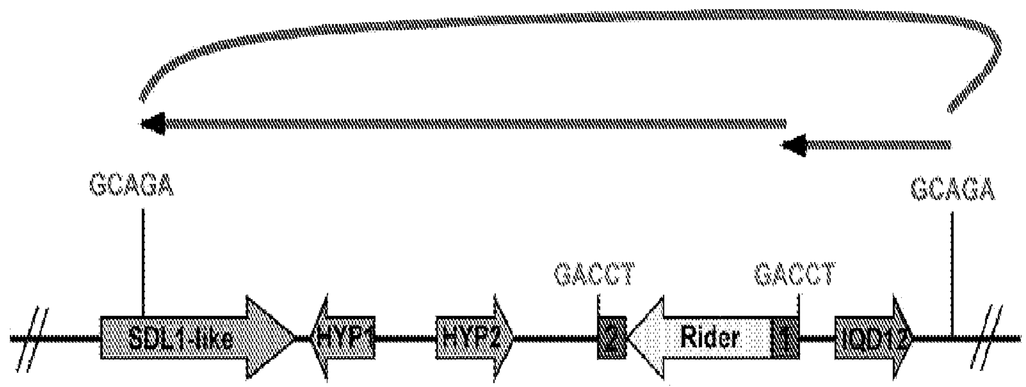

FIG. 6B shows that read-through transcription and template switch by Rider on chromosome 10. The red line and loop above the genome structure indicate the formation of the 24.3 kb retroelement RNA. The nucleotides in red (GCAGA) indicate the proposed site for the template switch. The sequence analysis of the sun locus on chromosome 7 reveals that the 24.3 kb segment is duplicated from chromosome 10 via a transposition-mediated event under the control of the autonomous LTR retroelement Rider. Transcription of Rider, read through and 3' transduction, a template switch, followed by transposition repositions IQD12 farther away from the retroelement. The transposition positioned IQD12 in another genome context on chromosome 7, in the vicinity of the promoter of DEFL1, a gene whose function was abolished upon transposition.

Figure 6C:
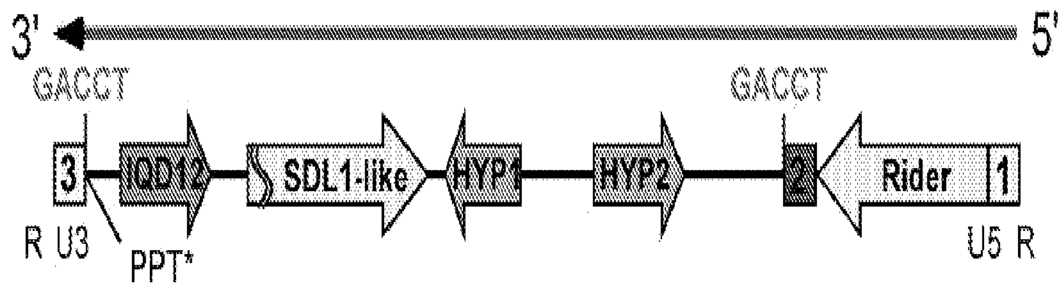

FIG. 6C shows the formation of one large retroelement.

Figure 6D:
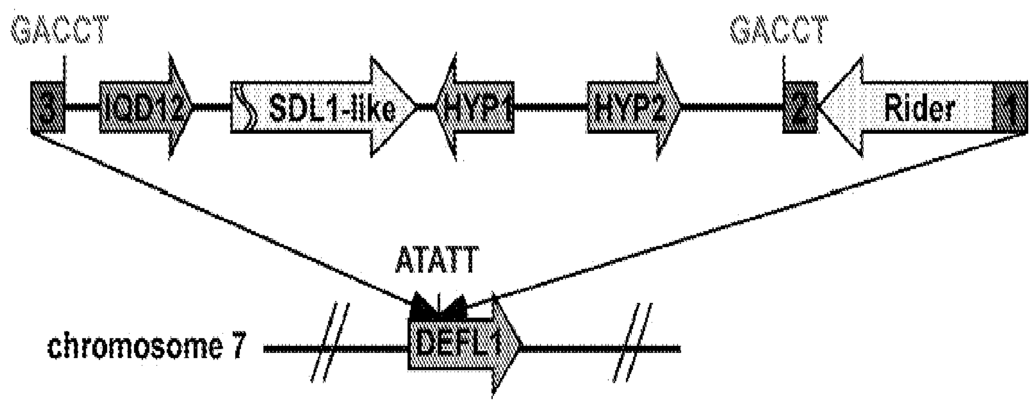

FIG. 6D shows the integration of Rider into chromosome 7 at the nucleotide site indicated in blue (ATATT).

Figure 6E:
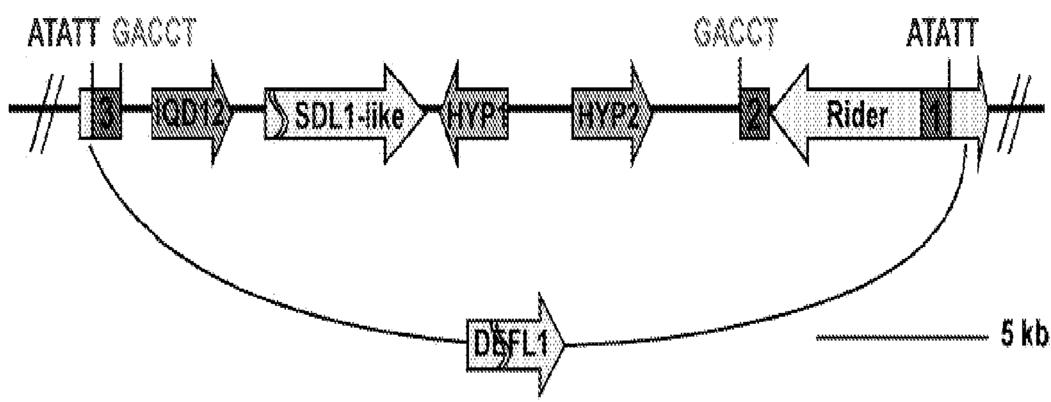

FIG. 6E shows the structure of the sun locus on chromosome 7 featuring the target site duplication (blue-lettered nucleotides, ATATT). The arrows represent the direction of transcription of the genes. Dark gene arrows (HYP1, HYP2) indicate expressed and predicted functional genes, purple arrows (IQD12) indicate the rearranged gene, light green arrows indicate the retroelement Rider, yellow arrows (SDL1-like, DEFL1, last arrow on right) indicate pseudogenes. The red boxes numbered 1-3 indicate the identical Rider LTR.

Figure 7A:
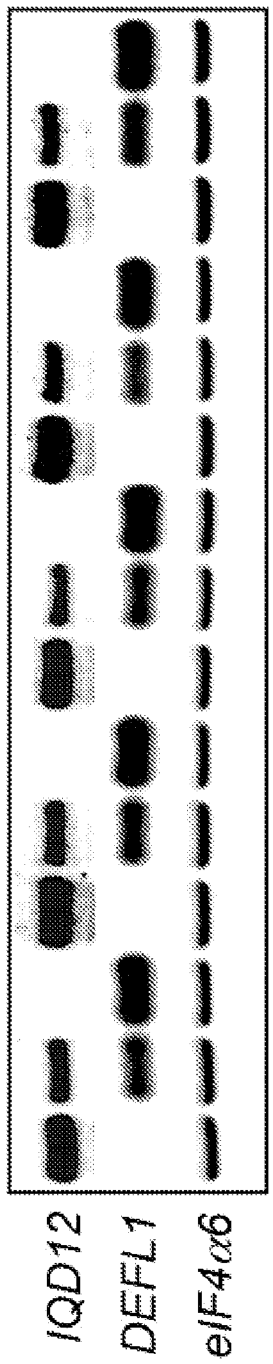
Figure 7B:
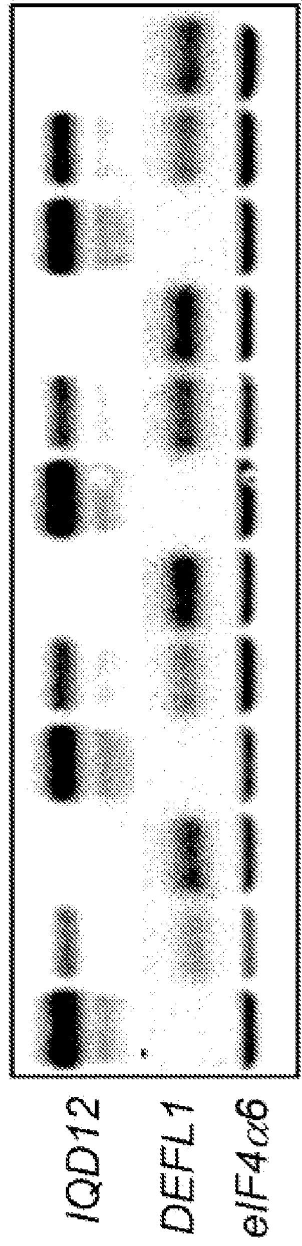
Figure 7C:
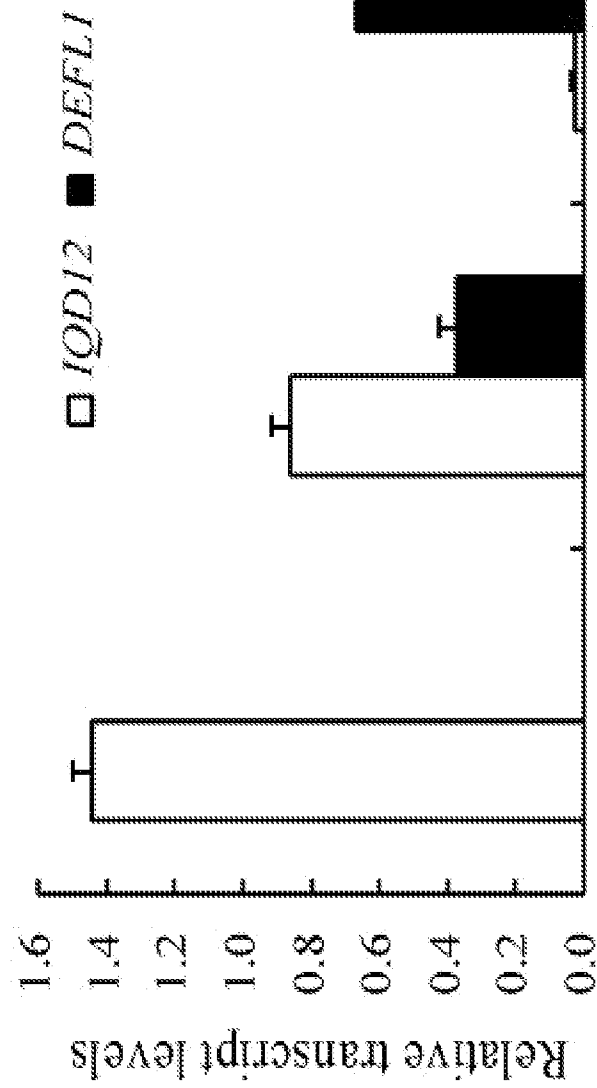

FIGS. 7A-7C show the dosage-dependent expression of IQD12 and DEFL1 gene in LA1589 and Sun1642 Nearly Isogenic Lines (NILs):

FIG. 7A shows the Northern blot of RNA from NILs in the LA1589 background harboring 0, 1 or 2 copies of the Sun1642 allele of sun. The plant numbers above the lanes correspond to pedigree 06S559-6 for plant no "6" etc.

FIG. 7B shows the Northern blot of RNA from NILs in Sun1642 background harboring 0, 1 or 2 copies of the Sun1642 allele of sun. The plant numbers above the lanes correspond to pedigree 06S22-5 for plant no "5" etc.

FIG. 7C shows a graph showing the average relative transcript levels of IQD12 and DEFL1, normalized to eIF4$\alpha$6 expression, in lines harboring 0, 1 or 2 copies of the Sun1642 allele of sun in the Sun1642 background. The data displayed in the graph are from the Northern blot shown in FIG. 9B. Error bar represents the standard deviation. The average mature stage fruit shape index is shown above the graph demonstrating that the degree of elongated fruit shape in the cultivated background is correlated to transcript levels of IQD12 and inversely correlated to transcript levels of DEFL1. Total RNA was isolated from 6-10 five days post anthesis (dpa) fruits of individual plants indicated above the lanes. The size-fractionated RNA was transferred to Hybond N membrane and hybridized sequentially to radioactivity-labeled tomato IQD12, DEFL1 and eIF4$\alpha$6 probes. The denotion "ee" signifies two copies of the Sun1642 allele at sun; "pp" two copies of the LA1589 allele at sun; "ep" one copy of each parental allele.

Figure 8A:
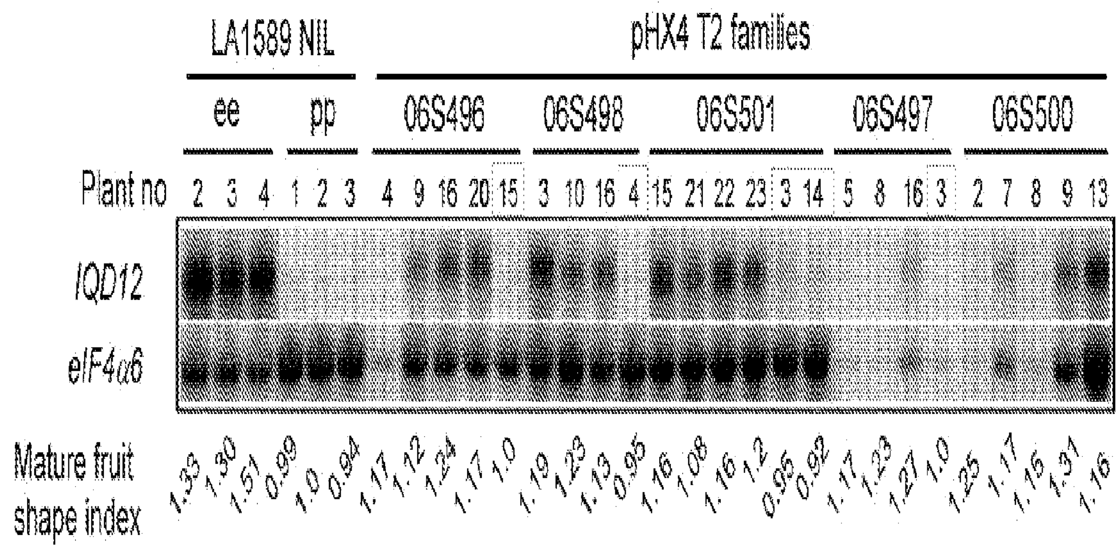
Figure 8B:
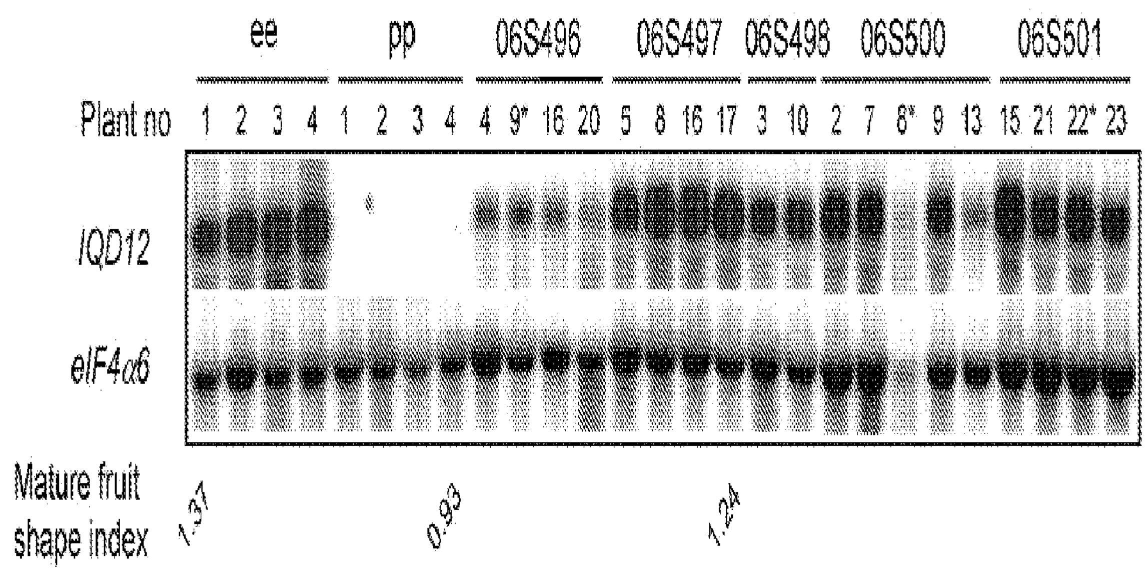
Figure 8C:
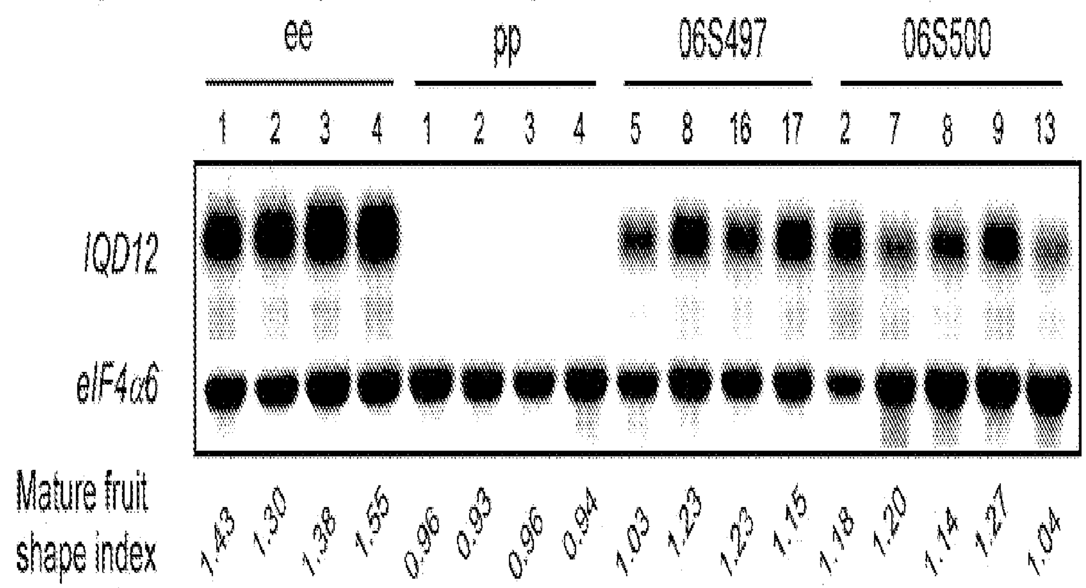

FIGS. 8A-8C show the Northern blot of IQD12 expression in five pHX4 transgenic T1-derived T2 families. Expression analyses were performed on total RNA isolated from 6-10 fruit at five days post anthesis (dpa). Homozygous transgenic plants were identified from the selfed progenies of hemizygous pHX4 T1 lines indicated in FIG. 10—Table 1. The selection was based on signal intensity on a Southern blot and confirmed by examining the segregation of the kanamycin gene via PCR in the 48 T3 progenies from each of these T2 plants. For each blot shown, the transgenic plants and the NILs were grown simultaneously in the same greenhouse and tissues for RNA extraction were harvested at simultaneously as well.

FIG. 8A shows the Northern blot showing IQD12 expression in 5 dpa fruits of NILs in the LA1589 background compared to individual T2 plants derived pHX4 transgenic T1 lines. Plants were three months old when the fruits were harvested. The boxed plant numbers indicate the non-transgenic sibs of the T2 family. The non-transgenic T2 sibs show much lower IQD12 expression and a smaller fruit shape index, demonstrating that both increased IQD12 expression and fruit shape index is controlled by the pHX4 transgene. Most of the RNA from plants in the families 06S497 and 06S500 had degraded during extraction.

FIG. 8B shows the IQD12 expression in 5 dpa fruits of same plants as in FIG. 8A albeit at five months of age. The transcript levels obtained in FIG. 8B were used in the graph of FIG. 3D. The plant numbers marked by an asterisk (*) were excluded from the analysis because plant 9 of 06S496 and 22 of 06S501 were heterozygous whereas for plant number 8 of 06S500 the RNA had degraded during extraction. The fruit shape index for the plants displayed in FIGS. 8A and 8B was collected once.

FIG. 8C shows that cuttings of two transgenic families (06S497 and 06S500) were taken. The plants were three months after asexual propagation when 5 dpa fruits were harvested for RNA extraction. IQD12 expression was compared to that of the LA1589 NIL controls. The fruit shape index was recorded from these plants and shown below the lanes on the Northern blot. The results from these experiments convincingly showed that increase in expression of the transgenically introduced IQD12 resulted in increased fruit shape index which strongly suggested that this gene encodes SUN.

FIGS. 9A-9E show the IQD12 expression in P35S:IQD12 and RNAi:IQD12 transgenic lines:

FIG. 9A shows that constitutive expression of IQD12 leads to extremely elongated fruit in both the cultivated (Sun1642) and the wild type (LA1589) backgrounds. Round-fruited lines were transformed with P35S:IQD12. Total RNA was extracted from 5 dpa fruits except for lines 109-017, -019, -023 and -028. In the latter cases, anthesis-stage flowers were used instead because of irregular fruit set in these lines. The transgenic lines marked with an asterisk (*) (100-002 and 100-003), were obtained from P35S:IQD12 transformed into the round-fruited Sun1642 background, lacking the duplication. The fruit shape index for each line is shown below the Northern blot.

Figure 9B:
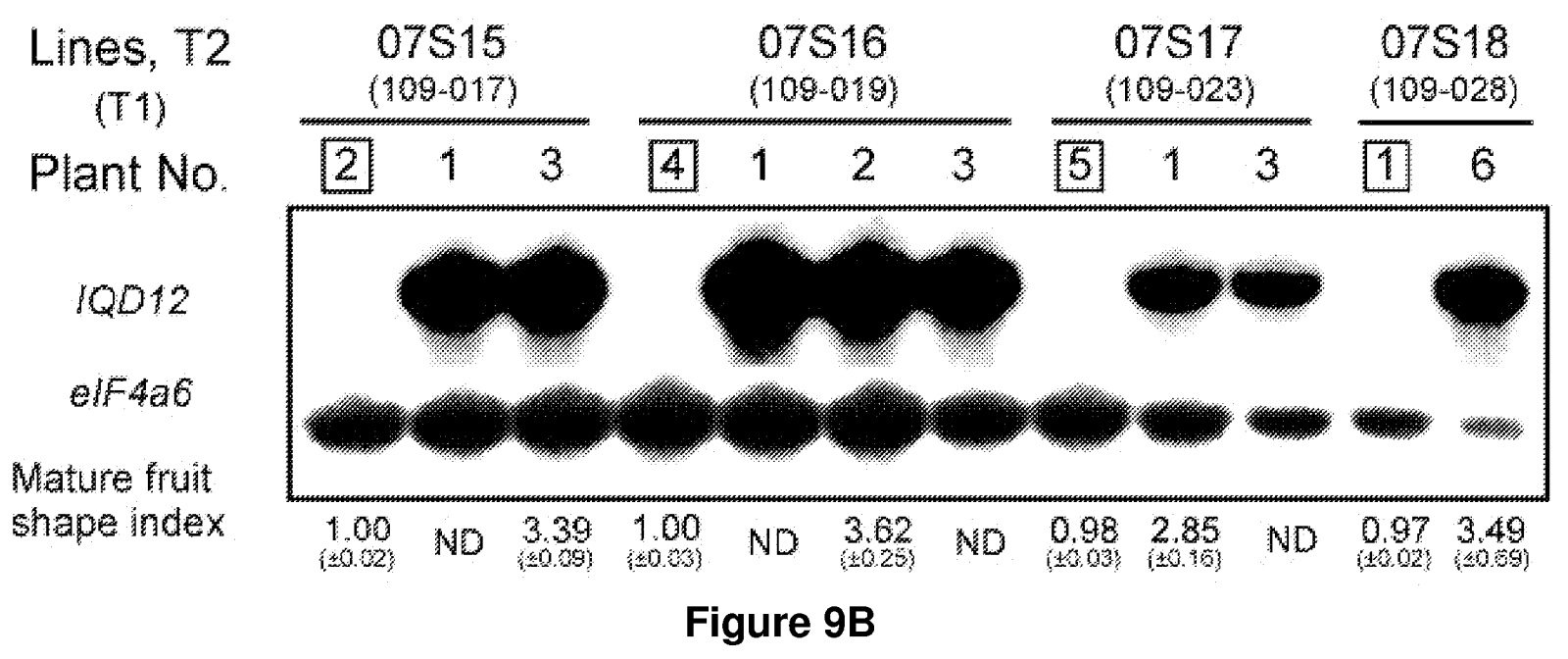

FIG. 9B shows that the elongated fruit shape and high expression of IQD12 under control of the CaMV 35S promoter is transmitted to next generation. Northern blot analysis was performed on total RNA isolated from anthesis-stage flowers of P35S:IQD12 T2 plants indicated above the lanes. To maintain these overexpressing lines which are essentially seedless, pollen of the primary transformants 109-017, -019, -023 and -028 were crossed to LA1589 pistils. ND, not determined. Boxed numbers indicate the non-transgenic sibs.

Figures 9C, 9D:
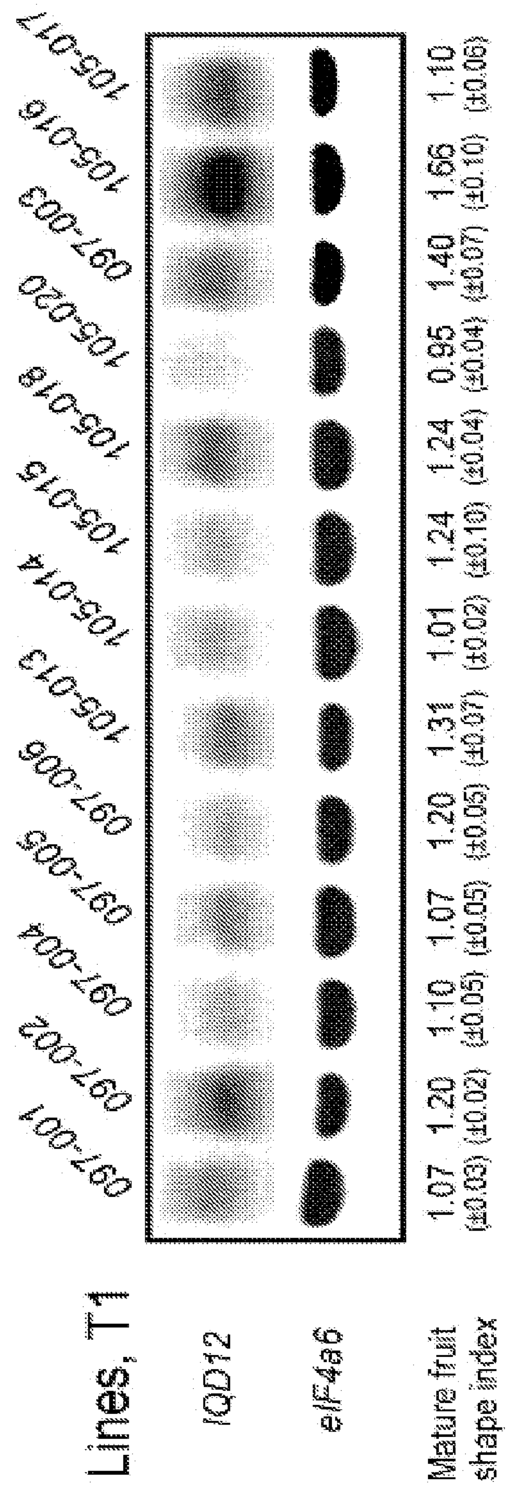

FIG. 9C shows the RNA knock down of IQD12 in the LA1589 NIL carrying the transposed segment, resulted in rounder fruit. Northern blot showing reduced transcript levels of IQD12 in 5 dpa fruit from each of the independent primary transgenic lines. Mature fruit shape index for each line was shown below the Northern blot.

FIG. 9D shows that the reduction of IQD12 transcript levels and fruit shape index is heritable to the $T_2$ generation. The Northern blot shows IQD12 transcript levels in the non-transformed NILs (first 6 lanes; lines 07S27 and 07S26) compared to two transgenic families that knock down IQD12 transcript level. Total RNA was isolated from 5 dpa fruits of each plant. Boxed numbers indicate the non-transgenic sibs.

Figure 9E:
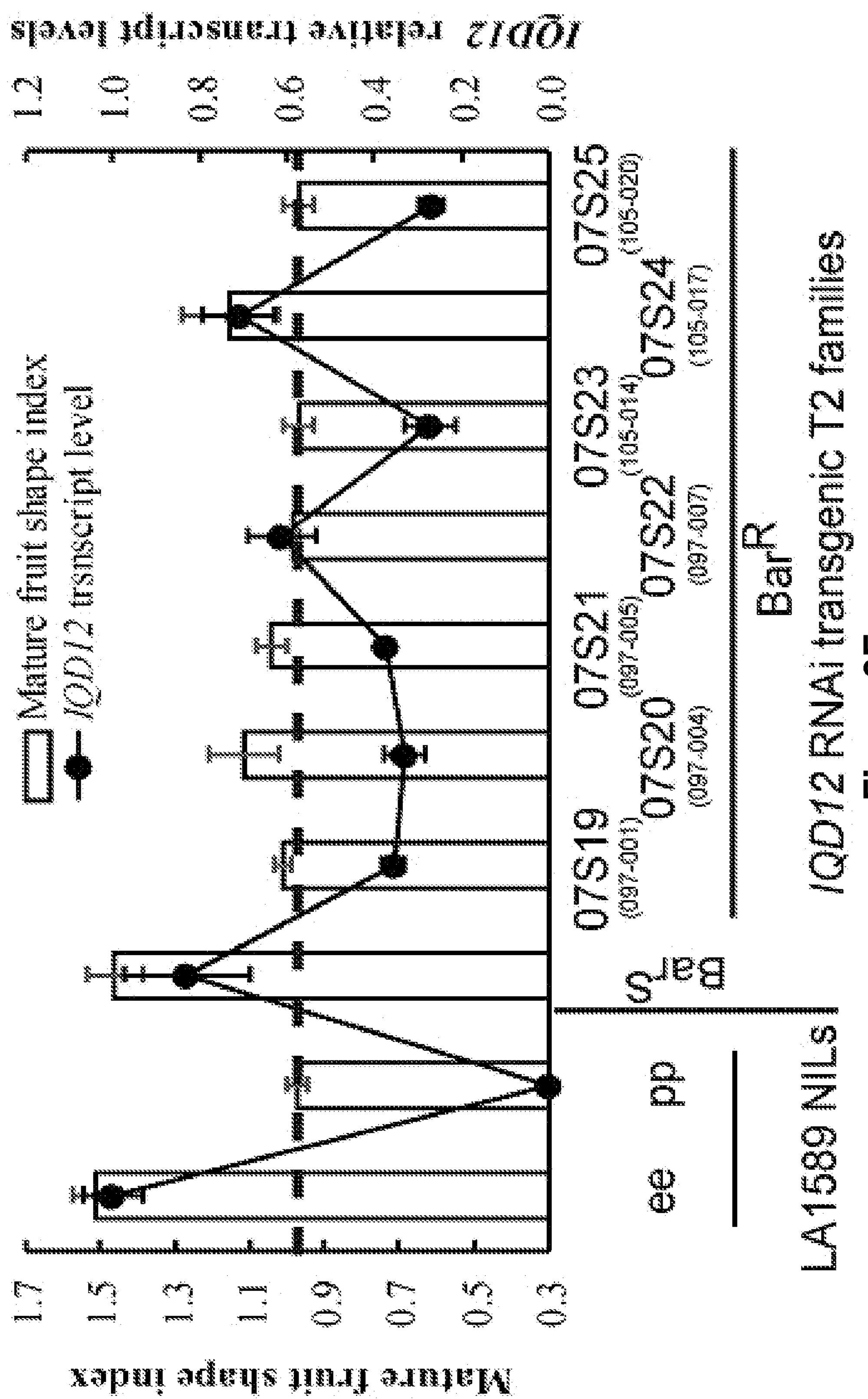

FIG. 9E shows a graph showing mature fruit shape index and IQD12 transcript level in the NILs compared to seven independent T2 families that down regulate IQD12 expression. The reduction of IQD12 transcript level led to a reduction in mature fruit shape index. Transcript levels of IQD12 in the transgenic plants was normalized to the transcript levels of eIF4α6 and expressed relative to that of the NIL carrying the Sun1642 allele of sun, which is set at "1". A dashed line set at a fruit shape index value of 0.97 was drawn to facilitate the comparisons of the transgenic IQD12 knock down lines to that of the non-transformed NILs. Data for the $Bar^s$ column was pooled from the 6 nontransgenic sib plants that segregated in the transgenic T2 progenies. The non-transgenic sibs came from three families (one from 07S21, one from 07S23 and four of 07S24).

FIG. 10 shows Table 1, listing the mature fruit shape index, IQD12 transcript levels and progeny testing of selected transformant in the round-fruited LA1589 background.

FIG. 11 shows Table 2, listing the mature fruit shape index of pHX2 and pHX4 primary transformants in the round-fruited Sun1642 background carrying the LA1589 allele of sun.

FIG. 12 shows Table 3, listing the fruit shape index of plants that over or under express IQD12.

FIG. 13 shows Table 4, listing the primers [SEQ ID NOS: 14-14], respectively in order of appearance, as used in the examples described herein.

Figure 14A:
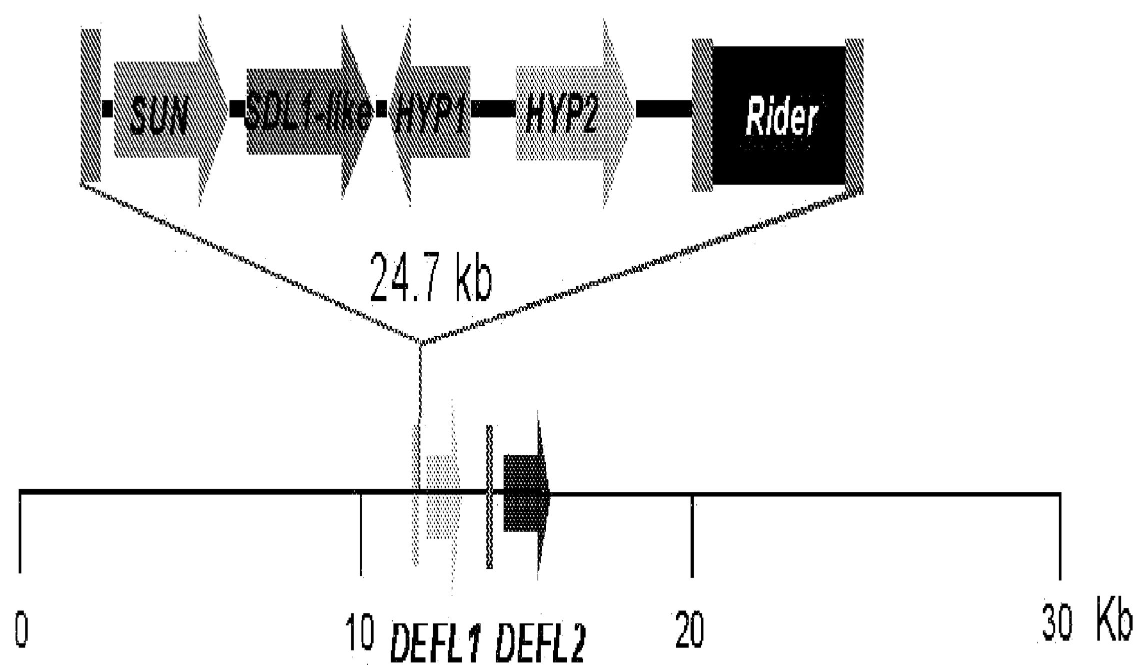
Figure 14B:
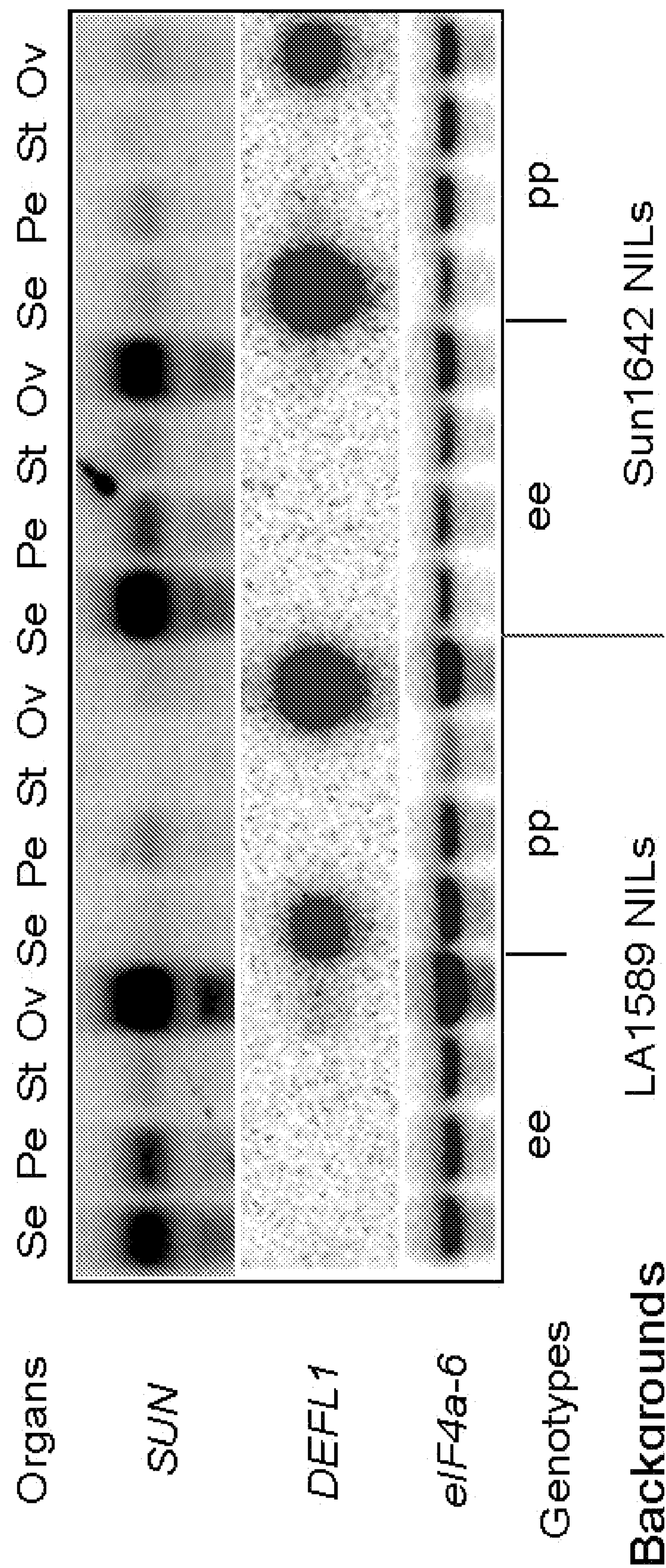
Figure 14C:
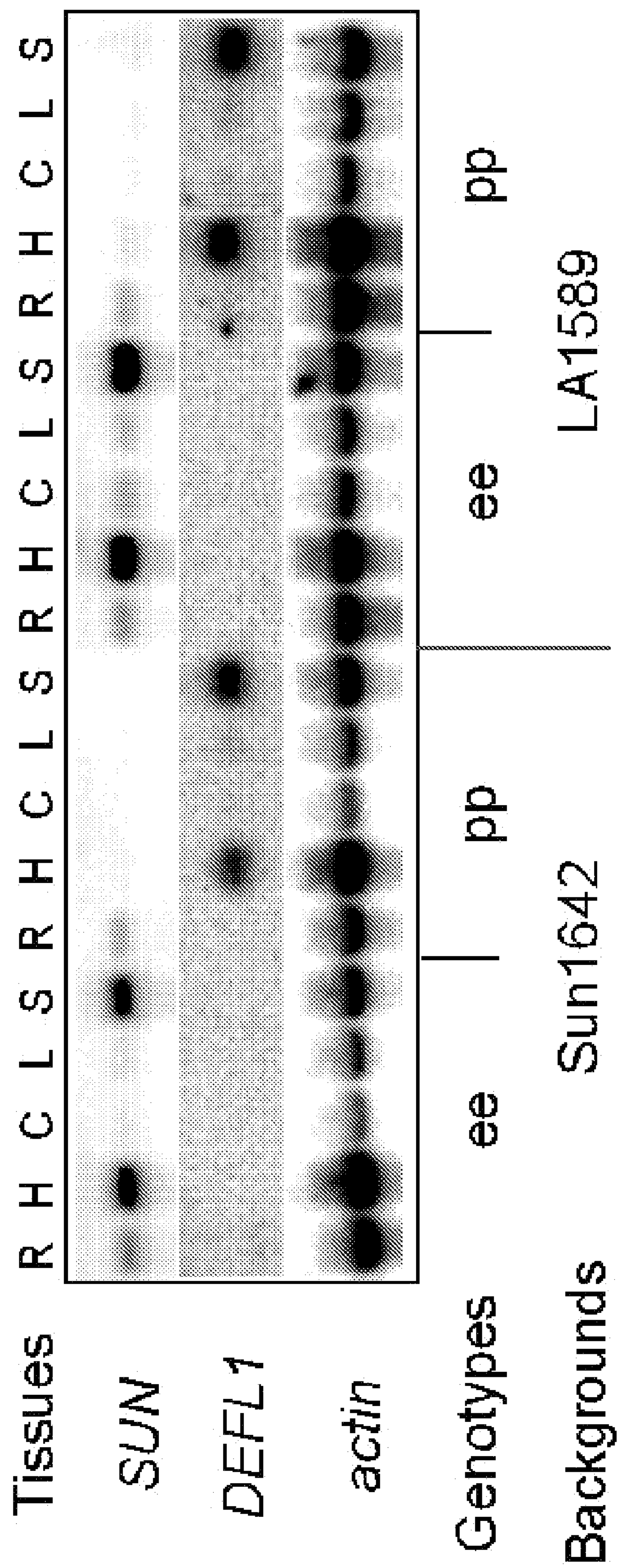

FIGS. 14A-14C show expression of SUN in different tissues:

FIG. 14A shows the gene structure at the sun locus. The 24.7 kb duplication, including SUN, disrupted the expression of DEFL1.

FIG. 14B shows the expression of SUN and DEFL1 in floral tissues. Northern blot containing RNA isolated from floral organs at the time of anthesis. The blot was sequentially probed with SUN, DEFL1 and lastly with eIF4α-6 as loading control. Se, sepal; Pe, petal; St, stamen; Ov, ovary. Tissues were isolated from the LA1589 and Sun1642 NILs that differ at the sun locus. ee, containing an extra copy of SUN; pp, lacking the extra copy of SUN.

FIG. 14C shows the expression of SUN and DEFL1 in different tissues. Tissues were isolated from the LA1589 and Sun1642 NILs that differ at the sun locus. ee, containing an extra copy of SUN; pp, lacking the extra copy of SUN. R, root; H, hypocotyl; C, cotelydon; L, leaf; S, shoot apex. In lines carrying the duplication, SUN is highly expressed in sepals, ovaries, hypocotyl and shoot apex. The ancestral SUN gene is expressed in roots and at low levels in other tissues. DEFL1 is expressed in the same tissues as the duplicated copy of SUN in plants that lack the 24.7 kb duplication (pp, lacking an extra copy of SUN). This indicates that the promoter of DEFL1 is driving expression of the duplicated copy of SUN.

Figure 15A:
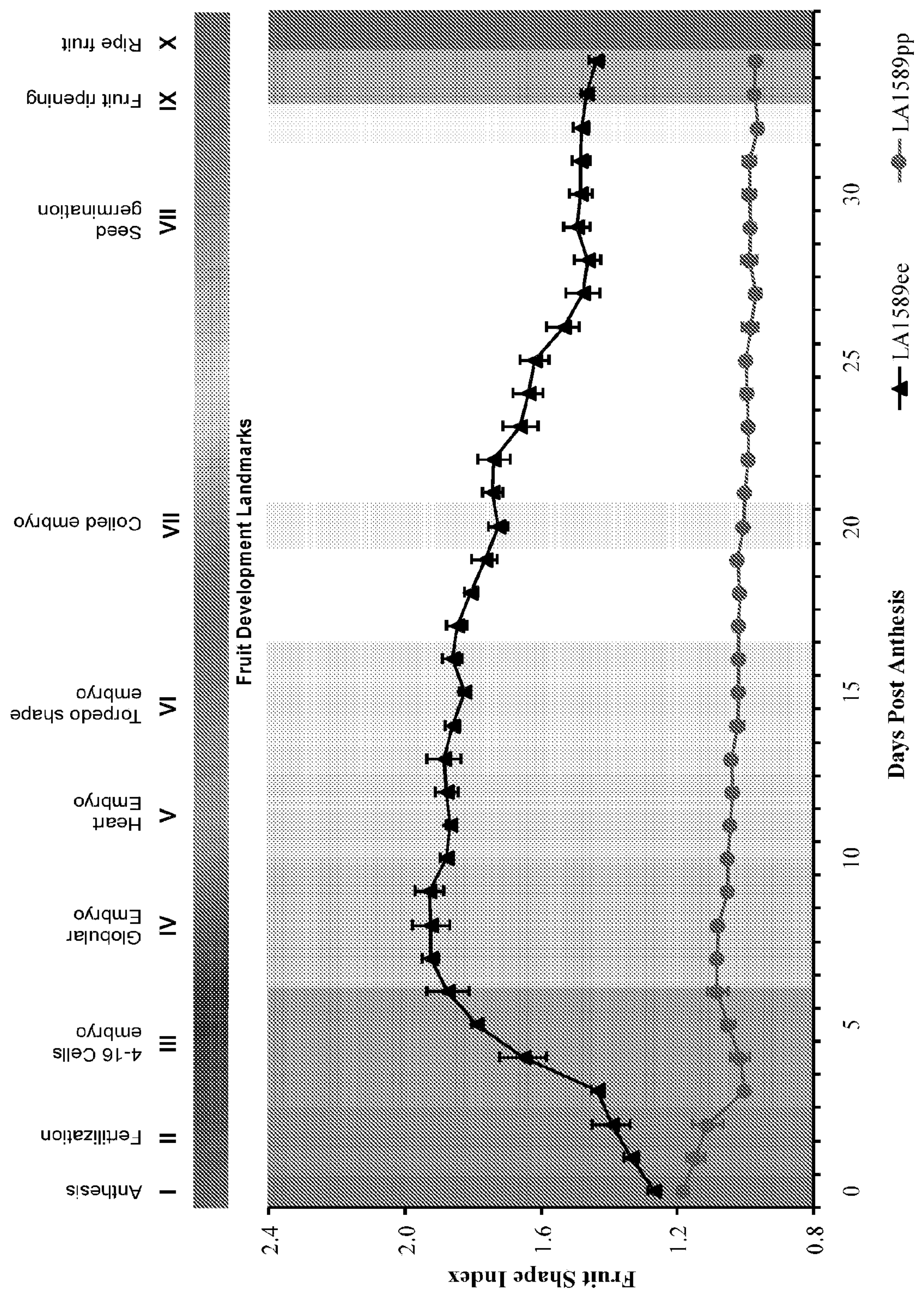
Figure 15B:
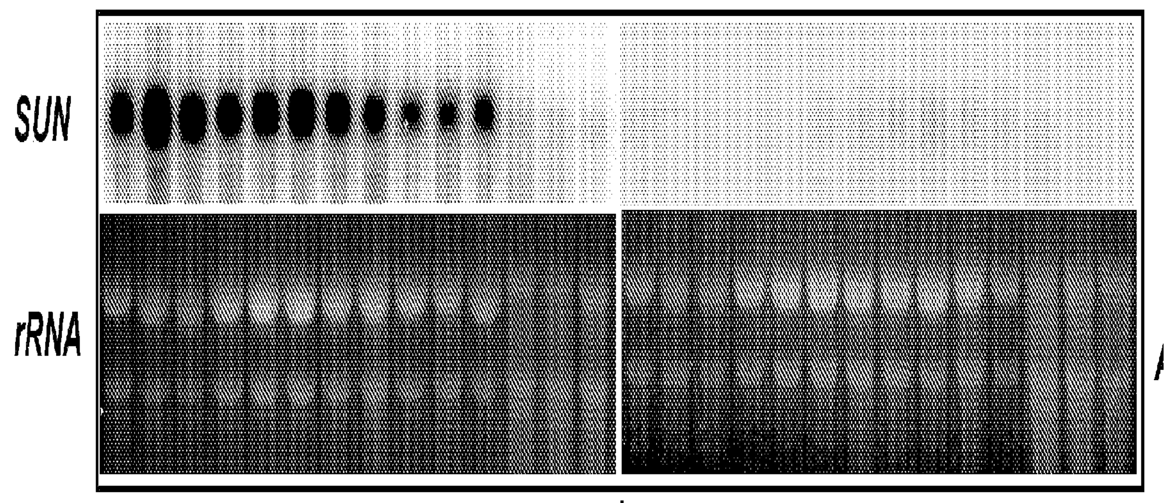
Figure 15C:
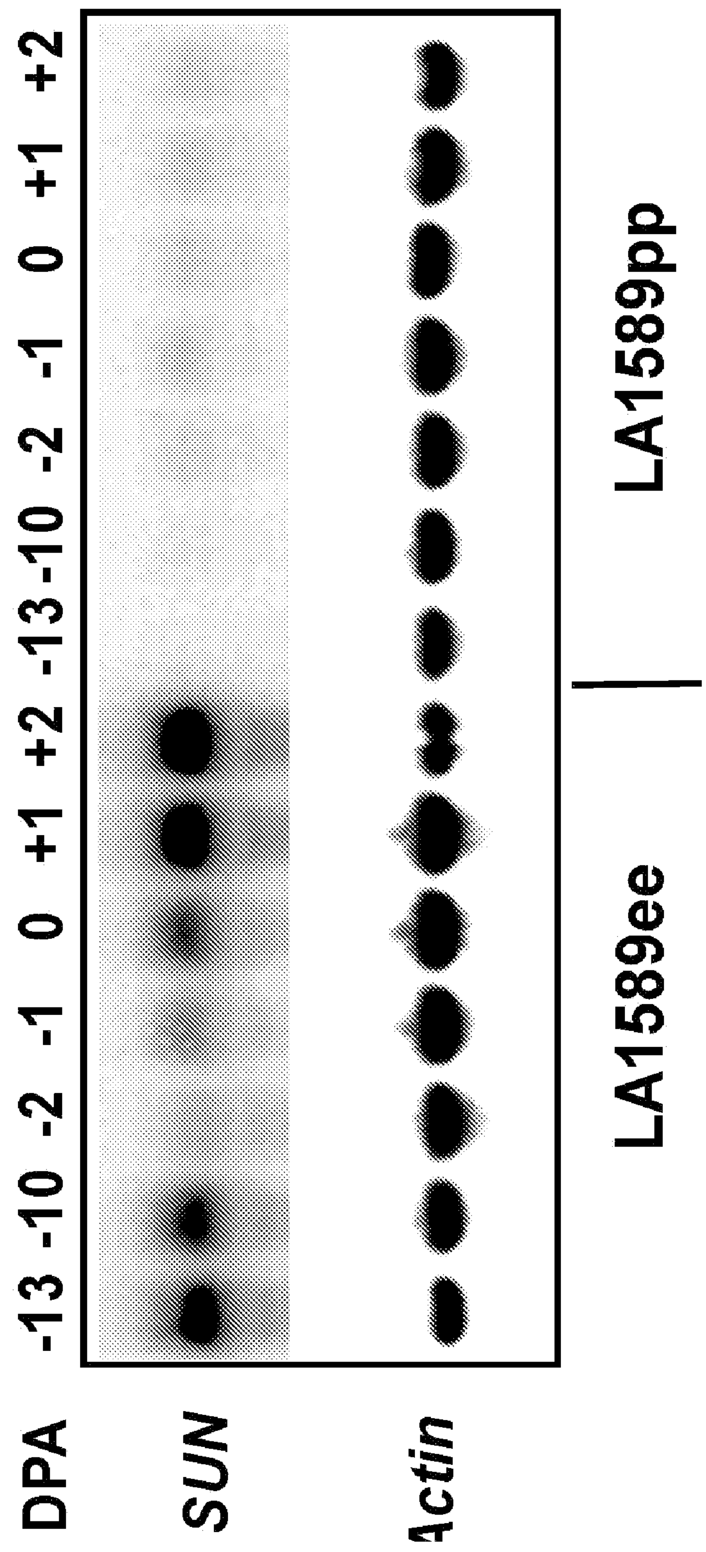

FIGS. 15A-15C: Fruit shape index and SUN expression changes during tomato flower and fruit development:

FIG. 15A shows the fruit shape index (length/width ratio) as a function of the number of days post anthesis. Fruit shape changes overlay the fruit/seed developmental landmarks indicated above the graph. The black triangles represent the fruit shape indices of the near isogenic lines (NILs) carrying two copies of the SUN gene whereas the grey circles represent the NILs with only one copy of SUN. The largest difference in fruit shape index is achieved at fruit landmark 3 and 4, coinciding with the landmarks 4-16 cell and globular stage of the embryo. Fruit shape index were collected from three inflorescences per plants of five for each genotype. Data shown are mean±standard error.

FIG. 15B shows SUN expression in the developing fruits of LA1589 NILs. Northern blots were performed on LA1589ee (carrying two copies of the SUN gene) and LA1589pp (carrying one copy of SUN). Total RNA was extracted from pooled tissues of five plants per genotype and hybridizations were conducted with SUN as probe. SUN expression is very high starting at anthesis until 20 days post anthesis. Its expression has dropped dramatically 25 days post anthesis which is prior to the fruit ripening and seed germination stage.

FIG. 15C shows SUN expression in floral buds of LA1589 NILs. Northern blots were performed on total RNA isolated from entire flowers or buds at the times indicated above the lanes (in days). The "0" timepoint denotes anthesis, the other values indicate days prior (−) or post (+) anthesis. SUN's expression is low 2 days pre-anthesis but increases dramatically until 2 days post pollination in the lines carrying two copies of SUN (LA1589ee). The increase in SUN expression precedes the change in fruit shape index shown in FIG. 15A. In the lines carrying only one copy of SUN (LA1589pp), SUN expression is low, however DEFL1 expression in LA1589pp follows a similar kinetic as SUN expression in the LA1589ee indicating that the DEFL1 promoter drives SUN expression (see also FIG. 15).

Figure 16A:
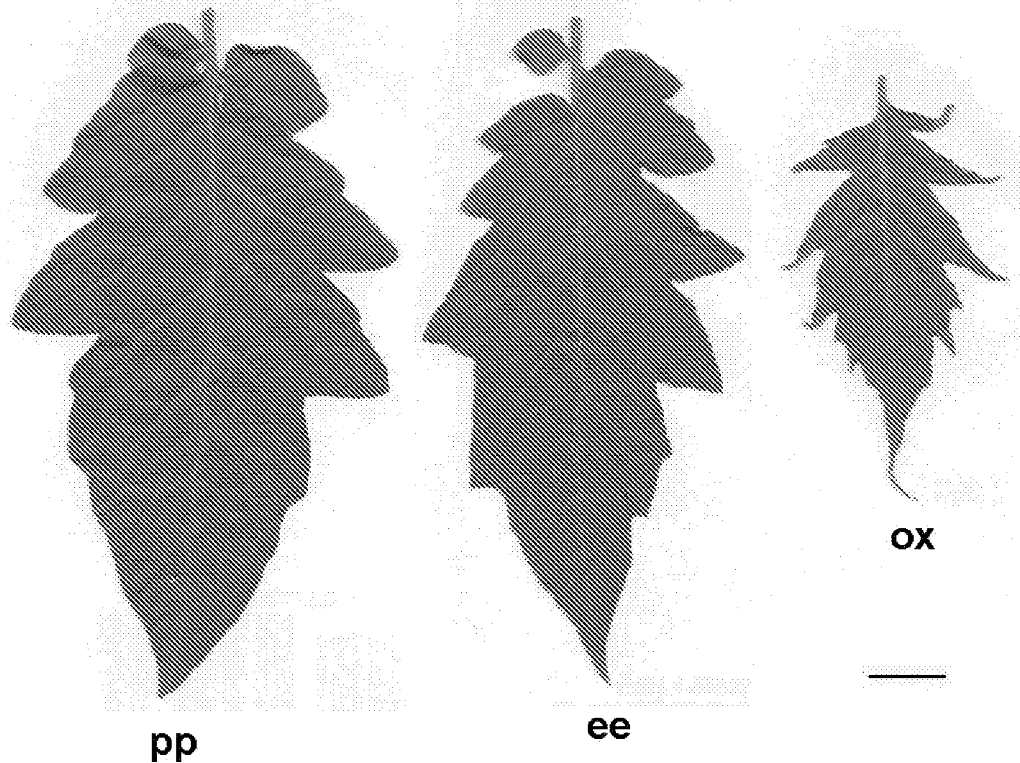
Figure 16B:
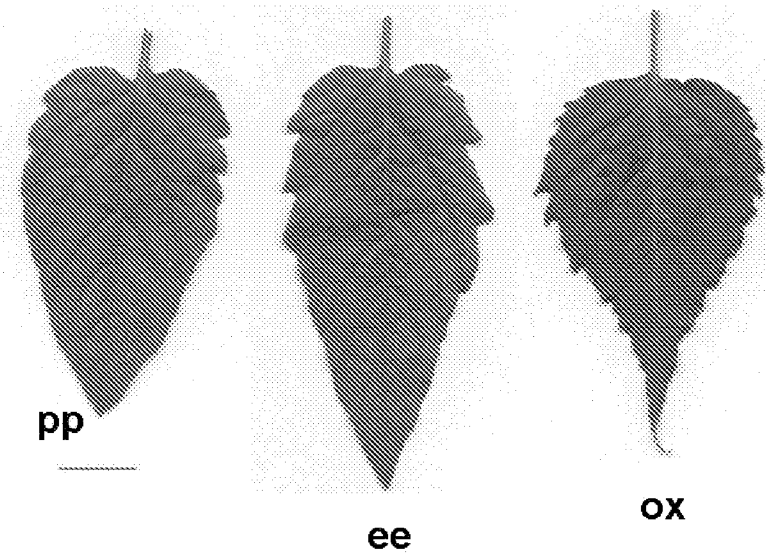

FIGS. 16A-16B: The effect of SUN on leaflet shape:

FIG. 16A shows the leaflets of cultivated tomato.

FIG. 16B shows leaflets of the wild relative *S. pimpinellifolium* accession LA1589. The leaves shown are from plants without the extra copy of SUN (pp), with the extra copy of SUN (ee) or SUN expressed under the constitutive 35S promoter (ox). The most notable feature is the pointed shape of the leaf and increased serrated margins when SUN is expressed (compare pp and ee). These features are accentuated when SUN is overexpressed (compare ee and ox). These results indicate that in addition to fruit shape, leaf shape is dramatically altered as well.

Figure 17A:
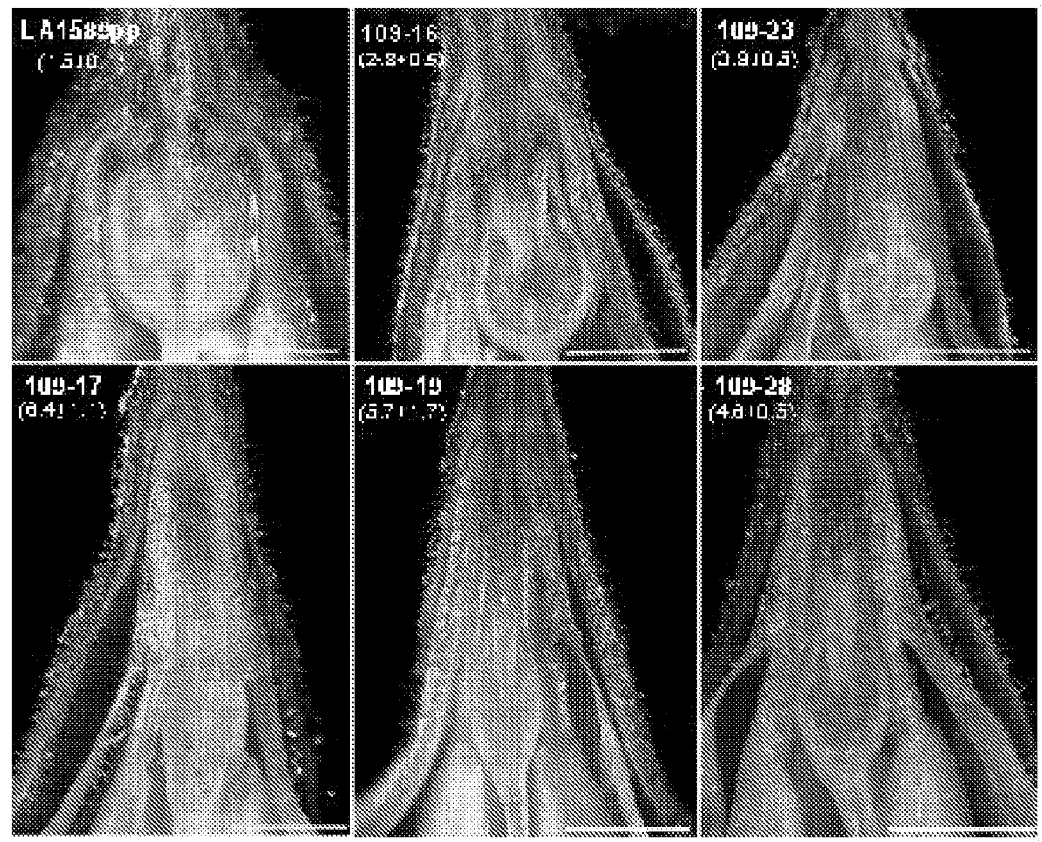
Figure 17B:
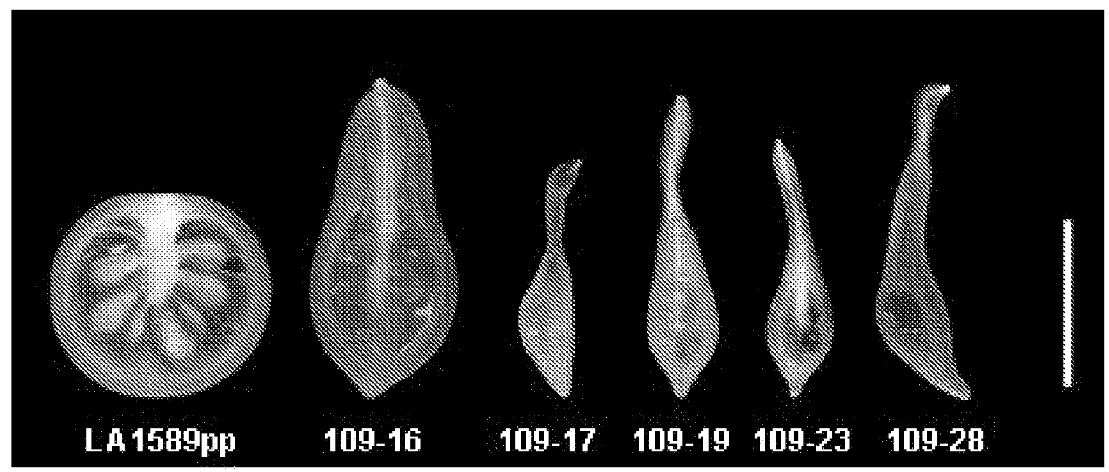
Figure 17C:
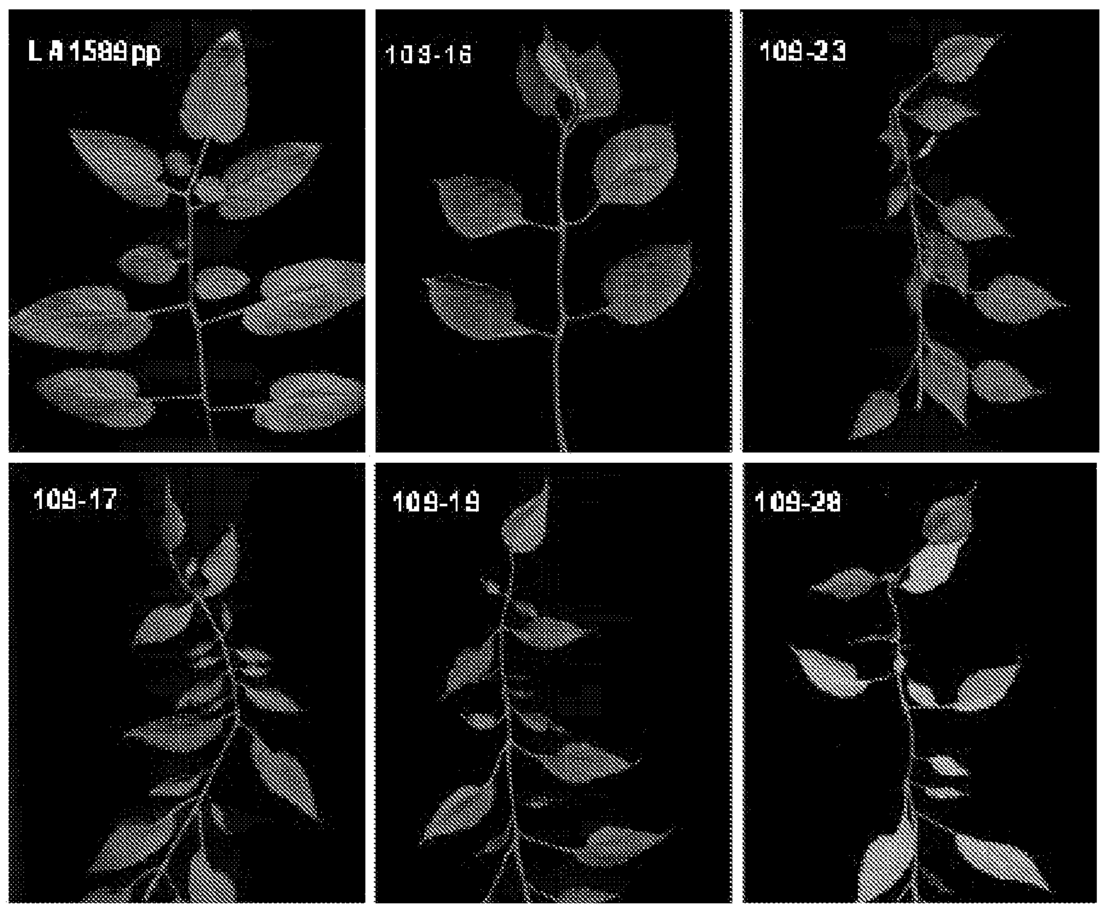

FIGS. 17A-17F shows the effect of overexpression of SUN on ovary, fruit and compound leaf shape in tomato:

FIGS. 17A-17C show the *S. pimpinellifolium* LA1589 background. Ovary shape of anthesis-stage flowers (FIG. 17A), fruit shape (FIG. 17B) and compound leaf shape (FIG. 17C) of wild type (LA1589pp) and 5 independent transformants. Note the very elongated slender shape of the ovary, fruit and the twisted shape of the leaves.

Figure 17D:
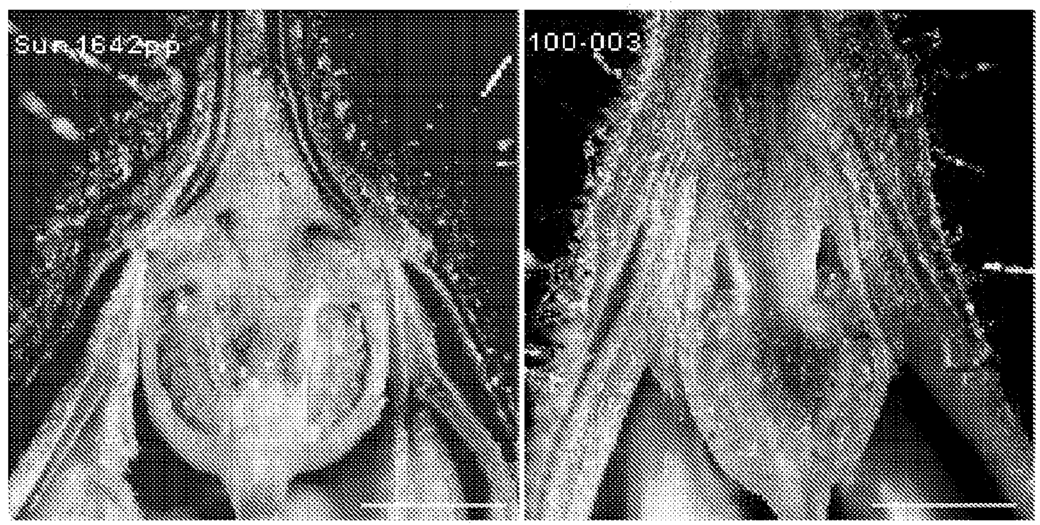
Figure 17E:
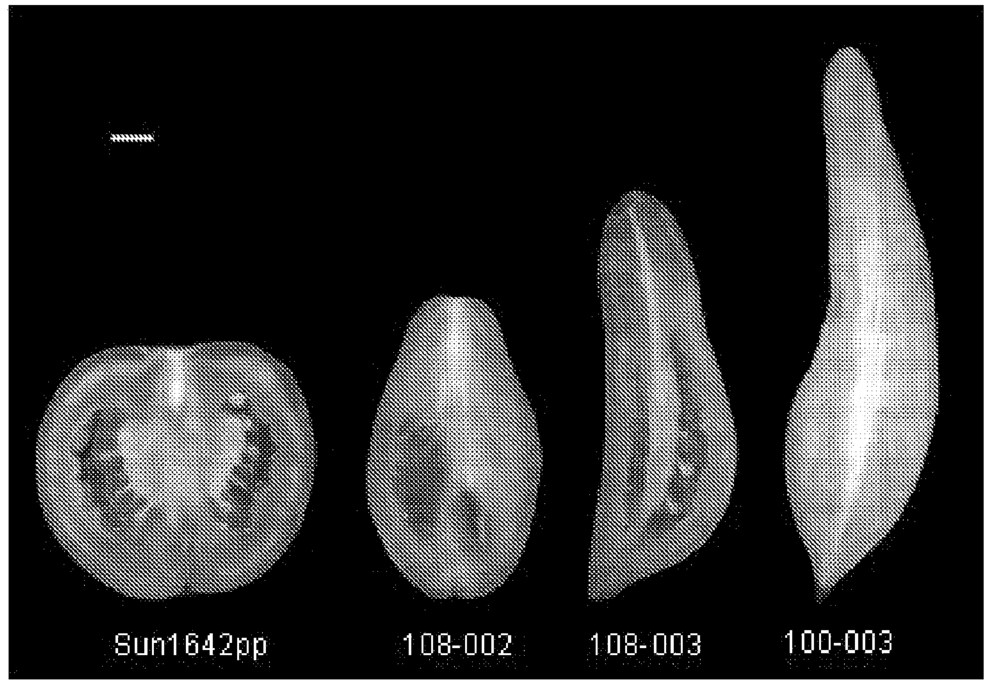
Figure 17F:
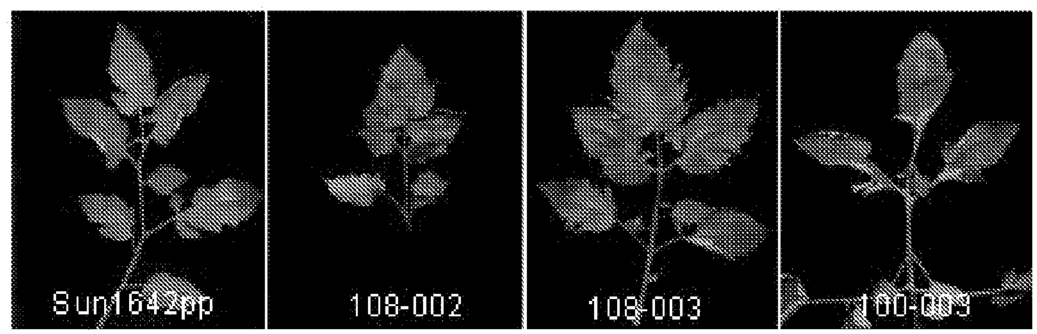

FIGS. 17D-17F show the *S. lycopersicum* Sun1642 background. Ovary shape of anthesis-stage flowers (FIG. 17D), fruit shape (FIG. 17E) and compound leaf shape (FIG. 17F) of wild type (Sun1642pp) and several independent transformants. When SUN is overexpressed under control of the 35S promoter, the fruit shape is already determined at the time of anthesis. Moreover, leaflets and compound leaf shape is also greatly affected when SUN is overexpressed. The leaves are twisted and the leaflets are more pointed in shape.

Figure 18A:
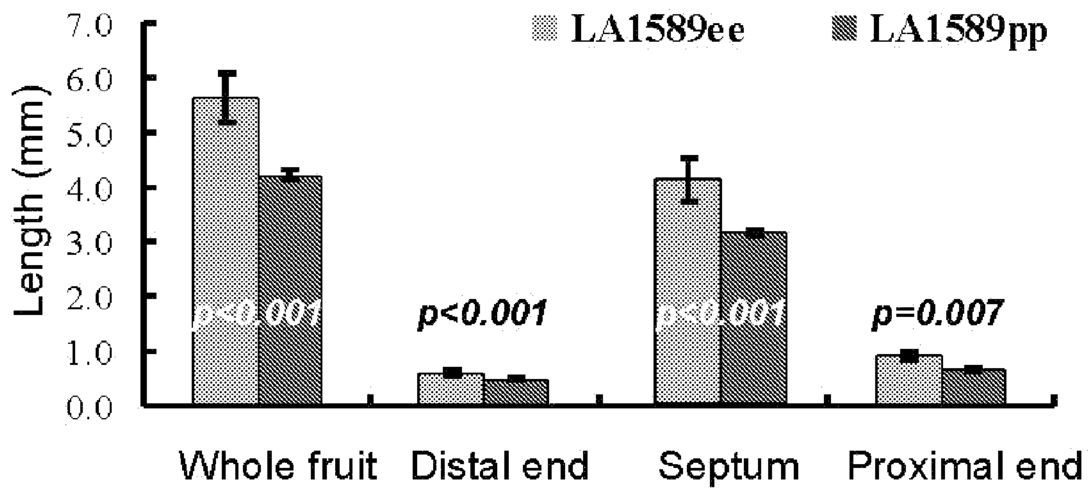
Figure 18B:
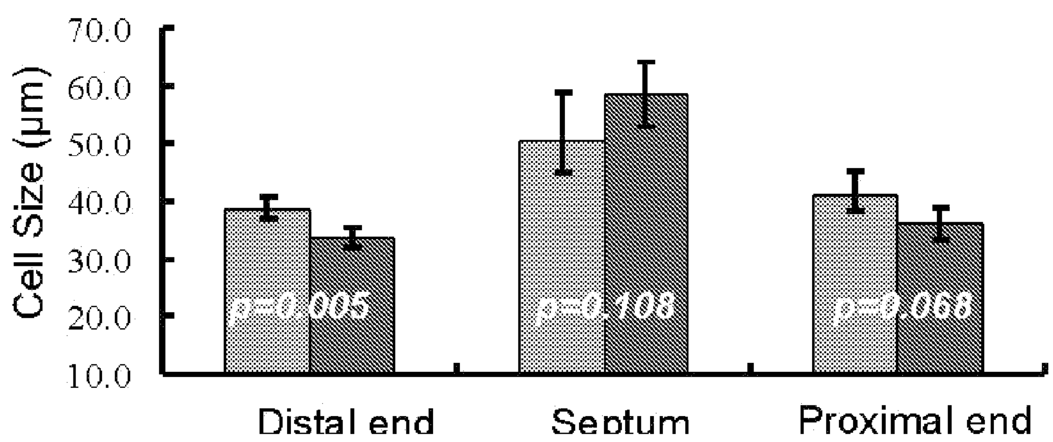
Figure 18C:
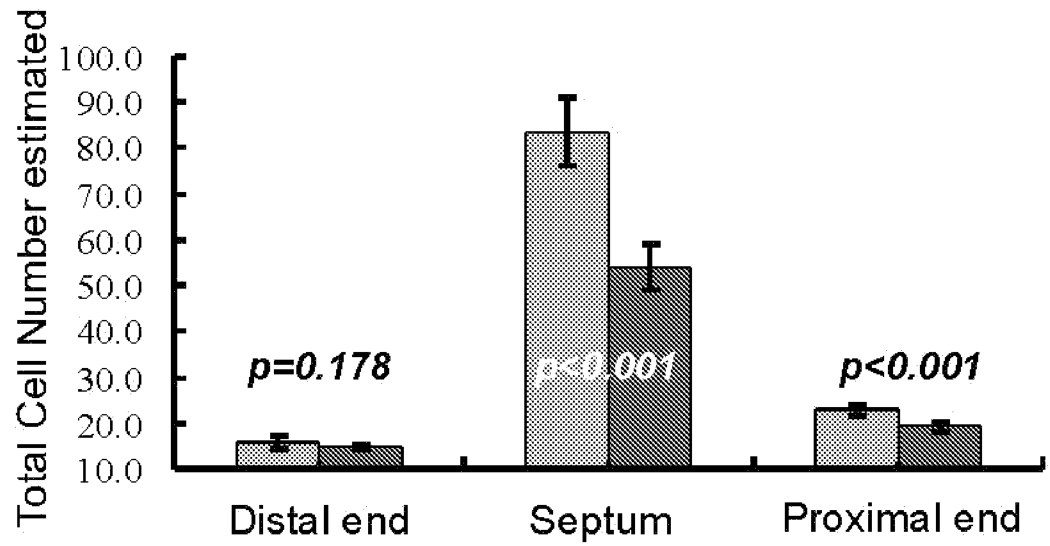

FIGS. 18A-18C show the cell size and number differences in the longitudinal direction of LA1589 NIL fruit differing at sun.

FIG. 18A shows the length of different parts of the fruit at 5 days post anthesis. All fruit parts are more elongated in the presence of SUN.

FIG. 18B shows the cell size is only significantly different in the distal end of the fruit.

FIG. 18C shows the ratio of fruit length and cell size shows that the septum and proximal end of the fruit have significantly more cells.

Figure 19A:
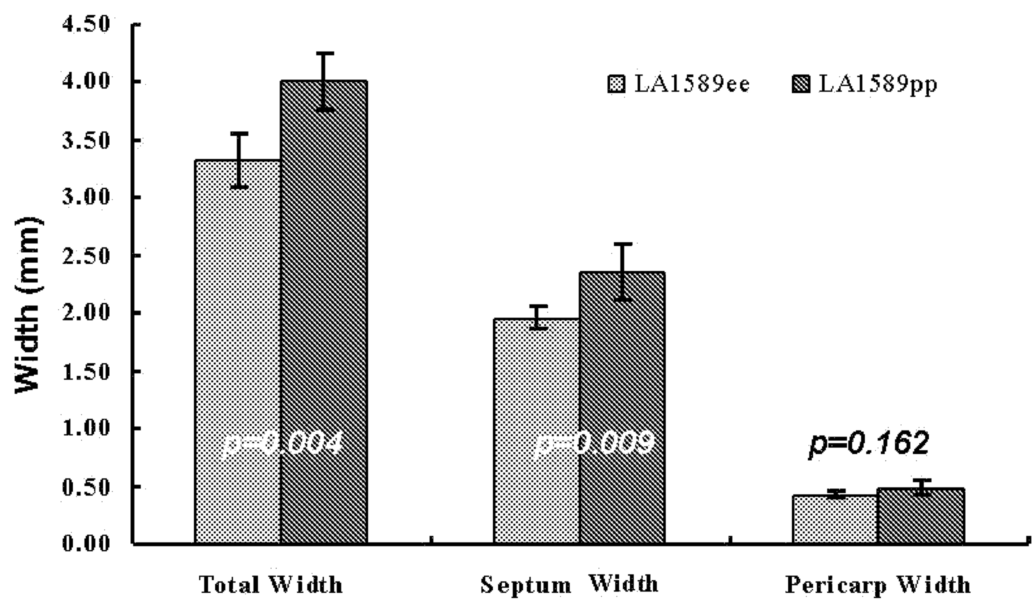
Figure 19B:
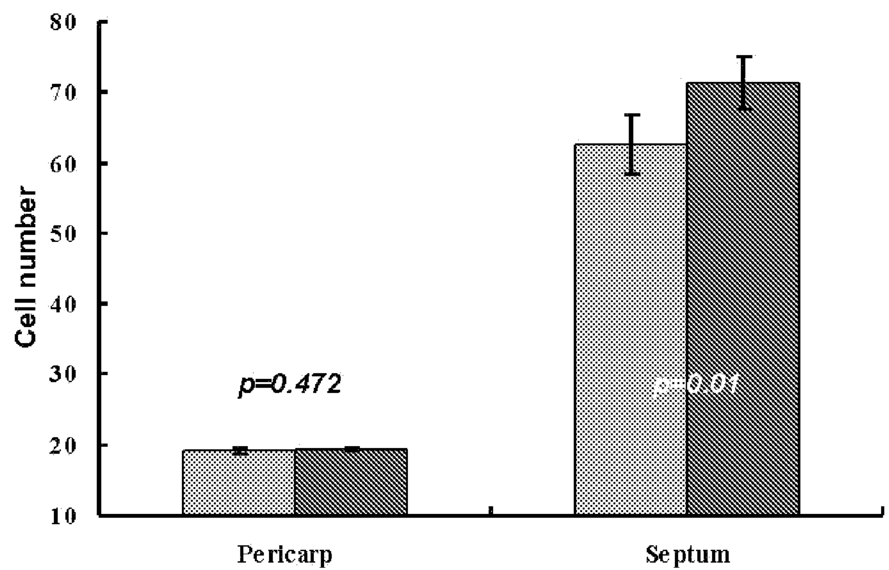
Figure 19C:
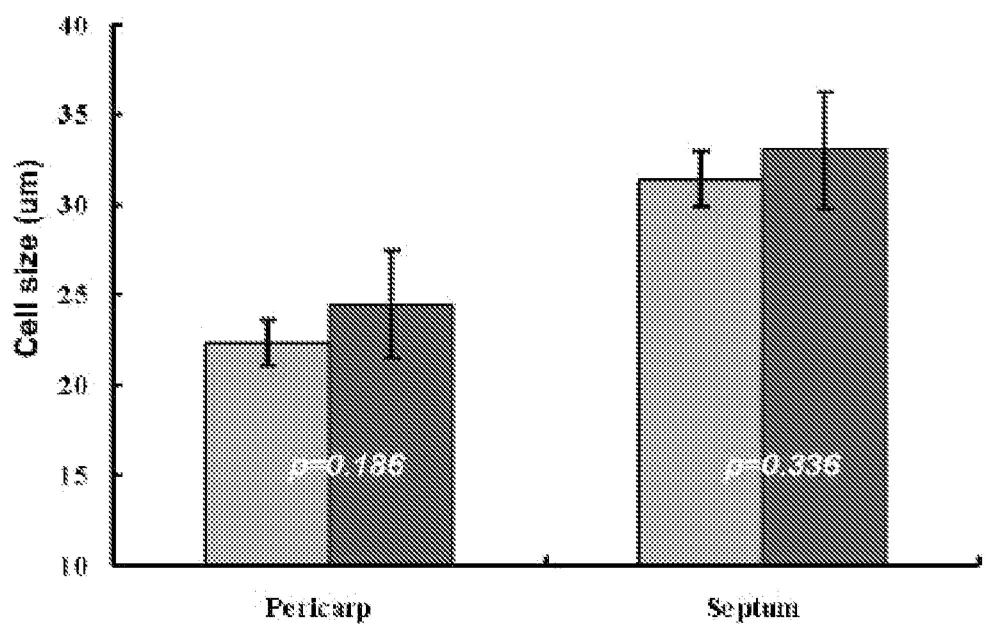

FIGS. 19A-19C show the cell size and number differences in the latitudinal direction of LA1589 NIL that differ at sun:

FIG. 19A shows the width of the fruit at 5 days post pollination. Total fruit and septum width are significantly smaller in the NILs carrying the SUN duplication.

FIG. 19B shows the cell number in the septum is significantly lower in the NILs carrying the SUN duplication.

FIG. 19C shows the cell size is not significantly different in the septum or pericarp. The results shown in FIGS. 18 and 19 demonstrate that SUN controls directional cell division predominantly in the septum and proximal end of the fruit. High expression of SUN leads to increased cell division in the longitudinal direction and reduced cell division in the latitudinal direction. This suggests that SUN can affect the shape of any organ in any plant species depending on where and when the gene is expressed.

Figure 20:
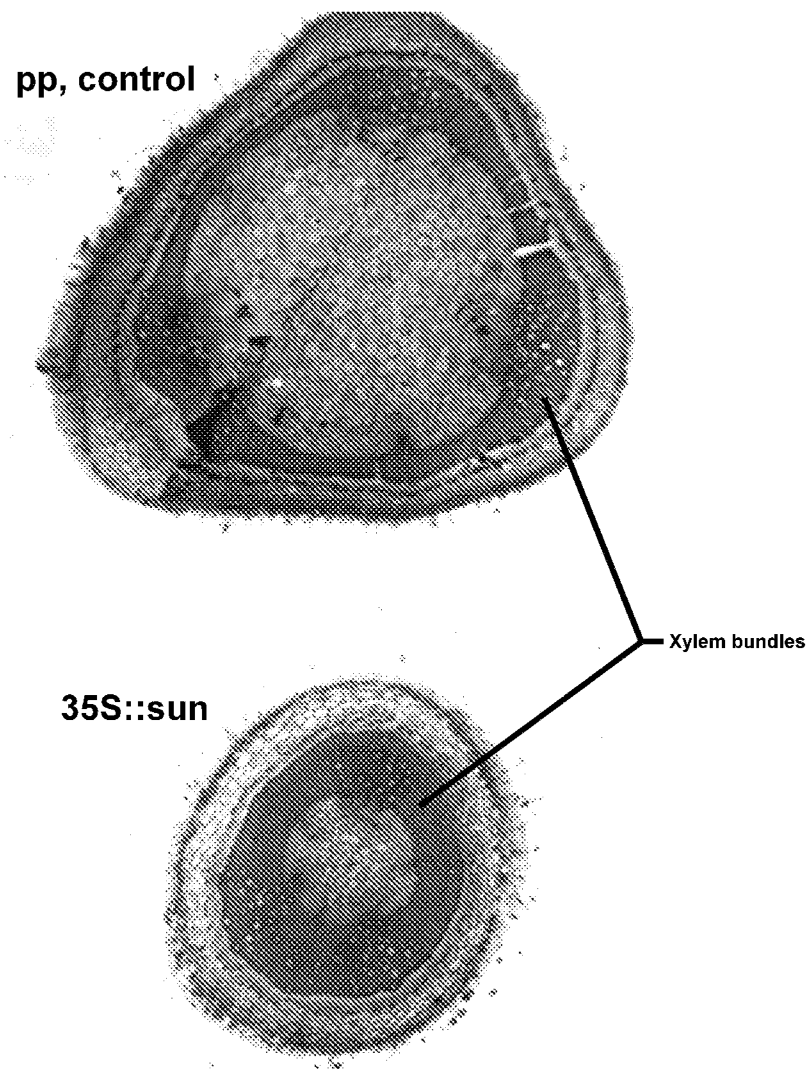

FIG. 20 shows the stem structure of *S. lycopersicum* cv Sun1642pp (without the SUN duplication and carrying round fruit) and Sun1642pp overexpressing SUN.

FIG. 21 shows Table 5 shows the near isogenic lines that differ at sun in both the Sun1642 and the LA1589 background show changes in fruit shape index, leaflet shape index (see also FIG. 16), sepal and ovary shape index and to a lesser extent petal shape index, and seed weight. Fruit weight, number of seed per fruit, hypocotyl and internode length is not altered. The fact that SUN does not affect fruit weight but only the shape strongly indicates that the gene acts to redirect growth without increasing growth. Again, this finding shows that SUN may be able to alter direction of growth of any plant organ.

FIG. 22 shows Table 6 shows that leaf shape, fruit shape, seed number per fruit, seed and fruit weight are similar in the line expressing SUN under its own promoter compared to the NIL carrying the SUN gene duplication. This shows that only SUN but neither DEFL1 nor one of the HYP genes (hypothetical, see FIG. 14) affect shape of plant organs and seed weight.

The Sequence Listing provides exemplary polynucleotide and polypeptide sequences of the invention. The traits associated with the use of the sequences are included in the Examples.

The GenBank accession number EF094939 [SEQ ID NO:1] for nucleotide sequence: file BAC_72D08_Lycopersicum_es, corresponds to the sequence on chromosome 10.

The GenBank accession number EF094940 [SEQ ID NO:2] for nucleotide sequence: file sunLesc_Lycopersicu_escul corresponds to the entire sequence of the sun locus in some cultivated tomato (the varieties that carry the duplication).

SUN Exon/Intron Positions in EF094940 [SEQ ID No:2] are as follows

| EXON | Genomic coordinates | mRNA coordinates |
|---|---|---|
| Exon 1 | 13386-13522 | 1-137 |
| Intron 1 | 13523-13964 | |
| Exon 2 | 13965-14051 | 138-224 |
| Intron 2 | 14052-14135 | |
| Exon 3 | 14136-14447 | 225-536 |
| Intron 3 | 14448-15013 | |
| Exon 4 | 15014-15238 | 537-761 |
| Intron 4 | 15239-15386 | |
| Exon 5 | 15387-15518 | 762-893 |
| Intron 5 | 15519-15685 | |
| Exon 6 | 15686-16858 | 894-2066 |

The GenBank accession number EF094941 [SEQ ID NO:3] for nucleotide sequence: file sunLpip_Lycopersicum_pimp corresponds to the sequence of the sun locus in the wild species.

The SUN gene amino acid sequence [SEQ ID NO:4]:

```
MGKRRNWFTFVKRLFIPETESTADQKKPKRWRCCFLRKFKLRKCPAITSA
PQQTLPEAKGTPQQTLTEAKEQQRKHAFAVAIATAAAAEAAVAAANAAAD
VIRLTDAPSEFKRKRKQAAIRIQSAYRAHLAQKALRALKGVVKLQAVIRG
EIVRGRLIAKLKFMLPLHQKSKTRVNQIRVPTFEDHHDKKLINSPREIMK
AKELKLKCKSLSTWNFNLASEQDSEALWSRREEAIDKREHLMKYSFSHRE
RRNDQTLQDLLNRKQNRRSYRIDQLVELDAPRKAGLLEKLRSFTDSNVPL
TDMDGMTQLQVRKMHRSDCIEDLHSPSSLPRRSFSNAKRKSNVDDNSLPS
SPIFPTYMAATESAKAKTRSNSTAKQHLRLHETLSGQHSPYNLKISSWRL
SNGEMYDSARTSRTSSSYMLI
```

The DNA sequence listing the clone that, when transformed into plants resulted in elongated fruit. The DNA sequence is shown in EU491503_suncdna [SEQ ID No:5] SunLesc.txt/genbank [SEQ ID Nos:4, 7, 8, 9, 10, 10, 11, 12, 13].

The construct that is encompassed by pHX4 (EK60): nt 7305-21371 [SEQ ID No:6], when transformed into tomato plants, confers an elongated fruit phenotype. The regulatory element for elevated transcription is located from 7305 to 10528 nt. The entire promoter of SUN spans from 7305-13386. The coding region of SUN starts in exon 2 at nt 13974. The 3' UTR of SUN starts in exon 6 at nt 16204. The 3' downstream region of the SUN spans from nt 16858-21371.

DETAILED DESCRIPTION OF THE PREFERRED EMBODIMENT(S)

The principles and operation of the present invention may be better understood with reference to the accompanying descriptions.

Before explaining at least one embodiment of the invention in detail, it is to be understood that the invention is not limited in its application to the details set forth in the following description. The invention is capable of other embodiments or of being practiced or carried out in various ways. Also, it is to be understood that the phraseology and terminology employed herein is for the purpose of description and should not be regarded as limiting.

In an important aspect, the present invention relates to polynucleotides and polypeptides, for example, for modifying phenotypes of plants. Throughout this disclosure, various information sources are referred to and/or are specifically incorporated. The information sources include scientific journal articles, patent documents, textbooks, and World Wide Web browser-inactive page addresses, for example. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

Unless defined otherwise, all technical and scientific terms used have the same meaning as commonly understood by one of ordinary skill in the art to which this invention belongs. Generally, the nomenclature used and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Where a term is provided in the singular, it is also contemplated that aspects of the invention described by the plural of that term. The nomenclature used and the laboratory procedures described below are those well known and commonly employed in the art. Where there are discrepancies in terms and definitions used in references that are incorporated by reference, the terms used in this application shall have the definitions given. Other technical terms used have their ordinary meaning in the art that they are used, as exemplified by a variety of technical dictionaries. The inventors do not intend to be limited to a mechanism or mode of action. Reference thereto is provided for illustrative purposes only.

It must be noted that as used herein and in the appended claims, the singular forms "a," "an," and "the" include plural reference unless the context clearly dictates otherwise. Thus, for example, a reference to "a plant" includes a plurality of such plants, and a reference to "a stress" is a reference to one or more stresses and equivalents thereof known to those skilled in the art, and so forth.

An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Hybridization complex" refers to a complex between two nucleic acid molecules by virtue of the formation of hydrogen bonds between purines and pyrimidines.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences.

"Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences.

An "IQ motif" is defined as an amino acid sequence of 20-40 amino acids in length containing an isoleucine residue (designated "I") immediately followed by a glutamine residue (designated "Q") which has at least 50% sequence similarity to the consensus sequence.

"Alignment" refers to a number of DNA or amino acid sequences aligned by lengthwise comparison so that components in common (i.e., nucleotide bases or amino acid residues) may be readily and graphically identified. The number of components in common is related to the homology or identity between the sequences. Alignments may be used to identify "conserved domains" and relatedness within these domains. An alignment may suitably be determined by means of computer programs known in the art.

A "conserved domain" or "conserved region" as used herein refers to a region in heterologous polynucleotide or polypeptide sequences where there is a relatively high degree of sequence identity between the distinct sequences.

A "conserved domain", with respect to presently disclosed polypeptides refers to a domain that exhibits a higher degree of sequence homology, such as at least 26% sequence similarity, at least 16% sequence identity, preferably at least 40% sequence identity, preferably at least 65% sequence identity including conservative substitutions, and more preferably at least 80% sequence identity, and even more preferably at least 85%, or at least about 86%, or at least about 87%, or at least about 88%, or at least about 90%, or at least about 95%, or at least about 98% amino acid residue sequence identity of a polypeptide of consecutive amino acid residues. It is to be understood that ranges within these percentages is also within the contemplated scope of the disclosure herein.

A fragment or domain can be referred to as outside a conserved domain, outside a consensus sequence. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

"Complementary" refers to the natural hydrogen bonding by base pairing between purines and pyrimidines. For example, the sequence A-C-G-T (5'→3') forms hydrogen bonds with its complements A-C-G-T (5'→3') or A-C-G-U (5'→3'). Two single-stranded molecules may be considered partially complementary, if only some of the nucleotides bond, or "completely complementary" if all of the nucleotides bond. The degree of complementarity between nucleic acid strands affects the efficiency and strength of the hybridization and amplification reactions.

"Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are known to those skilled in the art.

In general, stringency is determined by the temperature, ionic strength, and concentration of denaturing agents (e.g., formamide) used in a hybridization and washing procedure. The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known sequences. Numerous variations are possible in the conditions and means by which nucleic acid hybridization can be performed to isolate sequences having similarity to sequences known in the art and are not limited to those explicitly disclosed herein. Such an approach may be used to isolate polynucleotide sequences having various degrees of similarity with disclosed sequences, such as, for example, sequences having 60% identity, or more preferably greater than about 70% identity, most preferably 72% or greater identity with disclosed sequences.

The term "variant", as used herein, may refer to polynucleotides or polypeptides that differ from the presently disclosed polynucleotides or polypeptides, respectively, in sequence from each other, and as set forth herein.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent polypeptide. Thus, it will be readily appreciated by those of skill in the art, that any of a variety of polynucleotide sequences is capable of encoding the polypeptide and homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as the functional or biological activity of the polypeptide is retained.

The term "plant" includes whole plants, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. A plant also refers to plant cells or any other plant material, e.g., a plant explant, as well as to progeny thereof, and to in vitro systems that mimic biochemical or cellular components or processes in a cell.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of polypeptide. The expression cassette can be introduced into a plant by transformation or by breeding after transformation of a parent plant.

"Control plant" refers to a plant that serves as a standard of comparison for testing the results of a treatment or genetic alteration, or the degree of altered expression of a gene or gene product. Examples of control plants include plants that are untreated, or genetically unaltered (i.e., wild-type).

"Wild type", as used herein, refers to a cell, tissue or plant that has not been genetically modified to knock out or overexpress one or more of the presently disclosed transcription factors. Wild-type cells, tissue or plants may be used as controls to compare levels of expression and the extent and nature of trait modification with cells, tissue or plants in which expression is altered or ectopically expressed, e.g., in that it has been knocked out or overexpressed.

The term "growing" or "regeneration" as used herein means growing a whole plant from a plant cell, a group of plant cells, a plant part (including seeds), or a plant piece (e.g., from a protoplast, callus, or tissue part).

A "trait" refers to a physiological, morphological, biochemical, or physical characteristic of a plant or particular plant material or cell. In some non-limiting instances, this characteristic is visible to the human eye, such as seed, plant size or fruit or vegetable shape, or can be measured by biochemical techniques, such as detecting the protein, starch, or oil content of seed or leaves, or by observation of a metabolic or physiological process, e.g. by measuring uptake of carbon dioxide, altered expression or suppression of a hormone, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease in an observed trait (difference), at least a 5% difference, at least about a 10% difference, at least about a 20% difference, at least about a 30%, at least about a 50%, at least about a 70%, or at least about a 100%, or an even greater difference compared with a wild-type plant. It is known that there can be a natural variation in the modified trait. Therefore, the trait modification observed entails a change of the normal distribution of the trait in the plants compared with the distribution observed in wild-type plants.

The term "transcript profile" refers to the expression levels of a set of genes in a cell in a particular state, particularly by comparison with the expression levels of that same set of genes in a cell of the same type in a reference state. For example, the transcript profile of a particular gene in a suspension cell is the expression levels of a set of genes in a cell overexpressing that gene compared with the expression levels of that same set of genes in a suspension cell that has normal levels of that gene. The transcript profile can be presented as a list of those genes whose expression level is significantly different between the two treatments, and the difference ratios. Differences and similarities between expression levels may also be evaluated and calculated using statistical and clustering methods.

"Altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a strong expression signal, such as one of the promoters described herein (e.g., the cauliflower mosaic virus 35S transcription initiation region). Overexpression may occur throughout a plant or in specific tissues of the plant, depending on the promoter used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

Similarly, the term "under expression" as used herein refers to a lesser expression level of a gene in a plant, plant cell or plant tissue, compared to expression in a wild-type plant, cell or tissue, at any developmental or temporal stage for the gene. Under expression can occur when, for example, the genes encoding one or more polypeptides are under the control of a strong expression signal, such as one of the promoters described herein (e.g., the cauliflower mosaic virus 35S transcription initiation region). Under expression may occur throughout a plant or in specific tissues of the plant, depending on the promoter used.

Under expression may take place in plant cells normally having expression of polypeptides functionally equivalent or identical to the present polypeptides. Under expression may also occur in plant cells where endogenous expression of the present transcription factors or functionally equivalent molecules normally occurs, but such normal expression is at a higher level. Under expression thus results in a lesser than normal production, or "under" of the polypeptides in the plant, cell or tissue.

Thus, in a first broad aspect, there is provided herein a chromosome 7 region, which region, when introduced into a cultivated plant genetic background alters at least one trait in the plant.

Non-limiting examples of plants for which one or more traits can be altered include gymnosperms, angiosperms and mosses.

Non-limiting examples include including monocots and dicots, such as crop plants, ornamental plants, and non-domesticated or wild plants. Further examples include plants of commercial or agricultural interest, such as crop plants (especially crop plants used for human food or animal feed), wood- or pulp-producing trees, vegetable plants, fruit plants, and ornamental plants. Non-limiting examples of plants of interest include grain crop plants (such as wheat, oat, barley, maize, rye, triticale, rice, millet, sorghum, quinoa, amaranth, and buckwheat); forage crop plants (such as forage grasses and forage dicots including alfalfa, vetch, clover, and the like); oilseed crop plants (such as cotton, safflower, sunflower, soybean, canola, rapeseed, flax, peanuts, and oil palm); tree nuts (such as walnut, cashew, hazelnut, pecan, almond, and the like); sugarcane, coconut, date palm, olive, sugarbeet, tea, and coffee; wood- or pulp-producing trees; vegetable crop plants such as legumes (for example, beans, peas, lentils, alfalfa, peanut), lettuce, asparagus, artichoke, celery, carrot, radish, the brassicas (for example, cabbages, kales, mustards, and other leafy brassicas, broccoli, cauliflower, Brussels sprouts, turnip, kohlrabi), edible cucurbits (for example, cucumbers, melons, summer squashes, winter squashes), edible alliums (for example, onions, garlic, leeks, shallots, chives), edible members of the Solanaceae (for example, tomatoes, eggplants, potatoes, peppers, groundcherries), and edible members of the Chenopodiaceae (for example, beet, chard, spinach, quinoa, amaranth); fruit crop plants such as apple, pear, citrus fruits (for example, orange, lime, lemon, grapefruit, and others), stone fruits (for example, apricot, peach, plum, nectarine), banana, pineapple, grape, kiwifruit, papaya, avocado, and berries; and ornamental plants including ornamental flowering plants, ornamental trees and shrubs, ornamental groundcovers, and ornamental grasses. Further examples of dicot plants include, but are not limited to, canola, cotton, potato, quinoa, amaranth, buckwheat, safflower, soybean, sugarbeet, and sunflower, more preferably soybean, canola, and cotton. Further examples of monocots include, but are not limited to, wheat, oat, barley, maize, rye, triticale, rice, ornamental and forage grasses, sorghum, millet, and sugarcane, more preferably maize, wheat, and rice.

Non-limiting examples of suitable members of the Solanaceae family include tomato plants that may have a range of genotypes used in the production of commercial tomato varieties. Suitable plants can be used for processing into tomato paste, dice and whole peel production, fresh market tomatoes for open field production, staked cultivation in the open field and protected cultivation such as in a glasshouse.

In one particular aspect, there is provided herein a portion of a targeted site duplication into chromosome 7 resulting in elongated-fruited tomato. This duplicated chromosome 7 fragment which spans from a region between tomato markers Lp81B9-F and Lp61O2-R is capable of, when introduced into the genetic background of a cultivated tomato, altering the fruit shape index of fruits produced thereby, while at the same time maintaining the desired phenotypic traits of the cultivated plant.

Thus, in another aspect, there is provided cultivated tomato plants producing fruits and seeds, such as, for example, hybrid seeds, of commercial value, which plants are generated according to the teachings of the present invention by introducing a chromosomal region associated with a high fruit shape index, into a genetic background of a cultivated tomato.

In a first aspect, there is are provided herein isolated polynucleotides, including: (a) a sequence encoding a polypeptide, wherein the sequence is at least one of SEQ ID NOs: 1, 2, 3, 4 and 5, or segments thereof; (b) a variant of any of the sequences of (a) or (b) that has at least 70% sequence identity to a sequence of (a); (c) an orthologous sequence of any of the sequences of (a) or (b) that has at least 70% identity to a sequence of (a); (d) a paralogous sequence of any of the sequences of (a) or (b) that has at least 70% identity to a sequence of (a) or a paralogous sequence with 70% identity to the IQ motif thereof; (e) a sequence that hybridizes to any of the sequence of (a) under stringent conditions; and (f) a sequence encoding a polypeptide comprising a conserved domain that has at least 70% sequence homology with a conserved domain of a polypeptide encoded by any of the sequences of (a)-(e), wherein the conserved domain is required for the function of the polypeptide encoded by any of the sequences of (a)-(e) in regulating expression of the nucleotide and altering a trait in a transgenic plant.

In on embodiment, wherein the recombinant polynucleotide is operably linked to at least one regulatory element being effective in controlling expression of the recombinant polynucleotide when the recombinant polynucleotide is transformed into a plant. In certain embodiments, the polynucleotide is incorporated within an expression vector.

Also, in certain embodiments, there is provided herein a polynucleotide comprising one or more constitutive, inducible, or tissue-specific promoters operably linked to the polynucleotide sequence as described above. In certain embodiments, the expression vector is incorporated into a cultured host cell.

In another aspect, there is provided herein a transgenic plant that expresses at least one polynucleotide described herein, where at least a part of the transgenic plant has an altered trait as compared to a non-transgenic plant or wild-type plant.

In certain embodiments, the altered trait is one or more of: sensitivity to hormone levels, altered shape of at least part of the plant, altered plant size; altered leaf shape; altered vegetable shape, altered fruit shape; at least partially parthenocarpic fruit, increased SUN levels, and decreased SUN levels. Also, in certain embodiments, the altered trait is an overexpression of at least a portion of one of the isolated polynucleotides wherein the altered trait comprised a parthenocarpic fruit. Also, in certain embodiments, the altered trait is an expression of at least a portion of one of the isolated polynucleotides wherein the altered trait comprises an elongated fruit shape.

In a further aspect, there is provided herein transgenic plants where the plant is a plant that expresses one or more proteins from the IQD family of proteins. Such transgenic plants can be selected from one or more of: gymnosperms, angiosperms and mosses.

In certain embodiments, the plant is selected from one or more of: monocots and dicots, including, but not limited to crop plants, ornamental plants, and non-domesticated or wild plants.

In certain embodiments, the transgenic plant is selected from the Solanaceae family. In certain embodiments, the transgenic plant is a tomato plant. In certain embodiments, the transgenic plant is a tomato plant near isogenic line as described herein.

In another aspect, there is provided herein a method for producing a transgenic plant having an altered trait as compared to a non-transgenic or wild-type plant where the method includes: (a) providing an expression vector comprising: (i) a polynucleotide as described herein; and (ii) at least one regulatory element flanking the polynucleotide sequence, the at lest one regulatory element being effective in controlling expression of the recombinant polynucleotide in a target plant; (b) introducing the expression vector into a plant cell, thereby producing a transgenic plant cell; (c) growing the transgenic plant cell into a transgenic plant and allowing the transgenic plant to express or suppress a polypeptide encoded by the polynucleotide, the polypeptide having the property of altering a trait in a plant as compared to a non-transgenic plant that does not express or suppress the polypeptide; and (d) identifying at least one transgenic plant with an altered trait by comparing the transgenic plant with the non-transgenic plant.

In certain embodiments, the method further includes: (e) selfing or crossing the at least one transgenic plant with an altered trait with itself or another plant, respectively; and (f) growing a progeny plant from seed that develops as a result of the selfing or crossing, thus producing a transgenic progeny plant having an altered trait.

In another aspect there is provided herein a cell transformed with at least one polynucleotide described herein. In certain embodiments, the cell is a plant cell. Also provided herein is plant or plant tissue grown from such plant cell.

In another aspect, there is provided herein a transformed or transgenic plant, plant part, plant seed, plant cell, or the transgenic progeny thereof, comprising a sequence encoding a polypeptide, wherein the nucleotide sequence is at least one of: SEQ ID NO: 1, 2, 3, 4 and 6, and combinations thereof. In certain embodiments, the transgenic plant is selected from the Solanaceae family, such as, but not limited to a tomato plant. In certain embodiments, the plant is a tomato plant near isogenic line as described herein.

In another aspect, there is provided herein a transformed plant comprising in its genome at least one stably incorporated nucleotide construct comprising a promoter that drives expression in a plant operably linked to at least on of the isolated polypeptides described herein.

In another aspect, there is provided herein a mRNA molecule flanked by part of two LTRs, the R segment and U5 region at the 5' end of the mRNA and the R segment and U3 region at the 3' end of the mRNA, substantially as shown in FIG. 6C. In another aspect, there is provided herein a molecule where the LTR1 and LTR3 are on chromosome 7 and flank an entire duplicated fragment, and immediately flanking LTR1 and LTR3 are a 5 bp motifs "ATATT".

In another aspect, there is provided herein a clone, pHX4, comprising a full length SUN gene.

In another aspect, there is provided herein a plant transformed with the pHX4 clone.

In another aspect, there is provided herein a clone further including a cis-element located in a 3.2 kb region upstream of DEFL1.

In another aspect, there is provided herein a method for altering at least one trait of a plant, comprising causing a duplication event mediated by an autonomous Long Terminal Repeat retroelement, wherein the transposition of the retroelement results in the placement of a SUN gene proximal to a regulatory sequence of another gene results in an altered expression compared to its paralog at an ancestral location. In certain embodiments, a gain-of-function mutation results from the transposition event mediated by the autonomous LTR-retroelement, and wherein the transposition of the retroelement is associated with 3' transduction of nearby genes as well as a second rearrangement that moves the SUN gene from upstream of the retroelement to 20 kb downstream of the retroelement.

In another aspect, there is provided herein a method for making a plant having at least one fruit having a shape that is different from a naturally occurring fruit, comprising transforming a SUN inverted repeat construct into a near isogenic line of the fruit, and growing the plant.

In another aspect, there is provided herein a method of producing a fruit, comprising: a) growing a plant having at least one polypeptide described herein to produce a fruit, and b) harvesting the fruit.

In another aspect, there is provided herein a method of vegetatively propagating a plant comprising: collecting part of a plant grown; and obtaining a plantlet from the part. The method can further comprise growing a plant from the plantlet. Also, in certain embodiments, method can further include harvesting a fruit from the plant grown from the plantlet.

In another aspect, there is provided herein food and food products comprising the fruit of the plants described herein.

In another aspect, there is provided herein a near isogenic line (NIL) comprising a Sun1642 background.

In another aspect, there is provided herein a near isogenic line (NIL) comprising a LA1589 background.

In another aspect, there is provided herein a 17.2 kb pHX2 construct containing IQD12, SDL1-like, HYP1 and nucleotides encoding the first 415 amino acids of HYP2.

In another aspect, there is provided herein a 14 kb pHX4 construct containing IQD12 and terminating 180 nucleotides upstream of the SDL1-like stop codon.

In another aspect, there is provided herein a transformation construct made by subcloning the entire phage subclone insert of plasmids pEK59 and pEK60, respectively (released by NotI and blunted-ended using Klenow) into the Klenow-blunted ended BamHI-digested binary vector pCIB10G. In certain embodiments, the transformation construct comprises pHX2. In certain embodiments, the transformation construct comprises pHX4.

In another aspect, there is provided herein a RNAi:IQD12 construct, pHX8, generated by cloning 512 bp fragments of the IQD12 cDNA (from nucleotide 16,154 to 16,646 of the genomic sequence EF094940 [SEQ ID NO:2]), amplified using primer EP527 and EP528 from reverse transcribed mRNA, in the sense and antisense directions into pFGC5941.

In another aspect, there is provided herein a method for over expressing IQD12, a 1.4 kb fragment of IQD12 cDNA (corresponding to nucleotide 13,460-16,280 of the genomic sequence EF094940 [SEQ ID NO:2]), comprising: amplifying from reverse transcribed mRNA using primers EP519 and EP520 and subcloning between a CaMV 35S RNA promoter and NOS terminator of pCIB710.

In another aspect, there is provided herein a method for probe labeling expressing IQD12, a 1.4 kb fragment of IQD12 cDNA (corresponding to nucleotide 13,460-16,280 of the genomic sequence EF094940 [SEQ ID NO:2], comprising amplifying from reverse transcribed mRNA using primers CME5F and CME5R.

In another aspect, there is provided herein a method for silencing expressing IQD12, a 1.4 kb fragment of IQD12 cDNA (corresponding to nucleotide 13,460-16,280 of the genomic sequence EF094940 [SEQ ID NO:2]), comprising amplifying from reverse transcribed mRNA using primers EP527 and EP528.

In another aspect, there is provided herein a construct comprising plasmid pHX8.

In another aspect, there is provided herein a plasmid construct pHX8 transformed into near isogenic line (NIL) carrying a Sun1642 allele in a LA1589 background.

In another aspect, there is provided herein a construct comprising plasmid pHX2.

In another aspect, there is provided herein a plasmid construct pHX2 useful to transform round-fruited NIL plants in both the LA1589 and Sun1642 backgrounds.

In another aspect, there is provided herein a construct comprising plasmid pHX4.

In another aspect, there is provided herein a plasmid constructs pHX4 useful to transform round-fruited NIL plants in both the LA1589 and Sun1642 backgrounds.

In another aspect, there is provided herein a construct comprising plasmid pEK69.

In another aspect, there is provided herein a plasmid construct pEK69 useful to transform round-fruited NIL plants in both the LA1589 and Sun1642 backgrounds.

In another aspect, there is provided herein a near isogenic line (NIL) comprising a plant differing at sun constructed in Sun1642 background or LA1589 backgrounds, wherein the plant is made by sequential backcrosses to a recurrent parent using marker-assisted selection.

In another aspect, there is provided herein a 6.08 kb upstream region DEFL1 used as a promoter.

In another aspect, there is provided herein a vector comprising at least one of the polypeptides described herein. In another aspect, there is provided herein a plant cell transformed with such vector. In another aspect, there is provided herein a plant transformant comprising such plant cell. In another aspect, the plant transformant is tomato. In another aspect, there is provided herein a progeny or a clone of such plant transformant.

In another aspect, there is provided herein a method for producing a plant, comprising introducing at least one of the polypeptides described herein into a plant cell, and regenerating a plant transformant from the plant cell.

In another aspect, there is provided herein a method for altering at least one of a leaf and fruit shape of a plant, comprising introducing and expressing the polypeptide in the plant wherein the expressing the polypeptide alters the shape of the leaf and/or fruit, as compared to a plant that does not express at least one of the polypeptides described herein.

In another aspect, there is provided herein an isolated host cell transformed with a vector comprising at least one polypeptide described herein.

In another aspect, there is provided herein a process for altering at least one trait of a plant, or part thereof, comprising increasing SUN activity in the plant, or part thereof. In certain embodiments, the SUN has the amino acid sequence of SEQ ID NO:4 or an amino acid sequence with at least 60% sequence homology to SEQ ID NO:4 and which has SUN activity. In certain embodiments, the process includes introducing into the plant, or part thereof, a mutation into the polynucleotide sequence encoding the amino acid sequence of SEQ ID NO:4 or into a polynucleotide sequence encoding an amino acid sequence with at least 70% sequence homology to SEQ ID NO:4 and which has SUN activity.

In certain embodiments, the process includes introducing into the genome of the plant, or part thereof, in a sense or antisense orientation, a polynucleotide sequence of SEQ ID NO:4 or a polynucleotide sequence with at least 70% sequence homology to SEQ ID NO:4, wherein the homologous polynucleotide sequence inhibits SUN activity.

In another aspect, there is provided herein an isolated polynucleotide sequence encoding the amino acid sequence of SEQ ID NO:4 or encoding an amino acid sequence with at least 95% sequence homology with the amino acid sequence of SEQ ID NO:4. In another aspect, there is provided herein a vector comprising such polynucleotide.

In another aspect, there is provided herein an isolated polypeptide involved in the determination of fruit shape of plants, wherein the polypeptide is selected from one or more of: (a) a DNA encoding a protein comprising the amino acid sequence of SEQ ID NO:4; (b) a DNA comprising a coding region of the nucleotide sequence of SEQ ID NO:2; (c) a DNA encoding a protein comprising an amino acid sequence with one or more amino acid substitutions, deletions, additions, and/or insertions in the amino acid sequence of SEQ ID NO:4; and (d) a DNA that hybridizes under stringent conditions with a DNA comprising the nucleotide sequence of SEQ ID NO:2.

In another aspect, there is provided herein an isolated polypeptide encoding a partial peptide of a protein comprising at least one of the sequence of SEQ ID NO:4 or 6.

In another aspect, there is provided herein an isolated polypeptide comprising a promoter region of the nucleotide sequence of SEQ ID: NO:2. In another aspect, there is provided herein a vector comprising such polypeptides having one or more of SEQ ID NOS: 2, 4 or 6. In another aspect, there is provided herein a host cell carrying such vector. In another aspect, there is provided herein a plant cell carrying such vector. In another aspect, there is provided herein a plant transformant comprising such plant cell. In another aspect, there is provided herein a plant transformant that is a progeny or a clone of such plant transformant. In another aspect, there is provided herein a propagation material of such plant transformant.

In another aspect, there is provided herein a method for producing a plant transformant, wherein the method comprises the steps of introducing at least one polypeptide described herein into a plant cell, and regenerating a plant from the plant cell.

In another aspect, there is provided herein an isolated polynucleotide comprising at least 15 continuous nucleotides that are complementary to the nucleotide sequence of SEQ ID NO:2, or a sequence complementary thereto.

In another aspect, there is provided herein a method for increasing the regeneration ability of a plant, wherein the method comprises the step of expressing at least one polypeptide described herein in a cell of a plant.

In another aspect, there is provided herein an agent for altering at least one trait of a plant, wherein the agent comprises at least one polypeptide described herein, or a vector thereof as an active ingredient.

In another aspect, there is provided herein a method for determining the ability of a plant cell to produce a fruit with an altered shape, wherein the method comprises detecting the expression of at least one polypeptide described herein or a protein expressed thereby in the plant cell.

In another aspect, there is provided herein a method for determining the ability of a plant cell to produce a fruit with an altered shape, comprising detecting the expression of the polypeptide in the plant cell.

In another aspect, there is provided herein a method for improving the ability of a plant to produce a fruit with an altered shape, comprising regulating the activity of at least one protein produced by expression of at least one polypeptide described herein in the plant.

In another aspect, there is provided herein a method for selecting a transformed plant cell, comprising: (a) introducing a plant cell with a vector comprising at least one polypeptide described herein as a selection marker; (b) culturing the plant cells; and, (c) selecting plant cells that have acquired regeneration ability.

In another aspect, there is provided herein a method for altering the ability of a plant to produce a fruit with an altered shape, comprising substituting an endogenous polypeptide in a plant by crossing.

In another aspect, there is provided herein a plant cell transformed by an expression vector comprising an isolated molecule in antisense orientation, wherein expression of the vector in the plant cell results in an altered fruit shape index as compared to a corresponding wild-type plant, and wherein the molecule comprises (a) the sequence shown in SEQ ID NOS: 1, 2, 3, 4 or 6, or variants thereof, or (b) a sequence encoding the same sequence as the sequence of (a), but which is degenerate in accordance with the degeneracy of the genetic code. In certain embodiments, the molecule is SUN, SEQ ID NO:4.

In another aspect, there is provided herein a seed produced by a transgenic plant comprising the plant cell, where the seed is true breeding for an altered fruit shape index of a daughter plant as compared to a wild-type variety of plant cell.

In another aspect, there is provided herein a recombinant antisense expression vector comprising: (a) a promoter functional in a plant cell; and (b) an isolated molecule comprising SUN, SEQ ID NO: 4, wherein the molecule is operably linked in antisense orientation to a promoter. In another aspect, there is provided herein a method for producing a transgenic plant having an altered fruit shape as compared to the corresponding wild-type plant, comprising: (a) transforming plant cells by introducing the recombinant antisense expression vector; (b) producing plants from the transformed cells and (c) selecting a whole plant exhibiting an altered fruit shape index.

In another aspect, there is provided herein a method for altering the size of the fruit of a plant, comprising: (a) introducing the recombinant antisense expression vector into a plant cell; (b) regenerating the plant cell into a transgenic plant; (c) evaluating the whole plant for an altered fruit shape by comparing the plant with the introduced expression vector to a corresponding wild-type plant. In certain embodiments, the transgenic plant exhibits increased fruit shape index growth as compared to the corresponding wild-type plant.

In another aspect, there is provided herein a plant cell transformed with an isolated amino acid sequence in antisense orientation, wherein the amino acid sequence is SUN, SEQ ID NO:4, or the complement thereof, or a molecule encoding the same amino acid sequence as SEQ ID NO:4, but which is degenerate in accordance with the degeneracy of the genetic code, wherein expression of the sequence in the plant cell results in an altered fruit shape of a resulting plant as compared to a corresponding wild-type plant.

In another aspect, there is provided herein a transgenic plant comprising the plant cell as described herein.

In another aspect, there is provided herein a seed produced by the transgenic plant described herein where the seed comprises the isolated nucleotide sequence in antisense orientation.

In a particular embodiment, the sequence, as describe herein may be from any tomato species, particularly the *S. lycopersicum* fruit tomato plant species, in a naturally occurring form or from any source whether natural, synthetic, semi-synthetic or recombinant. The sequences of the invention may also include fragments of the present amino acid sequences.

EXAMPLES

According to one particular aspect, there is provided herein a cultivated tomato plant having a genome including an altered expressing through duplication and reposition of a gene derived from an elongated fruit tomato line. The elongated-fruited tomato is characterized by fruits having a high fruit shape index, i.e., where the fruit's height is greater that its width. The duplication/reposition gene, identified herein as IQD12 and/or SUN, includes a portion of chromosome 10 present as a duplicated fragment on chromosome 7. The SUN gene is responsible for a desired fruit elongation trait as compared to a wild-type tomato plant.

According to another aspect, there is provided herein a method of generating a tomato plant having fruits characterized by an increased fruit shape index, the method comprising the step of introducing to a genome of the tomato plant a construct derived from a elongated-fruited tomato, the construct including a portion of chromosome 10 of the elongated-fruited tomato duplicated on the chromosome 7.

As such, an evidence of the altered fruit shape index property may come by an introduction thereof into any cultivated variety of a construct that includes at least the SUN gene, as if further exemplified and described in the Examples section which follows.

Also, it is to be noted that, according to further features in preferred embodiments, the construct includes a regulatory elements, such as a promoter, as described herein.

According to still further features in the described preferred embodiments the fruits of the cultivated plants are characterized by an average elongated length-to-width aspect ratio. In certain embodiments, the plants are from the Solanaceae family, including tomato, potato, pepper, eggplant, petunia and the like.

The present invention is based, at least in part, on the discovery that a change in the size and shape of a plant fruit can be achieved by altering the level of SUN expression.

One specific aspect is a transgenic plant cell transformed by a SUN coding nucleic acid expression vector, wherein expression of the nucleic acid sequence in the plant cell results in an alteration in the fruit shape of the resulting plant as compared to a corresponding wild-type variety of the plant cell. In one embodiment, the SUN coding nucleic acid sequence is the SUN from *Solannum lycopersicum.*

Another specific aspect is a transgenic plant cell transformed by a SUN antisense coding nucleic acid expression vector, wherein expression of the nucleic acid sequence in the plant cell results in an altered fruit shape of the resulting plant as compared to a corresponding wild-type variety of the plant cell. In one embodiment, the SUN antisense coding nucleic acid sequence is the SUN from *Solananum lycopersicum.*

Another specific aspect is an agricultural product produced by any of the transgenic plants, plant parts or seeds described herein.

Another specific aspect is an isolated SUN as described below. In one embodiment, the SUN is SEQ ID NO: 4. Another aspect of the invention is an isolated SUN coding nucleic acid, wherein the SUN coding nucleic acid codes for SUN as described herein.

Another specific aspect is an isolated recombinant antisense expression vector comprising: (a) a promoter, the promoter being functional in a plant cell; and (b) a *Solananum lycopersicum* SUN antisense coding nucleic acid, the promoter being operably linked to the SUN antisense coding nucleic acid and the antisense coding nucleic acid oriented with respect to the promoter such that the RNA produced is complementary in nucleotide sequence and capable of hybridizing in a stringent manner to mRNA encoding SUN, wherein the SUN antisense coding nucleic acid comprises a nucleotide sequence of at least 15 contiguous nucleotides of SEQ ID NO: 4 compared to a corresponding wild-type variety of the host cell.

Another specific aspect is a method for producing a transgenic plant having altered fruit shape as compared to the corresponding wild-type plant, the method comprising: (a) transforming plant cells by introducing a nucleic acid vector encoding SUN; (b) producing plants from the transformed plant cells.

Another specific aspect is a method for altering the fruit shape of a plant, the method comprising: (a) introducing a nucleic acid vector encoding SUN into a plant cell; (b) regenerating the plant cell into a transgenic plant; and (c) evaluating the change in fruit shape by comparing the plant obtained by introducing the nucleic acid molecule with the size of a corresponding wild-type plant.

According to still further features in the described preferred embodiments, the fruits of the cultivated tomato plant are characterized by an average elongated length-to-width aspect ratio. According to still further features in the described preferred embodiments the fruits of the cultivated tomato plant are characterized by an average fruit shape index greater than 1.

According to still further features in the described preferred embodiments the elongated-fruited tomato is *S. Lycopersicum.*

According to still further features in the described preferred embodiments the cultivated tomato is selected from a range of genotypes used in the production of commercial tomato varieties.

According to still further features in the described preferred embodiments there is claimed a tomato fruit derived from the tomato plant. According to still further features in the described preferred embodiments there is claimed a tomato product derived from the tomato fruit.

According to still further features in the described preferred embodiments there is claimed a tomato seed derived from a crossing in which at least one of the parents is the tomato plant.

According to still further features in the described preferred embodiments the tomato seed of claim is a hybrid tomato seed.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Referring now to the FIG. 1A, fine mapping the tomato fruit shape locus sun showed that it was located in a 0.2 cM interval on chromosome 7. Fibre-Fluorescent In Situ Hybridization (Fibre-FISH) experiments using flanking bacterial artificial chromosome (BAC) clones showed that the physical distance in the elongated fruit genotype Sun1642, was approximately 30 kb larger than that of the round-fruited LA1589[9]. However these two BAC clones represented the end points of coverage of the tomato genome as no additional clone from publicly-available genomic large-insert libraries spanned this gap.

To clone the region, bacteriophage lambda genomic libraries were constructed from both the round-fruited LA1589 and the elongate-fruited Sun1642 tomato parents. These libraries were screened initially with probes derived from the ends of the BAC clones used in Fibre-FISH, and subsequently with the ends of recovered phage clones (FIG. 1B).

Comparative sequence analysis of overlapping phage clones showed that the size difference between LA1589 and Sun1642 at the locus was due to the insertion of a 24.3 kb segment present in Sun1642 but absent from LA1589 (FIGS. 1B, 1C).

Genetic analysis indicated the insertion completely co-assorted with the fruit shape phenotype (FIG. 1B). This result strongly implied that the 24.3 kb insertion was the causative mutation that underlied the molecular basis of elongated fruit shape mediated by sun. To determine the origin of the inserted segment, one phage clone end encompassing part of the 24.3 kb segment was used as Restriction Fragment Length Polymorphism (RFLP) probe and hybridized to a set of mapping filters containing genomic DNA from Sun1642×LA1589 $F_2$ progeny. The data showed that LA1589 contained only one copy of this sequence, whereas Sun1642 contained two copies. The copy that was shared between these two tomato accessions mapped to chromosome 10 (see FIG. 5).

Therefore, the data strongly supported the notion that the inserted segment on chromosome 7 originated from chromosome 10. The inventor herein subsequently screened a BAC library constructed from *S. lycopersicum* cultivar Heinz 1706[25] and selected one clone from the ancestral location, HBa072D08 for sequence analysis. The data showed that the entire 24.3 kb segment that inserted into chromosome 7 was present on chromosome 10 (FIG. 1C). Interestingly however, despite the near 100% identity at the nucleotide level, the 24.3 kb duplication was not completely colinear with its ancestral copy and comprised another rearrangement (FIG. 1C). The breakpoint of this rearrangement harbored a 3-bp mismatch, which in addition to the rearrangement were the only nucleotide sequence features that distinguished the chromosome 7 and 10 paralogous segments from one another.

Duplication at Sun was the Result of a Retrotransposition Event

The near-identity of the duplication and its ancestor made it likely that the sequence features that resulted in the formation of this copy number variant would be preserved and recognizable. Close inspection of the chromosome 7 and 10 genomic sequences suggested that a Copia-like autonomous retroelement present at both genomic locations might underlie molecular basis of the duplication. The chromosome 10 retroelement element was flanked by identical 398 bp Long Terminal Repeats (LTR) (FIG. 1C, designated in red (dark boxes) as 1 and 2), and a 5 bp target site duplication (TSD) of the signature "GACCT" which are both features of LTR retroelement transposition. Intriguingly, the chromosome 7 region possessed three identical 398 bp LTRs. Two LTRs (LTR 1 and 2) flanked the core retroelement whereas one LTR was further upstream (LTR3) (FIG. 1C).

LTR1 and LTR3 on chromosome 7 flanked the entire duplicated fragment. At the site of the presumed integration and immediately flanking LTR1 and LTR3, a 5 bp motif "ATATT" resembled the TSD of the transposition event (FIG. 1C). In LA1589, which lacked the segmental duplication, only a single copy of the "ATATT" motif was found, which supported the observation that integration of the entire element occurred at this 5 bp motif. Another feature typical of LTR retroelements is the polypurine tract (PPT) which is located immediately upstream of the second LTR (FIG. 1C). The PPT is important for the initiation of the second strand synthesis of the cDNA as well as the subsequent cleavage of PPT from the cDNA. The PPT of the core retroelement was a 15 bp region that started 3 nucleotides upstream of LTR2. A putative PPT that was 70% identical to the PPT upstream of LTR2 was found immediately upstream of LTR3 (PTT* in FIG. 1C). Therefore, the putative PPT was likely to serve as the actual PPT* during transposition of the core element and associated host DNA. This actual PPT* would permit double stranded cDNA synthesis and subsequent integration of the entire retroelement as one single fragment into chromosome 7. Taken together, the sequence features on chromosomes 7 and 10 strongly suggested that the duplication arose via a transposition event mediated by the LTR retroelement.

This novel Copia-like autonomous element was named "Rider" because it traversed the genome and brought along a segment of the host genome on its journey.

Candidate Genes at Sun

The fruit shape phenotype at sun was entirely linked to the inserted segment (FIG. 1B). It was then considered that the elongated fruit shape may be due to genes present on the transposed fragment, or the disruption of a gene at the preexisting locus. Ab initio gene prediction using FGENESH combined with BLAST searches identified four putative genes shared by the chromosome 7 and 10 regions. Present on the duplication were IQD12, SDL1-like, and two hypothetical genes coded HYP1 and HYP2, in addition to the LTR element Rider. In addition, a fifth gene DEFL1 on chromosome 7 was most likely disrupted after the transposition of Rider into this gene (FIG. 1C). IQD12 was most similar to *Arabidopsis* IQD12, a member of the IQ67 motif-containing plant proteins having calmodulin binding activity[26]. IQD12 was comprised of 6 exons, all of which were present on the transposed fragment. SDL1-like had high sequence similarity to *Nicotiana plumbaginifolia* SDL1 gene[27] and *Arabidopsis* ELD1[28]. SDL1-like encoded an 11 exon-containing gene on the parent chromosome 10, but lacked exon 1 and the upstream promoter on the transposed fragment. It now believed by the inventor herein that the transposed copy of the SDL1-like gene was probably not functional and not likely to underlie sun. HYP1, hypothetical 1, was a single exon gene predicted to encode a polypeptide of 350 amino acids having weak similarity to CUC1, an *Arabidopsis* protein that regulates lateral organ boundary formation[29]. HYP2 was also a single exon gene, and was predicted to encode a 487 amino acid protein. The best hit to HYP2 was a *Solanum tuberosum* protein of unknown function (GenBank accession AY737314).

Rider was a single exon retroelement which encoded a 1307 amino acid protein containing the integrase core domain and reverse transcriptase proteins that are required for cDNA synthesis and integration in the host genome. The fifth gene at the locus was DEFL1, consisting of two exons and encoding a secreted defensin protein. The transposition into the intron of this gene strongly suggested that DEFL1 in Sun1642 was inactivated (FIG. 1C). Plant defensins are reported to have anti-microbial and insecticidal properties and are members of a large gene family with up to 317 members in *Arabidopsis*[30, 31]. A role in plant development has not been described for any member of this large family.

To test the effect of the sun locus on fruit shape in a homogeneous background and to ascertain whether difference in expression of one of the candidate genes could underlie the phenotype, a set of Near Isogenic Lines (NIL) that differed at sun was generated. The developmental analyses of the NIL in the LA1589 background indicated that ovary shape differences were negligible in floral buds 10 days prior to flower opening (FIGS. 2A and 2B).

At anthesis, ovary shapes began to show significant differences albeit slightly. The most significant differences in shape however were found in developing fruit five days post anthesis (FIGS. 2A and 2B). This result indicated that shape change mediated by sun was manifested primarily following pollination and fertilization, consistent with earlier analyses of the parental genotypes[8].

Expression analysis of the five candidate genes during ovary and fruit development revealed much higher transcript levels of IQD12 in the NIL harboring the transposed copy on chromosome 7 in comparison to the NIL lacking the duplication (FIG. 2C). The highest transcript levels of IQD12 were found in young developing fruit five days after anthesis. However, transcript levels of the disrupted gene DEFL1 also significantly differed in the NIL and showed an expression pattern that was essentially the inverse of IQD12: when IQD12 was expressed, DEFL1 was not and vice versa (FIG. 2C).

Reverse transcription-PCR analyses failed to detect DEFL1 transcript in the NIL that carried the duplication. This finding strongly indicated that DEFL1 function was abolished as a result of Rider's transposition into this gene. The transcript levels of the other genes transposed by Rider, SDL1-like, HYP1, and HYP2 were not altered or undetectable and were deemed less-likely candidates of the SUN gene.

The fruit shape phenotype controlled by sun was dosage-dependent, e.g. NIL plants that were heterozygous at the sun locus exhibited a fruit shape phenotype between that of both parents which was indicative of a gain-of-function mutation (FIG. 2D). To investigate whether transcript levels of IQD12 and DEFL1 were also affected by a dosage effect, total RNA was isolated from developing fruits of individual plants homozygous for either the Sun1642 or LA1589 allele, or heterozygous. Northern blot analyses showed that IQD12 was indeed expressed approximately two-fold higher in individuals homozygous for the transposed fragment than it was in heterozygous plants. Similarly, DEFL1 was expressed about two-fold higher in homozygous individuals lacking the transposed fragment than in heterozygotes (FIG. 2D).

It was also observed that there was a similar dosage effect on fruit shape and expression levels of IQD12 and DEFL1 in the NIL in the Sun1642 background (FIG. 7).

Thus, only one gene was expressed in either homozygous situation, indicating that expression of IQD12 and DEFL1 were mutually exclusive and dosage-dependent. Moreover, these results suggested that the transposition event placed IQD12 in a genome environment in which it was now under the cis-regulatory control of factors that normally conferred high levels of DEFL1 expression in developing fruit.

Complementation of the Fruit Shape Phenotype

To determine whether genomic fragments encompassing IQD12 were capable of imparting an elongated phenotype to fruits, the entire insert from two overlapping Sun1642λ genomic clones were subcloned into an *Agrobacterium tumefaciens* binary vector and transformed into LA1589 and the round-fruited NIL in the Sun1642 background. These two clones, pHX2 and pHX4, harbored the full length IQD12 gene, including the promoter that was shared with the ancestral gene and the LTR, but contained different 5' as well as 3' end points (FIG. 3A).

In the LA1589 background, most of the primary plants transformed with the pHX4 construct ($T_1$) expressed IQD12 at very high levels, whereas this gene was very low or not at all expressed in the pHX2 primary transformants (FIG. 3B and FIG. 10—Table 1).

Moreover, pHX4 transformed $T_1$ plants exhibited a significantly greater fruit shape index, whereas those transformed with the pHX2 construct did not. Regression analysis confirmed that there was a highly significant correlation between IQD12 transcript levels and fruit shape index which was in turn correlated to transformation with the pHX4 construct (FIG. 3C). The transformation of the same constructs into the round-fruited NIL in the Sun1642 background produced similar results: lines transformed with pHX4 displayed a larger fruit shape index in comparison to control lines whereas none of the lines carrying pHX2 displayed significantly elongated fruit (FIG. 11—Table 2).

Increased expression of IQD12 and increased fruit shape index were inherited to the $T_2$ generation, and cosegregated with the presence of the pHX4 construct (FIG. 3D and FIG.

8A). The transcript levels of IQD12 and fruit shape index of the $T_2$ plants homozygous was compared to the pHX4 transgene to that of the NIL. These results indicated that for most transgenic plant families, the fruit shape index and the IQD12 transcript levels were nearly restored to the levels displayed by the NIL carrying the transposed segment (FIG. 3D, FIG. 10, FIG. 13).

Thus, the data obtained from the plants transformed with pHX4 indicated that the control of fruit shape in tomato was regulated at the level of transcription of IQD12. In addition, an important cis-element located in the 3.2 kb region upstream of DEFL1 was sufficient to drive high levels of IQD12 expression in the developing fruit as this region was present in the pHX4 transformants expressing IQD12 and absent from the pHX2 transformants that did not express this gene to appreciable levels (FIGS. 3A-3C).

Also, the results from the pHX2 and pHX4 transformations demonstrated that the SDL1-like and HYP1 genes were unlikely candidates in affecting fruit shape because these genes were present on the pHX2 construct that had no affect on fruit shape (FIGS. 3B, 3C).

Although transcript levels and fruit shape index were significantly increased in the transgenic lines carrying pHX4, they were not entirely restored to the levels of that in the NIL carrying the transposed segment. Thus, it was possible that additional cis-elements in the DEFL1 5' upstream region beyond the 5' end point of this construct were necessary to fully recover the fruit shape phenotype or that other genes were required (FIG. 3D and FIG. 8).

To determine whether IQD12 alone was sufficient to confer an elongated shape to tomato fruit, this gene was overexpressed in the round-fruited LA1589, and used an RNA interference (RNAi) strategy to knock-down expression in LA1589 carrying the transposed segment and exhibiting elongated fruit. Six of 13 LA1589 lines transformed with IQD12 under control of the constitutive CaMV 35S RNA promoter bore extremely elongated fruit and expressed IQD12 to high levels (FIG. 3E; FIG. 12—Table 3, FIG. 9A).

Since fruit and seed set were significantly reduced in the transgenic lines that overexpressed IQD12, these lines were maintained by using the transgenic pollen to pollinate wild type LA1589 pistils. The resulting $T_2$ plants showed that the extremely elongated fruit shape and associated high levels of expression of IQD12 were inherited in the next generation in the presence of the transgene (FIG. 3B, FIG. 13—Table 3).

Complimentary experiments using an RNAi strategy in which an IQD12 inverted repeat construct was transformed into NILs that carry the transposed segment resulted in reduced fruit shape index and decreased IQD12 expression in seven of the 14 primary $T_1$ transformants (FIG. 3F, FIG. 13—Table 4, FIG. 9C).

For three of these transformants, the fruit shape phenotype was essentially indistinguishable from the round-fruited non-transformed NIL (FIG. 12—Table 3).

Progeny testing of the seven primary transgenic plants that bore rounder fruit and comparison to the non-transformed NIL confirmed that reduction in IQD12 transcript levels resulted in rounder fruit which was dependent on the presence of the transgene (FIG. 12—Table 3, FIGS. 9D, 9E).

The results show that greatly enhanced transcript levels of IQD12 can control fruit shape phenotype controlled by the sun locus. As IQD12 conferred an elongated phenotype to tomato fruit controlled by the sun locus (renamed IQD12 gene as SUN).

SUN is a Member of the IQD Family of Proteins Found in Plants

The most prominent feature of the IQD family is a domain of 67 amino acids, the IQ67 domain, which is shared by all members and to date has only been found in plants[26]. The IQ67 domain of the founding member of this family, AtIQD1 is shown to bind calmodulin and localized in the nucleus[32]. Overexpression of AtIQD1 leads to increased glucosinolate levels in *Arabidopsis*[32]. Based on the shared domain structure and phylogenetic analysis, SUN was most closely related to AtIQD12 (FIG. 4) which was part of a subgroup of IQ67 domain-containing proteins that clustered in the subfamily II clade[26]. However, using the criterion of conservation of intron position, SUN was most closely related to AtIQD11 which is a member of the same subfamily II (FIG. 4A). Like SUN, AtIQD11 harbored six exons, including the first exon which did not code for part of the protein. However as noted by Abel et al[26], the *Arabidopsis IQD*12 displays an unusual genome structure because this gene is the only IQ67 domain member that lacks a highly conserved intron positioned within the IQ67 domain. Thus, it is possible that intron removal from the *Arabidopsis* IQD12 gene occurred subsequent to the divergence of this family and that SUN and AtIQD12 could share a common ancestor. Because of its closest similarity at the amino acid level, SUN was considered the likely tomato ortholog of the *Arabidopsis* IQD12. Plant EST and genomic database searches identified other IQ67 domain-containing proteins that were closely related SUN. None of these however, correspond to members of the monocotyledon lineage of plants including rice. The phylogenetic tree constructed using the IQ67 domain of these proteins indicated two clusters; one containing the *Arabidopsis* IQD11 and the other IQD12 (FIG. 4B). One tomato member in the IQD11 Glade and two tomato members in the IQD12 clade were identified. In addition, a close homolog of SUN was found in potato (BQ116231).

Presence of Sun in Other Tomato Varieties

Next, it was determined whether the sun locus played a role in the fruit shape phenotype that is observed in older accessions (heirloom) as well as other more recent tomato introductions. Although the origin of open pollinated heirloom varieties was often unclear, a few were likely to originate from Europe. The heirloom Spitze was likely brought over from Romania, whereas Howard German was likely from the "old country" and was presumably of German origin. Roma VF was introduced in 1963 as the *Verticillium* and *Fusarium*-resistant version of the heirloom Roma that originated from Italy. Banana Legs, Long John, Jersey Devil and Yellow Stuffer were more recent introductions although they were often listed with the heirloom and open pollinated varieties. Sun1642, M82, TA496 and Heinz1706 represented experimental processing tomato varieties. These genotypes were used for the construction of the tomato introgression lines (M82)[33], the large EST collection (TA496)[34], or were the resource for the tomato genome sequencing project (Heinz1706; SGN)[25].

To determine whether these accessions carried sun, all the varieties were crossed to *S. pimpinellifolium* LA1589. Via marker-assisted selection, plants that were homozygous *S. lycopersicum*, heterozygous and homozygous LA1589 at sun were identified from each of the resulting $F_2$ populations. The shape of mature fruit was analyzed in these plants, and the correlation of shape and marker score were assessed (FIG. 5A).

The results showed that varieties in which fruit shape segregated at sun (denoted "+") exhibited larger fruit shape indices compared to varieties that didn't segregate for fruit shape at sun (denoted "–") (FIG. 5A). Moreover, Southern blot hybridization using a probe derived from the duplication showed that varieties segregating for fruit shape at sun (FIG. 5A) carried the transposed copy of SUN (FIG. 5B).

Expression analysis confirmed that the genotypes harboring the duplication expressed SUN at high levels whereas those genotypes lacking the duplicated gene did not express SUN (FIG. 5C).

Genotyping these varieties for ovate which was another locus that controlled elongated fruit shape showed that Long John, Roma VF, and Heinz1706 carried the allele that conferred an elongated pear shape to fruit. Fruit shape in the less elongated and round varieties, M82 and Yellow Stuffer, respectively, did neither carry the elongated allele of sun nor ovate. Thus, based on the fruit shape index of the mature fruit, the varieties exhibiting the more elongated fruit carried sun, whereas the varieties displaying a less elongated shaped fruit carried ovate. Accessions that bore round or slightly oval shaped fruit, M82 and Yellow Stuffer, carried neither locus whereas Long John that carried the most extremely elongated tomato fruit had both the elongate shaped sun and ovate alleles (FIG. 5A). These results indicated that the transposed segment that gave rise to the sun locus was present in a subset of varieties carrying elongated fruit, some of which were heirloom and others that were modern types. Therefore, once the sun locus arose, it did spread through the germplasm and was maintained until present time.

Discussion

Provided herein is evidence of an unusual mutation event that resulted in an elongated fruit phenotype found in heirloom and modern varieties of tomato. The mutation was the result of a duplication of SUN into another genomic context. The new location of SUN on tomato chromosome 7 permitted high expression of this gene in developing ovaries and fruits which resulted in an elongated fruit shape. In plants, a translocation resulting in a copy number variant that resulted in phenotypic change have not been described to date.

SUN on chromosome 7 is positioned downstream of the promoter of DEFL1. Transformation with genomic constructs that harbor different promoter lengths indeed implied that the DEFL1 promoter acted as an enhancer for transcription of SUN.

Although LTR are known to carry promoter and enhancer activities, it is unlikely that Rider's LTR acted as an enhancer of SUN transcription since this LTR was present on both genomic constructs that were transformed into plants, and only one of them resulted in complementation of the fruit shape phenotype.

The gain-of-function mutation resulted from a transposition event mediated by the autonomous LTR-retroelement Rider. The transposition of the core retroelement was associated with 3' transduction of nearby genes as well as a second rearrangement that moved SUN from a few kb upstream of Rider to 20 kb downstream of this autonomous element. To explain how the transposition, associated gene transduction and second rearrangement occurred, a model is described in FIG. 6A.

Transcription of Rider on chromosome 10 began, as in all LTR retroelements, in LTR1. Typically, transcription would stop in LTR2; instead transcription read through occurred past the second LTR and continued far beyond into the flanking genomic region (FIG. 6B). In the first intron of the SDL1-like gene, the RNA polymerase switched to a region 3' of IQD12. Presumably, such a template switch would have required that these two regions were in proximity of one another. The 5-bp direct repeat "GCAGA" on each side of the breakpoint suggested that this was where the template switch occurred. Thereafter, elongation of the transcript continued until termination in LTR1 (FIG. 6B), resulting in a large mRNA molecule flanked by part of two LTRs, the R segment and U5 region at the 5' end of the mRNA and the R segment and U3 region at the 3' end of the mRNA[37] (FIG. 6C). Reverse transcription of the large mRNA, followed by second strand synthesis initiated at PPT*, resulted in a 24.3 kb element harboring three identical LTR; LTR1 and LTR3 flanking the entire element and LTR2 as an internal or solo LTR (FIG. 6D). This giant element then inserted into chromosome 7 (FIG. 6D) resulting in the genome structure that is found at the sun locus (FIG. 6E).

Several lines of evidences are in agreement with the proposed transposition mechanism. First, the 24.3 kb duplicated fragment is encompassed by two LTRs of Rider, indicating that Rider was directly involved in the duplication (FIG. 6C). Second, two signature TSD sequences "ATATT" are flanking the two outer LTRs (LTR1 and LTR3), strongly suggesting the entire fragment moved by a single transposition event (FIGS. 6C-6E). This explanation of the transposition is also supported by the observation that the original TSD of the retroelement on chromosome 10, "GACCT", was copied and now borders LTR2 and LTR3 on chromosome 7 (FIG. 6E). Also, this model explains the retention of the introns of IQD12 and SDL1-like genes since they are in the antisense orientation with regard to Rider. Therefore, the introns were not recognized and removed by the splicing machinery after RNA synthesis. Rider's 3' gene transduction and subsequent transposition event is very unusual since parts of the two flanking LTRs are absolutely required for reverse transcription and double stranded DNA synthesis of LTR retrotransposons[37]. Therefore, this element could not have been competitive for transposition, unless parts of the LTRs flanked the RNA molecule. Thus, transcription of a LTR retroelement past LTR2 will only result in an effective transposon if the transduction terminates in another LTR, as occurred with Rider via the template switch. The transcription read through and 3' transduction, followed by successful transposition is more commonly observed in non-LTR retroelements for which transcription does not need to end at a particular site.

Examples of 3' transduction and transposition to a second site are found certain L1-mediated retrotransposition events[38-40]. In fact, in humans 1% of the genomic sequence is estimated to have been transduced by such a mechanism that was mediated by the non-LTR L1 element[21]. An interesting example of a 3' transduction event which is perhaps most analogous to the transposition of Rider is mediated by the non-LTR SVA retrotransposon[41]. Duplications of human AMAC1, encoding acyl-malonyl condensing enzyme 1, were mediated by this element via a 3' sequence transduction mechanism and the entire gene including the promoter, which was located downstream of the SVA element, was duplicated and inserted into three different chromosomal regions along with the SVA retroelement[41]. Moreover, two of the three AMAC1 gene duplicates are differentially expressed in different tissues relative to the original gene, and thus new functionality may have been created for each of the AMAC1 duplicates following its retrotransposition[41]. However, the gene transduction and transposition event mediated by Rider is extremely rare for LTR retroelements given that those elements require flanking LTR for proper transposition.

As disclosed herein, the cloned SUN is one of the major genes controlling elongated shape in tomato. SUN encodes a IQ67 domain-containing protein which are found in diverse plant species from gymnosperm to angiosperm plants and even in moss[26, 32]. Moreover, SUN controls fruit shape in other accessions and therefore presents an important mutation in the tomato germplasm. The founding member of this family of proteins is the *Arabidopsis* IQD1 protein. IQD1 plays a role in glucosinolate production, binds calmodulin, and is nuclear localized[32]. The function of the other *Arabidopsis* members remains unknown. Glucosinolates are not produced by Solanaceous species and therefore, SUN is unlikely to affect the production of those metabolites in tomato. However, AtIQD1 is also thought to play a role in the transcriptional regulation of several cytochrome P450 genes including CYP79B3 and CYP79B2[32, 42]. CYP79B3 together with CYP79B2 catalyzes the conversion of tryptophan into indole-3-acetaldoxime (IAOx) in tryptophan-dependent auxin biosynthesis in *Arabidopsis*[43-45]. Although it is not clear whether AtIQD1 plays a role in the homeostatic control of auxin biosynthesis, the over and under expressing of AtIQD1 disturb plant growth slightly[32]. Regulating the production of and sensitivities to secondary metabolites as well as plant hormones is a common strategy that plants use to coordinate plant growth and responses to environmental and developmental pressures. Since the IQD protein family widely exists in the plant lineage, these proteins may play important roles in the life cycle and may affect diversity in plant form in other species. Their diverse amino acid sequences and protein structures may imply extensive selection pressures that persisted during their evolution[26]. Therefore, the IQD genes may have evolved into new functions to respond to selection pressures specific to each plant species.

In tomato, overexpression of SUN resulted in extremely elongated and often seedless fruit. These features are reminiscent of parthenocarpic and elongated and pointed fruit that are resulting from the expression of controlling auxin production in ovules.

The extremely elongated fruit shape and the lack of proper seed development when SUN is overexpressed, in addition to its potential biochemical function suggest that this protein may affect auxin levels or distribution in the fruit (FIG. 3E). Consequently, it is possible the involvement of SUN in shape variation is through the regulation of auxin homeostasis, thereby affecting the patterning of the fruit.

Examples

Methods

Plant Materials

The high-resolution screen to identify recombinants delineating the fruit shape locus was described previously[9]. Near Isogenic Lines (NILs) differing at sun were constructed in both Sun1642 and LA1589 backgrounds by sequential backcrosses to the recurrent parent using marker-assisted selection.

Primary transformants ($T_1$) carrying various constructs were generated through *Agrobacterium*-mediated transformation at Ralph M. Parsons Foundation Plant Transformation Facility, College of Agricultural and Environmental Sciences, University of California (Davis, USA).

Selection of $T_2$ transgenics was done by Southern blot analysis and homozygosity was confirmed by genotyping the progenies using $Kan^R$ specific primers EP551 and EP552 (pHX4 transgenic lines 06S496-501 and P35S:IQD12 transgenic lines 07S15-18) or using primers EP687 and EP688, which amplify the chalcone synthase intron in the RNAi vector, pFGC5941.

Primer sequences are listed in FIG. 13—Table 4 showing SEQ ID NOS:14-41. Plants used in this example were grown in the greenhouse at 25-32° C., 40-60% humidity, and supplemented with 200 μM $m^{-1}s^{-1}$ of light from high pressure sodium lamps. The RNA collected from the plants shown in FIG. 5 were field-grown during the summer of 2005 in Wooster, Ohio, USA.

Microscopy

Ovaries were harvested at 10 days pre anthesis, fixed and embedded in LR white resin, sectioned (5 μm) and stained with toluidine blue. Developing ovaries were visualized on a Leica DM IRB light microscope (Leica Microsystems Heidelberg GmbH, Germany) coupled to a digital camera (Optronics 60806, Olympus America Inc. USA).

Fresh anthesis stage ovaries and 5 dpa fruits were sectioned longitudinally and photographed using a Leica MZFLIII dissecting microscope equipped with an attached digital microscope camera (SPOT RT KE, Diagnostic Instruments, Inc. USA).

Construction and Screening of Phage Libraries.

Bacteriophage λ genomic libraries were constructed in the vector λ Fix® II using the components of the λ FixII Gigapack III XL kits from Stratagene (La Jolla, Calif.). Partially Sau3AI-digested genomic DNA of Sun1642 and LA1589 was ligated into XhoI-digested lambda FIX II vector. Complete details of library construction are available on the Stockinger Lab Web site (http://www.oardc.ohio-state.edu/stockingerlab/). The first probe used to screen the phage libraries and to initiate the chromosome walk was generated from BAC end Lp81B9-F using a genome walking approach and components of the GenomeWalker kit (Clontech, California, USA). For information on these BACs and end sequences, see Van der Knaap et al.,[9]. The fragment amplified with primers EP8 and EP9 mapped approximately 2 kb away from BAC end Lp81B9-F (FIG. 13—Table 4 for primer sequences).

Sun1642 phage clone EK36 was recovered after screening both parental libraries. At the other end of the gap, BAC end Lp61O2-F[9] was present in multiple copies in the genome and could therefore not be used in genomic library screens. Instead, Le33O1-R[9], which was uniquely represented in the genome, was used for the phage library screens resulting in several clones that were identified from both libraries. These screens were followed by sequential screening with $^{32}P$-labeled probes from unique end sequences of overlapping phage clones until the region was covered.

Sequencing of Large Insert Clones and Construction of the Sun Locus Contig.

Minimal overlapping λ clones were identified and the entire inserts were subcloned into the NotI site of pGEM11fz (+) vector. Shotgun libraries were generated from the plasmid inserts and sequenced using M13 forward and M13 reverse primers; complete details of all procedures are available on the Stockinger Lab Web site (http://www.oardc.ohio-state.edu/stockingerlab/). BAC clone HBa072D08 corresponding to the ancestral locus was identified from Heinz1706 library[25] using the phage clone end of EK36 that maps on the duplication (primers EP45 and EP46, FIG. 13—Table 4).

Sequencing was conducted at the Genome Sequencing Center, Washington University in St. Louis, Mo., USA, with the exception of clone, EK58, which was sequenced at the Purdue Genomics Core Facility, Purdue University. BAC HBa072D08 clone was shotgun subcloned, sequenced, and finished to completion at the Genome Sequencing Center, Washington University in St. Louis. The finishing of all phage clone insert sequences was done by primer walking using the large clones or the subclones as sequencing template at the Molecular and Cellular Imaging Center at Ohio State University, Wooster, Ohio on the ABI Prism 3100 Applied Biosystem, Foster City, USA. Sequences were assembled into one contig per clone using Sequencher 4.1.4 (Gene Code Corporation, USA) and manually corrected and edited. Questionable base calls in the assembled sequences were checked by PCR amplification using a genomic DNA template and sequencing of the PCR product.

Sequences of overlapping clones were assembled into a single contig representative for the two sun alleles present in Sun1642 and LA1589. The one exception was an approximate 3 kb gap in the Sun1642 contig (from nucleotides 27,755 to 30,601 in the deposited EF094940 GenBank sequence). This region was not recovered from the phage libraries because of 100% identity to the ancestral chromosome 10 locus. In this instance the sequence of the gap was inferred from the chromosome 10 HBa072D08 BAC sequence harboring the ancestral version. To confirm that these nucleotide sequences were present in the transposed chromosome 7 duplication, Southern blot hybridizations were performed using a PCR amplified fragment (primers EP293 and EP294) across this region as probe (FIG. 13—Table 4). This segment maps in the gap and showed two bands of the expected sizes on a Southern blot that carried Sun1642 DNA and digested with ScaI and XbaI (data not shown). Overlapping phage clones used in Fiber FISH experiments also showed that the distances between the clones were as predicted based on the complete sequence of the chromosome 10 locus (data not shown).

Sequence Annotation

Following assembly, the sequences were analyzed using the ab initio gene prediction program FGENESH. Final annotation of the genomic sequences using NCBI and TIGR databases was done at TIGR in the group of Dr. Robin Buell. Repetitive elements in the sequenced regions were identified by their repetitive features and by the presence of transposase coding sequences. Specifically, sequences were used as queries in Blast searches against tomato genomic sequences using a 1 kb window. The tomato genomic sequences were downloaded from SOL Genomics Network (27 Mb total size). Genomic fragments with five or more hits in the search were manually examined for features associated with transposable elements, including terminal sequence, terminal inverted repeats, direct repeats and target site duplications. All genomic sequences were searched against NCBI non-redundant protein database (Feb. 15, 2007) for proteins related to autonomous transposons. Rider was the only autonomous element detected in this region.

Constructs for Plant Transformation

Transformation constructs pHX2 and pHX4 were made by subcloning the entire phage subclone insert of plasmids pEK59 and pEK60, respectively (released by NotI and blunted-ended using Klenow) into the Klenow-blunted ended BamHI-digested binary vector pCIB10G[46]. End points of the clones are indicated in FIG. 3A.

The RNAi:IQD12 construct, pHX8, was generated by cloning 512 bp fragments of the IQD12 cDNA (from nucleotide 16,154 to 16,646 of the genomic sequence EF094940) that was amplified using primer EP527 and EP528 from reverse transcribed mRNA, in the sense and antisense directions into pFGC5941[47].

To over expresses IQD12, a 1.4 kb fragment of IQD12 cDNA (corresponding to nucleotide 13,460-16,280 of the genomic sequence EF094940) was amplified from reverse transcribed mRNA using primer EP519 and EP520 and subcloned between the CaMV 35S RNA promoter and NOS terminator of pCIB710[46] generating pEK67. Promoter, insert and terminator were released from the vector by KpnI and XbaI digestion and were subcloned into the corresponding sites of binary vector pCIB10G creating pEK69. Plasmid constructs were introduced into *Agrobacterium tumefaciens* strain LBA4404 using electroporation. Plasmid pHX8 was transformed into the NIL carrying the Sun1642 allele in the LA1589 background. Plasmid constructs pHX2, pHX4, and pEK69 were used to transform round-fruited NIL plants in both the LA1589 and Sun1642 backgrounds.

Northern and Southern Blot Analysis

Tissues for RNA extraction were harvested and immediately frozen in liquid nitrogen. Flower buds at 10 days pre-anthesis were identified as follows. Using a dissection microscope, the floral bud for which the sepals had just enclosed the remaining floral meristem was located on the inflorescence. Counting 4 to 5 buds upwards (older buds) on the same inflorescence marked the style and ovule initiation stage which occurred approximately 10 days prior to flower opening. To collect fruit five days post anthesis, recently opened flowers (within 24 hours) were hand pollinated to ensure sufficient seed and fruit set and the developing fruit was harvested 5 days later. Total RNA was isolated using Trizol® reagent (Invitrogen Inc. USA) following the recommendations of the manufacturer. Ten μg of total RNA from each sample was size-fractionated on a 1.2% agarose-formaldehyde gel prior to transfer to Hybond N membrane filters. A detailed protocol of the Northern and Southern blot hybridization are found at http://www.oardc.ohio-state.edu/stockingerlab/. Gene-specific probes were generated using a 3 cycle PCR step in the presence of [$\alpha$-$^{32}$P]dCTP as described previously[9].

After hybridization, filters were washed at high stringency 0.1×SSC, 0.1% SDS at 65° C. for 20 minutes. The blots were exposed to phosphorimager screens and visualized using the Storm 840 scanner (GE Life Sciences, USA). For quantification of gene expression, signals were quantified by ImageQuant 5.0 (Molecular Dynamic System Inc. USA) and normalized to the expression of the tomato eIF4α6 gene. Probe sizes and primers used for amplification of probe templates are listed in FIG. 13—Table 4.

Amino Acid Alignment and Phylogeny of SUN

Genes that are closely related to tomato IQD12/SUN were identified by BLAST searches using TBLASTN function against the public databases including the Solanaceae Genomics Network (SGN), Joint Genome Institute; and NCBI. The *Arabidopsis thaliana* IQ67-motif containing genes were directly retrieved from NCBI[26]. ClustalX (v1.83) was used for sequence alignments. The unrooted phylogenetic tree was also generated using ClustalX; bootstrap values represent 1000 trials. MEME v3.5.4 was used to predict motifs in IQD12/SUN and the 33 IQ67 *Arabidopsis thaliana* homologs[26]. Only motifs with p-value smaller than 1.0e-5 are shown.

Expression of SUN in Different Tissues:

FIG. 14A shows the Gene structure at the sun locus. The 24.7 kb duplication, including SUN, disrupted the expression of DEFL1. FIG. 14B shows the expression of SUN and DEFL1 in floral tissues. Northern blot containing RNA isolated from floral organs at the time of anthesis. The blot was sequentially probed with SUN, DEFL1 and lastly with eIF4α-6 as loading control. Se, sepal; Pe, petal; St, stamen; Ov, ovary. Tissues were isolated from the LA1589 and Sun1642 NILs that differ at the sun locus. ee, containing an extra copy of SUN; pp, lacking the extra copy of SUN.

FIG. 14C shows the expression of SUN and DEFL1 in different tissues. Tissues were isolated from the LA1589 and Sun1642 NILs that differ at the sun locus. ee, containing an extra copy of SUN; pp, lacking the extra copy of SUN. R, root; H, hypocotyl; C, cotelydon; L, leaf; S, shoot apex. In lines carrying the duplication, SUN is highly expressed in sepals, ovaries, hypocotyl and shoot apex. The ancestral SUN gene is expressed in roots and at low levels in other tissues. DEFL1 is expressed in the same tissues as the duplicated copy of SUN in plants that lack the 24.7 kb duplication (pp, lacking an extra copy of SUN). This indicates that the promoter of DEFL1 is driving expression of the duplicated copy of SUN.

Fruit Shape Index and SUN Expression Changes During Tomato Flower and Fruit Development:

FIG. 15A shows the fruit shape index (length/width ratio) as a function of the number of days post anthesis. Fruit shape changes overlay the fruit/seed developmental landmarks indicated above the graph. The black triangles represent the fruit shape indices of the near isogenic lines (NILs) carrying two copies of the SUN gene whereas the grey circles represent the NILs with only one copy of SUN. The largest difference in fruit shape index is achieved at fruit landmark 3 and 4, coinciding with the landmarks 4-16 cell and globular stage of the embryo. Fruit shape index were collected from three inflorescences per plants of five for each genotype. Data shown are mean±standard error.

FIG. 15B shows the SUN expression in the developing fruits of LA1589 NILs. Northern blots were performed on LA1589ee (carrying two copies of the SUN gene) and LA1589pp (carrying one copy of SUN). Total RNA was extracted from pooled tissues of five plants per genotype and hybridizations were conducted with SUN as probe. SUN expression is very high starting at anthesis until 20 days post anthesis. Its expression has dropped dramatically 25 days post anthesis which is prior to the fruit ripening and seed germination stage.

FIG. 15C shows the SUN expression in floral buds of LA1589 NILs. Northern blots were performed on total RNA isolated from entire flowers or buds at the times indicated above the lanes (in days). The "0" timepoint denotes anthesis, the other values indicate days prior (−) or post (+) anthesis. SUN's expression is low 2 days pre-anthesis but increases dramatically until 2 days post pollination in the lines carrying two copies of SUN (LA1589ee). The increase in SUN expression precedes the change in fruit shape index shown in FIG. 15A. In the lines carrying only one copy of SUN (LA1589pp), SUN expression is low, however DEFL1 expression in LA1589pp follows a similar kinetic as SUN expression in the LA1589ee indicating that the DEFL1 promoter drives SUN expression (see also FIG. 14).

The Effect of SUN on Leaflet Shape:

FIG. 16A shows the leaflets of cultivated tomato. FIG. 16B shows leaflets of the wild relative *S. pimpinellifolium* accession LA1589. The leaves shown are from plants without the extra copy of SUN (pp), with the extra copy of SUN (ee) or SUN expressed under the constitutive 35S promoter (ox). The most notable feature is the pointed shape of the leaf and increased serrated margins when SUN is expressed (compare pp and ee). These features are accentuated when SUN is overexpressed (compare ee and ox). These results indicate that in addition to fruit shape, leaf shape is dramatically altered as well.

Effect of Overexpression of SUN on Ovary, Fruit and Compound Leaf Shape in Tomato:

FIGS. 17A-17C show the *S. pimpinellifolium* LA1589 background. Ovary shape of anthesis-stage flowers (FIG. 17A), fruit shape (FIG. 17B) and compound leaf shape (FIG. 17C) of wild type (LA1589pp) and 5 independent transformants. Note the very elongated slender shape of the ovary, fruit and the twisted shape of the leaves.

FIGS. 17D-17F show the *S. lycopersicum* Sun1642 background. Ovary shape of anthesis-stage flowers (FIG. 17D), fruit shape (FIG. 17E) and compound leaf shape (FIG. 17F) of wild type (Sun1642pp) and several independent transformants. When SUN is overexpressed under control of the 35S promoter, the fruit shape is already determined at the time of anthesis. Moreover, leaflets and compound leaf shape is also greatly affected when SUN is overexpressed. The leaves are twisted and the leaflets are more pointed in shape.

Cell Size and Number Differences in the Longitudinal Direction of LA1589 NIL Fruit Differing at Sun:

FIG. 18A shows the length of different parts of the fruit at 5 days post anthesis. All fruit parts are more elongated in the presence of SUN. FIG. 18B shows that cell size is only significantly different in the distal end of the fruit. FIG. 18C shows that the ratio of fruit length and cell size shows that the septum and proximal end of the fruit have significantly more cells. Thus the effect of SUN is on increased cell division predominantly in the septum of the fruit thereby increasing fruit length.

Cell Size and Number Differences in the Latitudinal Direction of LA1589 NILs that Differ at Sun:

FIG. 19A shows the width of the fruit at 5 days post pollination. Total fruit and septum width are significantly smaller in the NILs carrying the SUN duplication. FIG. 19B shows that the eell number in the septum is significantly lower in the NILs carrying the SUN duplication. FIG. 19A-FIG. 19C shows that the cell size is not significantly different in the septum or pericarp. The results shown in FIGS. 18A-18C and FIGS. 19A-19C demonstrate that SUN controls directional cell division predominantly in the septum and proximal end of the fruit. High expression of SUN leads to increased cell division in the longitudinal direction and reduced cell division in the latitudinal direction. This suggests that SUN can affect the shape of any organ in any plant species depending on where and when the gene is expressed.

FIG. 20 shows the stem structure of *S. lycopersicum* cv Sun1642pp (without the SUN duplication and carrying round fruit) and Sun1642pp overexpressing SUN.

A cross section of the tomato stem at the sixth leaf of round-fruited tomato (pp, control) and overexpressors (35S::sun). The sections were hand cut and stained with Toluidine Blue. The xylem tissues of the vascular bundles stain blue. Note the round stem shape exhibited by the overexpressing lines compared to the triangular stem shape in the control plants. Also note the expansion of the xylem in the overexpressing lines at the expense of the pith cells (in the center of the stem). Thus, in the cultivated background, overexpression of SUN leads to altered stem structure and changes in cell identity where pith cells become xylem cells.

FIG. 21—Table 5 shows the near isogenic lines that differ at sun in both the Sun1642 and the LA1589 background show changes in fruit shape index, leaflet shape index (see also FIG. 16), sepal and ovary shape index and to a lesser extent petal shape index, and seed weight. Fruit weight, number of seed per fruit, hypocotyl and internode length is not altered. The fact that SUN does not affect fruit weight but only the shape strongly indicates that the gene acts to redirect growth without increasing growth. Again, this finding shows that SUN may be able to alter direction of growth of any plant organ.

FIG. 22—Table 6 shows that leaf shape, fruit shape, seed number per fruit, seed and fruit weight are similar in the line expressing SUN under its own promoter compared to the NIL carrying the SUN gene duplication. This shows that only SUN but neither DEFL1 nor one of the HYP genes (hypothetical, see FIG. 14) affect shape of plant organs and seed weight.

Expression of SUN in Additional Varieties of Tomatoes and Other Plants

The inventor has also established which of over 300 tomato varieties carry the SUN gene and has studied its expression pattern throughout fruit development.

SUN Expression in *Arabidopsis*

The inventor has also expressed the tomato gene in *Arabidopsis.*

SUN Expression in Other Plants

SUN can be expressed in other plants in addition to *Arabidopsis* using a constitutive promoter that works in all plants.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Brewer, M. T., Moyseenko, J. B., Monforte, A. J. & van der Knaap, E. Morphological variation in tomato: a comprehensive study of quantitative trait loci controlling fruit shape and development. J Exp Bot 58, 1339-1349 (2007).
2. Grandillo, S., Ku, H.-M. & Tanksley, S. D. Characterization of fs8 1, a major QTL influencing fruit shape in tomato. Mol Breeding 2, 251-260 (1996).
3. Ku, H. M., Doganlar, S., Chen, K. Y. & Tanksley, S. D. The genetic basis of pear-shaped tomato fruit. Theor Appl Genet 99, 844-850 (1999).
4. Van der Knaap, E., Lippman, Z. B. & Tanksley, S. D. Extremely elongated tomato fruit controlled by four quantitative trait loci with epistatic interactions. Theor Appl Genet 104, 241-247 (2002).
5. Van der Knaap, E. & Tanksley, S. D. The making of a bell pepper-shaped tomato fruit: identification of loci controlling fruit morphology in Yellow Stuffer tomato. Theor Appl Genet 107, 139-147 (2003).
6. Liu, J., Van Eck, J., Cong, B. & Tanksley, S. D. A new class of regulatory genes underlying the cause of pear-shaped tomato fruit. Proc Natl Acad Sci USA 99, 13302-13306 (2002).
7. Ku, H. M., Grandillo, S. & Tanksley, S. D. fs8.1, a major QTL, sets the pattern of tomato carpel shape well before anthesis. Theor Appl Genet 101, 873-878 (2000).
8. Van der Knaap, E. & Tanksley, S. D. Identification and characterization of a novel locus controlling early fruit development in tomato. Theor Appl Genet 103, 353-358 (2001).
9. Van der Knaap, E., Sanyal, A., Jackson, S. A. & Tanksley, S. D. High-resolution fine mapping and fluorescence in situ hybridization analysis of sun, a locus controlling tomato fruit shape, reveals a region of the tomato genome prone to DNA rearrangements. Genetics 168, 2127-2140 (2004).
10. Feuk, L., Marshall, C. R., Wintle, R. F. & Scherer, S. W. Structural variants: changing the landscape of chromosomes and design of disease studies. Hum Mol Genet 15 Spec No 1, R57-66 (2006).
11. Sharp, A. J., Cheng, Z. & Eichler, E. E. Structural variation of the human genome. Annu Rev Genomics Hum Genet 7, 407-442 (2006).
12. Redon, R. et al. Global variation in copy number in the human genome. Nature 444, 444-454 (2006).
13. Bennetzen, J. L. Transposable elements, gene creation and genome rearrangement in flowering plants. Curr Opin Genet Dev 15, 621-627 (2005).
14. Morgante, M., De Paoli, E. & Radovic, S. Transposable elements and the plant pan-genomes. Curr Opin Plant Biol 10, 149-155 (2007).
15. Brunner, S., Pea, G. & Rafalski, A. Origins, genetic organization and transcription of a family of non-autonomous helitron elements in maize. Plant J 43, 799-810 (2005).
16. Hoen, D. R. et al. Transposon-mediated expansion and diversification of a family of ULP-like genes. Mol Biol Evol 23, 1254-1268 (2006).
17. Holligan, D., Zhang, X., Jiang, N., Pritham, E. J. & Wessler, S. R. The transposable element landscape of the model legume *Lotus japonicus*. Genetics 174, 2215-2228 (2006).
18. Jiang, N., Bao, Z., Zhang, X., Eddy, S. R. & Wessler, S. R. Pack-MULE transposable elements mediate gene evolution in plants. Nature 431, 569-573 (2004).
19. Morgante, M. et al. Gene duplication and exon shuffling by helitron-like transposons generate intraspecies diversity in maize. Nat Genet 37, 997-1002 (2005).
20. Xu, J. H. & Messing, J. Maize haplotype with a helitron-amplified cytidine deaminase gene copy. BMC Genet 7, 52 (2006).
21. Pickeral, O. K., Makalowski, W., Boguski, M. S. & Boeke, J. D. Frequent human genomic DNA transduction driven by LINE-1 retrotransposition. Genome Res 10, 411-415 (2000).
22. Wang, W. et al. High rate of chimeric gene origination by retroposition in plant genomes. Plant Cell 18, 1791-1802 (2006).
23. Kong, H. et al. Patterns of gene duplication in the plant SKP1 gene family in angiosperms: evidence for multiple mechanisms of rapid gene birth. Plant J 50, 873-885 (2007).
24. Feschotte, C. & Wessler, S. R. Treasures in the attic: rolling circle transposons discovered in eukaryotic genomes. Proc Natl Acad Sci USA 98, 8923-8924 (2001).
25. Budiman, M. A., Mao, L., Wood, T. C. & Wing, R. A. A deep-coverage tomato BAC library and prospects toward development of an STC framework for genome sequencing. Genome Res 10, 129-136 (2000).
26. Abel, S., Savchenko, T. & Levy, M. Genome-wide comparative analysis of the IQD gene families in *Arabidopsis thaliana* and *Oryza sativa*. BMC Evol Biol 5, 72 (2005).
27. Majira, A., Domin, M., Grandjean, O., Gofron, K. & Houba-Herin, N. Seedling lethality in *Nicotiana plumbaginifolia* conferred by Ds transposable element insertion into a plant-specific gene. Plant Mol Biol 50, 551-562 (2002).
28. Lertpiriyapong, K. & Sung, Z. R. The elongation defective1 mutant of *Arabidopsis* is impaired in the gene encoding a serine-rich secreted protein. Plant Mol Biol 53, 581-595 (2003).

29. Takada, S., Hibara, K., Ishida, T. & Tasaka, M. The CUP-SHAPED COTYLEDON1 gene of *Arabidopsis* regulates shoot apical meristem formation. Development 128, 1127-1135 (2001).

30. Silverstein, K. A., Graham, M. A., Paape, T. D. & VandenBosch, K. A. Genome organization of more than 300 defensin-like genes in *Arabidopsis*. Plant Physiol 138, 600-610 (2005).

31. Thomma, B. P., Cammue, B. P. & Thevissen, K. Plant defensins. Planta 216, 193-202 (2002).

32. Levy, M., Wang, Q., Kaspi, R., Parrella, M. P. & Abel, S. *Arabidopsis* IQD1, a novel calmodulin-binding nuclear protein, stimulates glucosinolate accumulation and plant defense. Plant J 43, 79-96 (2005).

33. Eshed, Y. & Zamir, D. An introgression line population of *Lycopersicon pennellii* in the cultivated tomato enables the identification and fine mapping of yield-associated QTL. Genetics 141, 1147-1162 (1995).

34. Van der Hoeven, R., Ronning, C., Giovannoni, J., Martin, G. & Tanksley, S. Deductions about the number, organization, and evolution of genes in the tomato genome based on analysis of a large expressed sequence tag collection and selective genomic sequencing. Plant Cell 14, 1441-1456 (2002).

35. Doebley, J. F., Gaut, B. S. & Smith, B. D. The molecular genetics of crop domestication. Cell 127, 1309-1321 (2006).

36. Tanksley, S. D. The genetic, developmental, and molecular bases of fruit size and shape variation in tomato. Plant Cell 16 Suppl, S181-189 (2004).

37. Lewin, B. Genes IX (Jones and Bartlett Publishers, Sudbury, Mass., 2008).

38. Ejima, Y. & Yang, L. Trans mobilization of genomic DNA as a mechanism for retrotransposon-mediated exon shuffling. Hum Mol Genet 12, 1321-1328 (2003).

39. Lander, E. S. et al. Initial sequencing and analysis of the human genome. Nature 409, 860-921 (2001).

40. Moran, J. V., DeBerardinis, R. J. & Kazazian, H. H., Jr. Exon shuffling by L1 retrotransposition. Science 283, 1530-1534 (1999).

41. Xing, J. et al. Emergence of primate genes by retrotransposon-mediated sequence transduction. Proc Natl Acad Sci USA 103, 17608-17613 (2006).

42. Grubb, C. D. & Abel, S. Glucosinolate metabolism and its control. Trends Plant Sci 11, 89-100 (2006).

43. Hull, A. K., Vij, R. & Celenza, J. L. *Arabidopsis* cytochrome P450s that catalyze the first step of tryptophan-dependent indole-3-acetic acid biosynthesis. Proc Natl Acad Sci USA 97, 2379-2384 (2000).

44. Mikkelsen, M. D., Hansen, C. H., Wittstock, U. & Halkier, B. A. Cytochrome P450 CYP79B2 from *Arabidopsis* catalyzes the conversion of tryptophan to indole-3-acetaldoxime, a precursor of indole glucosinolates and indole-3-acetic acid. J Biol Chem 275, 33712-33717 (2000).

45. Zhao, Y. et al. Trp-dependent auxin biosynthesis in *Arabidopsis*: involvement of cytochrome P450s CYP79B2 and CYP79B3. Genes Dev 16, 3100-3112 (2002).

46. Rothstein, S. J. et al. Promoter cassettes, antibiotic-resistance genes, and vectors for plant transformation. Gene 53, 153-161 (1987).

47. Kerschen, A., Napoli, C. A., Jorgensen, R. A. & Muller, A. E. Effectiveness of RNA interference in transgenic plants. FEBS Lett 566, 223-228 (2004).

48. Bailey, T. L. & Elkan, C. Fitting a mixture model by expectation maximization to discover motifs in biopolymers. Proc Int Conf Intell Syst Mol Biol 2, 28-36 (1994).

What is claimed is:

1. A transgenic *Lycopersicon* plant transformed with an isolated nucleic acid sequence which encodes SEQ ID NO: 4 and an isolated DEFL1 promoter operably linked to the isolated nucleic acid sequence which encodes SEQ ID NO: 4.

2. The transgenic *Lycopersicon* plant of claim 1, wherein the transgenic *Lycopersicon* plant is a near isogenic line.

3. A plant part, plant seed, plant cell, or the transgenic progeny of the transgenic *Lycopersicon* plant of claim 1.

4. The plant part, plant seed, plant cell, or the transgenic progeny of claim 3, wherein the transgenic *Lycopersicon* plant is selected from the group consisting of: *Lycopersicon esculemm* and *Lycopersicon pimpinelliforlium.*

5. A method for making a transgenic *Lycopersicon* plant having altered fruit shape, comprising breeding the plant of claim 1 with another *Lycopersicon* plant.

* * * * *

UNITED STATES PATENT AND TRADEMARK OFFICE

CERTIFICATE OF CORRECTION

PATENT NO. : 8,653,330 B2
APPLICATION NO. : 12/678359
DATED : February 18, 2014
INVENTOR(S) : Esther van der Knaap It is certified that error appears in the above-identified patent and that said Letters Patent is hereby corrected as shown below:

In the Claims

Column 276, Claim 4, line 50, please delete “esculemm” and insert --esculentum--.

Signed and Sealed this
Thirteenth Day of May, 2014

Michelle K. Lee
*Deputy Director of the United States Patent and Trademark Office*